US008118872B2

(12) United States Patent
Trudeau et al.

(10) Patent No.: US 8,118,872 B2
(45) Date of Patent: Feb. 21, 2012

(54) SYSTEM AND METHODS FOR INSERTING A SPINAL DISC DEVICE INTO AN INTERVERTEBRAL SPACE

(75) Inventors: Jeffrey L. Trudeau, Marquette, MI (US); Qi-Bin Bao, Marquette, MI (US); Thomas Kilpela, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1091 days.

(21) Appl. No.: 11/836,621

(22) Filed: Aug. 9, 2007

(65) Prior Publication Data

US 2008/0109005 A1    May 8, 2008

Related U.S. Application Data

(60) Provisional application No. 60/822,027, filed on Aug. 10, 2006, provisional application No. 60/846,859, filed on Sep. 22, 2006.

(51) Int. Cl.
*A61F 2/44* (2006.01)

(52) U.S. Cl. ...................... 623/17.16; 606/99

(58) Field of Classification Search ............ 606/86 A, 606/99; 623/17.11–17.16
See application file for complete search history.

(56) References Cited

U.S. PATENT DOCUMENTS

| | | |
|---|---|---|
| 4,566,466 A | 1/1986 | Ripple et al. |
| 4,899,761 A | 2/1990 | Brown et al. |
| 5,562,736 A | 10/1996 | Ray et al. |
| 6,478,801 B1 | 11/2002 | Ralph et al. |
| 6,533,799 B1 | 3/2003 | Bouchier |
| 6,607,559 B2 | 8/2003 | Ralph et al. |
| 6,669,730 B2 | 12/2003 | Ralph et al. |
| 6,673,113 B2 | 1/2004 | Ralph et al. |
| 6,824,565 B2 | 11/2004 | Muhanna et al. |
| 6,863,689 B2 | 3/2005 | Ralph et al. |
| 6,984,246 B2 | 1/2006 | Huang |
| 2002/0065560 A1 | 5/2002 | Varga et al. |
| 2002/0111683 A1 | 8/2002 | Ralph et al. |
| 2002/0111687 A1 | 8/2002 | Ralph et al. |
| 2002/0151979 A1 | 10/2002 | Lambrecht et al. |
| 2003/0009227 A1 | 1/2003 | Lambrecht et al. |
| 2003/0014113 A1 | 1/2003 | Ralph et al. |
| 2003/0014115 A1 | 1/2003 | Ralph et al. |
| 2003/0069586 A1 | 4/2003 | Errico et al. |
| 2003/0069642 A1 | 4/2003 | Ralph et al. |
| 2003/0069643 A1 | 4/2003 | Ralph et al. |
| 2003/0078590 A1 | 4/2003 | Errico et al. |

(Continued)

FOREIGN PATENT DOCUMENTS

WO    9100713    1/1991

*Primary Examiner* — Nicholas Woodall
(74) *Attorney, Agent, or Firm* — Fitch, Even, Tabin & Flannery, LLP

(57) ABSTRACT

A system for replacing a natural nuclear disc in an intervertebral space has a spinal device configured for placement in the intervertebral space. An insertion tool is configured for holding the spinal device while the spinal device is inserted into the intervertebral space. A gripping member of the insertion tool has an end for adjustably holding the spinal device within the intervertebral space. A steering actuator of the insertion tool is operably connected to the spinal device and configured for pivoting the adjustably held spinal device within the intervertebral space while the steering actuator is controlled remotely from the intervertebral space.

9 Claims, 56 Drawing Sheets

U.S. PATENT DOCUMENTS

| | | |
|---|---|---|
| 2003/0078662 A1 | 4/2003 | Ralph et al. |
| 2003/0093155 A1 | 5/2003 | Lambrecht et al. |
| 2003/0130667 A1 | 7/2003 | Lin |
| 2003/0149438 A1 | 8/2003 | Nichols et al. |
| 2003/0204362 A1 | 10/2003 | Beresford et al. |
| 2003/0208203 A1* | 11/2003 | Lim et al. .................. 606/61 |
| 2003/0216810 A1 | 11/2003 | Ralph et al. |
| 2003/0229358 A1 | 12/2003 | Errico et al. |
| 2004/0010316 A1 | 1/2004 | William et al. |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034426 A1 | 2/2004 | Errico et al. |
| 2004/0049280 A1 | 3/2004 | Cauthen |
| 2004/0068321 A1 | 4/2004 | Ferree |
| 2004/0093088 A1 | 5/2004 | Ralph et al. |
| 2004/0098129 A1 | 5/2004 | Lin |
| 2004/0133132 A1 | 7/2004 | Chappuis |
| 2004/0133278 A1 | 7/2004 | Marino et al. |
| 2004/0133280 A1 | 7/2004 | Trieu |
| 2004/0143331 A1 | 7/2004 | Errico et al. |
| 2004/0143332 A1 | 7/2004 | Krueger et al. |
| 2004/0148027 A1 | 7/2004 | Errico et al. |
| 2004/0148028 A1 | 7/2004 | Ferree et al. |
| 2004/0153065 A1 | 8/2004 | Lim |
| 2004/0153158 A1 | 8/2004 | Errico et al. |
| 2004/0153159 A1 | 8/2004 | Cauthen |
| 2004/0167534 A1 | 8/2004 | Errico et al. |
| 2004/0167626 A1 | 8/2004 | Geremakis et al. |
| 2004/0167628 A1 | 8/2004 | Foley |
| 2004/0176843 A1 | 9/2004 | Zubok et al. |
| 2004/0176845 A1 | 9/2004 | Zubok et al. |
| 2004/0176848 A1 | 9/2004 | Zubok et al. |
| 2004/0186577 A1 | 9/2004 | Ferree |
| 2004/0225295 A1 | 11/2004 | Zubok et al. |
| 2005/0027360 A1 | 2/2005 | Webb et al. |
| 2005/0033305 A1 | 2/2005 | Schultz |
| 2005/0033437 A1 | 2/2005 | Bao et al. |
| 2005/0033438 A1 | 2/2005 | Schultz et al. |
| 2005/0038445 A1 | 2/2005 | Errico et al. |
| 2005/0038515 A1 | 2/2005 | Kunzler |
| 2005/0038516 A1 | 2/2005 | Spoonamore |
| 2005/0055097 A1 | 3/2005 | Grunberg |
| 2005/0060035 A1 | 3/2005 | Errico et al. |
| 2005/0071012 A1 | 3/2005 | Serhan et al. |
| 2005/0085917 A1 | 4/2005 | Marnay et al. |
| 2005/0096745 A1 | 5/2005 | Andre et al. |
| 2005/0113842 A1 | 5/2005 | Bertagnoli et al. |
| 2005/0119752 A1 | 6/2005 | Williams et al. |
| 2005/0131541 A1 | 6/2005 | Trieu |
| 2005/0143820 A1 | 6/2005 | Zucherman et al. |
| 2005/0143824 A1 | 6/2005 | Richelsoph et al. |
| 2005/0154463 A1 | 7/2005 | Trieu |
| 2005/0154464 A1 | 7/2005 | Humphreys et al. |
| 2005/0154466 A1 | 7/2005 | Humphreys et al. |
| 2005/0154468 A1 | 7/2005 | Rivin |
| 2005/0192670 A1 | 9/2005 | Zubok et al. |
| 2005/0192671 A1* | 9/2005 | Bao et al. .................. 623/17.14 |
| 2005/0203538 A1 | 9/2005 | Lo et al. |
| 2006/0069436 A1 | 3/2006 | Sutton et al. |
| 2006/0241761 A1* | 10/2006 | Gately .................. 623/17.11 |
| 2007/0213461 A1 | 9/2007 | Hu et al. |
| 2008/0091211 A1* | 4/2008 | Gately .................. 606/99 |

* cited by examiner

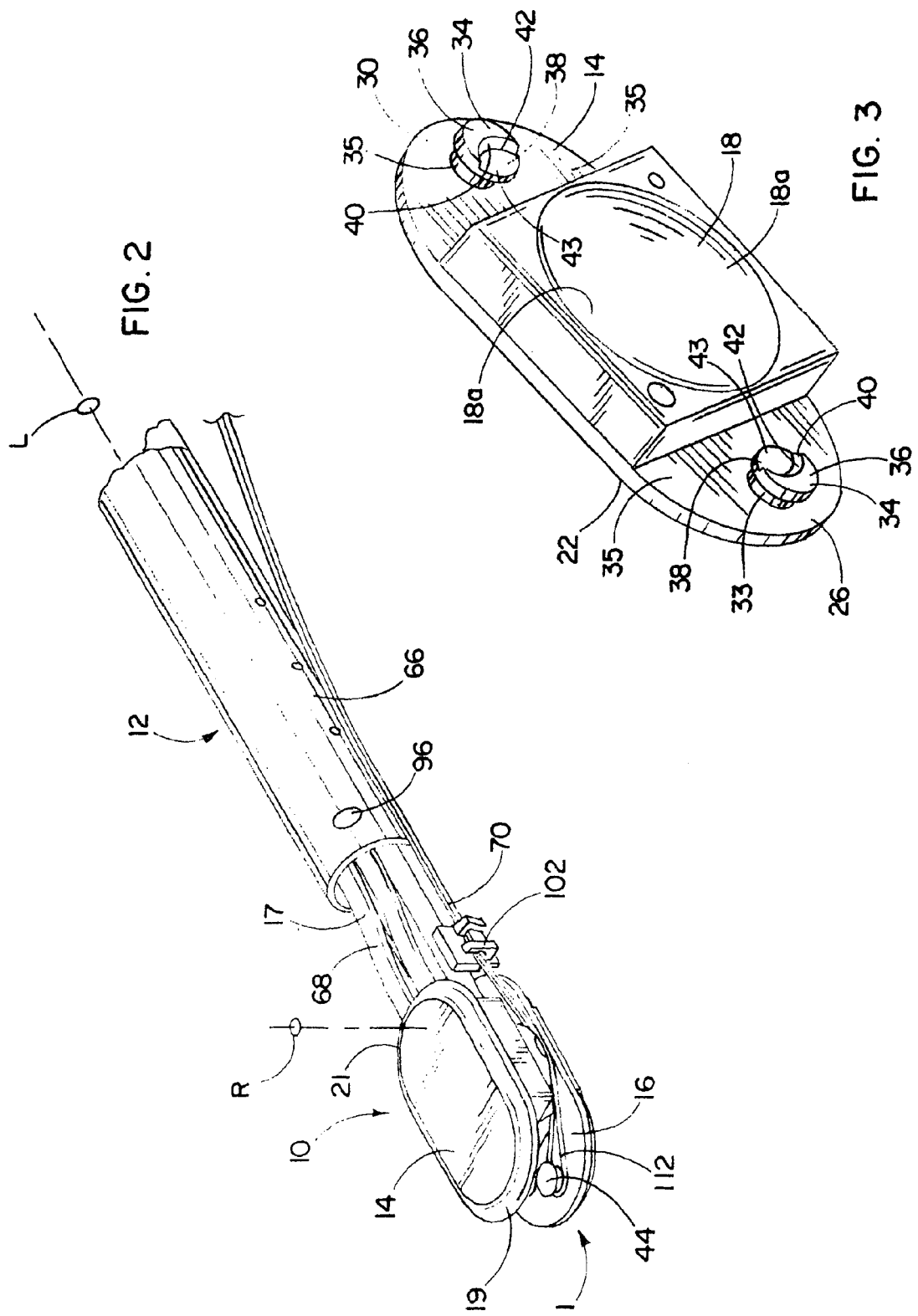

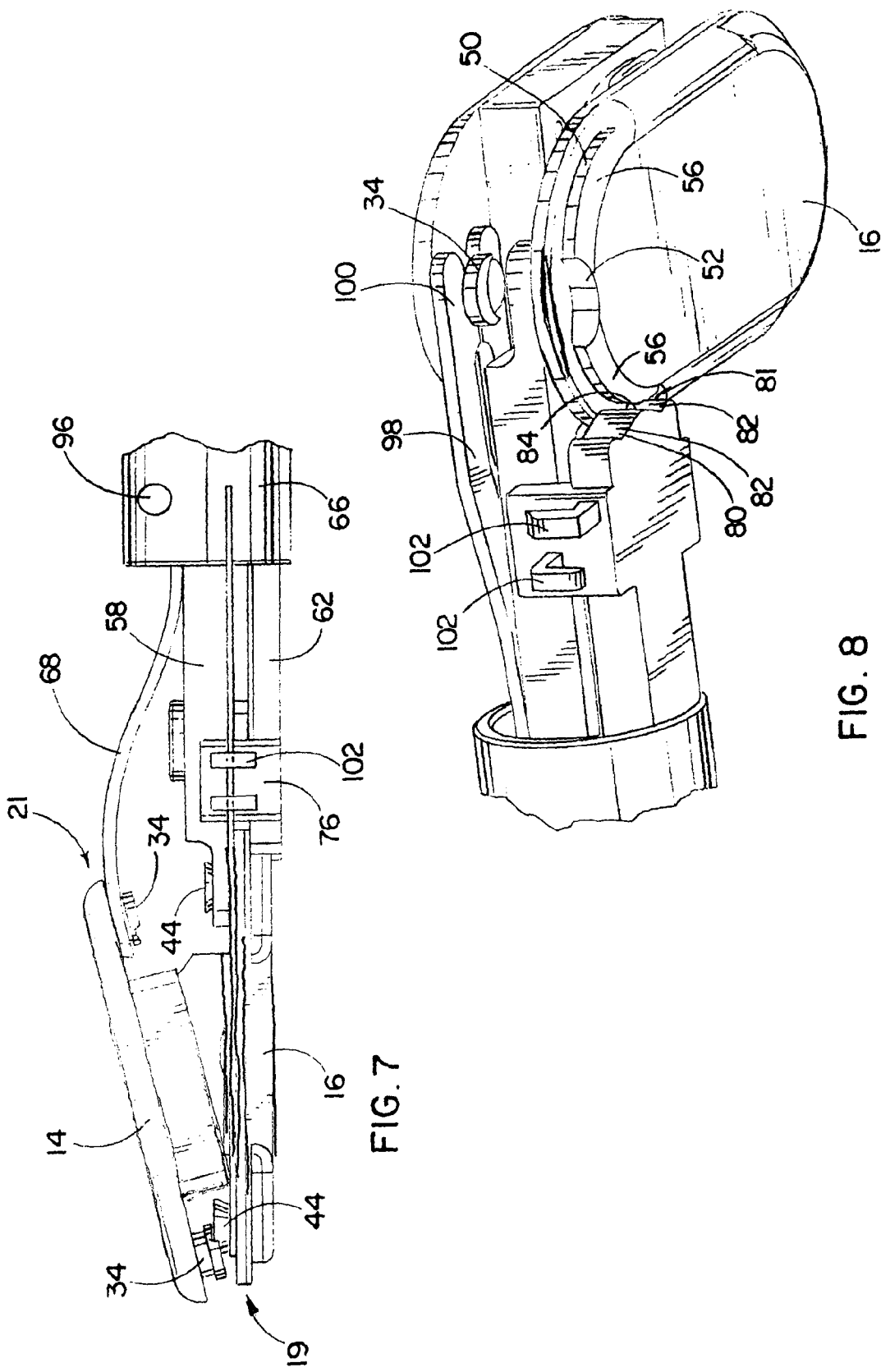

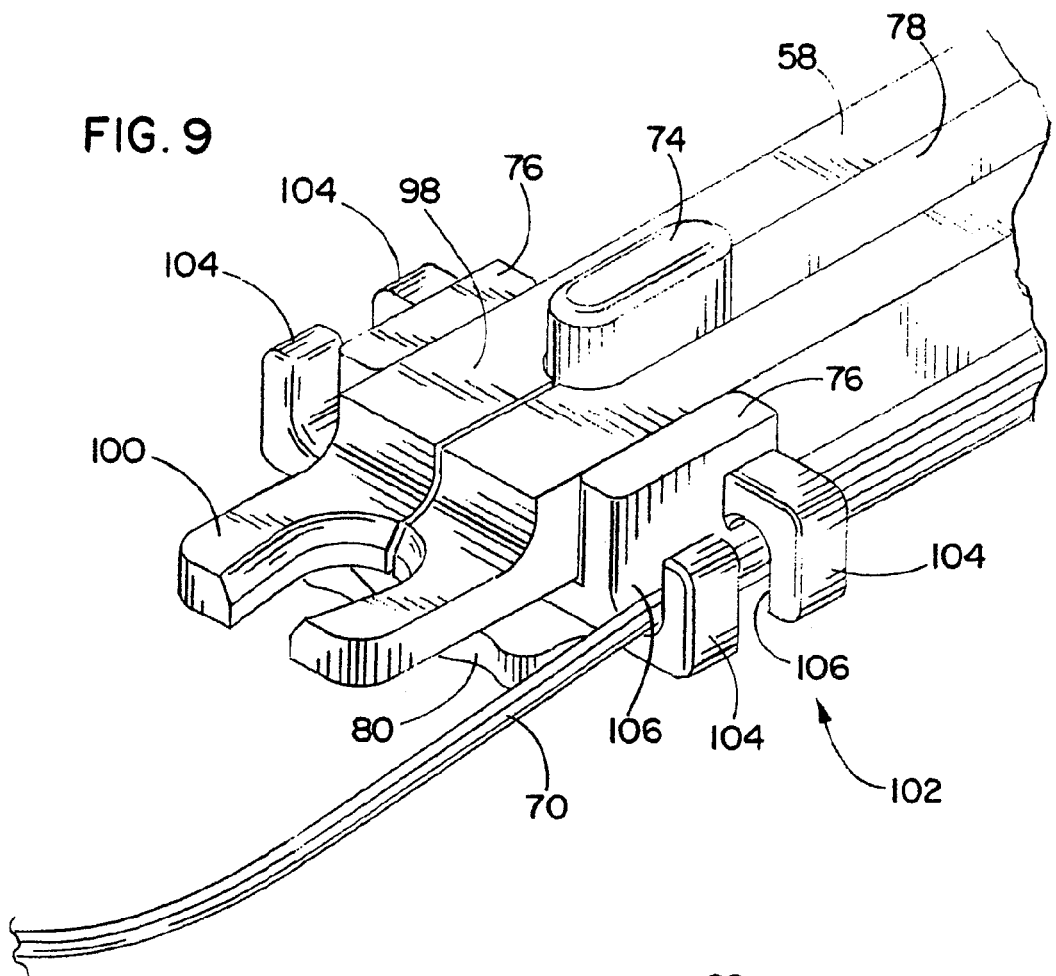
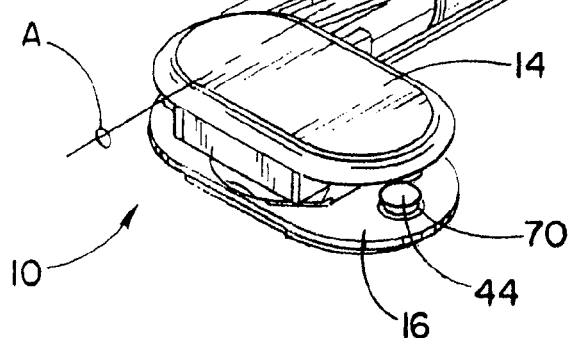

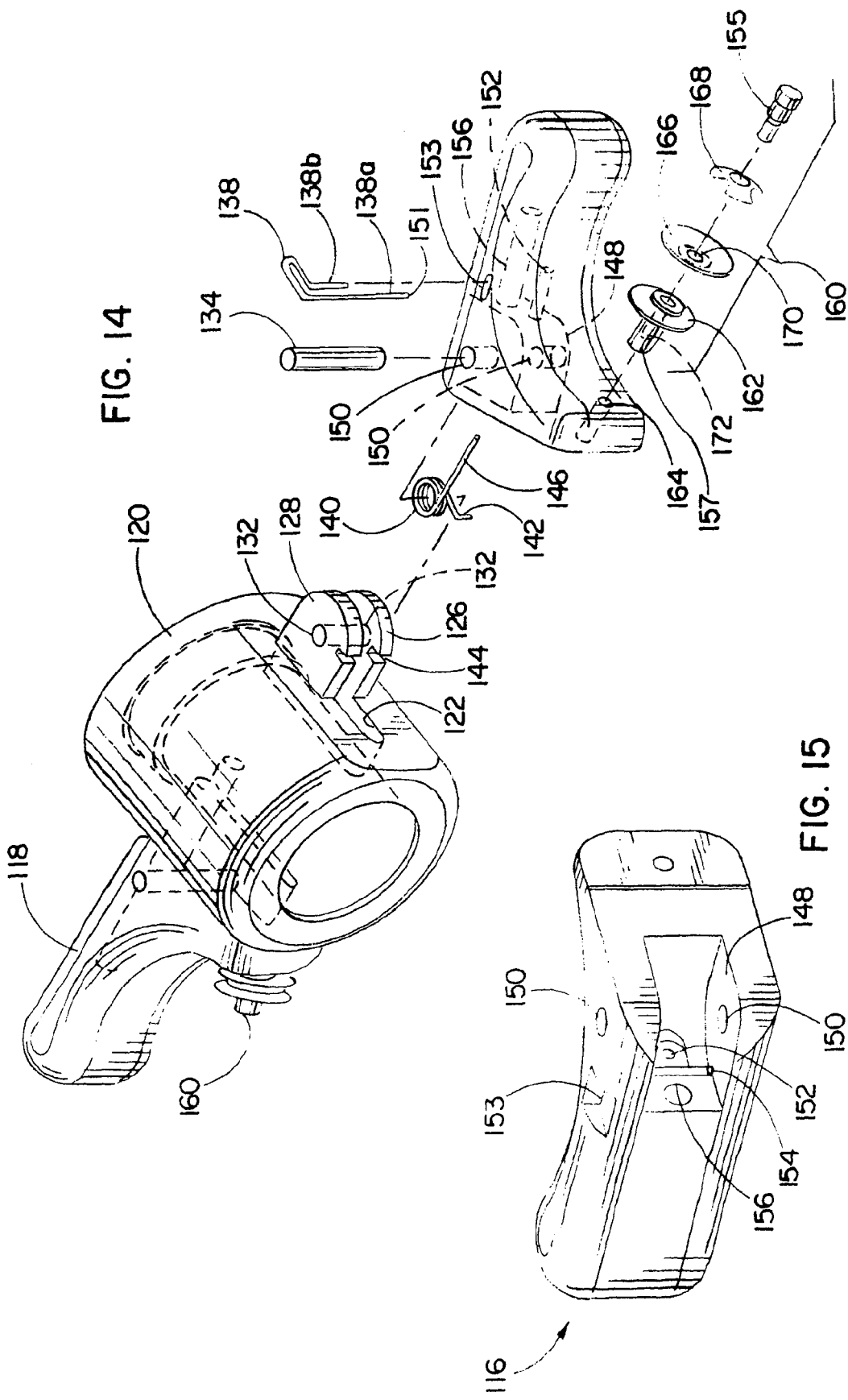

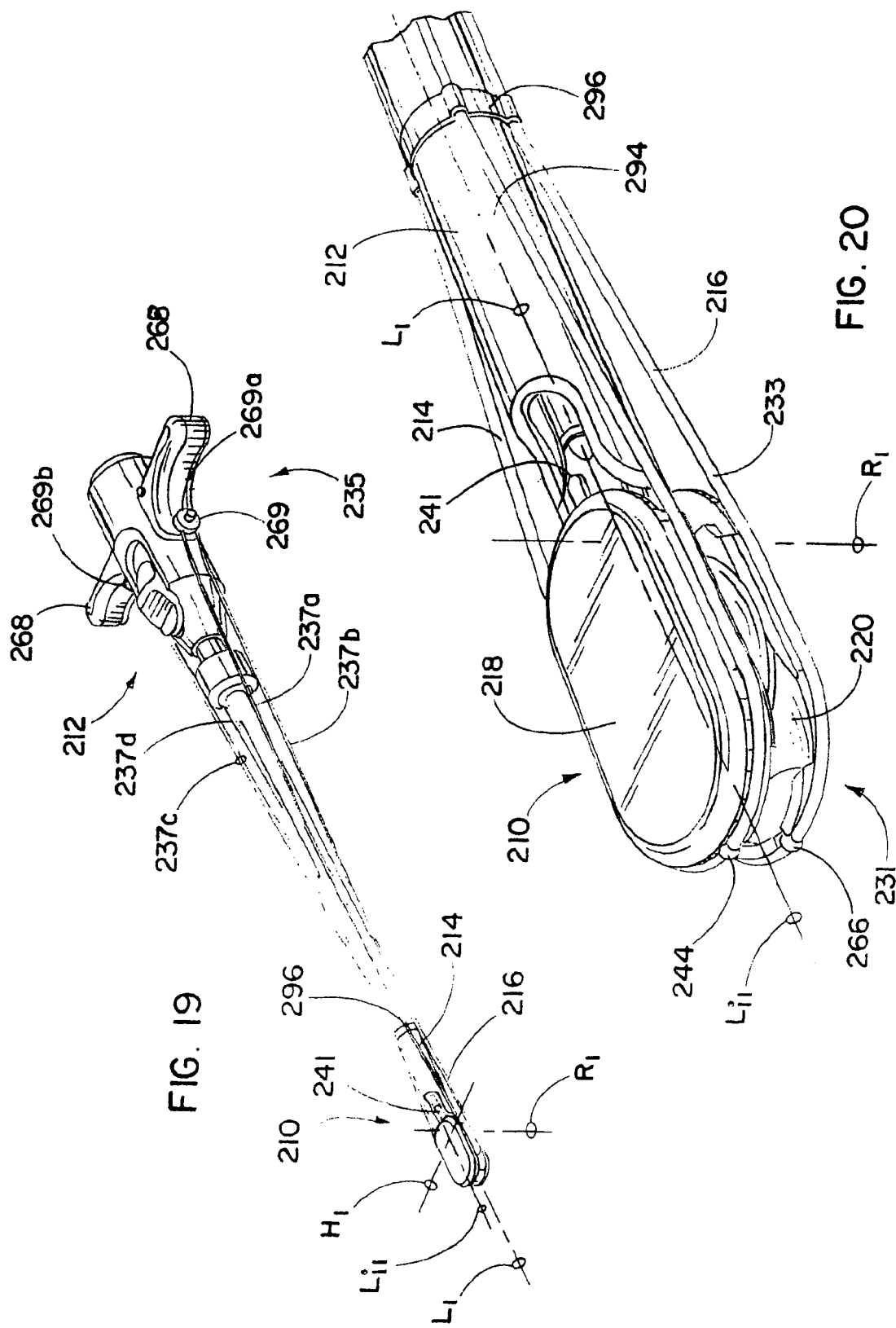

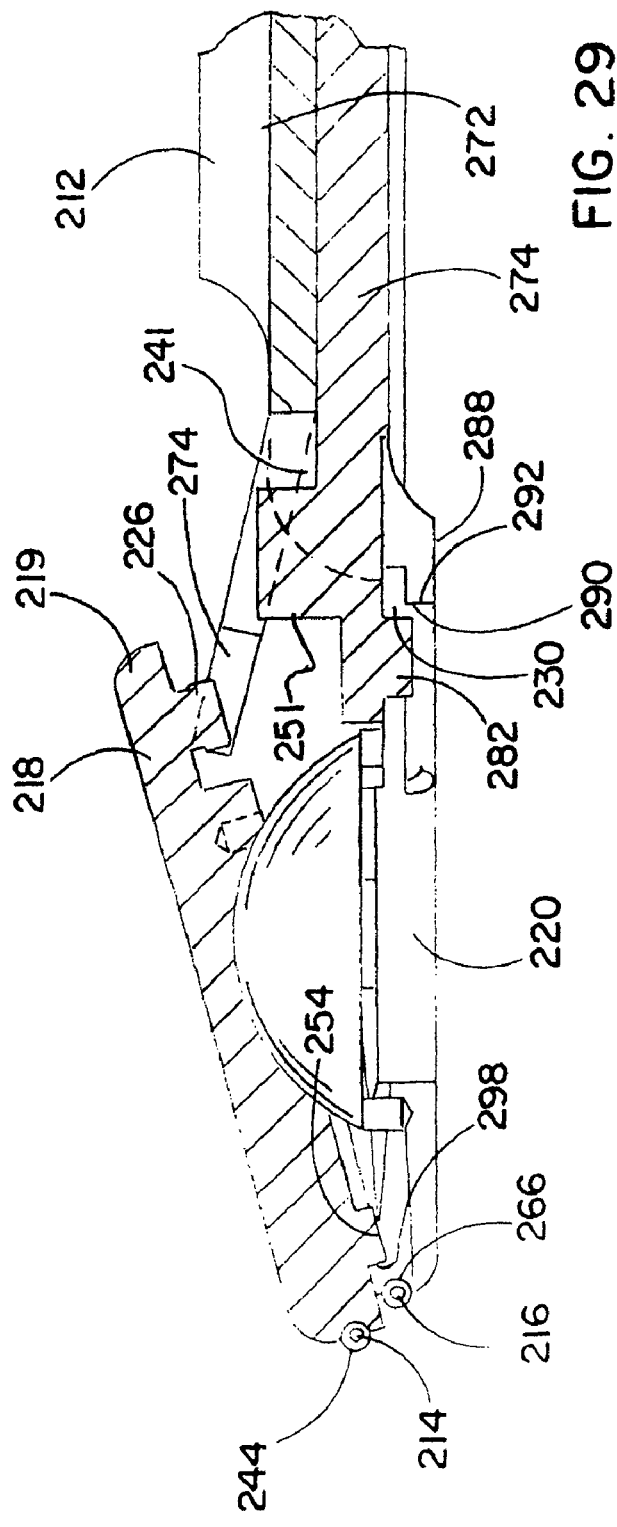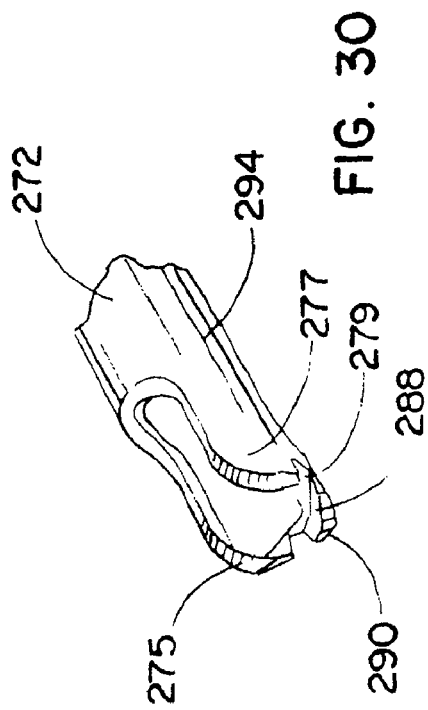

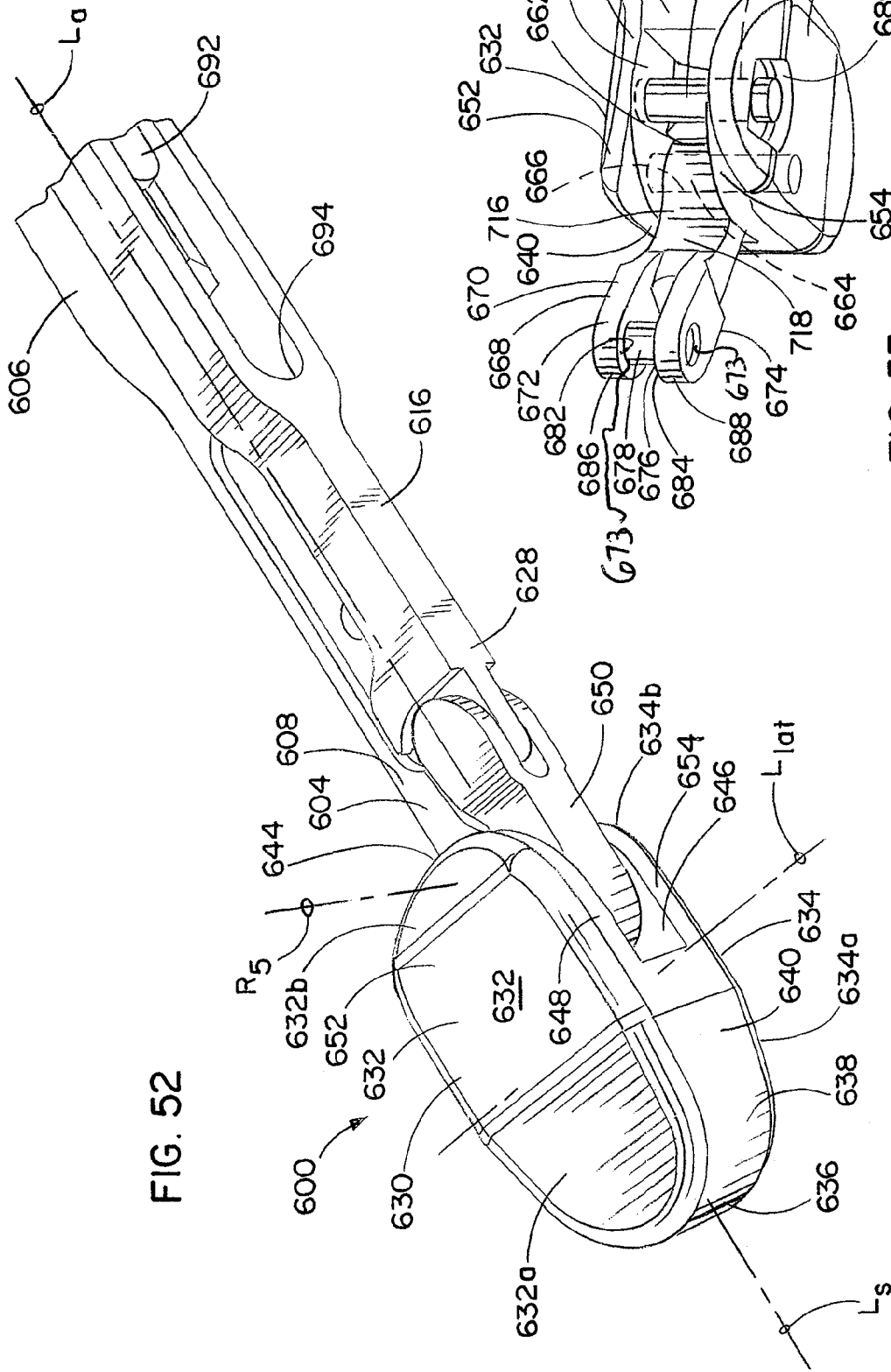

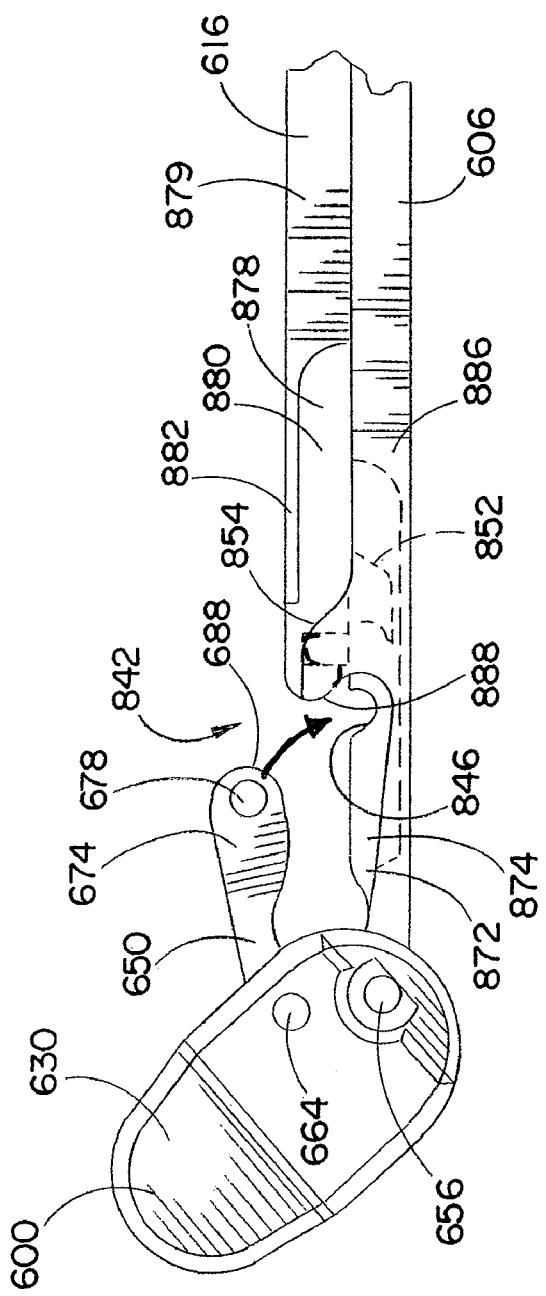
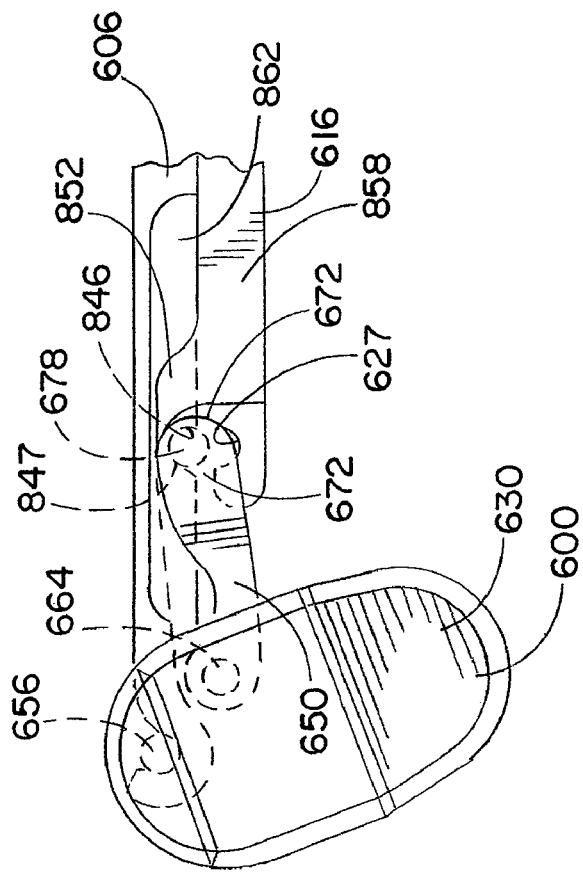
FIG. 61
FIG. 62A

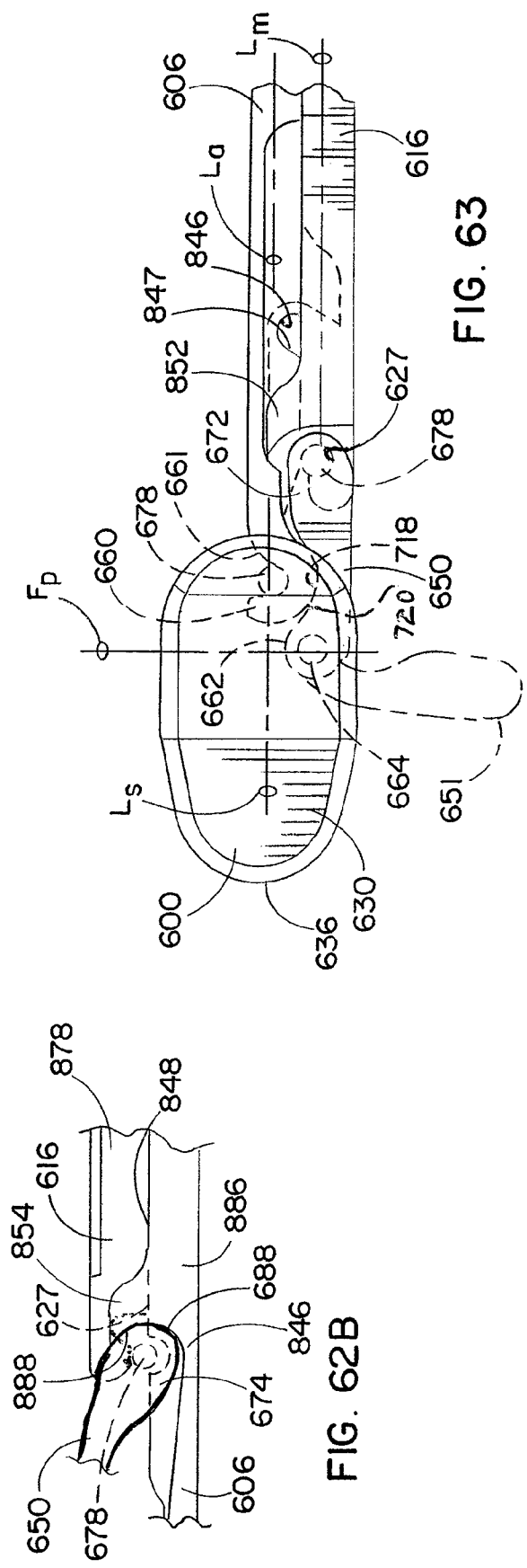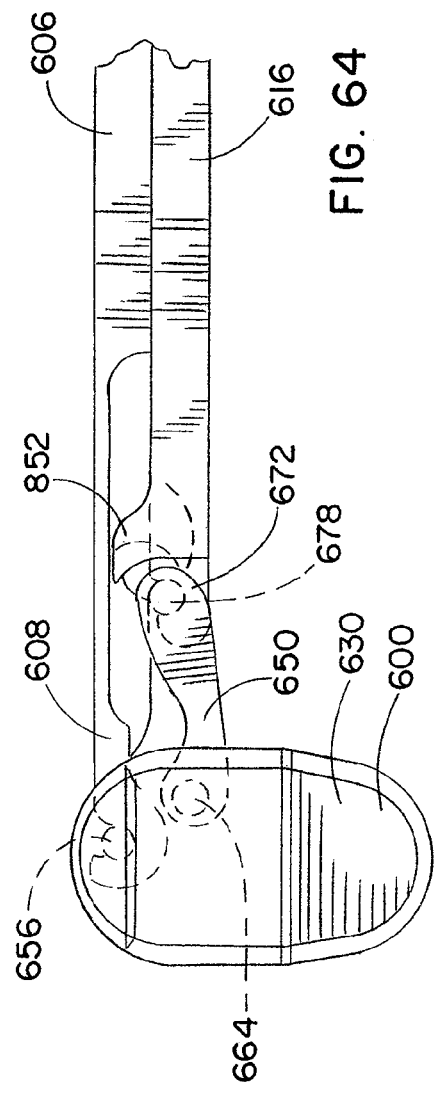

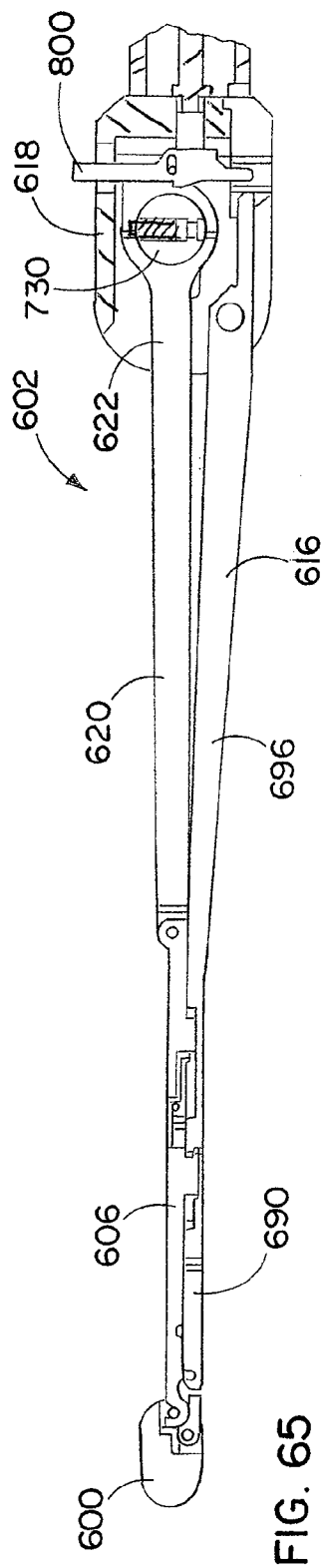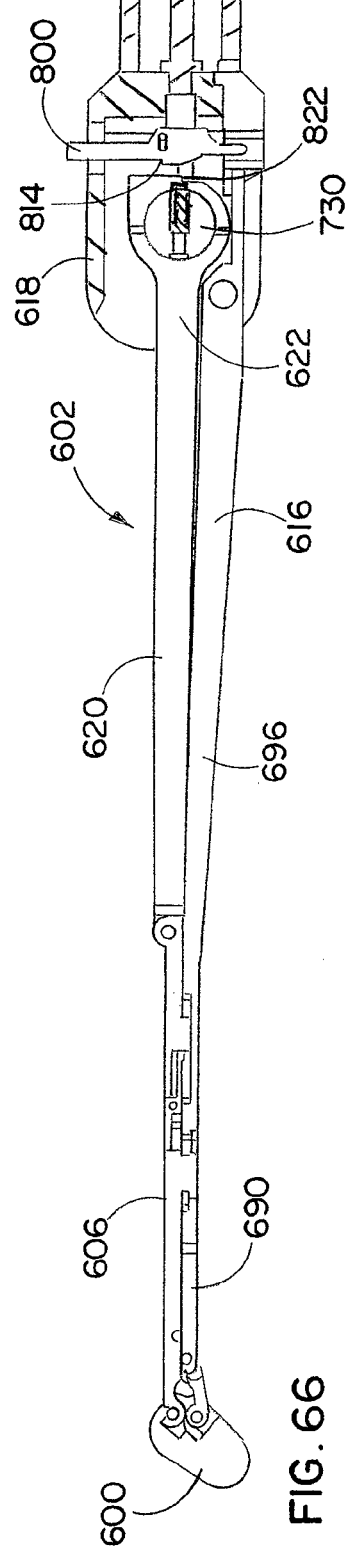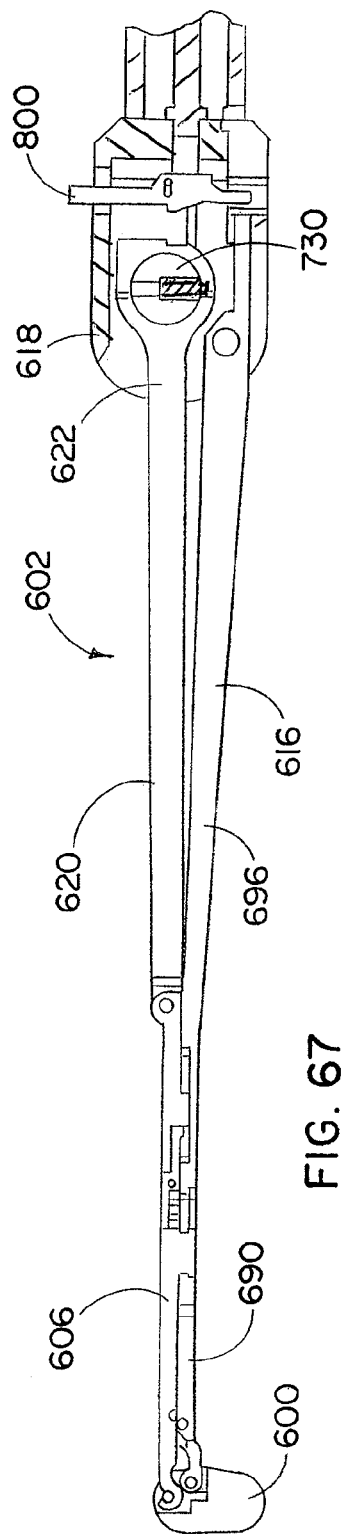

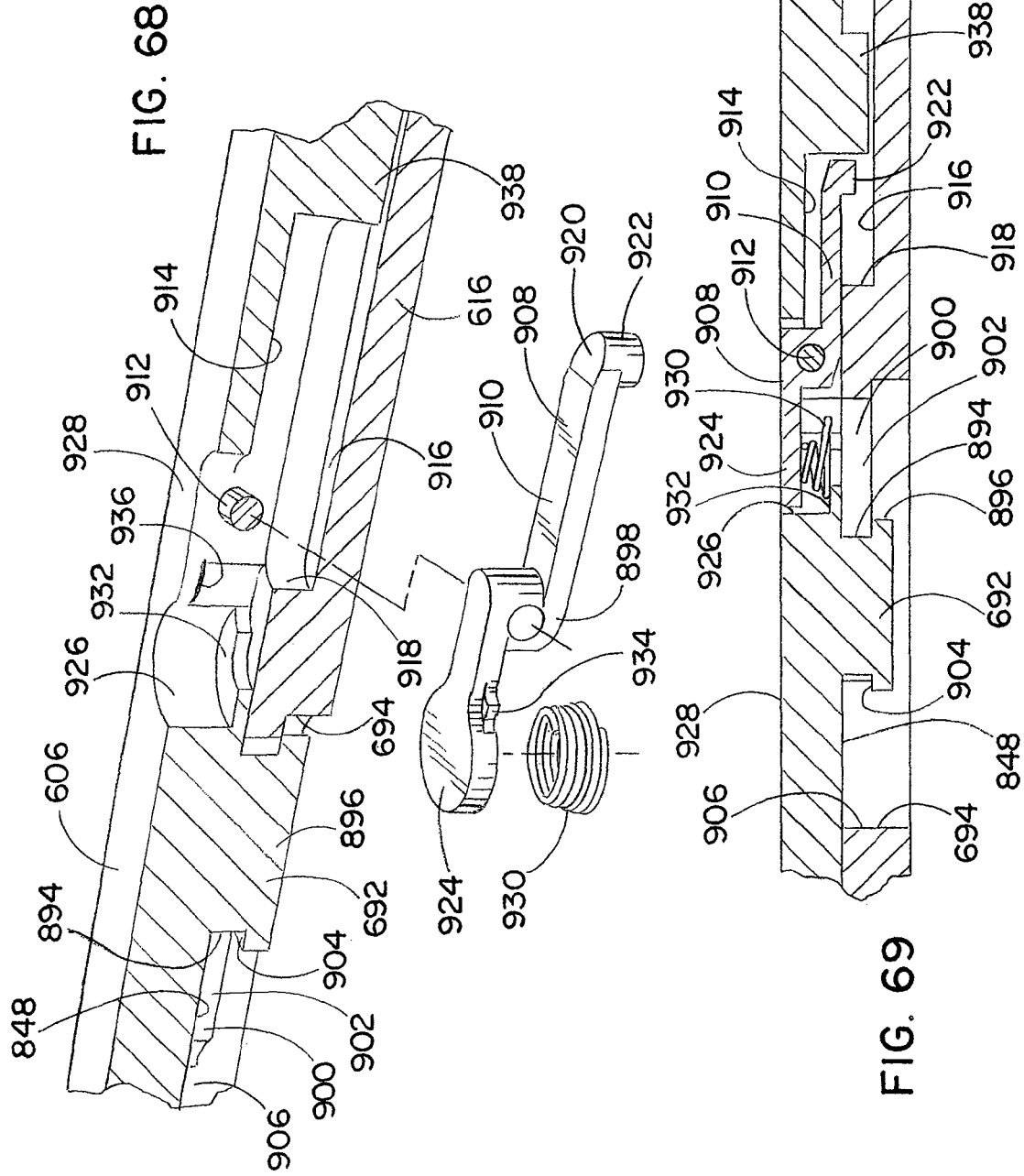

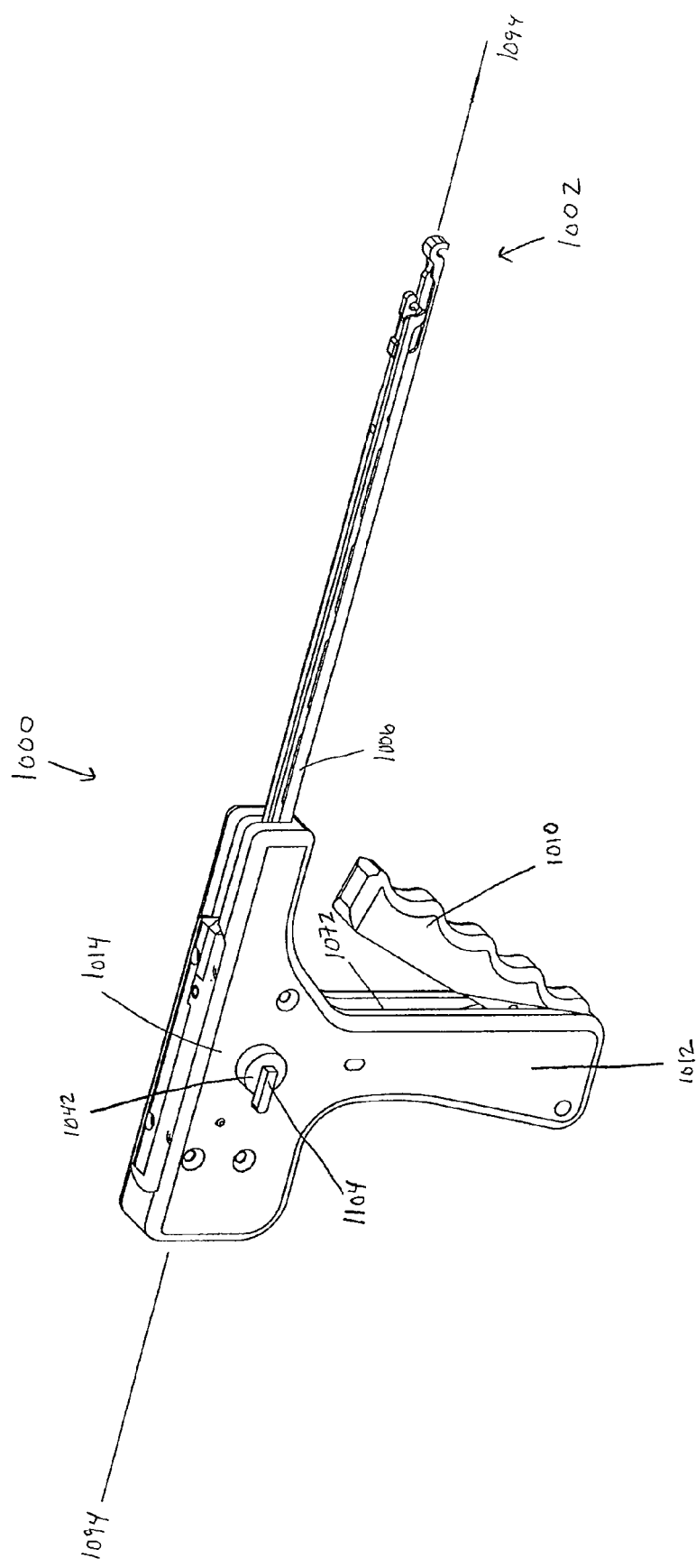

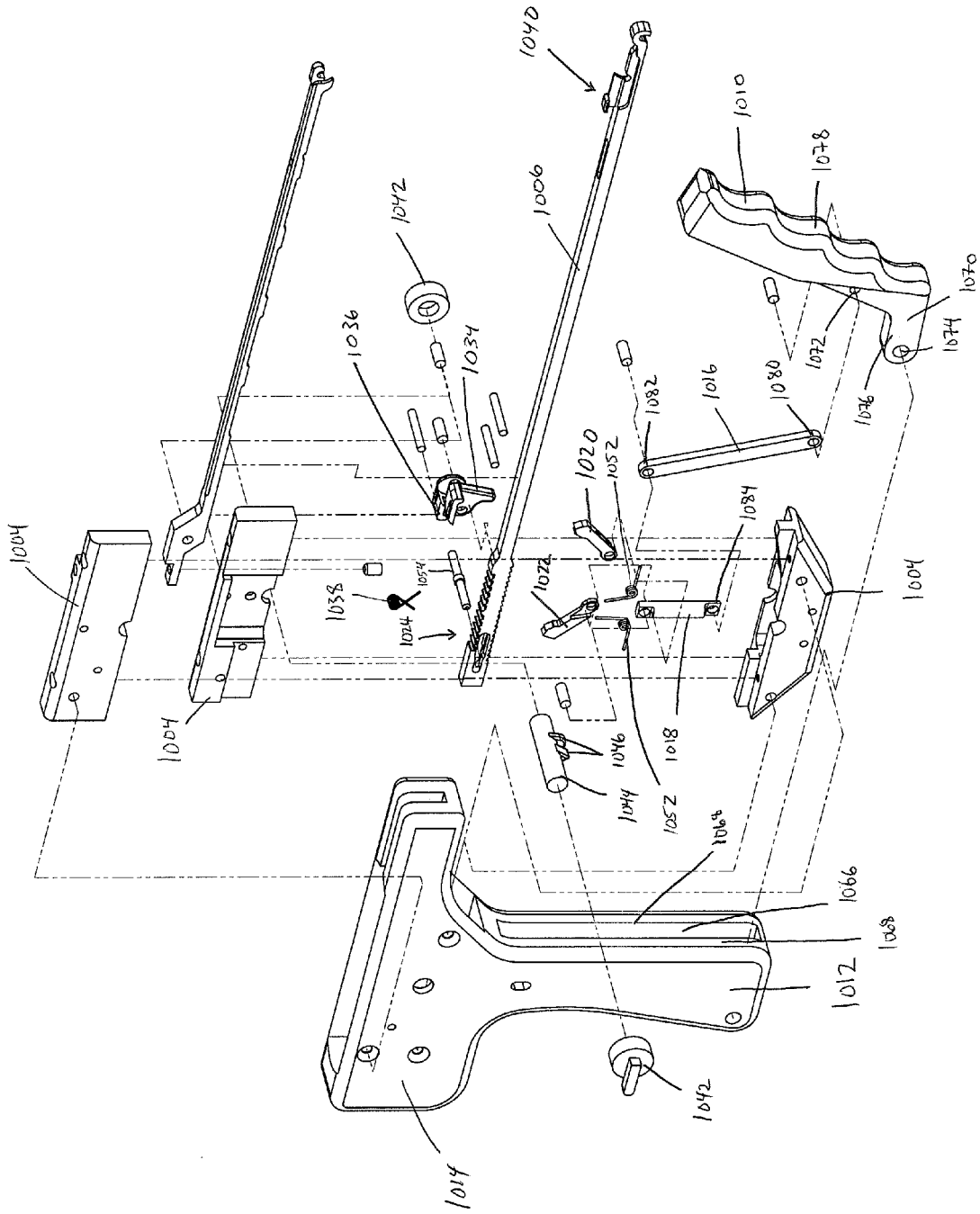

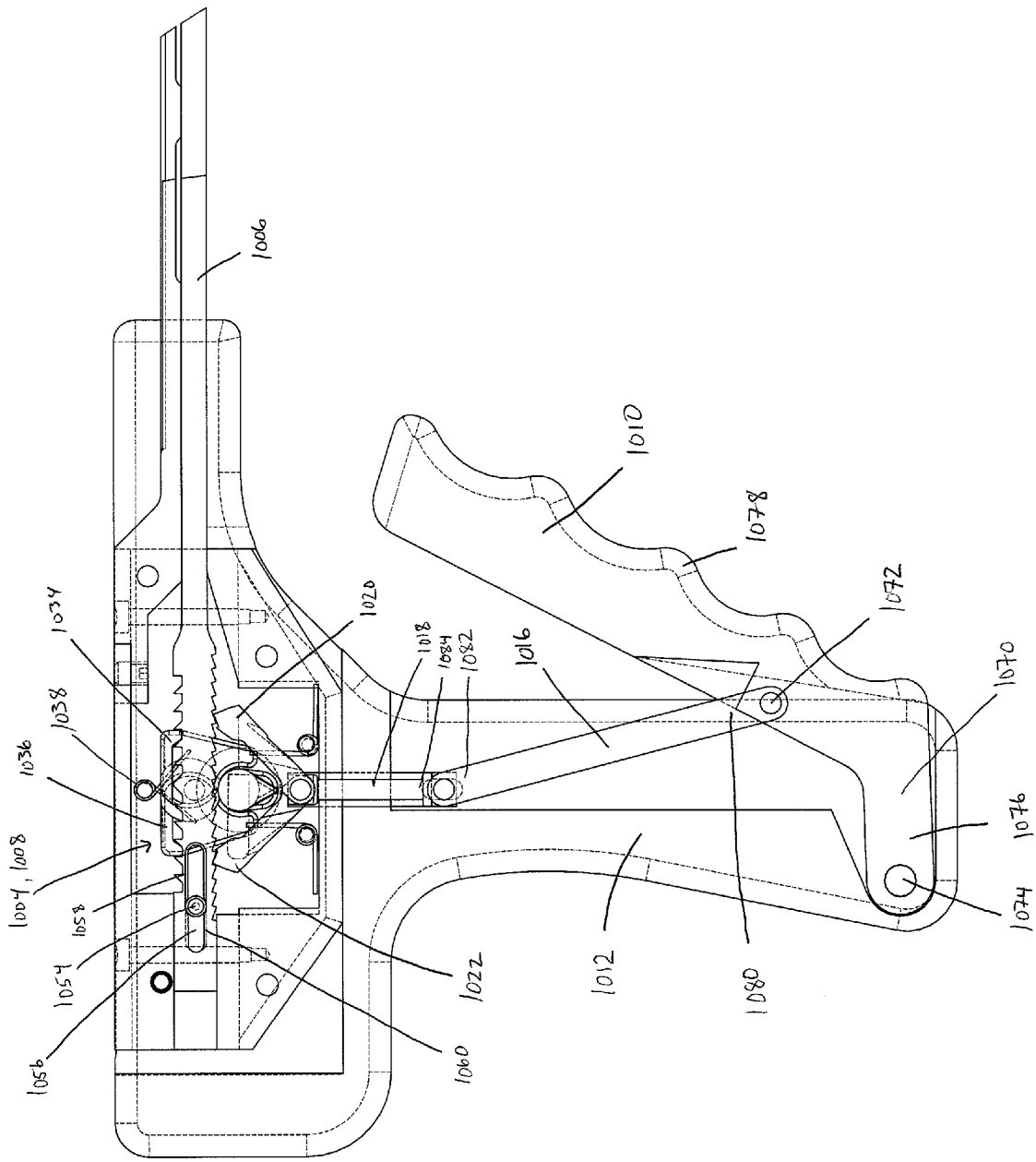

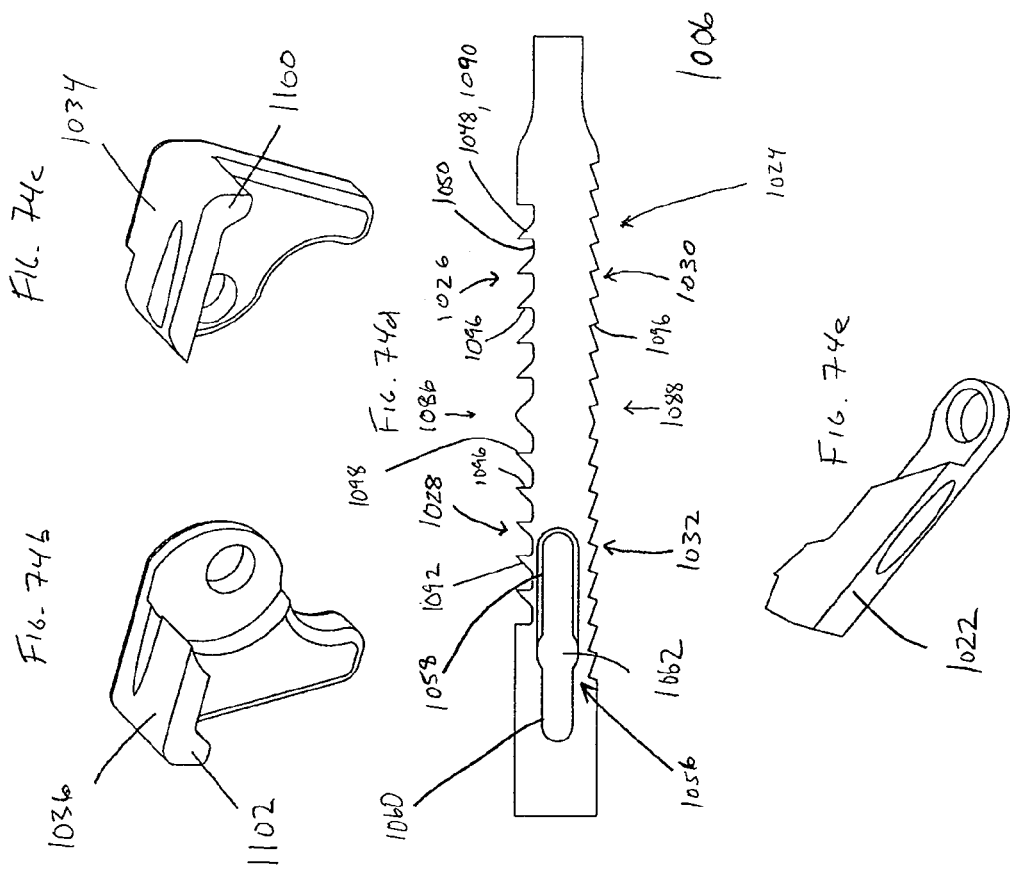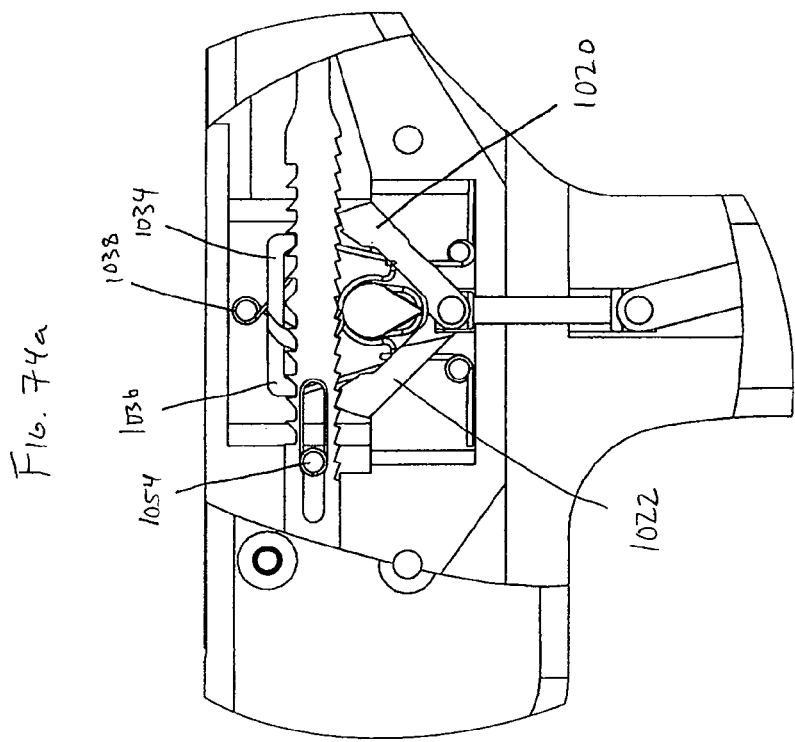

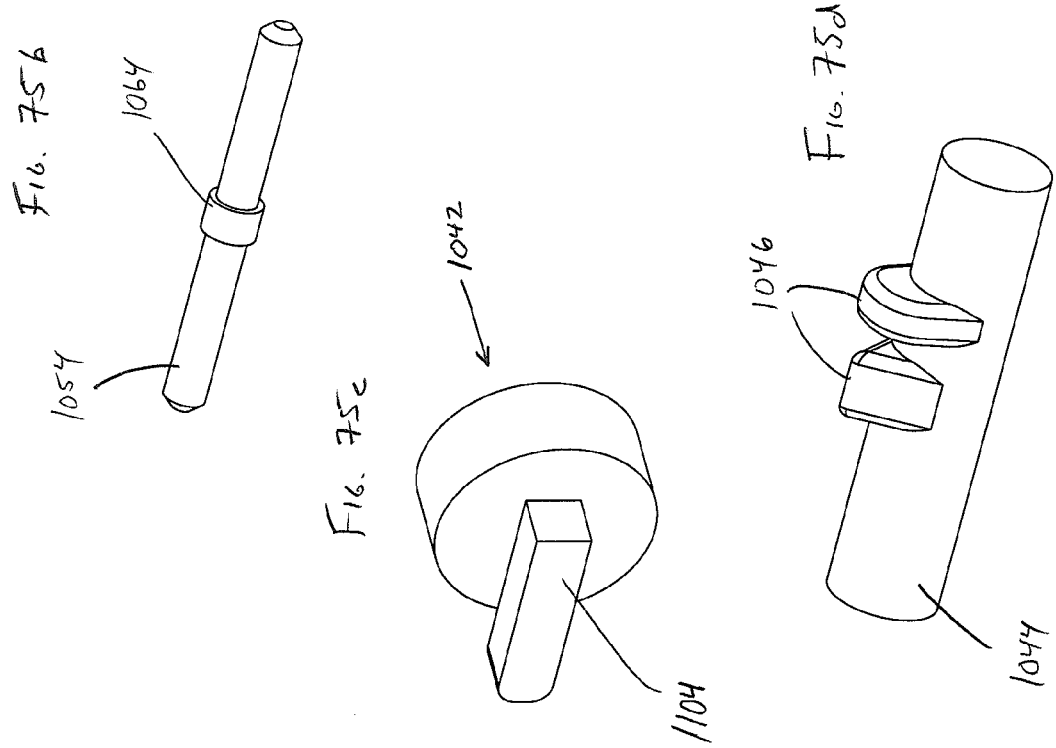
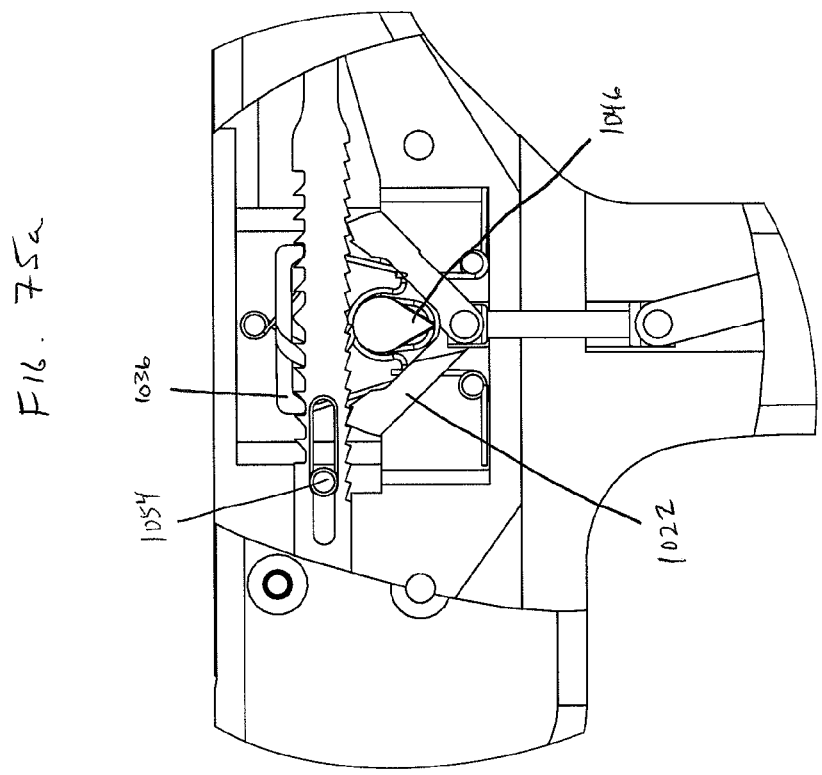

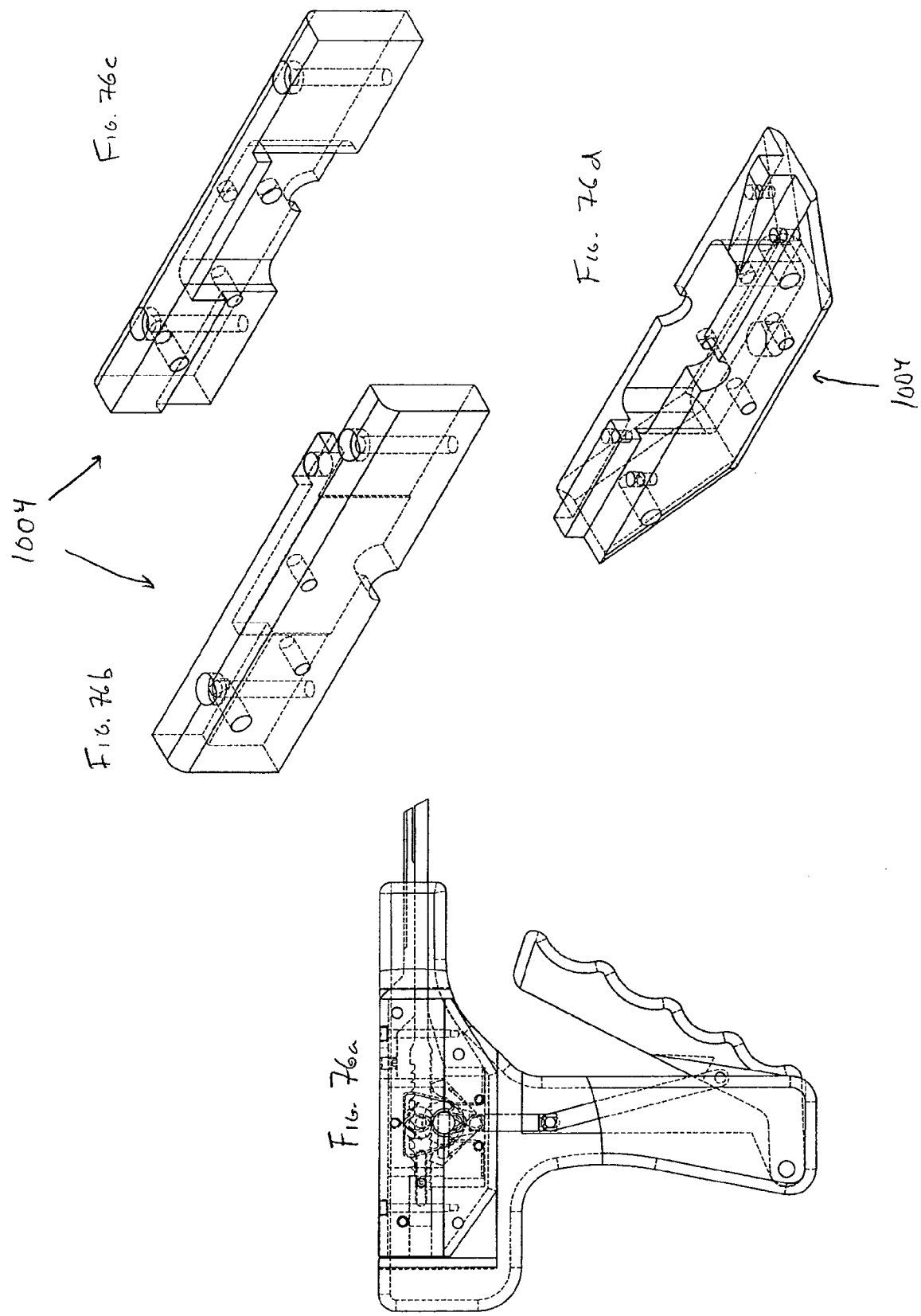

SYSTEM AND METHODS FOR INSERTING A SPINAL DISC DEVICE INTO AN INTERVERTEBRAL SPACE

CROSS REFERENCE TO RELATED APPLICATIONS

This application claims benefit of U.S. Provisional Application No. 60/822,027, filed Aug. 10, 2006 and U.S. Provisional Application No. 60/846,859, filed Sep. 22, 2006, all of which are hereby incorporated by reference as if reproduced herein in their entirety.

FIELD OF THE INVENTION

The present invention relates to artificial intervertebral implants and the tools to place the implants between vertebra, and in particular, to a steerable spinal disc device for placement of a sizing device or implant into an intervertebral space.

BACKGROUND OF THE INVENTION

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel-like viscous material capable of shock absorption and flowable to permit poly-axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried disc susceptible to damage. Because the nuclear material is flowable, extensive damage to the annulus is not necessary for leakage to occur.

Currently, approaches to treatment of spinal problems directly affecting the spinal cord are numerous. For instance, immobilization and high doses of corticosteroids may be employed. The dominant surgical procedures for treatment of these problems are spinal fusion and discectomy. Fusion is a method where adjacent vertebrae are immobilized so that they permanently secure to each other by having bone growth between and to the vertebrae, while discectomy involves removal of a portion or an entirety of a spinal disc.

However, the current practice of each of these procedures typically has certain limitations. With fusion, making a portion of the spine generally rigid produces a reduction in mobility, and drastically alters normal load distribution along the spinal column. Due to these factors, the non-fused portions of the spine experience stress and strain that are significantly increased over normal physiological motions. The increased stress and strain on the non-fused portions may lead to accelerated disc degeneration of the non-fused portions, particularly the adjacent levels of the spine.

Discectomy is effective for relieving sciatic pain by removing the damaged or herniated disc tissue compressing the spinal nerves. However, current discectomy often may lead to a reduction of the disc space between adjacent vertebrae, as well as instability in the affected portion of the spine. Such long-term effects with current discectomy often result in further surgery several years after the initial discectomy surgery.

A recent, though not new, development for spinal surgery of this type is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain. However, little success has been experienced with prosthetic disc implants due to the complexity of the natural disc structure and biomechanical properties of a natural spinal disc. As used herein, the term natural refers to normal tissue including portions of the spine and the disc.

Two types of prostheses for disc arthroplasty are currently believed to merit further development by medical science and research. One type is a total disc prosthesis, or TDP, where the entire spinal disc is replaced after radical discectomy. A typical TDP includes structures that together attempt to mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non-flowing prosthetic nucleus. Implantation of a DNP involves clearing of the natural nucleus from the annulus through the procedure known as nucleotomy, and inserting the DNP within the annulus. Accordingly, DNPs are typically smaller and require less extensive surgery than TDPs while still mimicking some of the biomechanical properties of a natural intervertebral disc. Herein, the term artificial disc device or implant can refer to either a TDP or a DNP.

In using disc implants, one problem relates to the preparation for the surgical procedure for implanting either the TDPs or DNPs. The time required for preparing for surgery, and specifically preparing the implants and inserters for use, can be important for both patient welfare and in terms of cost efficiency. For instance, if only one of the ends of the implant is configured for gripping by an inserter tool, this requires the medical personnel to locate the proper end of the implant and then connect it to the inserter. Extra time is wasted when an implant has otherwise similarly configured ends such that it is difficult to easily determine which end of the implant attaches to the inserter. The problem is compounded when the implant has multiple components (such as a top and bottom portion), and the medical personnel need to first properly match the disc components to each other so that the ends of each component configured to connect to each other are properly aligned with each other before attachment of the disc to the inserter. This can waste time during preparation for the surgical procedure. Accordingly, an artificial disc would be desirable that has portions that do not only connect with each other in one configuration and require that the disc be mounted on an inserter tool in a single orientation.

Other improvements specifically for the DNP procedure would be desirable. As mentioned above, a DNP requires less extensive surgery than for a TDP since it replaces only part of the disc. Implantation of most known DNPs with pre-formed dimensions generally requires a 5-6 mm, or larger, incision in the annulus for implantation. The incision, however, should be kept as small as possible to hold the DNP within the annulus without using anchors on the DNP that extend into the end plates of the vertebrae for securing the DNP. The minimal invasiveness of the procedure results in minimal recovery and post-surgical pain, and interbody fusion remains a viable revision surgery. Thus, maintaining a small incision and keeping damage to the annulus to a minimum is a high priority. Therefore, it would be desirable to provide a DNP and inserter that does not require an enlarged incision and does not significantly damage the annulus or other tissue during insertion and placement of the DNP.

Another problem with DNP structure and the surgical procedures involving DNP relate to the positioning of the artificial disc within the nuclear space. For some DNPs, once the implant is positioned in the nuclear space, it must be rotated in order to position it properly for providing its full range of motion and its full shock absorption capabilities to the patient. Thus, a DNP and an inserter that manipulates the DNP within the nuclear space without causing damage to the annulus are also desired.

As mentioned above, it is desirable that the implant match the size and shape of the natural disc because the implant may cause damage to the surrounding anatomical structure such as the annulus and may cause pain to the patient if the implant is too large or too small. Since the process of inserting, positioning and then releasing the implant can be complex, especially when an implant has multiple pieces, known sizing tool are used for measuring the nuclear space so that an implant that fits the shape and size of the nuclear space can be chosen before it is inserted into the nuclear space.

In order to determine the size of the nuclear space, conventional sizing tools are used such as a set of trial spacers disclosed by U.S. Pat. No. 6,478,801. In such a set, each spacer has a different size and is sequentially inserted into the nuclear space and then removed in trial and error fashion until the trial spacer fits the nuclear space which indicates the correct size of implant that should be used. The spacers may also be used to distract and stretch the tissue surrounding the nuclear space to make it easier to insert the implant. With some known spacers, however, connecting and disconnecting the spacer from the insertion tool that holds the spacer can be a cumbersome and time wasting process during the surgery while the patient is under anesthesia. This occurs when a surgeon is limited to tightening and loosening one or more fasteners to secure and unsecure the spacer to the insertion tool on each trial.

Other problems such as those mentioned above regarding proper orientation of the implant within the nuclear space also arise when attempting to measure the size of the nuclear space with trial spacers. In order to obtain an accurate measurement, some known spacers, similar to the implants, have elongated shapes to imitate the size and geometry of a natural disc, and in turn the artificial disc to be implanted, and the nuclear space to obtain a more accurate measurement. Thus, in order to minimize the size of the incision on the annulus surrounding the nuclear space to be measured, the spacer is mounted on an insertion tool with its longitudinal axis parallel to the longitudinal axis of the insertion tool on which it is mounted. The spacer is then inserted through the incision with its narrow end as the leading end of the spacer and facing the incision. With this configuration where the longitudinal axis of an elongated spacer is parallel to the longitudinal axis of the insertion tool, however, the surgeon is limited to more lateral surgical approaches (relative to the posterior-anterior direction) in order to orient the spacer with its longitudinal axis extending transverse to the anterior-posterior direction to imitate the orientation of the natural disc within the nuclear space. Thus, it would be desirable to have an insertion tool for inserting a spacer in a nuclear space that is not limited to certain surgical approaches.

SUMMARY OF THE INVENTION

In one aspect of the invention, a system for controllably inserting a spinal disc device, such as an artificial disc device or trial spacer device, between adjacent, superior and inferior vertebrae includes an inserter, and the spinal insertion device held by the inserter. With respect to the artificial disc device or implant, in order to reduce the risk of damage to the annulus and enlarging of the incision, which could permit the disc device or implant to back out of the nuclear space, the inserter includes a gripping member with a distal end configured to adjustably hold the disc device, and a steering control device that allows a user to actively steer the disc device while it is adjustably held by the gripping member. In a preferred form, the steering device includes an actuator connected to the disc device and configured to pivot the disc device relative to the distal end of the gripping member while the disc device is being shifted between the vertebrae. As mentioned, rather than an implant or an artificial disc device that is steered into a desired position between the vertebrae, a trial spacer device can be adjustably held by the inserter. In this manner, the inserter provides for active steering control over the trial spacer device to position it where desired between adjacent vertebrae similar to how the inserter provides for active steering of the artificial disc device. The trial spacer device is inserted into the intervertebral space for assessing the dimensions thereof for proper sizing of an artificial disc device to be subsequently inserted in the intervertebral space as explained in greater detail below.

In one form, the artificial disc device or implants have a generally elongated configuration such as a generally oval or racetrack shape to more closely match the kidney-shaped natural disc and nuclear space that are naturally oriented with their longitudinal dimensions orthogonal to the anterior-posterior direction (i.e. in the lateral direction relative to the spine). Thus, the implants described herein have a narrower lateral end that is the leading end of the implant during insertion of the implant providing for a smaller annulus incision. Desirably, once past the incision, the implant remains attached to the inserter and is then pivoted for orienting it so that its longitudinal dimension extends laterally within the nuclear space. To this end, an inserter is provided with a steering control device connected to the steering actuator and operative to actively steer the implant to pivot to the left or right and into the desired position described above. The active steering, where the inserter actually pulls or pushes on a portion of the implant to turn the implant, while retaining its hold and control over the implant, minimizes damage to the annulus as opposed to prior approaches relying solely on pushing the implant against the annulus or other tissue in order to passively rotate the implant as it is held by the insertion tool.

In another feature of the invention, to avoid enlarging the incision on the annulus, the inserter performs the pivoting of the implant by moving the steering actuator such as cable on the inserter generally parallel to the longitudinal axis of the inserter and through the incision in order to minimize lateral motion of the inserter against the edge of the incision. This avoids further damage or stretching of the annulus or other tissue by lateral motion of the inserter as may occur if the inserter must be rotated about the same superior-inferior axis that the implant is being rotated about. Thus, in one embodiment, the inserter has an actuator that can be operated to pivot the artificial disc without rotating the inserter about the rotational axis.

In another aspect of the invention, the implant or artificial disc may include at least a first superior member or portion, a second inferior member or portion, and a cooperating bearing portion on each member to provide at least one direction of movement between the upper and lower disc members, and preferably forming a polyaxial articulating joint between the two implant members. Alternatively, a separate bearing member may be pushed between the upper and lower disc members. The terms superior and inferior are merely used as references to differentiate the two disc members of the preferred implant but their positions may be reversed.

To facilitate the rotation of the artificial disc, the steering actuator is connected to at least one of the superior and inferior members of the implant. In one embodiment, the actuator includes at least one cable extending along the inserter, and attaching to the implant. The implant may have positioning structure such as grooves on either or both of the superior and inferior members and extending along the articulating bearing portion, and/or an outer peripheral wall of the implant members. The cable may be anchored to the implant by extending within one of the grooves on the implant, by having the implant secure a widened portion on the cable such as an anchoring bead, by being wound around a post on the implant designed for that purpose or even by being tied to, or threaded on, a separate steering anchor configured to attach to the implant. The separate anchor may be in the form of a flat clip or similar structure received by openings on the implant while being simultaneously attached to the cable. As is apparent, a wide variety of anchoring mechanisms for the cable anchors are contemplated.

In another aspect of the invention, the inserter has a control or handle portion such as a hilt, slide, trigger or other device for operating the actuator cable when the device is shifted by the user. In a preferred form, the steering control has a pivotal hilt with a spool mounted on a side of the hilt for securing the cable. Pivoting the hilt moves the spool back and away from the implant, which pulls on the cable, and in turn exerts a pulling force on the implant in the direction the cable is pulled. The control device could alternatively have rotatable handles or other devices directly connected to a spool or reel for securing an end of the cable. The cable is attached to the spool by pinching the cable between two biased disc pieces that form the spool.

In a further aspect of the invention, in order to decrease the preparation time for surgery, an artificial disc is provided with symmetrical opposing ends that are configured so that either end can be mounted to the inserter. In one example, the ends are the longitudinal ends of the artificial disc when the artificial disc is generally oval, rectangular or race-track shaped or otherwise has a length longer than its width. When the artificial disc has multiple components such as a superior member and an inferior member to be connected together, both implant members have symmetrical opposite ends so that the superior member can be mounted on the inferior member in different orientations. Thus, either longitudinal end of the superior member can be placed over, and aligned with, either longitudinal end of the inferior member. Further, the ends are configured so that no matter which orientation is chosen, any two of the aligned ends (one from the superior portion and one from the inferior portion) can be attached to the inserter.

In another embodiment of the invention, a multiple component implant may be provided with structure to secure the implant pieces in a particular orientation for implantation as a unit. The implant may be configured as a wedge to provide an insertion configuration to ease insertion of the implant into and through the annulus. The inserter used to form the wedge shape may have a lower forked grip member grasping the inferior implant member and an upper yoke grip or resilient member grasping the superior member. The resilient member has an original or initial shape with a distal portion that is upwardly bowed so that there are portions of the resilient member extending transverse to the tool axis at its distal end and so that the superior member is initially mounted on the inserter in a slanted orientation relative to the inferior member.

In the wedge or insertion configuration, an insertion or leading end of the implant is smaller than the trailing end for facilitating insertion into and through an incision in the annulus as well as between the vertebrae and within the nuclear space. Once placed in the nuclear space, the vertebrae can push the superior member downward to a flat orientation parallel to the inferior member. To accommodate the motion of the superior member, the resilient member has a longitudinally compressible, S-shaped, snaked or winding proximal portion to increase the compressibility of the resilient member.

The connection providing the insertion configuration is releasable so that as the disc is implanted, the connection is released and the disc members are free to shift relative to each other along their bearing interface. The constraint of the annulus and/or vertebrae during insertion applies separate forces upon the first and second implant members, particularly toward and at the larger trailing end thereof, to pivot the implant members in a fulcrum-like manner about the bearing interface formed therebetween, thereby releasing the connection.

In a preferred form, the inferior implant member has two upwardly extending posts and the superior implant member has two downwardly extending posts with one post being at each longitudinal (distal and proximal) end of the implant members. The posts on the proximal end of both implant members are grasped by gripping members of the inserter. An upper resilient grip member has fingers for grasping the neck of the proximal post or the upper implant member above a widened head on the post. The narrow neck of the post and the yoke grip are dimensioned to provide a tight connection so that the resilient member can hold the superior member in a stable slanted position for the wedge configuration with only the bearing portion as a support.

On the distal end of the implant, one of the two distal posts on the two implant members is configured to provide clearance for the other post so that the superior member can be placed in a slanted position at a desired angle to place the implant in the wedge configuration. For this purpose, the upper distal post has a groove or recess including a shoulder surface seated against the distal post on the inferior member. The upper and lower distal posts are not positively locked together but instead their interengagement provides extra support for the wedge configuration if it is needed and aids in locating the superior member in the wedge configuration. This structure is implemented when forming a symmetrical artificial disc or implant by providing the posts on both the proximal and distal end of each implant with the same structure as described above. The posts distal from the inserter may be attached to a steering actuator such as a cable while the inserter uses the distal end of its gripping members to hold the implant members.

In another example, in order to hold the disc members in a wedge configuration, one longitudinal end of the inferior member of the implant has an upwardly extending wall or flange that abuts a distal end of the superior member to act as a stop or support for the superior member. In this form, a relatively rigid yoke grip may be used to hold the superior member rather than the resilient member mentioned above. The distal end of the superior member has a stepped configuration with two offset, generally downwardly facing, flat surfaces interconnected by a distally facing, contoured shoulder surface. The shoulder surface is shaped to match and abut the corresponding proximally or rearwardly facing surface of the wall on the inferior member. One of the flat surfaces of the superior member sits on the top of the wall while the other flat surface rests on a slanted upper surface of the inferior member adjacent the wall. These three interfaces, in addition to the yoke grip, hold and stabilize the superior member in the slanted position thereof relative to the inferior member. Additionally, an outer facing surface of the wall or flange may include a recess or groove to receive a steering actuator such as cables or a cable anchoring bead. The contoured surface of the distal end of the superior member may be configured to provide clearance for the cable bead.

In order to further stabilize the implant in the wedge configuration, or for steering the implant in any configuration, one preferred implant has an undercut that extends into a lower portion of the bearing portion on the inferior implant member. The undercut receives an enlarged, generally flat, circular, stabilizing plate on the distal end of the inserter. The plate surrounds a boss that extends downward from a pivot arm on the inserter so that pivoting the arm in one direction places the boss in an opening on the implant and pivoting it in the opposite direction removes the boss from the opening. The plate aids in locking the boss with the inferior member while the inferior member is locked between the plate and another member on the distal end of the inserter. The plate and undercut are shaped so that the implant can still pivot even though it is locked on the inserter. The plate also provides for smooth pivoting and reduced rocking of the implant due to the relatively large surface area of the plate in contact with the implant.

As another aspect of the invention, a symmetrical, distal side of the inferior member can use the undercut to receive and secure a steering cable anchor such as a clip connected to cables extending to the actuator on the inserter. Pulling on the cables to steer the implant pulls the clip to one side of the inserter and thereby pulls the implant to that side. The clip is sufficiently flexible to place a portion of its body within the undercut while placing a pin on the bottom of its body within a recessed opening separate from the undercut on the inferior member. In this embodiment, a resilient member on the inserter grasps a proximal post on the superior member to hold it in the slanted position for the wedge configuration without any other assistance for support other than the bearing portion of the inferior member.

In an optional configuration for the distal end of the inserter, a yoke grip or resilient member is configured to facilitate connection to the superior member of the implant. As mentioned above, a yoke grip or resilient member has a distal end with a claw that has fingers to engage the superior member of the implant. The distal end of the resilient member is biased to bow in an arcuate configuration transversally up and down relative to the longitudinal axis of the inserter. This orients the superior member in a slanted orientation relative to the longitudinal axis of the inferior member of the implant to place the implant in the wedge configuration described previously. In order to make it easier to locate the claw on the neck of a post extending from an end of the superior member, the resilient member is configured with projections that minimize or eliminate the bowing on the claw and fingers. By providing non-bowed, linear fingers, it is easier to locate and insert the fingers on the post's neck between the head of the post and the main wall or surface of the superior implant member from which the post extends. This configuration also positions the fingers to lie flush against the main wall of the superior implant member providing further support for the superior member in the slanted orientation.

To accomplish this, the resilient member has two projections or wings extending downward from the left and right sides of the fingers on the distal end of the resilient member in order to increase the stiffness of the distal end. The wings add material in a plane extending in a direction transverse to the axis upon which the resilient member is bowed for the wedge configuration. This adds sufficient strength and stiffness to the fingers at the distal end of the resilient member to overcome the bias force of the resilient member and so that the fingers extend linearly and will not significantly bow.

This structure also reduces the independent action of the fingers which could make it harder to connect to the post on the implant and could cause the implant to detach from the fingers unintentionally. The independent action is reduced because the stiffness reduces the distances in the superior-inferior direction that the fingers are free to flex.

The wings also act to maintain the resilient member in lateral or transverse alignment with the gripping member upon which the resilient member is mounted. During pivoting or detachment of the implant from the inserter, the implant's post that is attached to the resilient member applies forces to the fingers of the resilient member and in a transverse direction relative to the longitudinal axis of the inserter. These forces could misalign the distal end of the resilient member from the gripping member.

To minimize the likelihood of this occurring, the wings extend downward and along both the left and right sides of the gripping member when the implant is held in a flat (non-wedge) configuration which occurs when the implant is disposed within an intervertebral space. So configured, when the post of the superior member applies a transverse force against one of the fingers on the resilient member which shifts the resilient member transversely, one of the wings abuts the left or right side of the gripping member and retains the resilient member in alignment with the gripping member.

This alternative resilient member also has the fingers configured to increase their flexibility in the lateral direction (from left to right and transverse to the longitudinal dimension of the inserter) so that it is easier to insert the post extending from the superior implant member between the fingers. For this purpose, the groove between the fingers has a widened end at the base of the fingers to reduce the amount of material between the groove at this location and the opposing, left and right edges of the resilient member. This reduction in material, and in turn reduction in strength and stiffness at this location, in the transverse, left-right dimension permits the fingers to flex transversely when the post is being pressed through a narrow portion of the groove between the fingers.

In another aspect of the present invention, a system for replacing a natural nuclear disc includes instruments for determining the size of the nuclear or intervertebral space before inserting an implant into the space. This is provided to ensure that an implant of a proper size is being inserted into a nuclear space in order to minimize damage to tissue and pain to the patient caused by an implant that is too large or too small. The sizing instruments are used rather than the implant itself to determine the size of the nuclear space because it is usually easier and more time efficient to use the sizing instruments rather than the implantation tools. This is particularly true when the implant is provided in multiple pieces and the implant is released from the implant insertion tool while the implant is within the nuclear space to determine if it is the correct size for the nuclear space. In such circumstances, reattaching a tool to an implant that does not fit and then removing the implant from the nuclear space is a relatively complex and time consuming procedure. Thus, the present invention also includes an insertion tool that remains connected to an intervertebral device inserted into the nuclear space and that indicates the size of the nuclear space such as a trial spacer also referred to herein as a spacer.

As with the inserter for the implants, the inserter for the trial spacer is configured to reduce the risk of damage to the annulus and enlarging of the incision on the annulus which could permit a subsequently inserted implant to back out of the nuclear space. For this purpose, the inserter includes a gripping member with a distal end configured to adjustably hold the trial spacer in the intervertebral space while a steering actuator on the insertion tool is connected to the trial spacer to pivot the adjustably held trial spacer within the intervertebral space. A steering control device is operatively connected to the actuator to permit a user to actively steer the trial spacer remotely from the intervertebral space and while the spacer is adjustably held by the gripping member in order to further minimize the potential for damaging the annulus as the spacer is pivoted.

In more detail, a set of trial spacers are provided where each spacer has the same general shape but a slightly different size or geometry. The size refers to the height of the spacer extending from one vertebra to the adjacent vertebra forming the nuclear spacer but may also refer to the width or length of the nuclear space. The geometry may refer to the angle of an outer surface such as a top surface of the spacer relative to the plane formed by the central lateral and longitudinal axes of the spacer so that the spacer can match the lordotic or kyphotic curvature of the vertebrae. Each spacer corresponds to one or more implants of a specific size or geometry. A surgeon inserts the spacers into the intervertebral space one at a time in trial and error fashion and preferably starting with the smaller spacers and increasing the size of the spacer with each trial. The spacers are inserted until one of the spacers fits the intervertebral space. Optionally, the spacers may also be used to distract the vertebrae and stretch the tissue surrounding the nuclear space as the spacers increase in size to make it easier to subsequently insert the implant into the nuclear space.

The surgeon determines whether or not the spacer fits properly within the intervertebral space by using imaging technology such as x-ray, MRI, fluoroscopic or other similar techniques and by determining how tightly the spacer fits in the intervertebral space by sensing how much force must be applied to the inserter to shift the spacer. Once the proper size of spacer is determined and the spacer is removed from the intervertebral space, the user can determine the proper size for the implant.

The inserter used to hold the spacer is configured to pivot the spacer relative to the distal end of a gripping member on the inserter to enable the spacer to be inserted into the nuclear space from any one of a number of different surgical approach angles relative to the anterior-posterior direction. A spacer body of the trial spacer, as with the implants described above, has an elongate shape such as a generally obround or oval shape with a narrow, lateral, and leading end for facing the incision on the annulus through which the spacer is to be inserted thereby minimizing the required size of the incision.

Also similar to the implants, once the spacer is placed through the incision, the spacer remains connected to the inserter and is then pivoted for orienting it so that its longitudinal dimension extends laterally relative to the posterior-anterior direction and within the nuclear space. The steering control device is held remotely from the intervertebral space and is operative to actively steer the implant into this desired position. As with the implant, the active steering minimizes damage to the annulus or other tissue as opposed to prior passive steering approaches relying solely on advancing the spacer against the anatomical structure in order to passively rotate the implant.

Since it is desirable to pivot the spacer within the nuclear space while the inserter extends through the annulus incision and into the nuclear space to adjustably hold the spacer, the inserter is configured to pivot the spacer without applying significant pressure against the incision on the annulus that could enlarge the incision or damage the annulus. In order to reduce the risk of enlarging the incision on the annulus, the inserter pivots the trial spacer relative to the distal end of the gripping member which holds the spacer. The spacer is rotated about an axis of rotation, extending in a superior-inferior axis in one example, without requiring the inserter itself to pivot about the rotational axis. In other words, even though the spacer is pivoted within the annulus, the inserter may generally remain extending along a stationary radius relative to the axis of rotation upon which the spacer pivots.

To accomplish this, in addition to the gripping member engaging the spacer, the steering actuator has an elongate main member that also connects to the spacer so that axial translation of one of these members relative to the other member through the incision causes the spacer to pivot. In the preferred form, the gripping member is translated relative to the axially stationary main member and is described hereafter in this way although the converse where the main member translates relative to the gripping member instead is also contemplated.

The main member has a first, elongate portion connected to the gripping member. In order to make it easier for the surgeon to understand and orient the position of the spacer within anatomical structure as well as to efficiently transfer spacer driving forces through the inserter, such as hammer blows at the back of the inserter, it is desirable to have an inserter that extends generally straight along a longitudinal axis extending to the back or handle used to hold the inserter and a spacer that pivots from that axis. Thus, the first portion of the main member that holds one part of the spacer is configured to extend generally parallel to the longitudinal axis of the inserter when the inserter is configured in an insertion or spacer pivoting orientation explained in more detail below. In order to maintain the gripping member in a parallel alignment with the longitudinal axis of the inserter during pivoting of the spacer, the gripping member has a protrusion that is removably and transversely secured in an axially extending slot on the first portion of the main member. The slot and protrusion are configured to permit the members to axially translate relative to each other in order to pivot the spacer.

To provide the inserter with a spacer changing orientation, a second, elongate portion of the main member adjacent the first portion is pivotally mounted on a housing and selectively secured in one orientation to hold the main member in place for insertion and pivoting of the spacer. The main member can be unlocked to pivot to provide the spacer changing orientation. In detail, the second portion of the main member bends from the longitudinal axis of the inserter and the first portion of the main member to extend to the housing that also holds the control device.

A housing end of the second portion of the main member is pivotally mounted by a pin to the housing and engages a release slide to secure the main member in the insertion and spacer pivoting orientations. In this orientation, the first portion of the main member extends parallel to the longitudinal axis of the inserter. The housing end of the second portion is secured within a retaining groove on the front end of the release slide facing the main member. The release slide is mounted on rails on two opposing, interior surfaces of the housing so that the release slide slides parallel to the longitudinal axis of the inserter to engage or disengage from the main member. Sliding the release away from the housing end of the main member permits the main member to pivot to a spacer changing orientation and a disassembly orientation.

In the preferred embodiment, in order to pivot the spacer, the spacer has a body and link extending from the body. The spacer body has an end proximal to the inserter or user and opposite the narrow, leading end of the spacer body. A port or pocket is formed on the spacer body and between an upper wall and a lower wall which is open at the proximal end and along at least a portion of one of the longitudinal sides of the spacer body in order to accommodate the swinging of the gripping member and the link within the pocket. A grip pin extends in a superior-inferior direction through the pocket and is removably engaged by a hook at the distal end of the gripping member that is configured to extend into the pocket to grasp the grip pin. The rotational axis for pivoting the spacer body is formed at the grip pin which intersects the central, longitudinal axis of the spacer body.

In order to secure the spacer to the main member, the spacer also has a rigid, elongate link with a first end pivotally mounted within the pocket by a first link pin. The link extends out of the pocket from a longitudinal side of the spacer body and has a second end opposite the first end. The second end of the link is pivotally connected to the main member by a second link pin that generally fixes the axial position of the link relative to the longitudinal axis of the inserter.

During insertion of the spacer, the spacer is held in a straight, non-pivoted orientation where the longitudinal axis of the spacer is generally parallel to the longitudinal axis of the inserter. In this straight orientation, the link extends axially and straight back from behind the spacer body so that the link does not press significantly against the annulus incision during insertion of the spacer. For this purpose, the first link pin is positioned close to one of the longitudinal sides of the spacer and within the pocket so that the link extends generally coaxially to the longitudinal axis of the main member when the spacer body is oriented in the straight orientation.

With this structure, axially translating the gripping member relative to the main member and the link shifts the position of the grip pin and in turn the proximal end of the spacer body axially forward or rearward while the link retains the first link pin in a generally axially fixed position relative to the longitudinal axis of the inserter. Since a longitudinal side of the spacer body is connected to the first link pin, this causes the spacer body to pivot about the grip pin and the first link pin and toward the side of the inserter that the link is located on. In the present embodiment, the gripping member and main member provide a sufficient axial distance of relative translation between them so that the spacer may be pivoted from a straight orientation where the longitudinal axis of the spacer body is parallel to the longitudinal axis of the inserter and up to about 90 degrees to the left or right of the longitudinal axis of the inserter depending on which side of the inserter the spacer link is disposed.

In another aspect of the invention, the steering control device is configured to selectively cause and control the axial translation of the gripping member to actively pivot the spacer. For this purpose, the steering control device includes a knob or dial rotatably mounted on an exterior, upper surface of the housing and a wide shank extending from the knob and into the housing. The shank has a reduced width portion that forms an eccentric cam and an axle portion rotatably mounted on a lower wall of the housing and concentric to the knob to secure the cam to the lower wall of the housing. The steering actuator includes a drive arm in addition to the main member, and the drive arm is operatively connected to the cam on one end and pivotally connected to an end of the gripping member on the opposite end of the drive arm. With this configuration, rotating the knob changes the axial position of the cam which in turn translates the drive arm axially and generally parallel to the longitudinal axis of the inserter. The axial translation of the drive arm then translates the gripping member relative to the main member to pivot the spacer.

In order to minimize the effort required for a surgeon to manipulate the spacer, the knob is relatively large to fit comfortably in the surgeon's hand and provides a large mechanical advantage such that the knob need only be rotated about one-half turn or 180 degrees in order to pivot the spacer through about 90 degrees. The cam is configured so that rotating the knob in one direction such as clockwise will pivot the spacer toward the left or right side of the inserter while pivoting the knob in the opposite direction will return the spacer to the straight orientation with its longitudinal axis parallel to the longitudinal axis of the inserter.

Another advantage of using a cam to connect the knob to the drive arm is that the cam is relatively durable due to its relatively large size that can dissipate a driving force compared to smaller, threaded fasteners that can wear easily or break when transferring driving forces to the drive arm. This occurs when the surgeon uses a driving tool such as a hammer to hit the proximal end of the inserter to thrust the spacer into a small, tight nuclear space between vertebrae. In the present embodiment, the inserter has a handle with a driving shaft connected to the back wall of the housing and extending through the handle and out of the proximal end of the handle. Hitting the shaft with a driving tool, transfers a driving force through both the handle and the shaft, into the housing and then through the cam, and in turn, through the drive arm, gripping member, and spacer.

In the preferred form, the drive arm has an end with an opening formed by two opposing, coaxial rings that are rotatably mounted on the cam. The rings are separated for about the rear half of the circumference of the rings to form a backward C-shaped slot therebetween. The rings are secured to the cam by a screw that extends through a diametrically extending bore on the cam. The screw is retained in the bore by a reduced diameter opening that permits a reduced diameter end of the screw to extend through the opening and into the C-shaped slot. The screw secures the rings laterally to the cam or relative to the central axis of curvature of the cam. Likewise, the screw also secures the cam to the rings so that the cam and knob cannot be pulled off of the housing without first removing the screw.

In order to orient the spacer in the straight orientation, also referred to hereinafter as the 0 degree orientation, the knob is rotated counter-clockwise to place the cam in its furthest rearward position closet to the handle on the inserter. The rotation of the cam translates the drive arm and in turn the gripping member rearward relative to the main member which positions the link and the spacer body in the straight or 0 degree orientation described above.

In the preferred embodiment, it is desirable to lock the spacer and the steering components of the inserter in the straight or 0 degree orientation for stable, non-pivoting insertion of the spacer through anatomy that may apply forces against the spacer or to remain aligned when the inserter is hit with a driving tool such as a hammer. In order to be able to retain the cam with a releasable locking lever that only blocks rotation of the cam in one direction, such as clockwise, the cam and in turn the knob, is limited to less than 360 degree rotation. Counter-clockwise rotation is blocked while the locking lever blocks clockwise rotation of the cam to lock the control device and actuator in place.

In a present form, the cam is limited to rotation in only about half of a circumference about the rotational axis of the knob on the control device. For this purpose, a first end of the C-shaped slot on the rings of the drive arm is configured to abut the screw on the cam to limit further counter-clockwise rotation of the cam to lock the cam in the 0 degree orientation while the locking lever is engaged.

In one preferred form, the locking lever is mounted within the housing and has a switch end extending out of an opening on the right wall of the housing and that is accessible to a user's fingers. The locking lever has an opposite T-shaped end that fits in a groove open to the right side of the release slide for reasons explained below. So configured, the locking lever swings back and forth in a direction parallel to the longitudinal axis of the inserter and about the end of the locking lever on the release slide. The locking lever also has a front surface with a ledge that faces the rings and cam. The locking lever is biased by a spring toward the rings which have opposing notches to engage the ledge on the locking lever to lock the cam and drive arm in the 0 degree orientation. Pushing the locking lever away from the drive arm and toward a back wall of the housing, releases the drive arm and cam to rotate clock-wise so that the spacer can be pivoted.

In order to pivot the spacer after the locking lever is released from the drive arm, the knob is rotated clockwise which rotates the cam to advance the drive arm and gripping member relative to the main member. Turning the knob a half-turn from the 0 degree orientation places the cam in its most distal or forward position for pivoting the spacer about 90 degrees relative to the longitudinal axis of the inserter. The lengths of the gripping member, main member, link and drive arm are chosen so that the cam limits rotation of the spacer to about 90 degrees when it is in its most forward position. A second end of the slot on rings of the drive arm is disposed on the diametrically opposing side of the cam as the first end of the slot and is configured to abut the screw on the cam to limit further clockwise motion of the cam. This limits the rotation of the cam about the central axis of the knob on the control device to less than 360 degrees as explained above.

In another aspect of the invention, providing the link on the spacer permits a surgeon to quickly and conveniently connect the spacer to the inserter as well as disconnect the spacer from the inserter without tightening or loosening any fasteners which saves time during the surgical procedure while the patient is under anesthesia. To accomplish this, each spacer in a set of spacers that may be inserted into the nuclear space is preassembled with the link, the first and second link pins and the grip pin as described above so that a surgeon does not need to waste time screwing or inserting the pins into positions on the spacer or inserter while the nuclear space on the patient's body is accessible. Instead, the inserter is configured to provide automatic loading and unloading of the link on the inserter. The surgeon need only place the main body and link on the inserter when the inserter is in the spacer changing orientation and then swing the main member to a pivoting orientation of the inserter to secure the spacer to the inserter. The process is performed in reverse to remove the spacer from the inserter as explained in more detail below.

In the preferred embodiment, in order to connect the spacer to the inserter, first the gripping member is translated to the spacer changing orientation that places the gripping member farther forward or more distally than its axial position for holding the spacer at 90 degrees. As explained above, the cam limits further translation of the gripping member past the 90 degree orientation while the main member retains the gripping member parallel to the longitudinal axis of the inserter and when the main member is secured to the release slide that prevents the swinging of the main member.

In order to disengage the release slide from the main member to permit the main member to swing, the locking lever is also pivotally mounted on a pin that extends within the housing and that extends through a centrally located slot on the locking lever. The slot extends generally parallel to the longitudinal axis of the inserter so that the locking lever is free to swing back and forth over the pin for locking and unlocking the drive arm and cam as described above for the steering operation. When the cam is rotated to the 90 degree orientation, the drive arm is disengaged from the locking lever so that a spring between the locking lever and the back wall of the housing biases the left end of locking lever forward and locates the central pin at an end of the central slot. This biases the release slide forward since it is connected to the left end of the locking lever. This configuration also permits the locking lever to pivot about the central pin.

So configured, a user can press the accessible end of the locking lever forward to pivot the locking lever about the central pin extending through the central slot. This in turn pivots the end of the lock lever connected to the release slide rearward and toward the handle. This causes the release slide to shift rearward and release the main member from the release slide. Once the release slide is shifted back and away from the main member, the end of the main member disengages from the groove on the release slide which frees the main member so that a surgeon can manually swing the main member left and right relative to the longitudinal axis of the inserter and about its pivot pin at the housing. For explanatory purposes, the longitudinal axis of the inserter remains fixed relative to the housing even though the main member and gripping member swing out of parallel alignment with the longitudinal axis as explained below.

Since the gripping member is secured to the main member, the swinging of the main member causes the gripping member and drive arm to shift with the main member and pivot about the cam. Since the gripping member is axially secured to the drive arm, and since the gripping member and main member have different but fixed centers of rotation, swinging the main member to the right and toward the gripping member axially translates the gripping member forward relative to the main member and distally into the spacer changing orientation.

In a preferred form, once the gripping member is in the spacer changing orientation a surgeon uses his fingers to manually place the grip pin of the spacer body on the hook at the distal end of the gripping member to mount the spacer body on the gripping member. The surgeon then manually places the second link pin on the second end of the link on a locating portion on the gripping member that is axially displaced from the hook on the distal end of the gripping member. The locating portion on the gripping member holds the second end of the link in an orientation for being automatically and subsequently shifted to engagement with a holding portion on the main member that secures the link for pivoting the spacer.

Also in a preferred form, the locating portion is a notch that opens on a left side of the gripping member that faces the main member. In the spacer changing orientation, the notch on the gripping member is positioned forwardly of the distal end of the main member so that the notch is accessible for a surgeon to manually place the second link pin in the notch.

The holding portion is a groove at the distal end of the main member that receives the second link pin for pivoting and securing the spacer. The groove has an opening that faces toward the gripping member so that translating the gripping member relative to the main member selectively aligns the groove with the notch to shift the second link pin from one to the other and back again as desired and as explained further below.

In a preferred configuration, the inserter includes shifting structure that shifts the second end of the link from engagement with the locating portion to engagement with the holding portion when loading a spacer onto the main member and for the reverse process when the spacer is to be removed from the main member. For automatic operation, the shifting structure is also connected to the gripping member and/or main member so that a surgeon can load or unload the spacer link by translating the gripping and main members relative to each other. Axially translating the gripping and main members relative to each other causes the shifting structure to press against the second end of the link to cam the second end from the locating structure to the holding structure or vice versa.

In more detail, the shifting structure is configured to correspond and engage with particular structure on the second end of the link. The second end of the link forms a clevis with an upper wall spaced from an opposing lower wall and a cavity therebetween. The walls extend parallel to each other and parallel to a plane formed by the longitudinal and lateral axis of the spacer body. The second link pin extends from the upper wall, through the cavity and onto the lower wall. The upper and lower walls also extend radially outward from the second link pin so that an overhang or setback exists on each wall from the outer edges of the upper and lower walls to the second link pin. The outer edges of both walls have a convex curve to engage the shifting structure of the inserter.

In order to automatically shift the second link pin out of the notch of the locating portion and into the groove of the holding portion, the shifting structure includes an engagement hook or protrusion to engage the upper wall of the link. The shifting structure also has a disengagement protrusion to engage the lower wall of the link to remove the spacer as described further below.

The engagement protrusion extends from the main member so that the engagement protrusion translates with the main member. The engagement protrusion also extends laterally from a longitudinal side and top side of the main member and over a top surface of the gripping member. Thus, the engagement protrusion engages the outer edge of the upper wall on the link as the engagement protrusion is being translated. For this purpose, the engagement protrusion is generally cusp-shaped with a convex, curved front edge configured for corresponding to and engaging the upper wall of the link. The front edge extends from the main member slightly rearward and set back from the notch on the gripping member in order to match the overhang on the upper wall of the link so that the front edge engages the outer edge of the upper wall while the second link pin is disposed in the notch on the gripping member.

With the configuration described, in order to automatically shift the second end of the link from the notch of the gripping member to the groove on the main member, a surgeon manually swings the main member and in turn the gripping member from the spacer changing orientation and back toward the longitudinal axis of the inserter (i.e. closer to parallel to the longitudinal axis). This causes the main member to translate forward relative to the gripping member so that the engagement protrusion engages the upper wall of the link. Continued translation of the gripping member causes the engagement protrusion to advance the upper wall of the link, and in turn the second link pin, until the second link pin engages a forward, tapered edge of the notch of the locating portion. The tapered edge extends toward the left side of the gripping member that faces the main member as the tapered edge extends forward so that translating the engagement protrusion forward shifts the second link pin against the tapered edge of the notch. This action slides or cams the second link pin against the tapered edge and toward the main member.

When the second link pin is engaged by the tapered edge, the gripping member and main member have translated so that the notch on the gripping member directly opposes the groove on the main member. Further translation and advancement of the main member relative to the gripping member by swinging the main member and gripping member closer to the longitudinal axis of the inserter causes the engagement protrusion to shift the second link pin into the groove on the main member.

After the second link pin is engaged in the groove on the main member, swinging the main member even closer to the longitudinal axis of the inserter places the housing end of the main member in position for reengagement with the release slide to hold the main member in a fixed position relative to the housing. In this orientation and during the pivoting of the spacer, the left longitudinal side wall of the gripping member opposes an opening of the groove on the main member and at a distance from the opening that is sufficiently close to the opening so that the second link pin does not have clearance to escape the groove.

Also in the preferred embodiment, in order to remove the spacer from the inserter, the main member and gripping member are swung to the spacer changing orientation from the pivoting orientation as explained above so that the gripping member is translated axially forward relative to the main member. As the gripping and main members translate relative to each other, the shifting structure automatically removes the second link pin from the groove of the holding portion on the main member, where the link is secured for pivoting of the spacer, and shifts the second link pin into the notch of the locating portion on the gripping member where the second link pin is accessible to be manually removed from the notch by a surgeon grasping the link with his fingers or a tool.

For this purpose, the shifting structure also includes a generally cusp-shaped, disengagement protrusion that extends from the bottom side and the left side of the gripping member facing the main member. The disengagement protrusion is configured to engage the lower wall of the link when the second link pin is held within the groove on the main member, and then shift the lower wall of the link toward the gripping member and over the notch on the gripping member to place the second link pin in the notch. To accomplish this, the disengagement protrusion extends transversely relative to the longitudinal dimension of the gripping member and underneath a bottom surface of the main member. Thus, the disengagement protrusion engages the lower wall of the link when the gripping member is translated forward relative to the main member.

The disengagement protrusion also has a front edge for engaging the lower wall of the link and for shifting the lower wall toward the gripping member as the disengagement protrusion is translated forward with the gripping member. The front edge of the disengagement protrusion is slanted relative to the longitudinal dimension of the main member and so that the front edge extends distally or forward as it extends transversely outward from the gripping member. The front edge is set back slightly rearward from the notch on the gripping member. This matches the setback from the second link pin to the outer edge of the lower wall of the link. So configured, when the disengagement protrusion is translated against the lower wall of the link, the front edge of the disengagement protrusion shifts the lower wall toward the gripping member and over the notch on the gripping member, and in turn, the second link pin is shifted from the groove on the main member and into the notch on the gripping member.

Once the second link pin is removed from the notch on the gripping member, the spacer body is free to pivot about the grip pin. The spacer body can be pivoted until the hook on the distal end of the gripping member has sufficient clearance within the pocket to be disengaged from the grip pin on the spacer. A different spacer can then be quickly and conveniently loaded on the inserter as explained above.

In another aspect of this embodiment, the front edge of the disengagement protrusion also is disposed and configured to aid the surgeon in first directing the link to the notch of the locating portion on the gripping member when the surgeon is first loading the link onto the inserter. For this reason, the front edge is continuous with a shoulder on the bottom surface of the gripping member to cooperatively form a concave, generally curved surface. This structure permits a surgeon to push the lower wall of the second end of the link against the curved surface to shift the lower wall of the link over the notch which shifts the second link pin into the notch. Thus, the curved surface is contoured to extend generally toward the notch and then around the notch but at a distance from the notch that corresponds to the length of the setback on the lower wall from the second link pin to the outer edge of the lower wall. So configured, the outer edge of the lower wall engages the curved surface while the second link pin is disposed in the notch.

Also in the preferred embodiment, a disassembly lock is pivotally mounted on the gripping member and extends onto the main member to limit further translation of the gripping member relative to the main member past the spacer-changing orientation unless the disassembly lock is released. The disassembly lock has an elongate body that extends axially relative to the longitudinal axis of the inserter and is pivotally mounted on the gripping member by a pin extending transversely up and down relative to the longitudinal axis of the inserter. The body has a button end accessible in an opening on the gripping member and an opposite end with a projection that is biased to extend into a recess or chamber on the main member. So configured, depressing the button, pivots the disassembly arm about its pin and retracts the projection from the main member so that the gripping member can translate relative to the main member and into a disassembly orientation.

In one form, the steering mechanism may provide incremental adjustment of the disc device position, in contrast to continuous adjustment, wherein the adjustment increments are infinitesimally small. For example, instead of actuating a drive arm of the inserter with an elliptical camming surface, which allows minute and continuous adjustment of the disc device position, the disc device may be actuated with an actuator that generates discrete, incremental movements, such as a ratchet mechanism. The ratchet mechanism actuates a drive arm in predetermined discrete increments to shift the disc device by a corresponding predetermined discrete increment. This configuration allows the surgeon to quickly and easily adjust the position of the disc device.

Because the disc device is not typically visible when inserted into the patient, a surgeon must determine the position of the disc device by other means. In a preferred form, the ratchet mechanism audibly emits a sound, such as a clicking sound produced by the ratchet mechanism components when actuated. Thus, a clicking sound will accompany each positional change of the disc device. As a result, a surgeon, knowing the predetermined increment that the disc device will shift with each actuation of the ratchet mechanism, may simply listen for the clicking sound to determine the orientation of the disc device. In this form, the steering mechanism generates audible feedback to provide information regarding the steered position of the disc device. In addition, the steering mechanism may emit tactile feedback through the inserter, such that the surgeon can feel with his hand when the mechanism has been actuated, and thus determine the steered position of the disc device.

In one embodiment, the ratchet mechanism is actuated by a trigger operatively connected thereto. Each depression of the trigger actuates the ratchet mechanism, which selectively advances or retracts the drive arm connected to the disc device, causing the disc device to be shifted by a predetermined increment correlating to the positional change of the drive arm. The number of predetermined increments within the full range of motion of the disc device may vary. However, in a preferred form, the normal operating range of the disc device is 90 degrees, and each depression of the trigger results in a 30 degree shift of the disc device, such that three depressions of the trigger will shift the disc device through its full range of motion.

In another embodiment, an inserter for a spinal disc device such as a trial spacer or an artificial disc may have a pistol-grip style handle for holding the inserter. The pistol-grip style handle enables the surgeon to grasp the inserter with his wrist in a substantially neutral position, wherein the wrist is positioned without substantial deviation from its natural resting position. Thus, this embodiment reduces unnecessary and potentially awkward movements by the surgeon that could result in discomfort to the surgeon, accidental and potentially disabling or even fatal trauma to the patient, or improper placement of the disc device, leading to the potential failure of the procedure.

BRIEF DESCRIPTION OF THE DRAWINGS

In the drawings,

FIG. 2 is an enlarged, fragmentary view of an implant-holding end portion of the inserter of FIG. 1 showing the implant with its longitudinal dimension extending parallel to the longitudinal axis of the inserter;

FIG. 3 is a perspective view of a superior member of the implant showing symmetrical posts at opposite ends and a concave bearing surface;

FIG. 7 is an enlarged, elevational view of the implant and implant-holding end portion of the inserter showing the implant in a wedge configuration for insertion of the implant;

FIG. 8 is a perspective view of the implant and implant-holding end portion of the inserter showing the implant pivoted left about 90 degrees for positioning of the implant between the vertebrae;

FIG. 9 is an enlarged, perspective view of the implant-holding end portion of the inserter without the implant and showing cable guides for laterally securing steering actuator cables;

FIG. 10 is an enlarged, perspective view of the implant-holding end portion of the inserter showing the implant pivoted to the left about 90 degrees for positioning between vertebrae;

FIG. 14 is an exploded view of the steering control device showing the components for pivotally securing the hilt;

FIG. 15 is a perspective view of a portion of the hilt on the inserter showing a pocket for the steering control components;

FIG. 19 is a perspective view of an alternative form of an implant connected to an inserter in accordance with the present invention;

FIG. 20 is an enlarged, fragmentary view of an implant-holding end of the inserter showing the implant and the inserter adjustably connected via cables extending from the inserter;

FIG. 29 is an enlarged, cross-sectional view of the implant connected to the inserter of FIG. 19 showing the implant in a wedge configuration;

FIG. 30 is an enlarged perspective view of a distal end of a shaft on the inserter of FIG. 19 showing a contoured braking surface on the shaft for abutting the implant and guiding the steering of the implant;

FIG. 43 is an enlarged, perspective view of the steering clip of the inserter of FIG. 31 showing the securing arm and a cable engaging bore;

FIG. 44 is an enlarged, bottom perspective view of the steering clip of the inserter of FIG. 31 showing the securing arm and an anchoring pin;

FIG. 52 is an enlarged fragmentary view of a spacer-holding end portion of the inserter of FIG. 50 showing the spacer and the inserter in coaxial relation with each other;

FIG. 53 is an enlarged perspective view of the trial spacer showing a spacer body connected to a pivoting link;

FIG. 61 is a bottom enlarged, plan view of the spacer partially connected to the inserter showing a spacer-holding end of the inserter in an orientation for locating the spacer link on the gripping member;

FIG. 62A is an enlarged plan view of the spacer connected to the inserter showing a spacer-holding end of the inserter in an orientation for automatically shifting the spacer link into engagement with a main member of the actuator;

FIG. 62B is an enlarged, fragmentary bottom plan view of a portion of the inserter showing an orientation for automatically shifting the spacer link into engagement with a gripping member of the actuator;

FIG. 63 is an enlarged plan view of the spacer-holding end of the inserter holding the spacer at a zero degree orientation relative to the longitudinal axis of the inserter;

FIG. 64 is an enlarged plan view of the spacer-holding end of the inserter holding the spacer at a 90 degree orientation relative to the longitudinal axis of the inserter;

FIGS. 65-67 are top cross-sectional views of the inserter holding the spacer at 0, 45 and 90 degrees, respectively, and showing a main member and a drive arm of the actuator and a cam of the control device in different orientations for holding the spacer;

FIG. 68 is a cross-sectional, perspective view of the main member and gripping member of the inserter and a disassembly lock disassembled from the members;

FIG. 69 is a top cross-sectional view of the main member and gripping member of the inserter assembled together;

FIG. 71 is a perspective view of the insertion tool;

FIG. 72 is an exploded perspective view of the insertion tool;

FIG. 73 is an enlarged plan view showing the ratchet mechanism and other internal components of the insertion tool;

FIG. 74a is an enlarged plan view of the ratchet mechanism;

FIG. 74b is a perspective view of the reverse locking wing;

FIG. 74c is a perspective view of the forward locking wing;

FIG. 74d is an enlarged plan view of the rearward portion of the drive arm including the toothed portion thereof;

FIG. 74e is a perspective view of the reverse pawl;

FIG. 75a is an enlarged plan view of the ratchet mechanism;

FIG. 75b is a perspective view of the release pin;

FIG. 75c is a perspective view of the directional knob;

FIG. 75d is a perspective view of the directional shaft;

FIG. 76a is a plan view of the housing portion of the insertion tool;

FIG. 76b is a perspective view of a right top portion of the ratchet mechanism housing;

FIG. 76c is a perspective view of a left top portion of the ratchet mechanism housing;

FIG. 76b is a perspective view of a bottom portion of the ratchet mechanism housing;

FIG. 77a is a plan view of the insertion tool and trial spacer in a trial spacer removal orientation;

DESCRIPTION OF THE PREFERRED EMBODIMENTS

Figure 1:
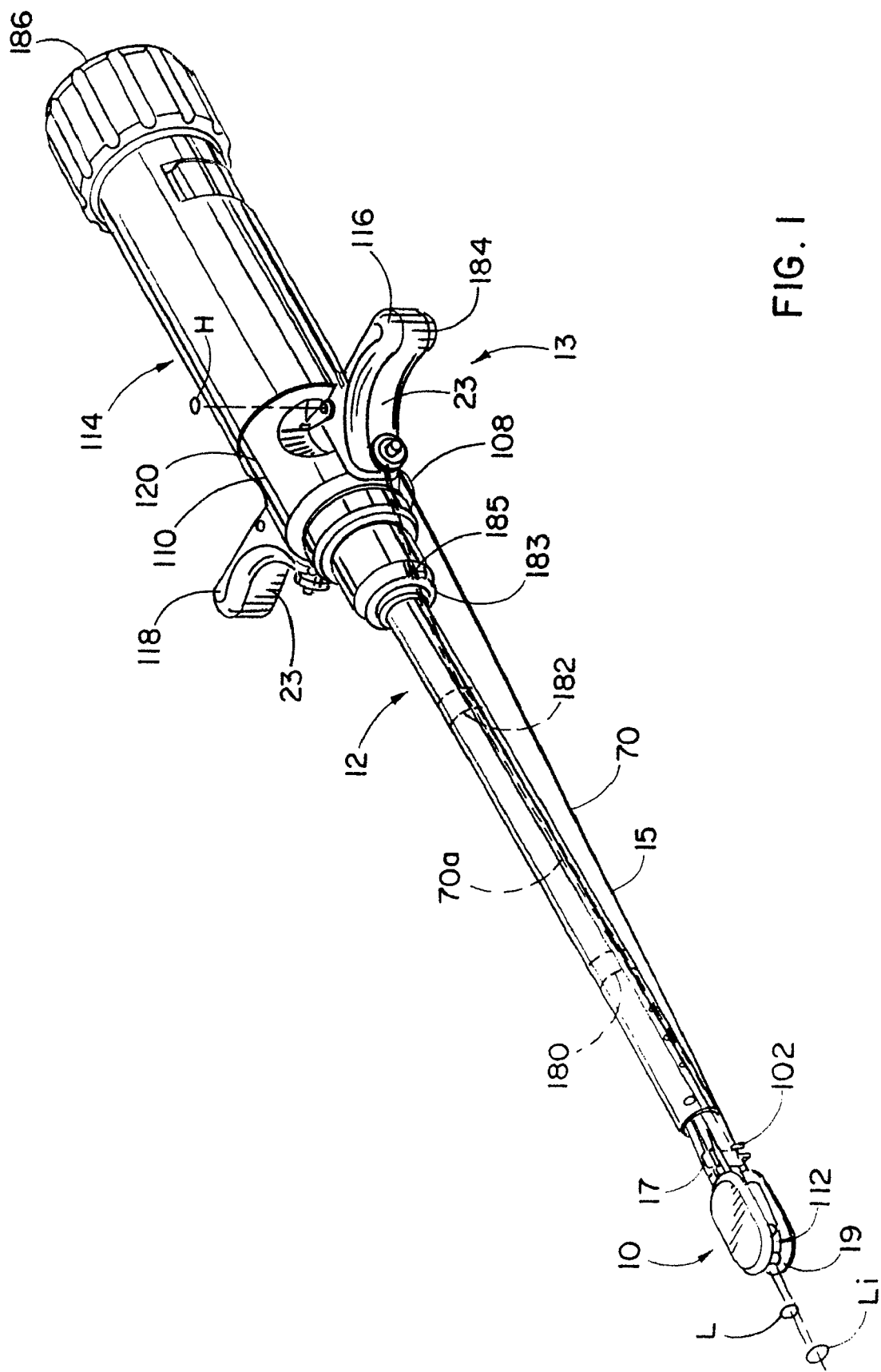
FIG. 1 is a perspective view of an implant connected to an inserter tool in accordance with the present invention.

Referring to FIGS. 1 and 2, a spinal implant 10, such as an artificial disc, is mounted on or connected to an inserter tool 12 for replacing a nucleus of a natural spinal disc between adjacent vertebrae preferably without removing the annulus surrounding the nuclear space. In order to minimize the size of the incision in the annulus, the implant 10 should be inserted by leading with its narrow side facing the incision and pivoting the implant once the implant is positioned within the nuclear space in order to place the implant with its longitudinal dimension or axis $L_i$ extending orthogonal to the posterior-anterior direction (i.e. lateral relative to the spine). To pivot the implant 10 without significantly pushing against the incision, which could enlarge or otherwise damage the incision, the inserter 12 has a distal end 17 that extends into the nuclear space and holds the implant 10 while cooperating structure 11 on the inserter 12 and implant 10 are configured to pivot the implant relative to the distal end of the inserter. The inserter provides active steering of the implant 10 by using a steering actuator 15 extending from the inserter and connected to the implant 10 and a steering control device 110 on the inserter that operates the steering actuator 15 to pivot the implant 10 described in further detail below.

The disc implant 10 is preferably configured for cooperating with insertion tool 12 to allow for the active steering thereof during the disc implantation procedure. In this regard, such structure will be described with respect to the preferred disc implants discussed herein including implants that can be held by inserter 12 in a releasable, wedge-shaped insertion configuration convenient for inserting the implant through the incision. However, it will be appreciated that the cooperating structure can be advantageously applied to other disc implants for use with the present insertion tools. So for instance, the insertion tool 12 including an active steering system generally designated 13 can be used with single or multiple component implants including implants that do not have a wedge insertion configuration. In fact, the inserter tool 12 is advantageous for any disc implant that needs to be dynamically redirected during the surgeon implantation procedure with the surgeon maintaining control thereover.

Figure 4:
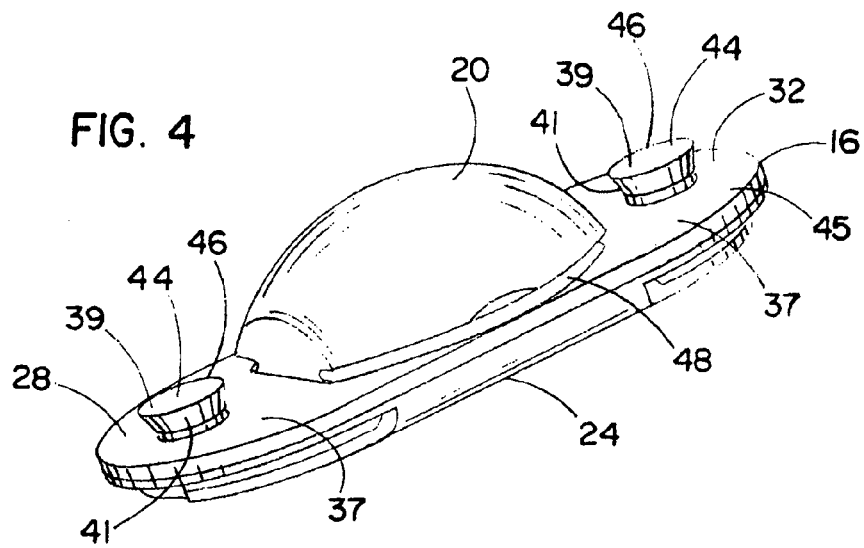
FIG. 4 is a perspective view of an inferior member of the implant showing symmetrical posts at either end and a convex bearing surface.
Figure 5:
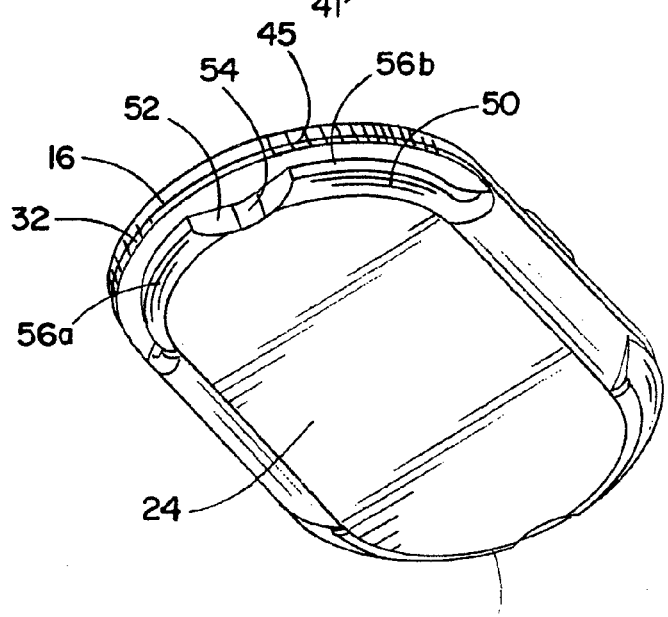
FIG. 5 is a perspective view of the inferior member of the implant showing lower positioning surfaces for controlled, active steering of the implant during implantation thereof.

Referring to FIGS. 1 and 2, a steering system 13 of the inserter 12 includes the steering control device 110 in the form of a trigger pull or hilt 116 or 118 and the steering actuator 15 in the form of an elongated steering cable 70 connected to the hilt 116 or 118 and the implant 10. Referring to FIGS. 3-5, the implant 10 has a number of positioning surfaces and structures configured to receive and/or hold steering cable 70 to control the pivoting of the implant for attachment to inserter 12 and/or for maintaining the implant 10 in a wedge configuration.

In more detail, one type of implant 10 is an artificial disc with multiple components including at least an upper or superior member 14 and a lower or inferior member 16. The superior member 14 has a concave bearing portion 18 that engages a convex bearing portion 20 on the inferior member 16 to form a polyaxial joint that imitates the motion of a natural disc. It is also contemplated that an intermediate bearing member may be provided between the superior and inferior implant members 14 and 16 to provide the desired relative motion therebetween. The disc portions or members 14 and 16 also have respective outer surfaces 22 and 24 configured to engage the end plates of adjacent vertebrae. The bearing portion 20 has symmetrical elongated grooves 48 (only one is shown) that extend along the bottom of the dome bearing portion 20 for receiving and guiding the steering cable 70 as described in further detail below. Otherwise, the details of the bearing portions or members 18 and 20 and the outer surfaces 22 and 24 as well as further explanation regarding the insertion and positioning of the implant through the annulus and between vertebrae are described in the related U.S. patent application Ser. Nos. 10/282,620; 10/692,468; and 10/971,234, which are fully incorporated herein.

In the illustrated form, both members 14 and 16 of the implant 10 are generally obround, race-track shaped or oval, although many other shapes are possible as long as they are capable of forming at least one of the configurations described below for placing the implant in a wedge configuration, steering the implant and/or conveniently mounting a symmetrical implant on the inserter 12. Here, the implant members 14 and 16 each have a longitudinal distal end 26 and 28 that preferably is respectively symmetrical in structure to a longitudinal proximal end 30 and 32. The symmetry of the members 14 and 16 conveniently permits a surgeon to place the superior member 14 on the inferior member 16 in at least two different orientations where either end 26 or 30 on the superior member 14 can be aligned over either end 28 or 32 on the inferior member 16. With this configuration, the inserter 12 can engage either longitudinal end of members 14 and 16 as long as one superior end 26 or 30 and one inferior end 28 or 32 is presented for connection to the inserter 12.

As shown in FIG. 3, in order to hold the implant 10 in a wedge configuration (best seen in FIG. 7), the superior member 14 has a pair of upper brace posts 34 that extend downwardly from a downwardly facing flat surface 35 which extends generally parallel to oppositely facing surface 22, one post 34 being disposed near each end 26 and 30 of the superior portion. Each post 34 has a narrow neck portion 33 and a widened head portion 36 with a groove or indent 38 opened downward and a curved shoulder or wall 40 formed by the indent 38. The indent 38 has a recessed, slanted surface 43 meeting the wall 40 at a rounded, concave corner 42. The recessed surface 43 extends obliquely to the flat surface 35. Thus, since the superior member 14 is of a symmetrical configuration, surfaces 43 of both posts 34 taper away from surface 35 of the superior implant member 14 while extending away from their respective ends 26 and 30 and toward the opposite end 26 or 30.

Referring to FIG. 4, the inferior member 16 has two posts 44 extending upward from a base or wall portion 45 and upper surface 37 thereof on opposing ends 28 and 32 of the inferior member 16. Each post 44 has a generally frusta-conical configuration including a flared end 46 that widens as it extends away from the base 45. The ends 46 are curved to correspond to the curve on walls 40 so that the walls 40 are connected partially thereabout. Further, the ends 46 each have an upper, flat surface 39 extending from flared, upwardly extending annular surface 41 itself extending from the base wall 45. These surfaces 39 are generally parallel to each other and parallel to outer surface 24 of the inferior implant member 16.

The flared post end 46 is received in the indent 38 so that the curved, flared end 46 engages flush against the corner 42 and the flat, upper post surface seat 39 is flush against the recessed surface 43. The indent 38 on the superior member's post 34 is deep enough to provide clearance for the post 44 on the inferior member 16 so that the superior member 14 can be placed at a desired angle in the wedge configuration. As explained below, the inserter has a resilient member 68 that holds the superior member 14 in a wedge configuration on the bearing portion 20 without the need for any other supports. The distal posts 34 and 44 aid in locating the members 14 and 16 in the wedge configuration and may act as a secondary or "back up" support in case they are needed to stabilize the superior member in the wedge configuration. Since the posts 34 and 44 are not positively locked to each other in a snap-fit, disengaging the disc members 14 and 16 from the wedge configuration cannot cause potentially harmful, high impact forces. Instead, the posts 34 and 44 easily separate since the surfaces 39 and 43 of the posts 34 and 44 merely abut to form a predetermined orientation of the posts and in turn the implant members 14 and 16 relative to one another without a positive locking structure.

Referring to FIG. 5, the wall portion 45 has a bottom shoulder 50 recessed back from each end 28 and 32. The shoulder 50 has a continuous surface with adjacent arcuate surfaces including an arcuate concave middle surface 52, which is disposed between two convex arcuate surfaces 56a and 56b. These positioning surfaces 52, 56a and 56b abut a contoured impact surface 80 on a distal end 72 of a braking member 62 of the inserter 12. The arcuate surfaces 56a-b are curved to provide a surface that can roll or slide against the impact surface 80 of the inserter 12 to a number of pivoted positions or be placed against the impact surface 80 to tightly hold the implant at a preset pivoted position.

Figure 5A:
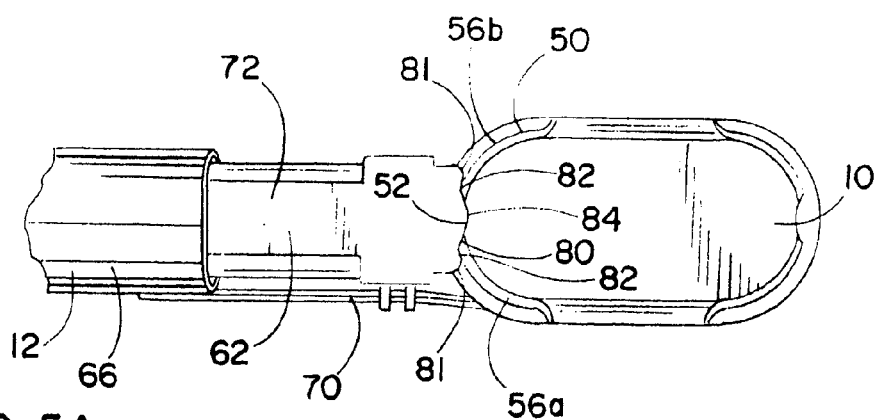
FIGS. 5A-5D are bottom plan views of the implant and implant-holding ends of the inserter showing pivoted positions of the implant and the rotation guiding surfaces progressing from an initial, inserter orientation (FIG. 5A) to a final, implant orientation (FIG. 5C) and an alternative steering configuration (FIG. 5D)
Figure 5B:
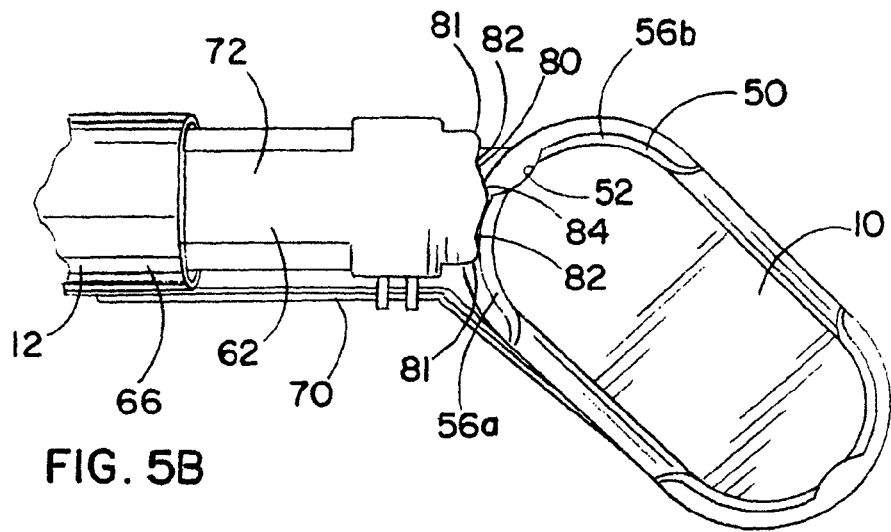
Figure 5C:
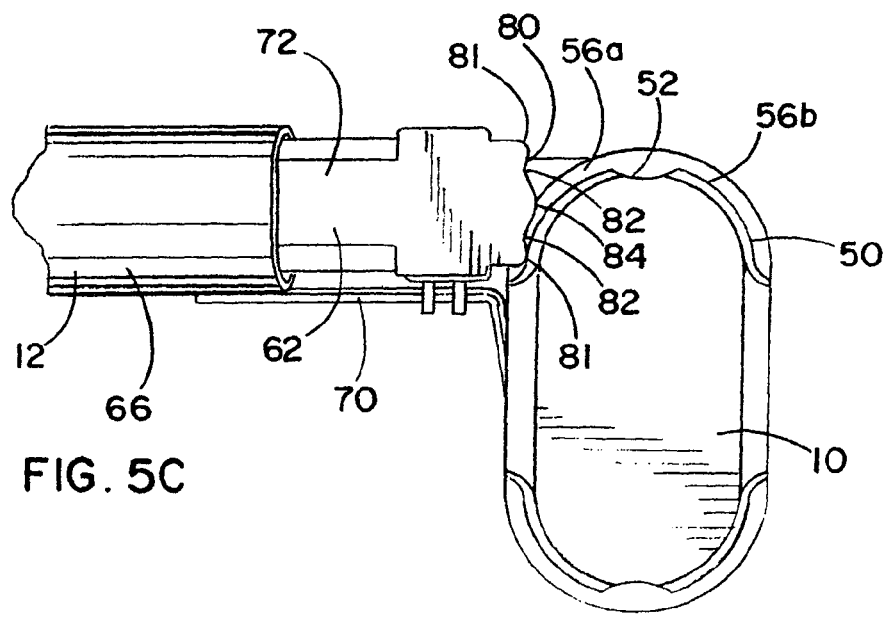
Figure 5D:
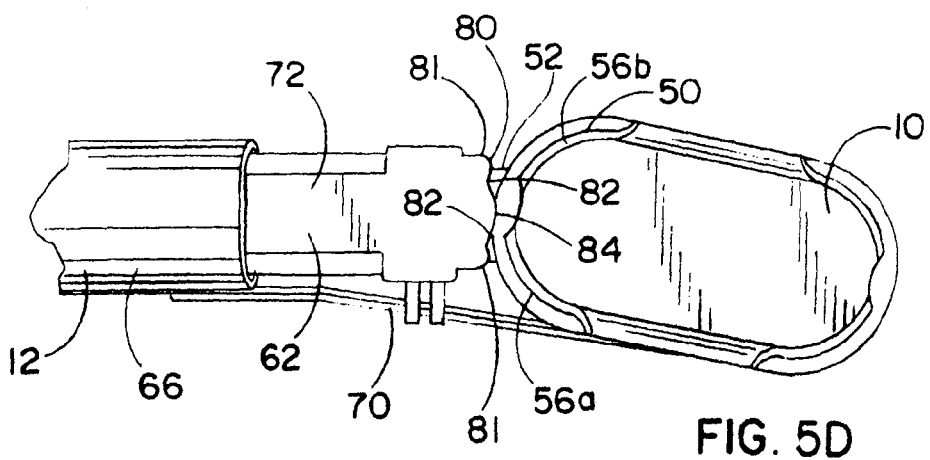

In the illustrated embodiment, the braking member 62 and impact surface 80 thereof are retracted away from the shoulder 50 while the implant is pivoted in order to avoid frictional forces that may need to be overcome if the impact surface is pressing against the shoulder 50 as shown in FIG. 5D. For this embodiment, the impact surface 80 is engaged to the shoulder 50 after the implant 10 is pivoted and with sufficient force to hold the proximal end 32 of the inferior member 16 in the pivoted position. The proximal end 32 is secured between the impact surface 80 and a gripping member 58 with a snap-fit claw 88 holding the proximal post 44 on the inferior member 16. The impact surface 80 also provides the main force from the inserter 12 that drives the implant forward and distally as the inserter is moved forward through any anatomy that pushes proximally against the implant 10 such as the vertebrae. The impact surface 80 can also be used to dislodge the inferior member 16 from the inserter 12 as described in further detail below with the description of the impact surface 80.

It will be appreciated that an alternative embodiment uses the impact surface 80 as a guide for the pivoting of the inferior member 16 of the implant 10. In this case, the shoulder 50 rolls and/or slides along impact surface 80 as it is being pivoted so that at least a contact point exists between the two guiding surfaces 50 and 80 as shown on FIGS. 5A-5C.

Figure 6:
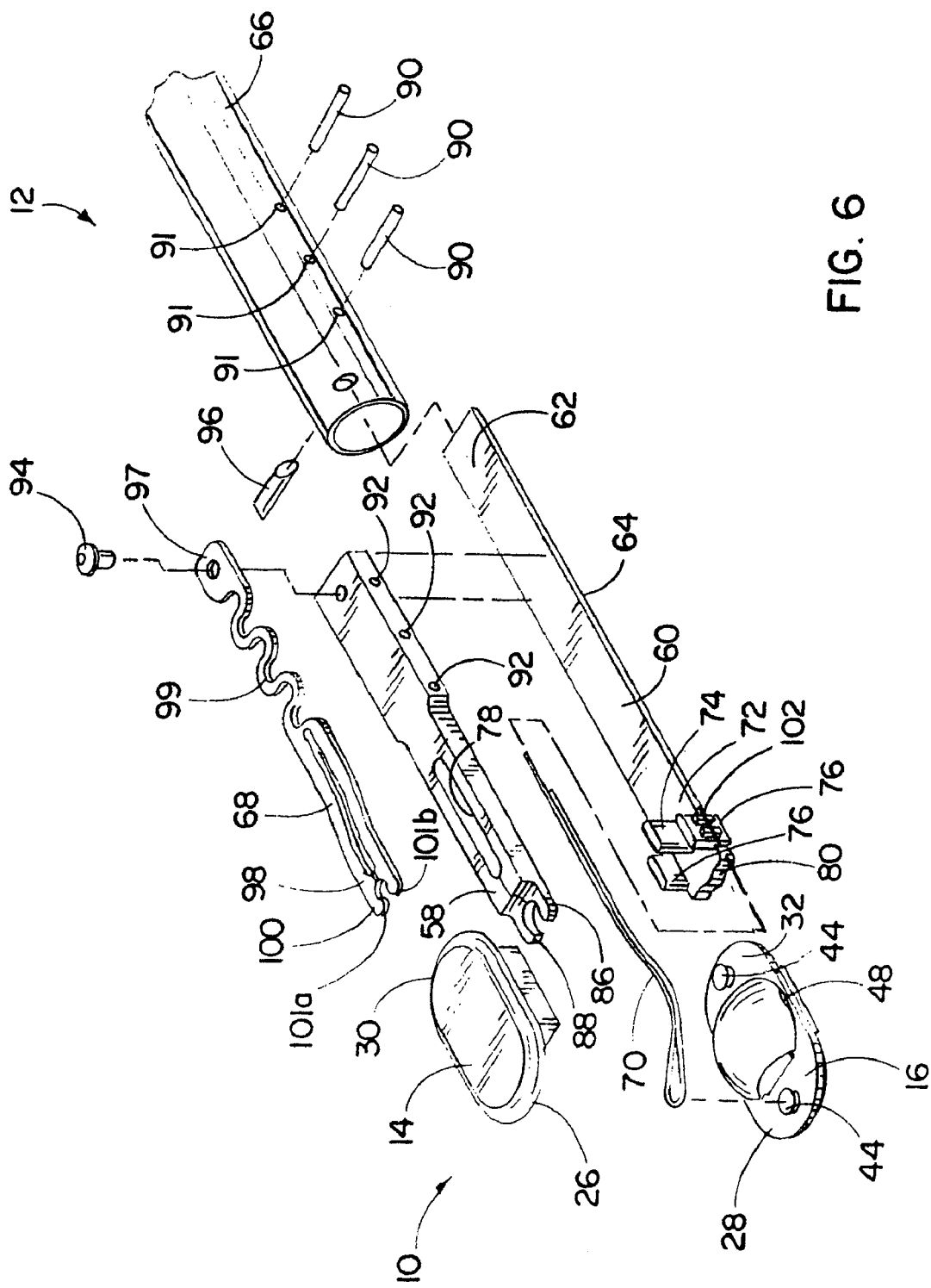
FIG. 6 is an exploded, perspective view of the implant and implant-holding end portion of the inserter showing the components that actuate and steer the implant.

Referring now to FIGS. 6 and 7, the inserter 12 is configured for selectively placing implant 10 in a wedge configuration and for actively steering and rotating the implant 10 relative to the inserter 12. As previously discussed, the wedge configuration assists in inserting and fitting the implant 10 through a relatively small incision in the annulus and into the nuclear space. Similarly, the active steering of the implant 10 allows the implant to fit through a relatively small incision in the annulus as the smaller width ends 19 and 21 of the implant 10 are advanced through the incision. With the implant in the nuclear space, the implant can then be steered via the inserter tool 12 so that the ends 19 and 21 are no longer aligned with the incision as explained above.

Figure 11:
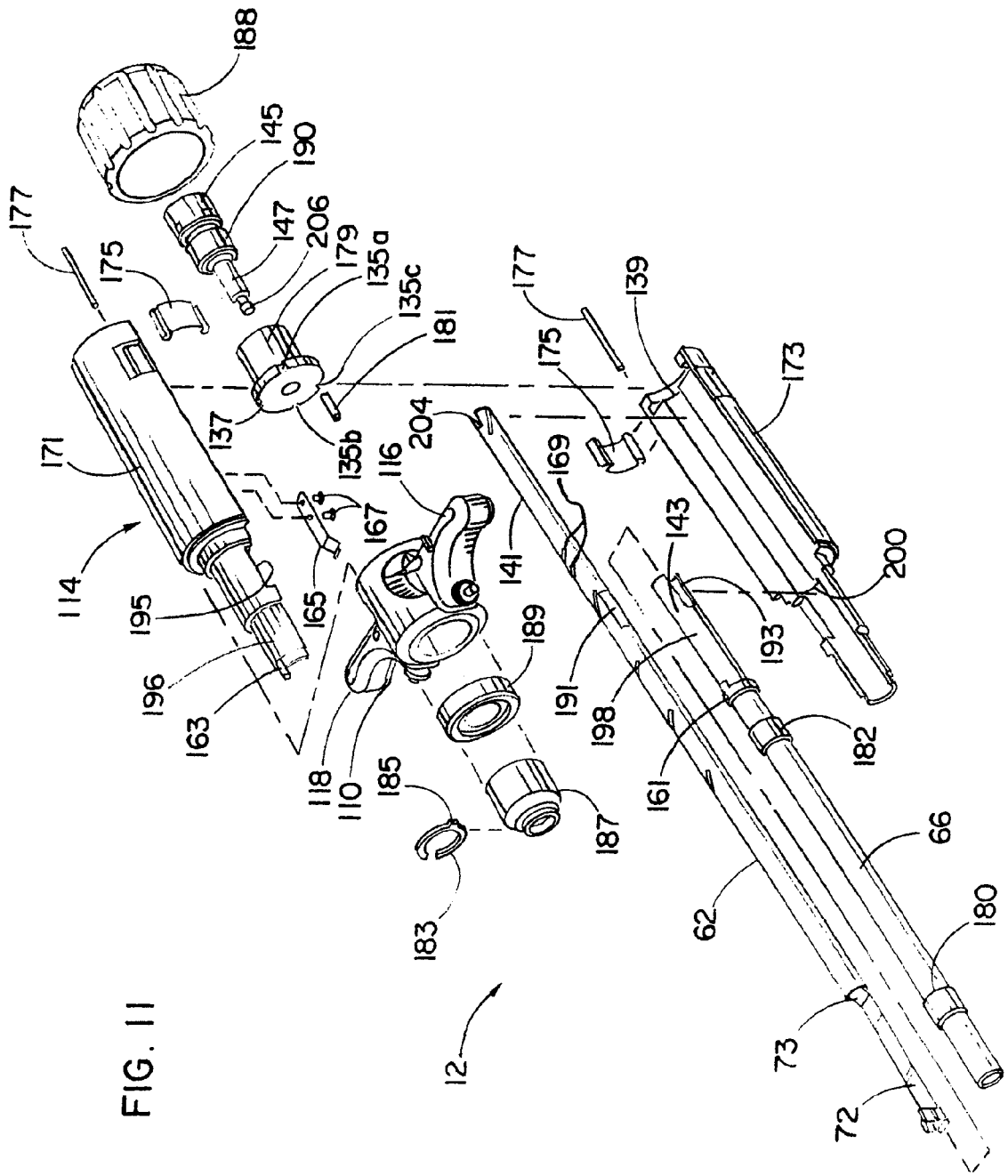
FIG. 11 is an exploded, perspective view of the inserter showing the components of the handle portion including a steering control device thereof.

Generally, the inserter 12 has the elongated gripping member 58 mounted on a top flat surface 60 of the braking member 62 for grasping the proximal post 44 on the inferior member 16. The resilient member 68 lays upon, and is secured to, the gripping member 58 to engage an upper, proximal post 34 on the superior member 14. All three members including the braking member 62, gripping member 58 and resilient member 68 are disposed within a cylindrical, outer shaft 66. The braking member 62 translates within the outer shaft 66. In this embodiment, the resilient member 68 and gripping member 58 do not extend to a handle portion 114 of the inserter and generally extend longitudinally relative to the inserter's longitudinal axis L until they both terminate before the widening of the braking member 62 at a ramp portion 73 (shown in FIG. 11).

As shown in FIG. 7, the gripping member 58 secures the inferior member 16 to the inserter 12. For this purpose, the gripping member 58 has a distal end 86 with opposing fingers 86a and 86b that form a claw 88 to grasp about the flared, annular surface 41 of the lower proximal post 44 on the proximal end 32 of the implant's inferior member 16. The fingers 86a and 86b are configured to provide a snap-fit connection with the post 44 so that the post cannot disengage from the gripping member 58 without applying a sufficient separation force between the gripping member 58 and implantable member 16.

The braking member 62 axially translates to abut the proximal end 32 of the inferior member 16. Once the braking member 62 abuts the proximal end 32, it is in position to provide the main driving force as the entire inserter is moved forward and the implant 10 is squeezed against or through any anatomy pushing proximally upon the implant 10. For inserting and pivoting the implant 10, the braking member 62 is held at an axial position that places its impact surface 80 against the inferior member 14 at a location relative to the gripping member 58 that does not push the inferior member away from the gripping member and disengage post 44 from the gripping member claw 88. In this position, the braking member 62 still provides sufficient force against the inferior member 16 to secure the proximal end 32 of the inferior member 16 as already explained. The handle portion 114 of the inserter 12 provides structure that indicates this predetermined position to the surgeon handling the inserter as explained in further detail below. Once the implant 10 is inserted and in a proper orientation between vertebrae, the braking member 62 can be translated distally to dislodge post 44 from gripping member 58 by pushing the inferior member 16, and in turn the post 44, distally away from claw 88 on grip member 58. This action also dislodges post 34 from claw 100 on the resilient member 68 in the same way.

The bottom 64 of the braking member 62 is curved to sit within, and translate axially within, the cylindrical shaft 66. The distal end 72 of the braking member 62 also has a central guide wall 74 that slides within a slot 78 on the gripping member 58 (as shown in FIG. 9) to maintain the longitudinal alignment between the two members 58 and 62. The braking member 62 has two laterally spaced guide walls 76 on either side of the braking member at the distal end 72 thereof provided to further constrain lateral movement of the gripping member 58 but are also used to support cable guides 102 described below.

The distal end 72 of the braking member 62 terminates with the contoured surface 80 recessed back and under the spaced gripping claw 88 of the gripping member 58, as seen in FIG. 9. The contoured surface 80 has two concave generally arcuate surfaces 82 interconnected by an intermediate, convex arcuate surface 84, while both concave surfaces 82 have an outer rounded end 81 as shown in FIG. 8. As shown in FIG. 5A, the central surface 84 is shaped to correspond to the shape of the center surface 52 of the shoulder 50 so that the two surfaces abut substantially flush with each other to maximize the surface contact and distribute the driving force from the inserter at least along surface 52 when the entire inserter is being moved forward or distally and against the implant 10. The surface 80 is referred to as an impact surface due to this driving function of the surface 80. With this configuration of the impact surface 80 and the shoulder 50, the implant 10 is stabilized in a straight position with the longitudinal axis $L_i$ of the implant generally aligned with the axis L of the inserter 12 when the projecting convex surface 84 of the braking member 62 engages the concave arcuate surface 52 of the implant member 16.

Referring to FIG. 5D, as mentioned previously, the inserter 12 of the illustrated embodiment retracts the braking member 62 to pivot the implant 10. The braking member 62 can then be reengaged with the implant once the implant is in a desired pivoted position as shown in FIGS. 5B and 5C. It will be understood, however, that FIGS. 5B and 5C also show the configurations as the implant pivots along and in engagement with the impact surface 80. For either of these embodiments, the surface 80 has rounded ends 81 to impact the convex surfaces 56a-b of the shoulder and to act as the main pivot points to better guide the rolling and sliding of the shoulder 50 against the impact surface 80. In the embodiment that pivots the implant 10 while in contact with impact surface 80, the inferior member 16 preferably has contact with the surface 80 at a single point (as viewed from the bottom view) along the rounded outer ends 81 although their may occasionally be contact with more than one point such as shown in FIG. 5B where the shoulder 50 of the inferior member 16 abuts both a rounded end 81 and the convex surface 84.

For the embodiment that pivots the implant 10 against the braking member 62, it will be appreciated that when the impact surface 80 of the braking member is maintained at a forward insertion and implant pivoting position and a constant longitudinal distance to the claw 88 of the gripping member 58, the impact surface 80 acts to limit further proximal rotation of the implant 10 more than about 90 degrees as shown in FIG. 5C. If the braking member 62 is moved from this position or the impact surface 80 has a different configuration, the braking member 62 may permit the implant 10 to rotate by a different amount from the longitudinal axis L of the inserter. For the embodiment that retracts the braking member 62 before pivoting the implant 10, the braking surface 80 may still limit the range the implant can pivot as long as it is positioned within the circular path of the implant as it is pivoted.

Referring again to FIG. 6, the gripping member 58 is mounted within the outer shaft 66 by three support dowels 90 that extend generally radially through holes 91 on the shaft and through apertures 92 extending through the gripping member 58. This configuration fixes the shaft 66 to the gripping member 58 while permitting the braking member 62 to translate within the shaft 66 for at least the length of the slot 78 on the gripping member 58.

The resilient member 68 is a generally flat, leaf-type spring made of suitable metal, plastic or other resilient material and mounted to the top of the gripping member 58 by a screw 94 or any other similar fastener at a proximal end 97 of the resilient member. A biasing dowel 96 is mounted through the shaft 66 and above the resilient member 68 to hold the resilient member 68 down against the gripping member 58 within the shaft 66. A distal end 98 of the resilient member 68 also has a claw-like structure 100 (shown best in FIG. 9) with fingers 101a-b for gripping the neck 33 of post 34 above the posts widened head 36 on the proximal end 30 of the superior portion 14 and in a snap-fit configuration that requires a separation force to be applied between the resilient member 68 and implant member 14 to disengage the fingers 101a-b from the proximal post 34. The thickness of the claw 100 is dimensioned to fit tightly between the flat surface 35 of the superior member 14 and the head 36 of post 34 so that the resilient member 68 holds the superior member 14 in the slanted position on the bearing portion 20 of the inferior member 16 without any other supports.

Referring to FIG. 7, the distal end 98 of the resilient member 68 has an initial or original vertically bowed configuration so that portions at the distal end 48 of the resilient member 68 extend transversely to the longitudinal axis L of the sizing tool 10. The resilient member 68 has sufficient strength and resiliency to hold the superior portion 14 in the wedge configuration as its initial or original configuration when the superior portion 14 is first attached to the inserter 12 outside of the nuclear space. Once the implant 10 is inserted into the nuclear space, the pressure from the vertebrae push the superior member 14 downward into a flat configuration where it extends generally parallel to the inferior member 16. The resilient member 68 is flexible enough to be pushed downward by the vertebral forces acting on the superior member 14 so that the resilient member 68 is shifted to a non-bowed orientation and still holds the post 34.

The resilient member 68 has an S-shaped, snaked or winding proximal portion 99 (FIG. 6) that winds transversely from side to side as it extends along the longitudinal dimension of the resilient member. As the superior member 14 shifts from the wedge configuration to a more parallel configuration, the proximal post 34 on the superior member 14 that is attached to the claw 160 pushes proximally against the distal end 98 of the resilient member 68. The winding portion 99 then compresses in a direction parallel to the longitudinal axis L of the inserter 10 by reducing the space between each pair of adjacent transverse windings and flexing the arcuate portions connecting each of the pair of adjacent windings.

Turning now to the steering aspects of the illustrated embodiment, the pivoting of the implant 10 takes place about the posts 34 and 44 at the proximal ends 30 and 32 of the superior and inferior portions 14 and 16 as they are respectively held by the resilient member 68 and gripping member 58 as explained in detail below.

With reference to FIG. 2, a cable actuator 70 for the disc implant 10 is wrapped around the distal post 44 on the inferior portion 16 and runs along the guide groove 48, alongside and generally under the dome bearing portion 20, and then through cable guide structure 102 on either one of the guide walls 76 on the braking member 62 depending on which side the disc implant is to be pulled during placement thereof in the nuclear space. This cable guide structure 102 permits the axial sliding of the cable. As shown in FIG. 9, the guiding structure 102 includes two L-shaped, oppositely extending hooks 104 with interior surfaces 106 that the cable 70 slides axially against or within.

Referring to FIGS. 1 and 2, a proximal end portion 108 of the cable 70 is connected to a steering control device or assembly 110 on a handle portion 114 of the inserter 12. With a distal end 112 of the cable 70 looped around or otherwise connected to the post 44 on the distal end 28 of the implant 10, pulling proximally on the cable 70 through the guide 102 pulls the distal ends 26 and 28 of the implant 10 toward the inserter 12 and toward the same side of the inserter 12 along which the cable 70 extends.

As shown in FIG. 10, by operation of hilts 116 and 118 on the control assembly 110, the implant 10 can be pivoted left or right up to approximately 90 degrees from the initial insertion orientation of the implant 10 with its longitudinal axis $L_i$ generally aligned with the axis L of the inserter tool 12. When the implant 10 is secured in a position with the shoulder 50 of the inferior member 16 abutting against the impact surface 80 of the braking member 62, the distal corners 81 of the braking member will limit further proximal pivoting of the implant at about 90 degrees as shown in FIG. 5C. As explained previously, when the impact surface 80 is maintained at a constant longitudinal distance from the distal end 86 of the gripping member 58, and in turn the rotational axis R about which the implant 10 pivots, the impact surface 80 blocks more than about 90° of rotation of the implant from longitudinal axis L. The implant 10 and inserter 12 could be used to pivot the implant 10 more than 90 degrees by retracting the braking member 62 far enough from the implant 10 to provide clearance for the implant to pivot to that extent. However, it is unlikely that this amount of pivoting would be required since any surgical approach should only need the implant 10 to pivot 90 degrees or less in order to orient the implant 10 with its longitudinal axis perpendicular to the anterior-posterior direction. It will be appreciated that while the cable 70 is shown to be attached to run along the left side of the inserter 12 to pivot the implant 10 to the left, the cable 70 can be positioned to run along the right side of the inserter 12 to pivot the implant 10 to the right instead.

Referring now to FIGS. 11-15, in the preferred and illustrated form, the steering control assembly 110 includes the two symmetrical, left and right finger holds or user operated, control hilts 116 and 118 respectively mounted on opposite sides of a collar 120 placed near the front of the handle portion 114. Only the braking member 62 and outer shaft 66 extend within the collar 120 since the members 58 and 68 terminate at the distal end 72 of the braking member 62.

Figure 12:
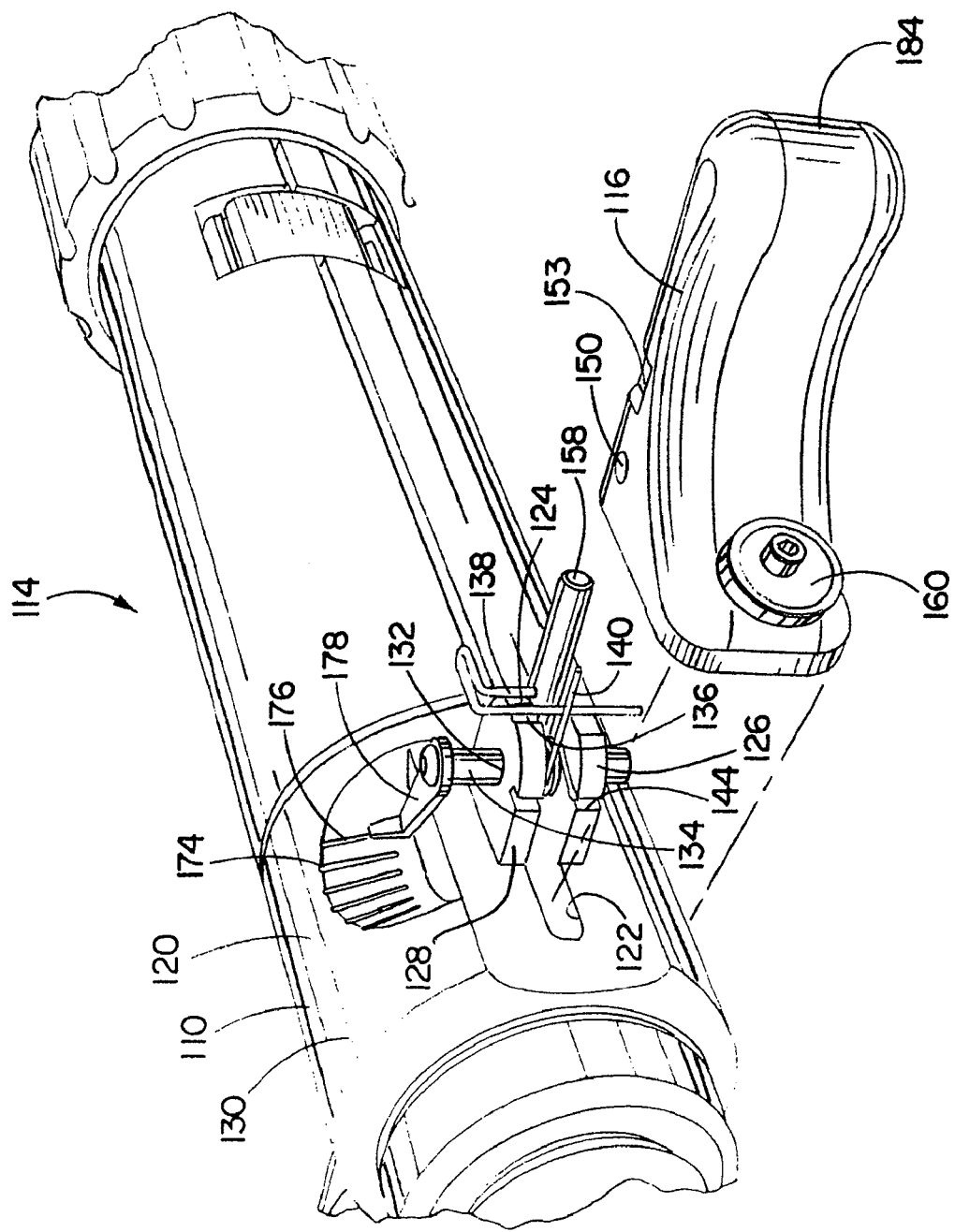
FIG. 12 is an enlarged, perspective view of a steering control on the inserter and including a hilt shown separated from a collar of the steering device and showing the interior structure of the steering control device within the hilt and that pivotally secures the hilt.

As shown in FIG. 12, the left side of collar 120 has a longitudinally extending slot 122. The collar 120 has a symmetrical construction so that there is identical structure on the other side to that described for the left side. Two support fins 126 and 128 extend outwardly and laterally from the generally cylindrical exterior surface 130 of the collar 120, and respectively extend below and above the slot 122. The fins 126 and 128 are shown to be integrally formed with the collar 120 and support the hilts 116 or 118.

The fins 126 and 128 have coaxial openings 132 (both visible in FIG. 14) dimensioned for tightly receiving a pin 134 such as with a friction fit, extending therethrough and for mounting a torsion spring 140 thereabout. The upper fin 128 has an edge 136 with teeth 124 (seen best in FIG. 13) for engaging a locking pawl 138. Of course the teeth could be disposed on either fin 126 and 128 or both of them.

Figure 13:
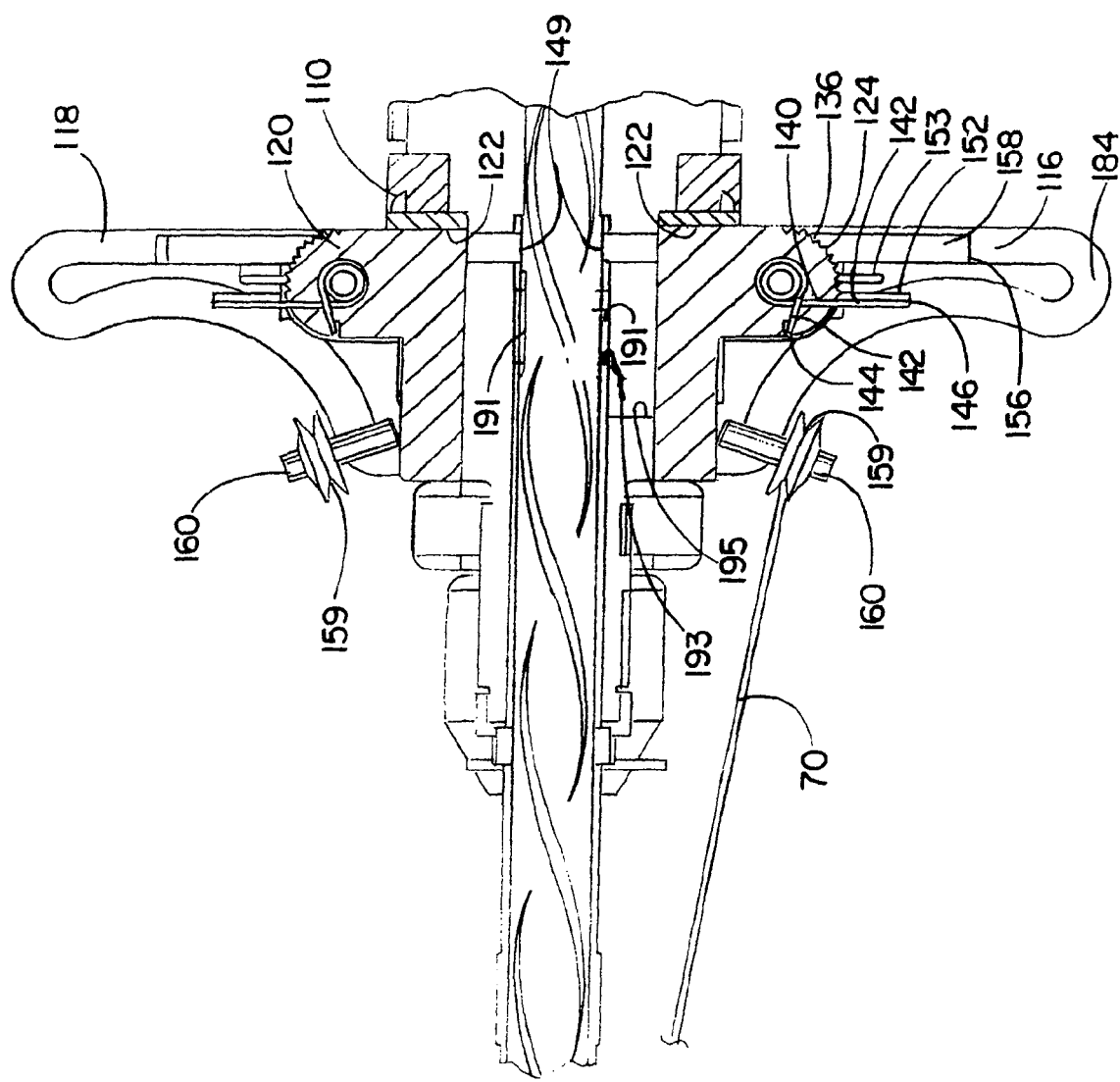
FIG. 13 is a cross-sectional view of the steering control device of FIG. 12 showing cables attached to the hilt and a torsion spring for biasing the hilt.

Coils of the torsion spring 140 are wound around the pin 138 between the fins 126 and 128, as shown in FIGS. 12 and 13. One projecting end 142 of the spring 140 is hooked and anchored in a notch 144 in either the top or bottom fin 126 and 128. The other projecting end 146 of the spring 140 extends straight out and laterally or radially from the collar 120 and toward the hilts 116 or 118 for being operatively engaged therewith.

Referring to FIGS. 14 and 15, the hilt 116 (and similarly hilt 118) has a pocket 148 configured for receiving the fins 126 and 128 and the spring 140. The ends of the pivot pin 134 extend in clearance through the apertures 150 that open to the pocket 148 and are coaxial with the through apertures 132 in order to pivotally mount the hilt 116 to the fins 126 and 128 about axis H extending through the aligned aperture 132 and 150 as shown in FIG. 1. A first bore 152 extends laterally from the pocket 148 to receive the straight end 146 of the spring 140 therein. The sizing and spacing of the spring ends 146 and 148 is such that when received in the notch 144 and bore 152, respectively, the hilt 116 is rotatively biased to the forward position shown in FIGS. 1 and 13.

The hilt 116 has a vertically extending slot 153 through which the pawl 138 is inserted and an aperture 154 for receiving the lower end of the locking pawl 138, as can be seen in FIGS. 13-15. The locking pawl 138 has two spaced, parallel legs 138a and 138b. The longer leg 138a extends through slot 153 where the slot opens to the pocket 148 so that the leg 138a can engage the teeth 124 of the fin 128 in order to releasably lock the hilt 116. The shorter leg 138b presses against the side of slot 153 and biases the longer leg 138a against the fin 128 while creating a tight fit within the slot 153. The pawl 138 holds the hilt 116 in one of a number of rotated hilt positions, and in turn a number of pivoted implant positions, determined by the circumferential position of the teeth 124 on the fin 128 relative to the axis of rotation H and the amount of teeth 124. The teeth 124, therefore, create a range of positions with limits that may or may not correspond to the limits of the pivoting range created by the contoured braking surface 80 when the braking surface abuts the implant member 14 turning the steering of the implant. The positions also may correspond to pivoted angles of the implant 10 relative to longitudinal axis L where one position is 90 degrees, another 45 degrees, etc. The pawl 138 holds the hilts 116 or 118, and in turn the implant 10, at certain angles so that a surgeon does not need to use one of his hands or his fingers, which may be uncomfortable, to hold the hilt 116 or 118 at a certain angle relative to the handle portion 114 of the inserter 12 when desirable. This may occur when the surgeon needs to hold other instruments or objects in his free hand while holding the implant 10 at a certain angle on the inserter 12 in the other hand.

A second laterally extending bore 156 is formed in the hilt 116 for securely receiving a guide dowel 158 therein (shown in FIGS. 12 and 13) and projecting out therefrom into the guide slot 122 on the side of the collar 120. The guide dowel 158 preferably restricts rotation of the implant 10 so that rotation occurs only when the brake member 62 and its impact surface 80 are retracted away from the inferior member 16 as explained in greater detail below.

Figure 16:
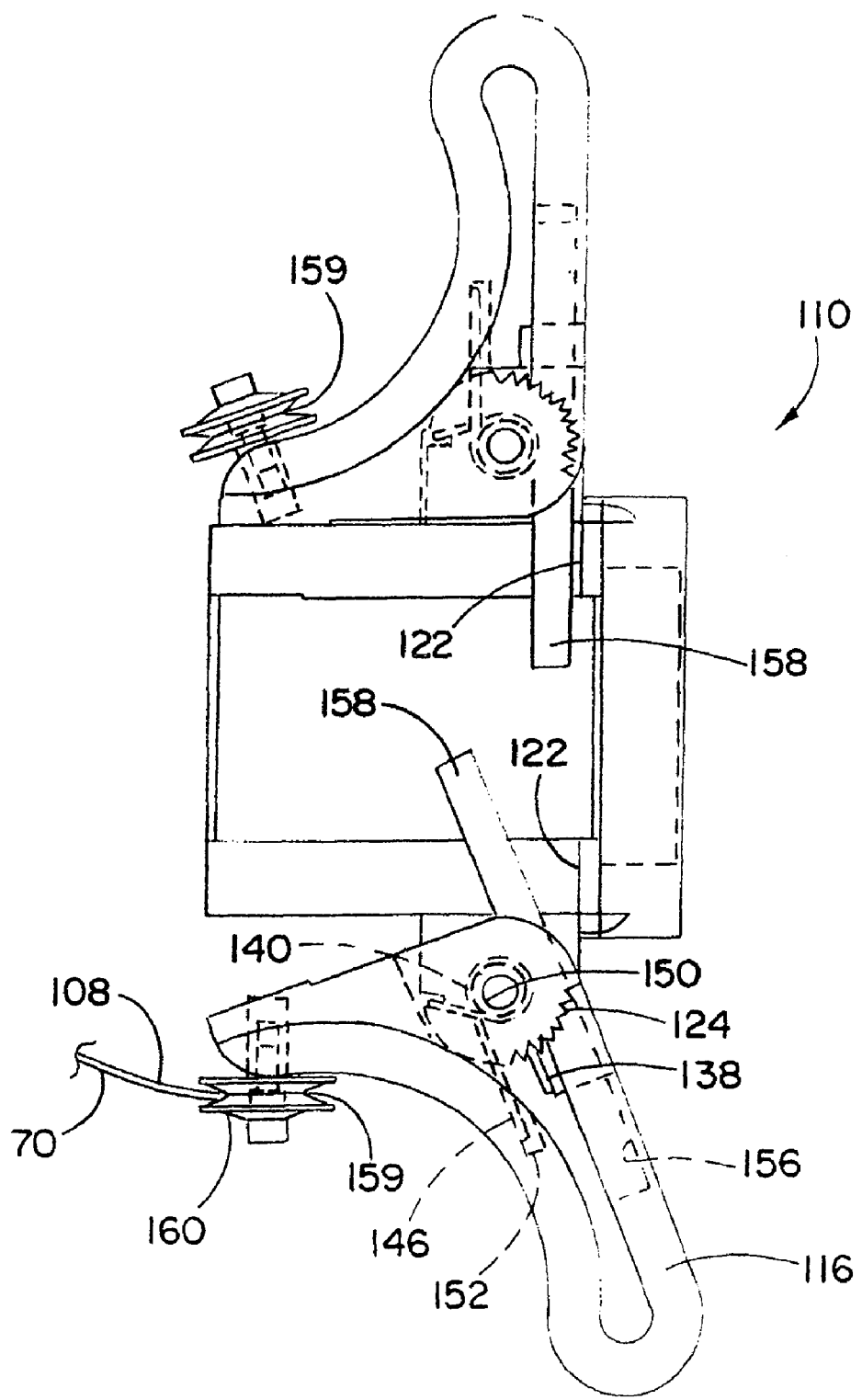
FIG. 16 is a top, cross-sectional view of the steering control device showing one of the hilts in a pivoted position for pivoting an implant held by the inserter.

Referring to FIG. 14, spools 160 are mounted to the hilts 116 and 118 for the actuator cable 70. The spools 160 can each include a dish shaped base 162 with a shank 157 received by friction fit in a third bore 164 in the hilt 116. A dish shaped cap 166 is secured to the dish shaped base 162 so that they open in generally opposite directions to form a cable receiving annular groove 159 (FIGS. 13 and 16). More specifically, the cap 166 and a spring washer 168 are fixed to the base 162 by a fastener, such as a screw 155 that fits through an opening 170 in the cap 166 and into an internally threaded bore 172 in the cylindrical shank 157 of the base 162. The screw 155 secures the cap 166 to the base 162. The spring washer 168 biases the cap 166 toward the base 162 so that winding the cable 70 around the spool and within the groove 159 with enough force, inserts the cable between the cap 166 and the base 162 against the bias force of the washer 168 so that the cap and base tightly grip the cable 70 therebetween to secure the cable to the spool.

Referring again to FIG. 12, one optional feature is an angle gauge 174 disposed within a recess 176 on the collar 120 adjacent the control hilt 116. The gauge 174 has an array of indicia 176 that are spaced to correspond to different angles of rotation of the implant 10. A pointer or dial member 178 is fixed to the pivot pin 134 extending radially toward the indicia 176. For this configuration and as previously mentioned, the pin 134 fits tightly within the apertures 150 on the hilt 116 and is able to rotate within the clearance through openings 132 on the fins 126 and 128 so that the pointer 178 rotates with the hilt 116 to indicate the appropriate angle on the gauge 174. It will be appreciated that the gauge 174 may have alternative configurations such as where the indicia are disposed on a wheel on the top of the shaft 134 and the pointer is on the collar 120, or gauges are provided on both the top and/or bottom of the inserter.

For the steering operation, generally, once the inferior member 16 is mounted on the distal end 17 of the inserter 12, the cable 70 is threaded from the spool 160, through the cable guides 102, 180, 182 and 185, and onto the distal post 44 on the inferior member 16. The inferior member 16 is mounted in a straight configuration with its longitudinal axis $L_i$ parallel to the longitudinal axis L of the inserter 12. The superior member 14 is then mounted on the inserter 12 in a slanted position to form the wedge insertion configuration, and the implant 10 is then inserted through an incision on an annulus with its narrow distal end 19 leading.

Upon insertion of the implant 10 within the nuclear space, the vertebrae presses down on the superior member 14 pushing it into a flat configuration while flattening the bowed resilient member 68 holding the superior member 14. The surgeon then removes the locking pawl 138 from the hilt 116 or 118 attached to the cable 70 and pulls the hilt which pulls the cable 70 proximally and in turn pivots the implant 10 toward the side (left or right) of the inserter 12 that has the cable 70. Pivoting of the hilt 116 or 118 is performed by using either finger in the hand gripping the handle portion 114 on the inserter 12 or by using the hand to hold the inserter and the other hand to turn the hilt. The surgeon may pull the hilt 116 or 118 to a desired angle for further manipulation of the implant 10 or until the longitudinal axis $L_i$ of the implant 10 extends orthogonally to the anterior-posterior direction of the nuclear space. The pawl 138 may then be placed back in the hilt 116 or 118 to hold the implant 10 at the desired angle if needed so that the inserter 12 can be held with one hand without keeping a finger on hilt 116 or 118, which may be uncomfortable.

Once the implant 10 is in place, the cable 70 is cut or untied from spool 160 and pulled off of post 44 on the inferior member 16 and longitudinally through the annulus incision. The braking member 62 is then translated distally to disengage the grip members 58 and 68 from the implant 10, and the inserter 12 is retracted longitudinally through the incision and out of the nuclear space. The longitudinal motion of the cable 70 and inserter 12 avoids enlarging the incision in the annulus.

Now describing the steering operation in detail, the cable 70 may be preliminarily wound around spool 160 and stored for later use. Spool 160 may then be attached to the hilt 116 when needed. Otherwise, the cable 70 is attached to the spool 160 as mentioned above. The cable 70 is then threaded through optional cable guides 180 and 182 on the outer shaft 66 (shown in dashed line on FIG. 1 and FIG. 11 with a cable 70a) and optional cable guide 185 that has a collar 183 (mounted on shaft nut 187 described below) to keep the cable 70 close to the tool shaft 66 and to extend therealong toward the disc implant 10 at the distal end 17 of the tool 12. Next, the cable 70 is placed through the oppositely oriented cable guides 102 on the distal end 72 of the braking member 62 which cooperate to keep the cable 70 from shifting laterally away from the tool, and also in upward and downward directions, respectively, as shown on FIG. 9. Keeping the cable 70 close to the tool 12 as well as the implant 10 is useful since the forward end portion 17 of the tool 12 is to be advanced through the annulus incision and into the nuclear space.

The cable 70 is then fit within groove 48 and around post 44 on the superior portion 16 of the implant 10, as shown best in FIG. 2. The cable 70 is drawn back to the spool 160 in and through the reverse order of the guides described above to complete a loop. The loop is desirable so that once the implant 10 is in place in the nuclear space, the loop need only be cut or untied and one end of the cable 70 pulled such as by rotating the spool 160 or by simply pulling it by hand until it is completely disengaged from the implant 10. The cable 70 may be wound around the post 44 a number of times although one turn around the post is preferred for easy removal of the cable. The cable 70 may also terminate at the post 44 if the post 44 and cable 70 are provided with a releasable connection therebetween such as an opening in the post or hook on the post 44 where the cable 70 has a releasable knot or frangible bead or similar structure that can be received by the post structure.

As shown in FIG. 1, the hilt 116 is biased in the forward position with the axis H extending generally orthogonal to the longitudinal axis L of the tool 12 which places the implant 10 in the initial straight or non-rotated position. In this position, the implant 10 has its lateral ends aligned with the tool axis L so that the implant's longitudinal axis $L_i$ and the tool axis L are aligned. In this manner, the surgeon can direct the narrow width, leading end 19 of the disc implant 10 through the incision by advancing the tool 12 along its axis L. As previously discussed, this end 19 is not only narrower than the length of the implant 10, but it also is of a smaller size in terms of its height than the reminder of the implant due to the wedge configuration of the implant for keeping the size of the incision in the natural disc annulus to a minimum.

Generally, and as mentioned above, once the larger trailing end 21 of the disc implant 10 has cleared the annulus wall so that the entire implant has been fit through the incision and into the nuclear space, the surgeon will want to reorient the implant in the nuclear space when the annulus incision is positioned to require the disc implant to be advanced through the incision into the nuclear space in a generally posterior-anterior or other non-lateral direction. In this instance, the surgeon can steer the implant 10 via the tool 12 still operatively connected thereto. This reorients the implant 10 without reliance on engagement with the annulus wall to assist the implant reorientation.

The steering control 110 is used to rotate or pivot the implant 10 so that the narrow width ends 19 and 21 are no longer generally aligned with the incision as may occur when the implant longitudinal axis $L_i$ extends in the posterior-anterior direction or only slightly offset therefrom. For instance, the implant 10 can be rotated up to about 90 degrees so that the narrow width ends 19 and 21 are disposed on either lateral side of the nuclear space with the implant longitudinal axis $L_i$ extending laterally there across. In addition to orienting the implant 10 more properly in the nuclear space from an anatomical perspective, having the long sides of the implant extending generally parallel to the length of the incision minimizes the chance that the implant may back out of the nuclear space through the incision after implantation. It should be noted that implant rotation by a lesser amount than 90 degrees may be sufficient where the incision is positioned so that the disc implant is advanced therethrough offset from or obliquely to the posterior-anterior direction.

Also, during implantation, it is contemplated that the implant 10 will shift from the wedge, insertion configuration to an operative configuration where the implant members 14 and 16 can move relative to each other at their bearing interface, as has been previously described. This shifting can occur as the implant is being pushed through the incision or in the nuclear space as force applied by the annulus wall surrounding the incision or by the vertebrae on locations along the implant 10 toward and at the large, trailing end 21 thereof cause the superior member 14 to pivot about the dome bearing portion 224 of the inferior member 16 so that the posts 34 and 44 disengage.

While this shift in configuration of the implant 10 occurs, the inserter tool 12 stays operatively connected thereto via the gripping members 58 and 68 as previously described. Accordingly, generally the implant 10 will be in its operative configuration of FIG. 2 in the nuclear space before it is turned or pivoted therein by the connected tool 12. The front or distal end 19 of the tool 12 is sized to fit through the incision and into the annular space for staying connected to the implant 10. In this regard, only the portions of the gripping members 58 and 68, and braking member 62 projecting from the larger diameter shaft 66 extend through the incision and into the nuclear space while the shaft 66 remains external thereof.

In order to rotate the implant 10, the locking pawl 138 is lifted upward and out of slot 153 in the hilt 116 to disengage its leg 138a from the teeth 124 of the fin 128. Then, the surgeon can pull the hilt 116 back toward the proximal end 186 of the inserter 12 with a finger engaged on a contoured surface 23 of the control hilt 116, with sufficient force to pivot the hilt 116 about axis H against the biasing force of the torsion spring 140. This pivot action turns the guide dowel 158 within slot 122 as shown in FIG. 16. Once the hilt 116 is rotated to a desired position as indicated on the angle gauge 174 for example, the pawl 138 can be reinserted within the slot 153 with a lower end 151 of its long leg 138a seated in recessed aperture 154 so that the long leg 138a reengages between the teeth 124 of the fin 128 to releasably lock the hilt 116 in the rotated position.

Referring to FIG. 2, as the hilt 116 is pivoted, it pulls the inferior member 16 at the distal post 44 in the direction the cable 70 is moving while the opposite proximal post 44 remains pivotally held by the gripping member 58 thereby rotating the inferior member about the proximal post 44. As the inferior member 16 is pivoted for steering the implant 10, its dome bearing portion 20 will push laterally against the concave bearing surface 18 of the superior member 14, causing the superior member 14 to pivot along with the inferior member 16 about pivot axis R. Since the steering takes place within the nuclear space, the vertebrae apply pressure to the superior and inferior members 14 and 16 so that they cannot separate. This increased connection between the bearing portion 18 and 20 will tend to make the implant members 14 and 16 pivot together. The concave bearing surface 18 of the superior member 14 extends downward a sufficient length alongside the convex bearing surface 20 so that the convex bearing surface 20 pushes on the side surface portions 18a of the concave surface 18 during pivoting of the lower inferior member 16 causing both implant members 14 and 16 to pivot together. This steering feature permits the implant 10 to be rotated about axis R of the proximally held post 44 of inferior member 16 and rotated to the laterally extending position within the nuclear space between vertebrae described above. This is accomplished without requiring rotation of the inserter 12 about axis R which avoids lateral motion of the forward insertion portion 17 extending through the incision on the annulus and into the nuclear space. Since the steering is active rather than passive, the implant 10 itself does not need to be pressed against any anatomy at the surgical site, and especially within the nuclear space and annulus, in order to turn the implant and therefore, the risk of damage to any tissue is lowered.

It will be appreciated, however, that the implant 10 as well as implants 210 and 300 described below for the other embodiments, may be pivoted partially by active steering and partially by passive steering either simultaneously or by performing one after the other. For example, the inserter 12 may actively steer the implant 10 to about 45 degrees relative to the longitudinal axis L of the inserter 12. Thereafter, now that the implant leans in the direction of pivoting and the driving force from the inserter and through the implant is directed at least partially laterally rather than longitudinally and is not pointed directly toward the annulus wall, the risk of damaging the annulus is less by passive steering. Thus, the implant 10 may be steered by passive steering from the 45 degree position by pushing the implant against the annulus to pivot the implant to about 90 degrees relative to the longitudinal axis L of the inserter. This applies to all of the inserter and implant embodiments described herein.

In an alternative configuration, the inserter 12 could have two cables 70, or a single cable with extra length, such that the ends of the cable(s) are attached to both spools 160 and to the post 44 on the distal end 28 of the inferior portion 16. With this configuration, rotating the left hilt 116 turns the implant 10 to the left, while rotating the right hilt 118 would rotate the implant to the right. Both spools 160 would have a sufficient amount of wound cable to provide enough slack when the implant is turned in the opposite direction relative to either of the spools. Desirably, this would permit the implant 10 to be pivoted to the left or right for about 90 degrees although this angle could be more or less depending on how far the hilt 116 can rotate and/or the configuration of the abutting contoured surfaces 50 and 80.

Figure 17:
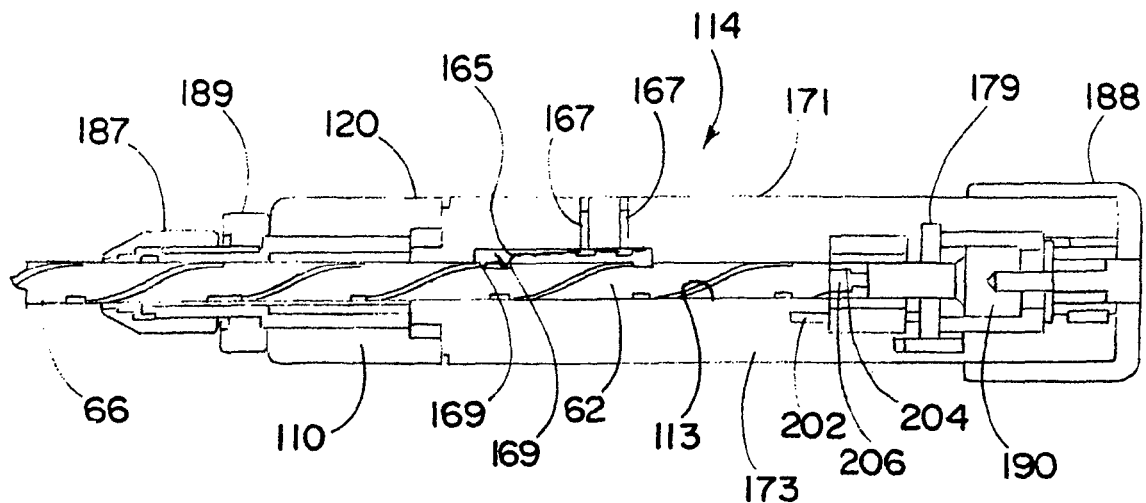
FIG. 17 is a cross-sectional view of the handle portion of the inserter showing a main shaft, braking member and steering control device secured to the handle portion of the inserter.
Figure 18:
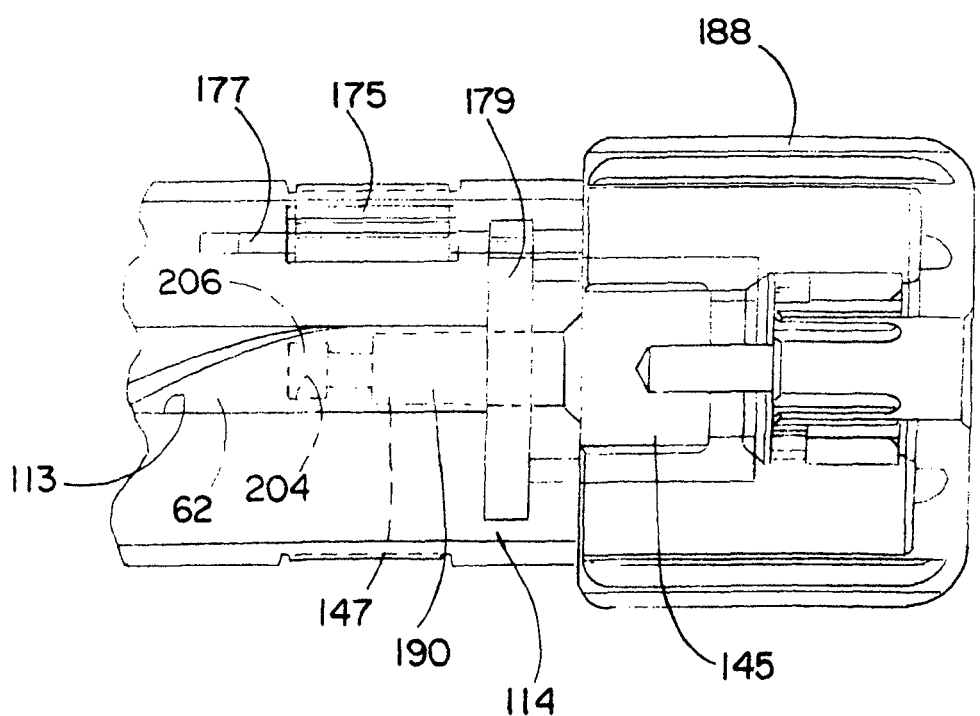
FIG. 18 is an enlarged, cross-sectional view of the handle portion of the inserter and showing a knob and braking screw used for axially driving a braking member.

Referring again to FIG. 11, the handle portion 114 of the inserter 12 can be operated to axially translate the braking member 62 to secure the implant 10 against the inserter. As shown in FIGS. 17 and 18, the handle portion 114 has a rotatable knob 188 at its proximal end 186 that is connected to a braking screw 190 with an outer rotatable body 145 that rotates with the knob 188 and an inner body or driving portion 147 connected to the outer body 145 and translating axially when the outer body is rotated. A driving connection between the outer and inner bodies 145 and 147 allows relative rotation therebetween and may be a threaded connection or a ratcheted torque limiting connection that permits the surgeon holding the handle portion 114 and knob 118 to sense an amount the knob 188 is turned, and in turn the axial length the braking member 62 has moved. To secure the inner body 147 to the braking member 62, the braking member 62 has a T-shaped slotted proximal end 204 that rotatably receives a distal enlarged head 206 of the inner body 147 of the braking screw 190 as shown in FIG. 18.

The handle portion 114 has an upper cover 171 and a lower cover 173 secured together by clips 175. The clips 175 cannot be removed without first removing axial locking dowels 177 inserted through aligned openings in the clips 175 and holes 202 in the covers 171 or 173 (shown in FIG. 17) which are not exposed unless the knob 188 is removed by pulling it axially and away from the upper and lower covers 113. The covers 171 and 173 have a generally semi-circular configuration and cooperate to form an internal space 113 into which rear portions 141 and 143 of the braking member 62 and outer shaft 66, extend respectively, and in which braking screw 190 is disposed, as shown in FIG. 18. A positioning leaf spring 165 is connected to the upper cover 171 by screws 167 to selectively engage notches 169 on the braking member 62 in order to provide an indication of the position to which the braking member has been shifted. Thus, the more proximal notch 169 indicates a predetermined position in which the impact surface 80 of the braking member 62 abuts the inferior member 16. The more distal notch 169 indicates a predetermined position where the impact surface 80 is disengaged from the inferior member 16. The surgeon is able to feel increased resistance to rotate the knob 188 once the spring 65 engages one of the notches 169 or hears a "click" or feels a vibration as the spring 65 snaps into the notches 169.

A collar insert 179 is provided in the handle space 113 to orient the forward drive portion or inner body 147 of the braking screw 190 for proper alignment of the rear slot 204 of the brake member 62. A forward, enlarged flange 137 of the collar 179 is received in an interior, annular groove 139 formed by the covers 171 and 173 so that the collar 179 is fixed in the handle interior space 113. Two locking dowels 177 and an additional locking dowel 181 fixes the insert 179 in a predetermined circumferential position by respectively extending through grooves 135*a-c* on an outer rim 133 of the flange 137.

The steering control 110 is mounted to the upper and lower covers 171 and 173 and secured to the covers by a shaft nut 187 and a housing nut 189 which are both releasably secured by threads 196 on the covers 171 and 173. The shaft 66 has a protrusion 161 that is axially and circumferentially secured between the shaft nut 187 and a notch 163 on the cover 171 within which the protrusion extends longitudinally. The interfit of the protrusion in the notch 163 in turn secures the shaft 66 both axially and circumferentially to the cover 171.

Referring to FIG. 13, in the illustrated embodiment, the braking member 62 has diametrically opposite, longitudinally extending grooves 191 that are selectively aligned with slot 122, while the outer shaft 66 and covers 171 and 173 both respectively have slots 193 and 195 that are permanently aligned with slot 122 in order to provide clearance space in the interior space 113 of the handle portion 114 that permits the swiveling of the guide dowel 158 and in turn the pivoting of the hilts 116 and 118 for the steering operation with the inserter tool 12 herein.

In the presently illustrated configuration, the slots 191 are positioned on the braking member 62 so that the braking member 62 must be retracted and the impact surface 80 must be pulled away from the contoured shoulder 50 of the inferior member 16 in order for the slots 191 to align with slot 122 to permit the pivoting of the guide dowel 158. When the slots 191 are not aligned with slots 122, the distal ends 149 of the guide dowels 158 abut the non-grooved areas of the braking member 62 which blocks pivoting of the dowels 158 and the hilts 116 and 118. Accordingly, the braking member 62 is shifted to an interfering position when steering of the implant 10 and/or operation of the hilts 116 and 118 is not desired. This structure is provided as an extra security measure to avoid accidental pivoting of the hilts 116 and 118. In this case, however, the implant 10 may pivot entirely about its posts 34 and 44 without active steering and contact with guiding surfaces on the inserter 12. In an alternative embodiment, the guide dowels 158 and slots 191, 193, 195 and 122 could be eliminated or the guide dowel 158 could be shortened when it is desirable to have the implant 10 rotate while its shoulder 50 abuts the impact surface 80 of the braking member 62.

Referring now to FIGS. 19-30, in an alternative embodiment of the invention, cooperating structure 231 is provided between an implant 210 and an inserter 212 for adjustably holding the implant with the inserter. A steering control device 235 operates a steering actuator 233 such as cables 214 and 216, respectively connected to both the superior and inferior members 218 and 220 of implant 210 to actively steer the implant. Implant 210 can be actively steered to the left or right or laterally up to about 90 degrees in either direction from the longitudinal axis $L_1$ of the inserter 212. The cables 214 and 216 in this embodiment, however, are first arranged on the inserter 212 and implant 210 to pivot the implant to one of the desired directions (left or right) before the implant 210 is inserted into an intervertebral space as explained below. Otherwise, the same general procedure for inserting implant 10 with inserter 12 explained above is also applicable for inserting the implant 210 with the inserter 212. This includes placing implant 210 in a wedge configuration, inserting the implant 210 through an incision on an annulus wall with its narrow or low profile end presented to the incision, collapsing the wedge configuration when the implant 210 is placed between the vertebrae, and steering the implant 210 left or right to orient the implant with its longitudinal dimension extending generally transverse, and preferably orthogonally to axis $L_1$ of the inserter 212 and laterally relative to the anterior-posterior direction of the vertebrae while still connected to the inserter 212.

In more detail, as shown in FIGS. 19 and 20, inserter 212 has an upper cable 214 wrapped around a superior member 218 and a lower cable 216 wrapped around an inferior member 220. For actively steering the implant 210, the steering control 235 has hilts 268 with the same structure as the hilts 116 and 118 of inserter 12 and connected here to the cables 214 and 216. With inserter 212, the hilts 268 connect directly to a main body 213 of the inserter 212 rather than to a collar of a steering control. The cables 214 and 216 are simultaneously pulled on one side 237*a* and 237*b* thereof in order to pivot the implant 210 in the direction the cable was pulled (the left or right) and relative to a distal end 241 of the inserter 212.

Referring to FIGS. 21-25, the basic structure of the superior member 218, inferior member 220, and bearing portions 222 and 224 of the implant 210 are similar to the structure of implant 10 previously described above. The implant members 218 and 220 are elongated with generally race-track or obround shapes. The proximal end portions 292 and 219 of the inferior and superior members 220 and 218 are connected to the distal end 241 of the inserter 212. For this purpose, the proximal end portion 219 of the superior member 218 has a post 226 (shown best in FIG. 25) extending downward from a downwardly facing, flat surface 243 that opposes the inferior member 220. The post 226 has a neck 247 that terminates in an enlarged head 249.

Figure 26A:
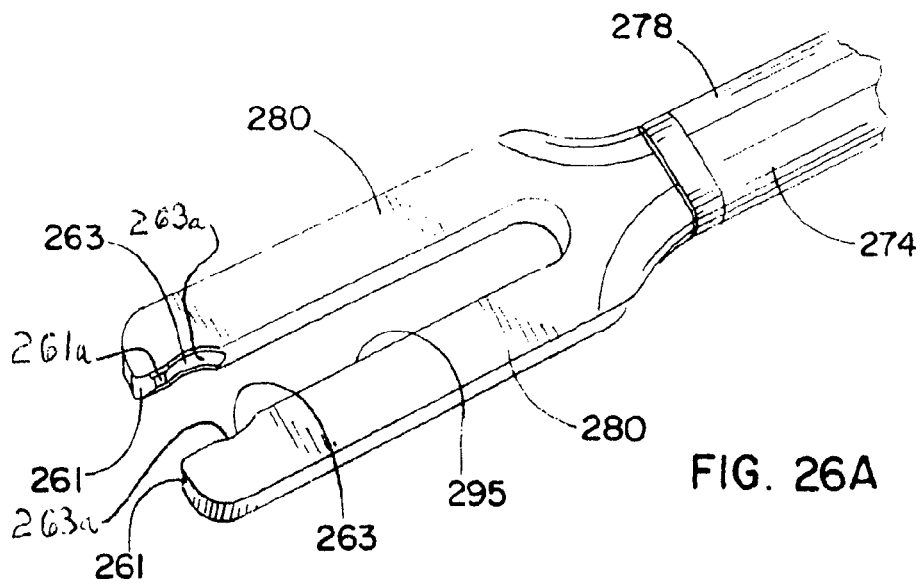
FIG. 26A is a perspective view of a distal end of a gripping member on the inserter.

A grip yoke 274 of the inserter 212 has a distal end 278 with fingers 280 shown on FIG. 26A. The fingers 280 are configured to adjustably grasp the head 249 so that the head 249 can rotate between the fingers 280. This enables the head 249 and in turn the superior member 218 to pivot left or right about rotational axis $R_1$ (shown in FIG. 20) and/or about a horizontal axis $H_1$ that extends orthogonally to both axes $R_1$ and $L_1$ as shown in FIG. 19. Pivoting the head 249 about axis $H_1$ allows the grip yoke 274 to lift the proximal end portion 219 of the superior member 218 upward to a slanted, wedge configuration as described in more detail below.

The proximal end portion 292 of the inferior member 220 has a recessed opening 228 formed on a flat, upwardly facing surface 243 for receiving a boss 282 extending downward from a distal end 284 of a base grip member 276 of the inserter 212. The opening 228 and boss 282 are configured and sized so that the inferior member 220 can pivot laterally left or right about the boss and about rotational axis $R_1$ as also explained in more detail below.

Figure 24:
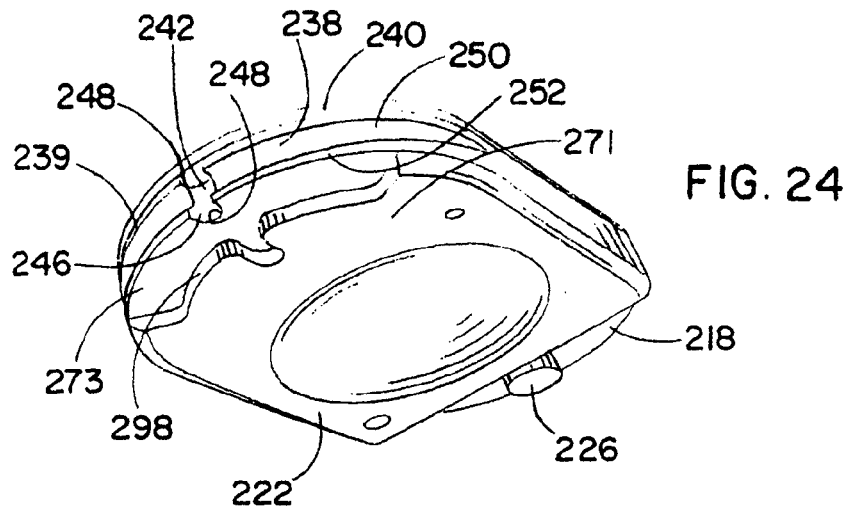
FIG. 24 is a perspective view of the superior member of the implant of FIG. 19 and showing a concave bearing surface, a post on one end, structures on the opposite end that receive a steering actuator, and a step for stabilizing the superior member in a slanted position.
Figure 25:
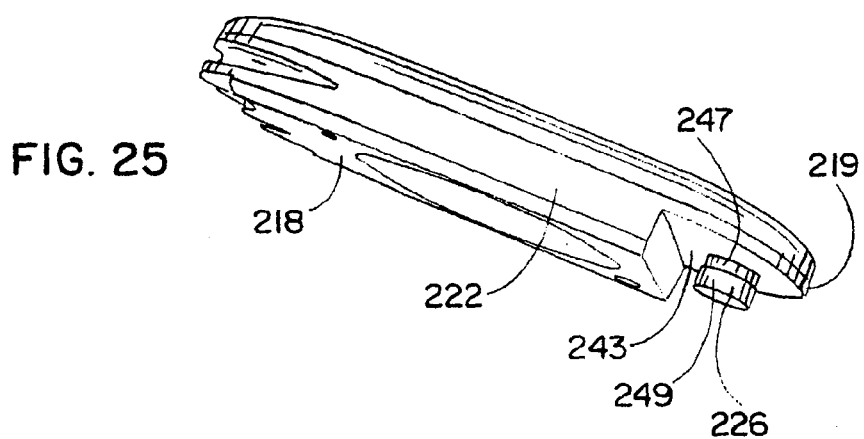
FIG. 25 is a side perspective view of the superior member of the implant of FIG. 19 and showing a post with a bearing neck.

Referring to FIG. 24, in order to pivot the implant 10, both of the superior and inferior members 218 and 220 have anchoring structure to hold a cable anchor beads 244 and 266, respectively. The beads 244 and 266 adhere or are otherwise fixed to or carried on the cables to releasably secure the cables 214 and 216 to the implant 210. For example, the beads 244 and 266 can be solid and the cables 214 and 216 are attached to opposite ends of the respective beads, or the cables 214 and 216 extend through a bore in the beads. Each bead 244 and 266 anchors a corresponding cable 214 or 216 to a respective implant member 218 or 220 so that pulling a cable pulls the bead which in turn pulls the implant member in the direction the cable is pulled.

An elongated groove 238 extends along a generally semicircular, outer periphery 239 of the longitudinal, distal end portion 240 of the superior member 218 for holding the upper cable 214. The groove 238 also has a generally semi-circular cross-section formed by two spaced flanges 250 and 252. The groove 238 is continuous along the outer periphery 239 at the distal end portion 240 except for a cut-out or notch 242 for receiving the anchor bead 244 (shown on FIG. 20) of the upper cable 214. The notch 242 is formed by anchoring structure such as a curved wall 246 that is recessed back toward the middle of the implant member from the groove 238 and forms cut-outs 248 in the flanges 250 and 252. The bead 244 is held snugly in the notch 242 so that pulling along one side or the other of the associated cable 214 causes the implant member 218 to shift or pivot in a corresponding direction.

Figure 21:
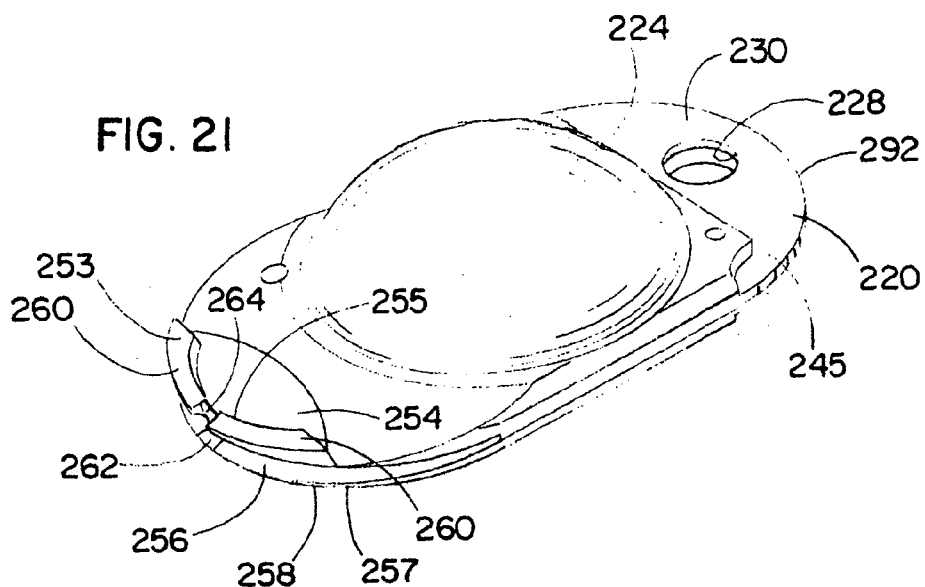
FIG. 21 is a top perspective view of the inferior member of the implant of FIG. 19 and showing a convex bearing surface, an aperture in the end, and a wall at the opposite end used for actively steering surfaces of the implant.
Figure 22:
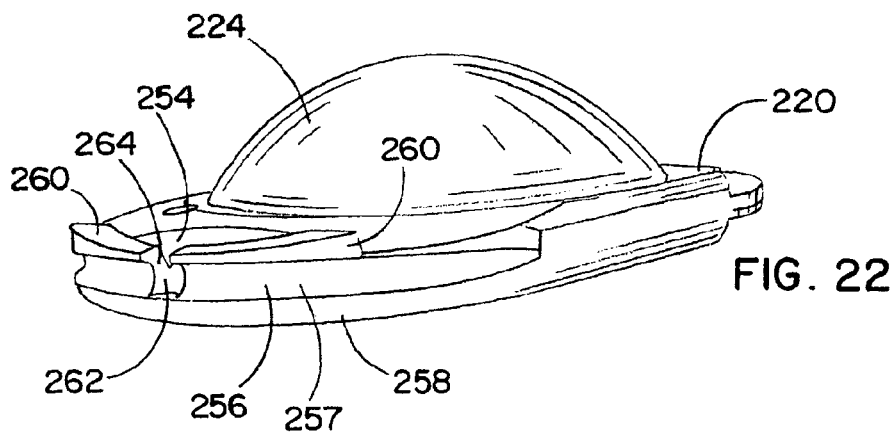
FIG. 22 is a perspective view of the inferior member of the implant of FIG. 19 and showing structures that receive a steering actuator.

As shown in FIGS. 21 and 22, the inferior member 220 also has an elongated groove 256 formed along a semi-circular peripheral edge 257 of the distal end portion 258 of the inferior member 220. Flanges or walls 260 extend upward from peripheral edge 257. In order to receive and hold anchor bead 266 (shown on FIG. 20) on cable 216, a notch 262 (shown on FIG. 21) is formed by a curved recessed surface 264 centrally at the distal end portion 258 of the inferior member 220. The recessed surface 264 extends centrally back toward the middle of the implant member from the groove 256. The bead 266 is received with a snug fit within the notch 262. Preferably this is a releasable connection such that the bead 266 can be disengaged from the notch 262 by pulling the cable 214 once the implant 210 is pivoted in place. Alternatively, the bead 266 may permanently reside in notch 262 and remain in situ post-procedure. In this case, pulling the cable 216 with a sufficiently strong force separates the cable from the bead 266 which is retained by the notch 262. After the implant member is properly oriented in the vertebral space, the cable 214 can then be pulled to disengage it from the bead and implant member 214.

Figure 23:
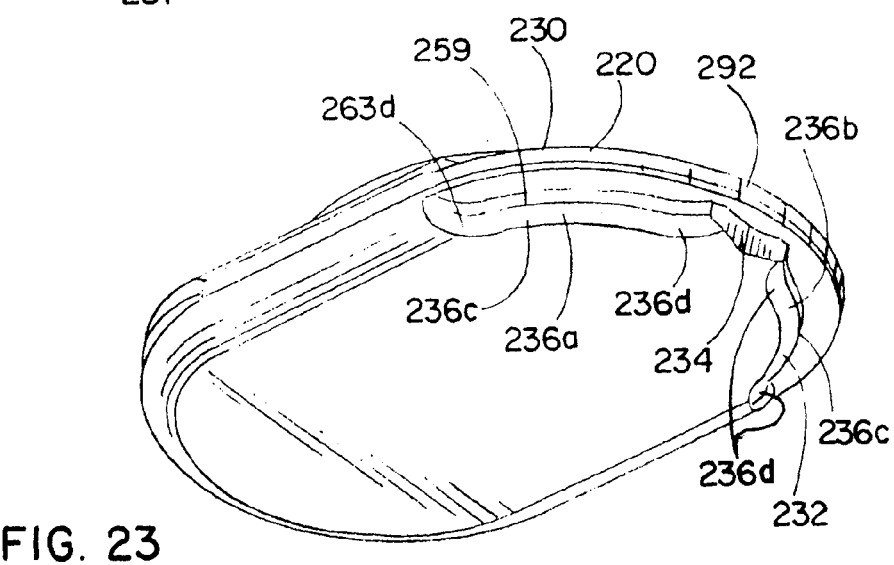
FIG. 23 is a bottom perspective view of the inferior member of the implant of FIG. 19 showing lower positioning surfaces for controlled, active steering of the implant during implantation thereof.

Referring to FIGS. 22 and 23, the inferior member 220 has a base or wall 230 with a downwardly extending shoulder 232. A contoured surface 259 is formed on the shoulder 232 for use in pivoting the implant. The contoured surface 259 has adjacent, arcuate surface portions. One of the portions includes an intermediate or central, concave surface 234 that is generally aligned with a longitudinal axis $L_{i1}$ of the implant 210. Thus, the surface 259 also is aligned with longitudinal axis $L_1$ of the inserter 212 when the longitudinal axis $L_{i1}$ of the implant 210 is generally coaxial with the longitudinal axis $L_1$. The central surface 234 is configured to receive an impact surface 290 on a grip shaft 272 of the inserter 212 (as shown on FIG. 30) for driving the implant 210 forward as the implant is pushed past or through any anatomical structure that applies a proximally directed force on the implant 210 such as the annulus or vertebrae. The impact surface 290 has a convex shape to correspond to the concave shape of the central surface 234 so that driving the impact surface 290 in a distal direction presses it substantially flush against the central surface 234. So structured, it is easier to maintain the longitudinal dimension of the implant 210 parallel to or coaxial with the longitudinal axis $L_1$. The continuous surface 259 also includes secondary, symmetrical, arcuate surface portions 236a and 236b on both sides of the central surface 234 and that have concave centers 236c with opposite convex ends 236d. During a steering operation, the shoulder 232 either abuts and rolls against the impact surface 290 or the implant is pivoted to a rotated position, and specifically the inferior member including the shoulder surface 257 thereof, and then the impact surface 290 is placed against the shoulder surface by translating the grip shaft 272 distally and longitudinally to hold the implant 210 in the pivoted orientation. This is accomplished by securing the proximal end portion 292 of the inferior member 216 between a boss 282 of the inserter 212 and the impact surface 290 on the grip shaft 272 as shown in FIG. 29.

Referring again to FIG. 19, the two hilts 268 on steering control device assembly 235 each have a spool 269a and 269b with the same structure as spools 160 described above for control 110. The cables 214 and 216 may be part of a single long cable looped around and secured by both spools 269a and 269b or each cable 214 and 216 may be a separate piece secured at their ends by both spools 269a and 269b.

In order for the hilts 268 to pivot the implant 210 in a desired direction (left or right), the cables 214 and 216 are attached to extend from the implant 210 to the two hilts 268 with different degrees of tautness on either side of the implant 210. For instance, it is desirable to provide the surgeon with precise control of the initial pivoting of the implant 210. Thus, when pivoting the implant 210 to the left, for example left, portions 237a-b of the cables 214 and 216 are preferably taut as they extend from the implant 210 to the left spool 269a. With the left cable portions 237a-b taut, the slightest pivoting of the left hilt 268 will pull the beads 244 and 266 on the implant 210 to pivot the implant. This also may minimize the chance that the hilt 268 runs out of clearance to pivot rearward toward the user before the implant 210 is pivoted to a desired angle.

On the right side of the inserter 212, right portions 237c-d of the cables 214 and 216 are attached to provide a sufficient length and/or play so that the cable portions 237c and 237d can extend around the implant 210 as the implant is pivoted to the left. Accordingly, prior to pivoting the implant, there will be slack in the cable portions 237c-d which is taken up by winding the cable around spool 269b.

The cables 214 and 216 may extend through at least one guide such as in the form of band 296 (shown in FIGS. 19 and 20) disposed on the exterior of the elongated grip shaft 272 near a distal end portion 294 of the grip shaft. The guide band 296 keeps the cables 214 and 216 close to the shaft 272 at the distal end portion 294 thereof and permits the cables 214 and 216 to translate axially underneath the band along the shaft 272. In this manner, the distal end portion 294 of the inserter tool 212 has a compact configuration for easier manipulation thereof in the surgical site during the implantation operation. It will be appreciated that more cable guides can be added along the shaft and a number of different types of cable guides are contemplated including the hook type and collar described previously for inserter 12.

To prepare for an implantation operation, the cables 214 and 216 are attached to the spools 269a and 269b and threaded through any cable guides 296. The inferior member 220 is connected to the distal end 284 of the grip member 276 while the superior member 218 is placed on the inferior member 220 and attached to the distal end 278 of the yoke grip 274. The cables 214 and 216, and the anchor beads 244 and 266 are then respectively secured to the implant members 218 and 220.

The grip shaft 272 is translated in the distal direction to place the impact surface 290 against the inferior member 220 to secure it in place. The yoke grip 274 is then translated distally to push the proximal end portion 219 of the superior member 220 upward into a slanted position for forming a wedge configuration as shown in FIG. 29 and explained in detail below. The inserter 212 and implant 210 are now ready for insertion with the low profile, distal end 241 of the implant 210 oriented as the leading end facing toward the annulus incision.

Figure 28:
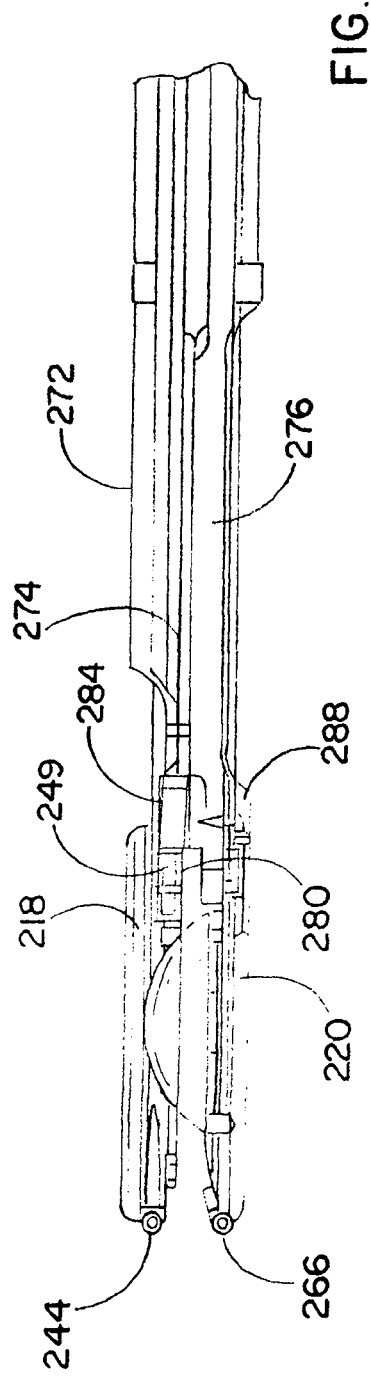
FIG. 28 is an enlarged, cross-sectional view of the implant and the implant-holding end of the inserter of FIG. 19 showing the superior and inferior members of the implant in a flat configuration.

Once the implant 210 is fit through the incision in the annulus, the upper vertebra will push down on the raised, proximal end portion 219 of the superior member 218 so that it pivots about the bearing interface between the implant members 218 and 220 until the superior member extends generally parallel to the inferior member 220 as shown in FIG. 28. One of the hilts 268 is then operated in the same manner as explained above and earlier for the hilts 116 and 118 of inserter 12. The surgeon operates the hilt 268 for pivoting the implant 210 about axis $R_1$ (shown in FIG. 20), about boss 282 of the grip member 276, and within yoke arms 280 of the yoke grip 274. The pivoting occurs either as the inferior member 220 slides and turns along the impact surface 290 on the grip member 272 or by first retracting the impact surface 290 away from the implant member 220, and specifically shoulder 232 thereof before pivoting the implant. Once the implant 210 is pivoted, the impact surface 290 may be reengaged against the shoulder 232 of the inferior member 220 to hold the implant at the pivoted orientation if desired.

The implant 210 is pivoted in the intervertebral space to a desired angle relative to longitudinal axis $L_1$ of the inserter tool 212. For instance, the implant may be placed with its longitudinal dimension or axis $L_i$ extending generally orthogonal to the anterior-posterior direction within the nuclear space. This operation is performed with axial or longitudinal motion of the cables 214 and 216 to avoid requiring that the annulus incision, through which the cables 214 and 216 extend, be enlarged over that needed to get the distal end of the inserter tool therethrough.

Once the implant 210 is in place, the cable loop is cut, untied and/or separated from the spools 269 and 269b and the cables 214 and 216 are removed from the implant 210. In one alternative, the cables 214 and 216 are removed by pulling on the cables with sufficient force to separate the cables from the beads 244 and 266. Alternatively, when the implant is oriented in a pivoted position, the cables 214 and 216 may be removed by using the cables to pull the beads 244 and 266 from the notches 242 and 262. In this case, sufficient cable slack is provided on one side of the inserter 212 and implant 210 while pulling the cable proximally on the other side of the inserter and implant.

Once the cables 214 and 216 are disengaged from the implant 210, the yoke grip 274 is then retracted to disengage the yoke arms 280 from the proximal post 226 on the superior member 218. The grip shaft 272 is then retracted and the base 282 on grip member 276 is lifted off of the inferior member 220 which separates the implant 210 from the inserter 212. The inserter is then pulled back longitudinally out of the annulus incision and nuclear space avoiding any sufficient lateral motion that could enlarge the incision or damage the annulus.

Referring to FIGS. 26-30, the inserter 212 will next be described in detail. The inserter tool 212 includes a handle portion 270 for holding the cylindrical grip shaft 272. The yoke grip 274 and the base grip member 276 are disposed within the grip shaft 272, and the yoke grip sits on a grooved top surface 281 of the base grip member 276.

Figure 26:
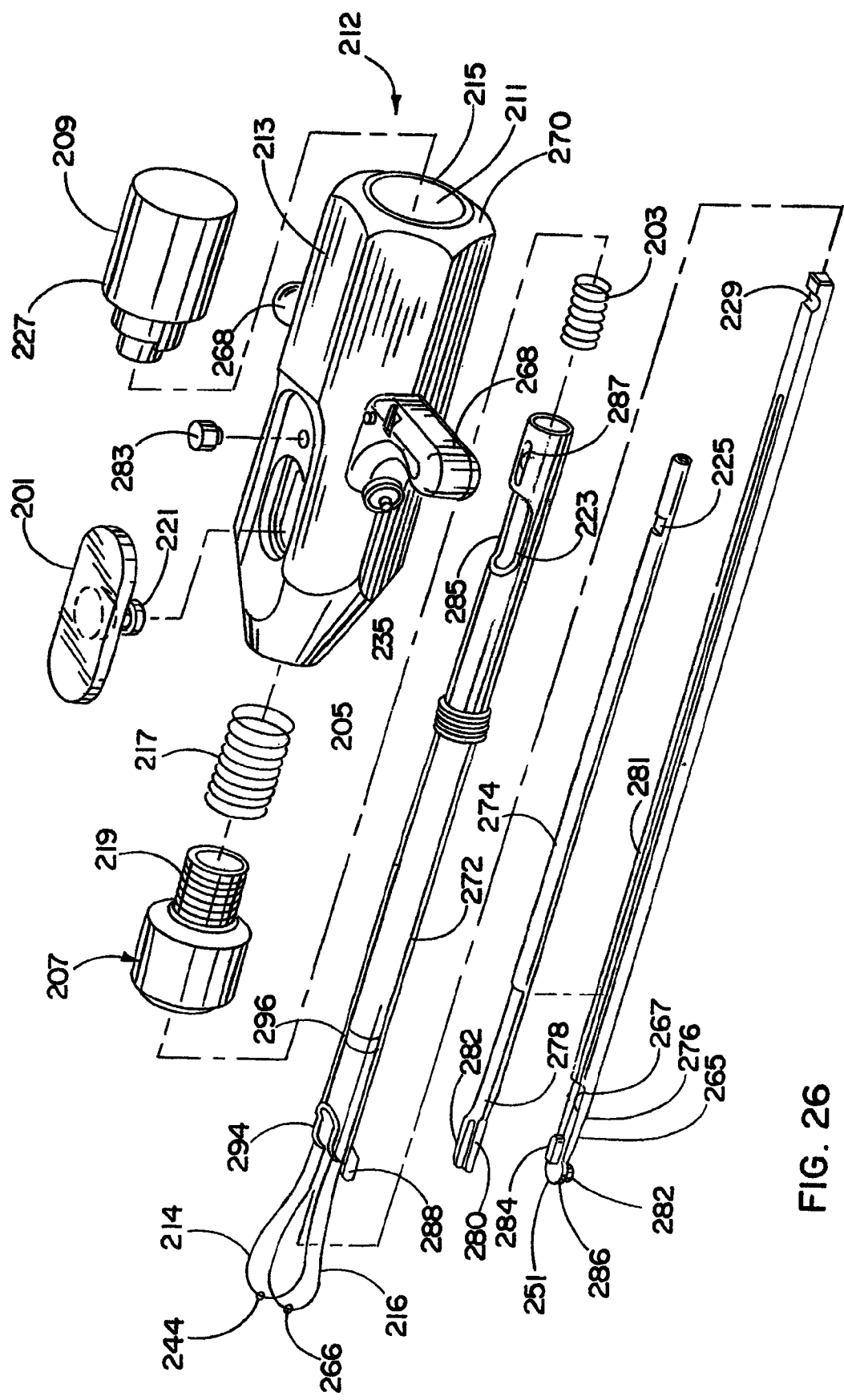
FIG. 26 is a perspective, exploded view of the inserter of FIG. 19 and showing the drive mechanism for the gripping shaft, and braking and gripping members that engage the implant.
Figure 27:
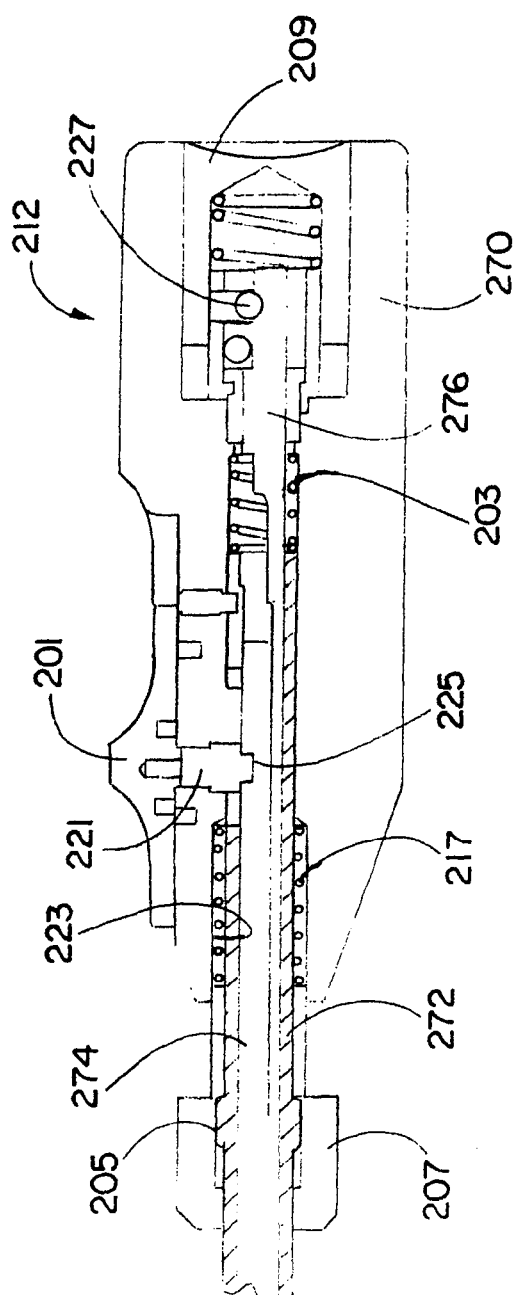
FIG. 27 is a cross-sectional view of a handle portion of the inserter of FIG. 19 and showing a main shaft and gripping and braking members secured to the handle portion of the inserter.

As shown in FIGS. 26 and 27, the inserter handle portion 270 has a slide member 201 connected to the yoke grip 274 by an integral actuator pin 221 for moving the yoke grip 274 axially relative to the base grip member 276. The pin 221 extends through a slot 285 in grip shaft 272 and into a notch 225 on the yoke grip 274 for translating the yoke grip back and forth. The yoke grip 274 translates distally or forward toward the implant 210 relative to grip member 276 that holds the inferior member 220 against axial translation. As the yoke grip 274 translates distally, its arms 280 flex upward and transversely outwardly away from each other as the inner cam surfaces 261 press against post 226 on the superior member 218. The cable 214 limits the distal movement of the superior member 218 so that the superior member 218 tilts about bearing portion 224 on the inferior member 220. This causes the proximal end portion 219 to shift upward placing the superior member 218 in a slanted orientation to place the implant 210 in the wedge configuration as shown in FIG. 29.

To hold the superior member 218 and shift it to a slanted orientation, the yoke grip 274 has a flexible, slightly upwardly bent distal end 278 (shown best in FIGS. 28 and 29) that extends out and beyond the distal end portion 294 of the main cylindrical shaft 272 of the insertion tool 212. The yoke grip's arms or fingers 280 hold the superior member 218 by engaging the head 249 of the depending post 226 on the superior member 218 of the implant 210. As shown on FIG. 26A, fingers 280 of the yoke grip 274 each have a curved, concave, opposing entry surface 261 along an inner side 263a of the finger 280. The entry surfaces 261 direct the post head 249 between the fingers 280 and provide a camming surface that directs the fingers 280 to flex outwardly for receiving the head 249. Thus, the entry surfaces 261 extend diagonally relative to longitudinal axis $L_1$ so that the surfaces 261 face forward as well as toward each other. The surfaces 261 also extend toward each other as they extend rearwardly. A rear edge 261a of both entry surfaces 261 is biased laterally (from side to side) to be spaced from each other a distance that is slightly less than the diameter of the post head 249 to receive and secure the head between the fingers 280 with an interference fit.

The entry surfaces 261 are spaced along the fingers 280 forwardly of arcuate, concave holding grooves 263 that hold the post head 249 during insertion and pivoting of the implant. The holding grooves 263 are recessed into the inner sides 263a of the fingers 280, and are spaced from each other a sufficient distance so that the head 249 may be snap-fit into the holding surfaces 263. The grooves 263 are configured to permit the post head 249 to rotate similar to a ball-joint, as mentioned above. In this regard, the grooves 263 are curved about axis $R_1$ to permit the side-to-side pivoting of the implant relative to the yoke grip fingers 280 and about axis $R_1$ as well as being curved about the axis $H_1$ (shown in FIG. 19) to allow for pivoting of the head 249 about the horizontal or lateral axis $H_1$. Pivoting about axis $H_1$ permits the yoke grip 274 to push the superior member 218 into a slanted orientation for the wedge configuration as shown in FIG. 29.

The grip shaft 272 translates axially relative to the grip member 276 to secure the base or wall 230 of the inferior member 220 between the boss 282 and the impact surface 290 of the grip shaft as described in detail below. For this purpose, the grip shaft 272 is biased forward by spring 203 mounted within cavity 223 formed in the main handle body 213 of the handle portion 270 as shown in FIG. 27. Internal threads on an axially adjustable securement sleeve 207 mounted on the shaft 272 threadedly engages intermediate outer threads 205 formed along the grip shaft intermediate the ends thereof. The securement sleeve 207 is attached to the front of main body 213 and is itself biased forward by a large spring 217 while being threaded to the main body 213 over a small diameter, threaded projection extending rearwardly in order to hold the securement sleeve tightly against the threads and reduce play. A set screw 283, which is normally covered by the slide member 201, extends through the main body 213 and extends into a slot 287 of the grip shaft 272 to avoid accidental removal of the grip shaft from the main body 13 without first releasing the screw. The slot 287 has an axial extent sized to permit the grip shaft 272 to translate axially for steering control over the implant as has been previously discussed.

The handle portion 270 also includes a release device 209 configured to be mounted in an opening 211 at the back or proximal end 215 of the main body 213. The device 209 releasably secures the gripping member 276 to the main body 213 of the handle portion 270. The release device 209 carries a horizontal, laterally extending pin 227 that extends in a rear notch 229 in the elongate gripping member 276. So configured, the pin 227 releasably secures the gripping member 276 in fixed axial position relative to the release device 209. In order to disengage the gripping member 276 from the release device 209, the pin 227 is mounted within a diagonal slot in the release device 209. The diagonal slot extends upwardly and proximally from adjacent lateral ends of the notch 229. So configured, pressing the release device 209 in the distal direction cams the pin 227 upward in the diagonal slot and out of notch 229. The gripping member 276 can then be removed from the release 209 for disassembly.

The distal end portion 284 of the inserter grip member 276 includes the boss 282 extending downward from a bottom surface 265 thereof. The boss 282 is fit in the upwardly facing opening 228 of the inferior member 220. The peripheral surfaces of the boss 282 and opening 228 have annular configurations so that steering the implant 210 pivots the implant about the boss 282 while the proximal end portion 292 of the inferior member 220 is adjustably held between the boss 282 and the impact surface 290 of the grip shaft 272.

The base grip member 276 also has a dislodging wall or post 286 extending upward from an upper surface 267 thereof. The wall 286 is aligned with the slot 295 formed between the fingers 280 on the yoke grip 274. The dislodging wall 286 is used to abut the proximal end portion 219 of the superior member 218 when the yoke grip 274 is retracted in order to disengage the post head 249 of the superior member 218 from its gripped position between the yoke fingers 280. The dislodging wall 286 stops the proximal motion of the post head 249 and superior member 220 as the holding grooves 263 of the fingers 280 are retracted past a front edge 251 of the dislodging wall 286.

As shown in FIG. 28, the initial upwardly inclined angle of the bent distal end portion 278 of the yoke grip 274 is sufficiently small to permit the fingers 280 to hold the superior member 218 even when the implant is in the illustrated flat orientation and the superior member 218 generally extends parallel to the inferior member 220. When the yoke grip 274 is moved forward (FIG. 29), the superior member 218 is held in place in the axial or longitudinal direction by the cable 214 so that the post head 249 rotates between the fingers 280 and the proximal end portion 219 of the superior member 218 is forced upward which places the implant 210 in the wedge configuration. Also, it can be seen that the grip end portion 278 is flexible as it bends to extend in an upward direction at a greater angle to the tool axis when the grip member 274 is pushed forwardly to shift the implant from its generally flat configuration (FIG. 28) to its wedge insertion configuration (FIG. 29).

In one embodiment, the yoke grip 274 can hold and maintain the implant 210 in the wedge configuration without the need for further support structure other than the bearing portions 222 and 224 of the implant members 218 and 220. The yoke grip 274, however, may be assisted in shifting the superior member 218 in the wedge configuration and/or assisted in holding the wedge configuration by corresponding structure of the distal ends 240 and 258 of the superior and inferior members 218 and 220. Specifically, the distal end portion 240 of the superior member 218 has a downwardly facing bottom, flat surface 271 offset from a recessed downwardly facing lower, flat surface 273 by a contoured edge or shoulder surface 298 that extends from surface 271 to surface 273 as shown in FIG. 24. As shown in FIG. 29, when oriented in the wedge configuration, the contoured surface 298 is configured to abut the surfaces 255 of the upstanding flanges 260 on the inferior member 220. The downwardly facing surface 271 sits flush against the sloped, upwardly facing surface 254 of the inferior member 220 while the downwardly facing surface 273 sits flush on the top 253 of the flanges in the wedge configuration of the implant 210. This structure further aids in locating the two implant members 218 and 220 in the wedge configuration and stabilizes the superior member 218 on the inferior member 220.

Referring to FIG. 30, projection 288 extends downward and forwardly from sidewalls 275 and 277 on the distal end of the grip shaft 272. The contoured impact surface 290 is found at the front end of the projection 288 and is used to abut the shoulder 232 (FIG. 23) on the proximal end portion 292 of the inferior member 220 as mentioned above. As explained above for implant 10 and inserter 12, the grip shaft 272 is configured to create easier and smoother pivoting of the implant by reducing frictional forces against the implant 10 while the implant pivots. Thus, while the grip shaft 272 could be configured to abut the inferior member 220 while the superior member 220 pivots, in an alternative form the grip shaft 272 is retracted to disengage the impact surface 290 from the shoulder 232. This eliminates or minimizes the frictional force between the shoulder 232 and the impact surface 290 that could make it more difficult to pivot the implant 200. The impact surface 290 can then be abutted against the shoulder 232 once the inferior member 220 has been steered to a desired pivoted position.

To provide a further structure for securing the implant 210, the grip shaft 272 also has its opposing side grip walls 275 and 279 extending distally and spaced above the lower projection 288 to form side grooves 279 therebetween. The grooves 279 receive and hold the base wall 230 of the proximal end portion 292 of the inferior member 220. As shown in FIGS. 28 and 29, moving the grip shaft 272 distally or forwardly so that the impact surface 290 abuts the shoulder 232 releasably secures the proximal end portion 292 of the wall 230 of the inferior member 220 between the boss 282 and the impact surface 290. This configuration secures the inferior member 220 against axial movement relative to the grip shaft 272 while still permitting the inferior member 220 to pivot about boss 282 due to the contoured shape of the impact surface 290.

Figure 31:
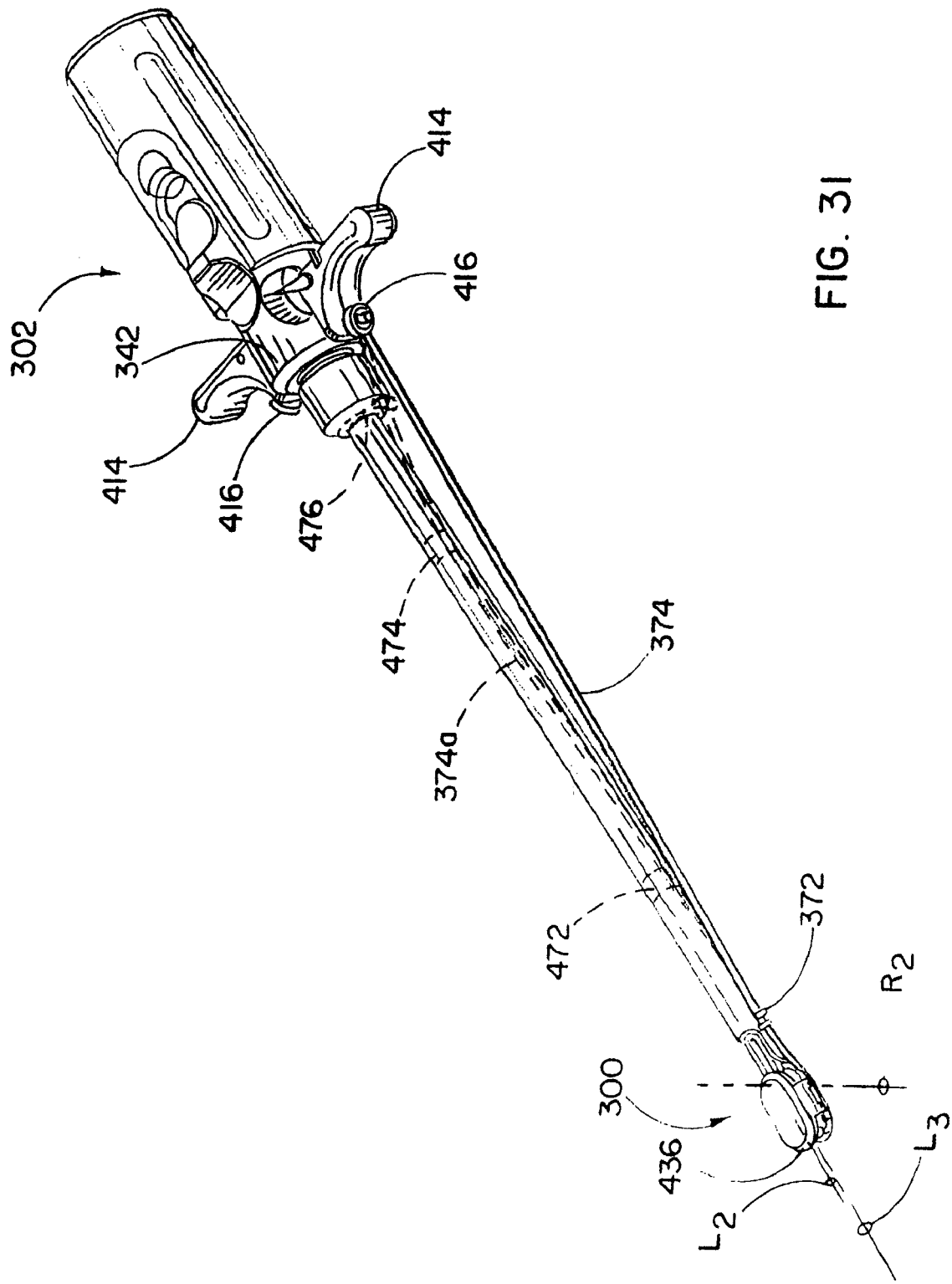
FIG. 31 is a perspective view of another embodiment of the inserter and an implant adjustably held by the inserter in accordance with the present invention.

Referring now to FIGS. 31-45, another form of the invention provides active steering, a stable and easily disengaged wedge configuration, and convenient symmetrical implants. As shown in FIG. 31, an artificial disc or implant 300 is connected to an inserter 302 for placement in the nuclear or intervertebral space between adjacent inferior and superior vertebrae. The implant 300 is elongated in an obround shape to provide a narrow width, distal or leading end 436 that faces the annulus incision for insertion therethrough to permit a narrower width incision. In order to orient the longitudinal dimension of the implant 300 orthogonally to the anterior posterior direction, the inserter 302 pivots the implant 300 about a rotational axis $R_2$ and relative to a distal end 362 of the inserter 302. With this structure, the inserter 302 does not need to be rotated laterally about axis $R_2$ which reduces the risk of damage or enlarging of the incision on the annulus around the nuclear space.

For actively pivoting the implant 300, the inserter 302 has a steering actuator 410 (shown best in FIG. 38) connected to the implant 300 and a steering control assembly 342 on the inserter for operating the steering actuator. In one form, the steering actuator 342 includes hilts 414 and the steering actuator 410 is a cable or cables 374 connecting implant 300 to at least one of the hilts 414. As with inserters 12 and 212, operating the hilt 414 shifts the cable 374 to pivot the implant 300.

Also in this embodiment, a symmetrical inferior member 306 of the implant 300 has opposite, symmetrical undercuts 328a and 328b that extend into the lower portion of the bearing portion 310 at the proximal and distal sides thereof. The undercuts 328a and 328b are sized to receive either an actuator clip 412 for actively steering the implant 300 or a stabilizing plate 378 of a base grip member 356 of the inserter tool 302 for more stable pivoting of the implant 300.

In another aspect of this embodiment, the inserter 302 has a holding arm 358 pivotally mounted on the grip member 356 and that is configured to facilitate detachment of the grip member 356 from the inferior member 306. Specifically, after the implant is positioned between vertebrae, some known inserters must be pulled with significant force to detach the inserter from the implant. This force may cause sudden detachment of the inserter which may in turn cause the inserter and/or the implant to impact against, and damage, the vertebrae or annulus. To avoid this occurrence, the holding arm 358 is configured with an end 394 that smoothly pivots into and out of engagement with the implant by shifting members on the inserter as explained in greater detail below.

Figure 32:
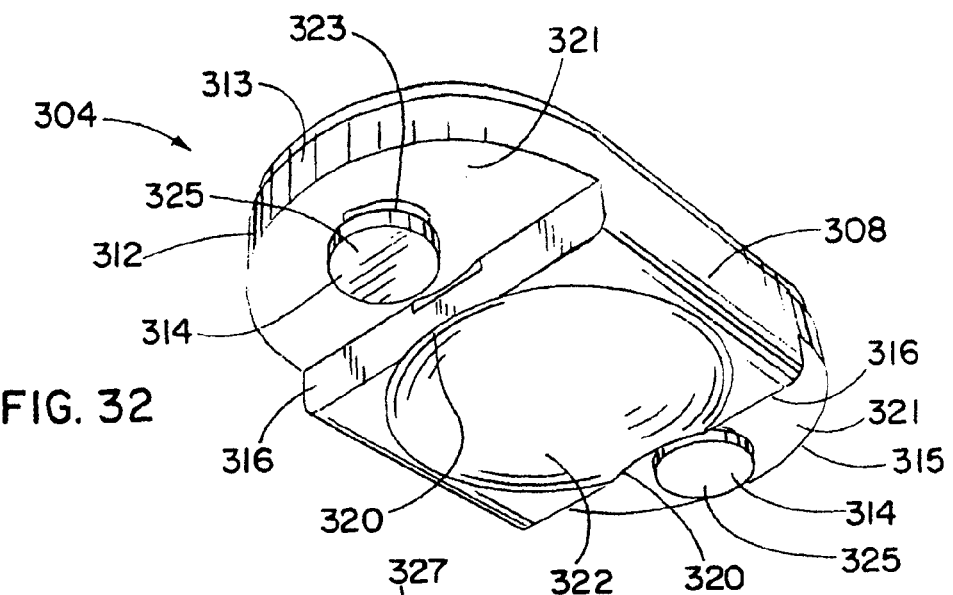
FIG. 32 is a bottom perspective view of the superior member of the implant of FIG. 31 showing symmetrical posts at opposite ends and a concave bearing surface.
Figure 33:
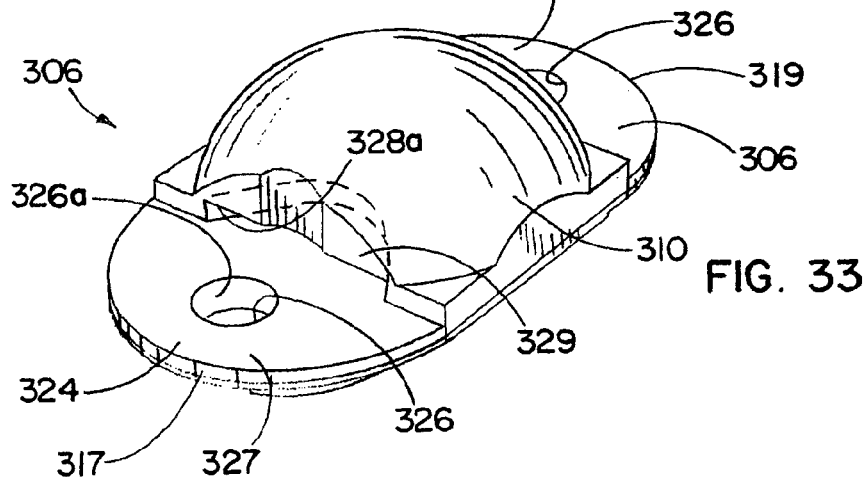
FIG. 33 is a top perspective view of the inferior member of the implant of FIG. 31 showing symmetrical anchoring openings and a convex bearing portion with an undercut for stable steering of the implant during implantation thereof.
Figure 34:
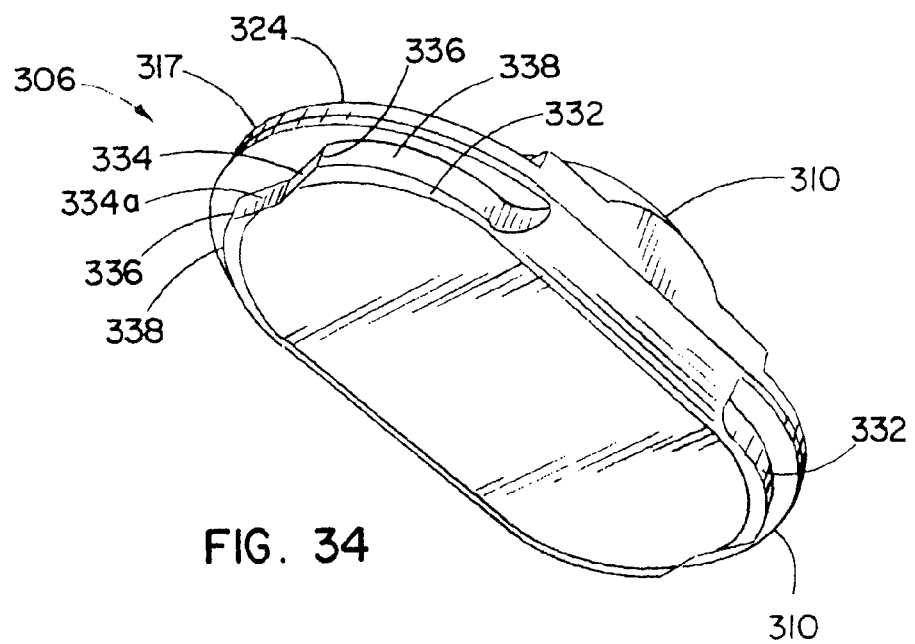
FIG. 34 is a bottom perspective view of the inferior member of the implant of FIG. 31 showing lower positioning surfaces for controlled, active steering of the implant during implantation thereof.

Turning now to FIGS. 32-34, the implant 300 has a superior member 304 as well as the inferior member 306. The implant members 304 and 306 respectively have concave and convex mating, bearing portions 308 and 310 that engage each other as described for implant 10. The implant 300 is symmetrical like implant 10 so that either opposing longitudinal end 313 or 315 on the superior member 304 can be aligned over either longitudinal end 317 and 319 of the inferior member 306. Additionally, any of the ends 313, 315, 317, and 319 can be attached to the inserter 302. Although reversible due to their symmetrical configuration, superior end 313 and inferior end 317 will be referred to as the distal ends, and superior end 315 and inferior end 319 will be referred to as the proximal ends relative to the inserter 302 or user.

Referring to FIG. 32, the superior member 304 has a wall or base 312 and at least two opposite posts 314 that extend downwardly from downwardly facing flat surfaces 321 on the base 312. The posts 314 each have necks 323 that terminate in enlarged heads 325 used for connection to the inserter as described below. Two oppositely facing, symmetrical sidewalls 316 extend downwardly from the surface 321 alongside the bearing portion 308 adjacent to and facing the corresponding posts 314. The side walls 316 are positioned inwardly toward the center of the implant member 304 to provide sufficient clearance for a yoke grip 352 to grasp the proximal post 314. A slight indent 320 may also be provided at lower edges on the sidewalls 316 where it intersects with a dome recess 322 to allow for a minimum dome radius to be maintained with smaller implant sizes.

With reference to FIG. 33, the inferior member 306 has a base 324 with two upwardly facing, flat surfaces 327 each with recessed opening 326 at either implant end portion 317 and 319 adjacent the convex or domed bearing portion 310. The openings 326 are so disposed for receiving either the boss 386 from the inserter 302 (shown in FIG. 36) or a steering cable anchor such as the clip 412 (shown in FIGS. 42 and 43) as described below. As shown in FIGS. 39-42, the undercuts 328a-b of the bearing portion 310 are generally semi-circular and are sized for pivotally receiving stabilizing plate 378 of the base grip member 356 on the proximal side 319 of the inferior member 306 or a portion of the clip 412 on the distal side 317 of the inferior member. The bearing portion 310 also has two opposing sidewalls 329, squaring off the ends of the domed bearing portion 310 or cutting the domed bearing portion 310 short for providing clearance for the inserter grip member 356 as also explained in greater detail below.

Referring to FIG. 34, the wall or base 324 of the inferior member 306 has a shoulder surface 332 with the same or similar configuration to shoulder 50 on implant 10 for impacting the inserter 302. Thus, the shoulder surface 332 also has a generally central, concave surface portion 334 having its center aligned with a longitudinal axis $L_3$ of the implant 300 prior to pivoting of the implant. The central surface portion 334 has opposite, common ends 336 with symmetrical, convex surface portions 338 on either side of the central, concave surface portion 334. Together the surface portions 338 and 334 provide for stable driving and pivoting of the implant 300 against the inserter 302 as with shoulder 50.

In order to maintain implant 300 in generally parallel alignment with longitudinal axis $L_3$ as the grip shaft 348 advances the implant forward during insertion, shoulder 332 has a wider central, concave surface portion 334, albeit shallower, than the concave surface 52 on the shoulder 50. The larger arcuate or concave surface portion 334 provides a wide contact area 334a for engaging an impact surface 370 similar to impact surfaces 80 and 290 on inserters 10 and 212. So configured, it is less likely that the anatomical structure pressing transversely or proximally against the implant, such as the vertebrae or annulus, will shift the implant 300 away from the longitudinal axis $L_3$. Otherwise, the function of the shoulders 50, 232 and 332 are generally the same and will not be repeated in great detail here.

Figure 35:
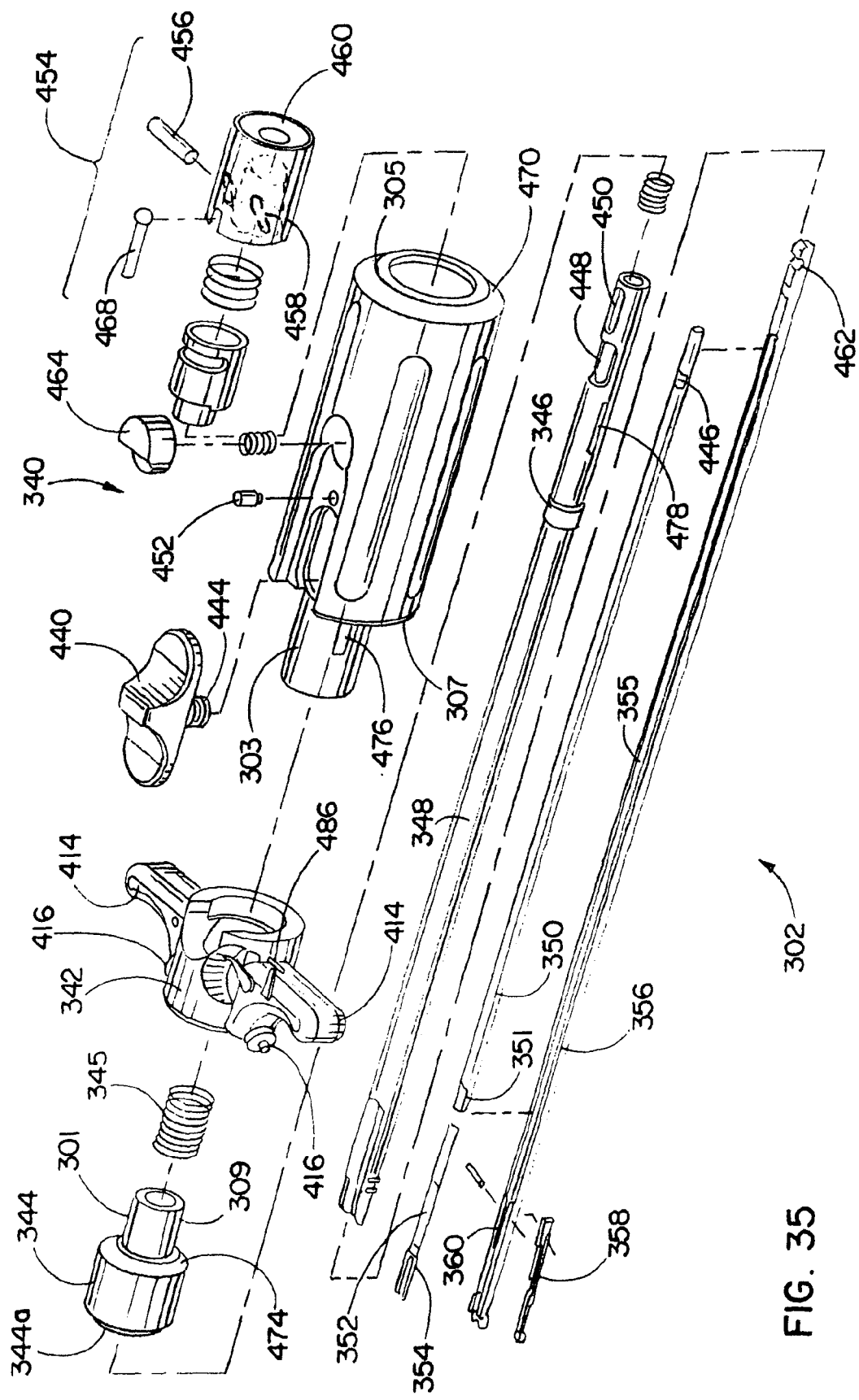
FIG. 35 is an exploded perspective view of the inserter of FIG. 31 showing a steering control device, and grip and yoke shafts for being secured to a handle portion of the inserter.

Referring now to FIG. 35, the inserter 302 has a handle portion 340 for operating the inserter 302. The handle portion 340 has a main housing or body 470 with a generally cylindrical, large diameter portion 305 and a smaller diameter, front collar portion 303 with interior threads. The collar portion 303 extends distally from a distally facing forward shoulder 307 on the large diameter portion 305.

In order to secure the steering control assembly unit 342 on the handle portion 340, the control assembly unit 342 has an annular body portion or collar 466 mounted over the collar portion 303 and abutting shoulder 307. A securement sleeve 344 has a cylindrical, small diameter portion 309 that extends rearwardly from a proximally facing shoulder 474 formed on a cylindrical, large diameter portion 311 of the securement sleeve. The small diameter portion 309 is sized to fit through the annular body 343 and is externally threaded for being threaded into the internally threaded collar portion 303. Securing the securement sleeve 344 into the collar portion 303 clamps the control assembly unit 342 and preferably the annular body portion 466 thereof between the shoulder surfaces 307 and 474 of the respective handle portion 305 and sleeve 344.

The steering control assembly unit 342 has hilts 414 mounted on opposite sides of the annular body portion and spools 416 mounted on the hilts. Control assembly 342 has the same or similar structure as control assembly 110 on the inserter 12 such that a detailed description will not be repeated.

As with sizing tool 10 and control assembly 110, in order to provide an extra security measure to avoid accidental pivoting of the hilts 414 when steering of the implant 300 is not desired, the grip shaft 348 has an axial, interfering position in which the grip shaft 348 engages a portion of the control assembly unit 342 to block the pivoting of the hilts 414. The grip shaft 348 also has an axial, non-interfering position that permits the hilts 414 to pivot. In one form, the grip shaft 348 blocks pivoting of the hilts 414 unless the impact surface 370 is separated from implant 300 to reduce friction against the implant during pivoting.

In more detail, the collar 303 has opposite, longitudinally extending slots 476 (only one is shown on FIG. 35). Grip shaft 348 has opposite, longitudinally extending, flat grooves 478 that selectively and axially align with the slots 476 to provide the non-interfering position, as was previously described with respect to inserter 12. In the non-interfering position, the groove 478 is positioned adjacent to each slot 476 in radial alignment therewith to receive laterally extending guide dowels 486 extending from the respective hilts 414, similar to guide dowel 158 of inserter 12, extending through both the slot 476 and groove 478. So aligned, the slots 476 and grooves 478 provide clearance for the guide dowels 486 to pivot which permits the hilts 414 to pivot. In the interfering position, the grip shaft 348 is shifted axially so that grooves 478 do not align with slots 476. In this configuration, the guide dowels 486 engage the grip shaft 478 so that neither the dowel 486 nor the hilts 414 to which they are connected can be pivoted.

Figure 45:
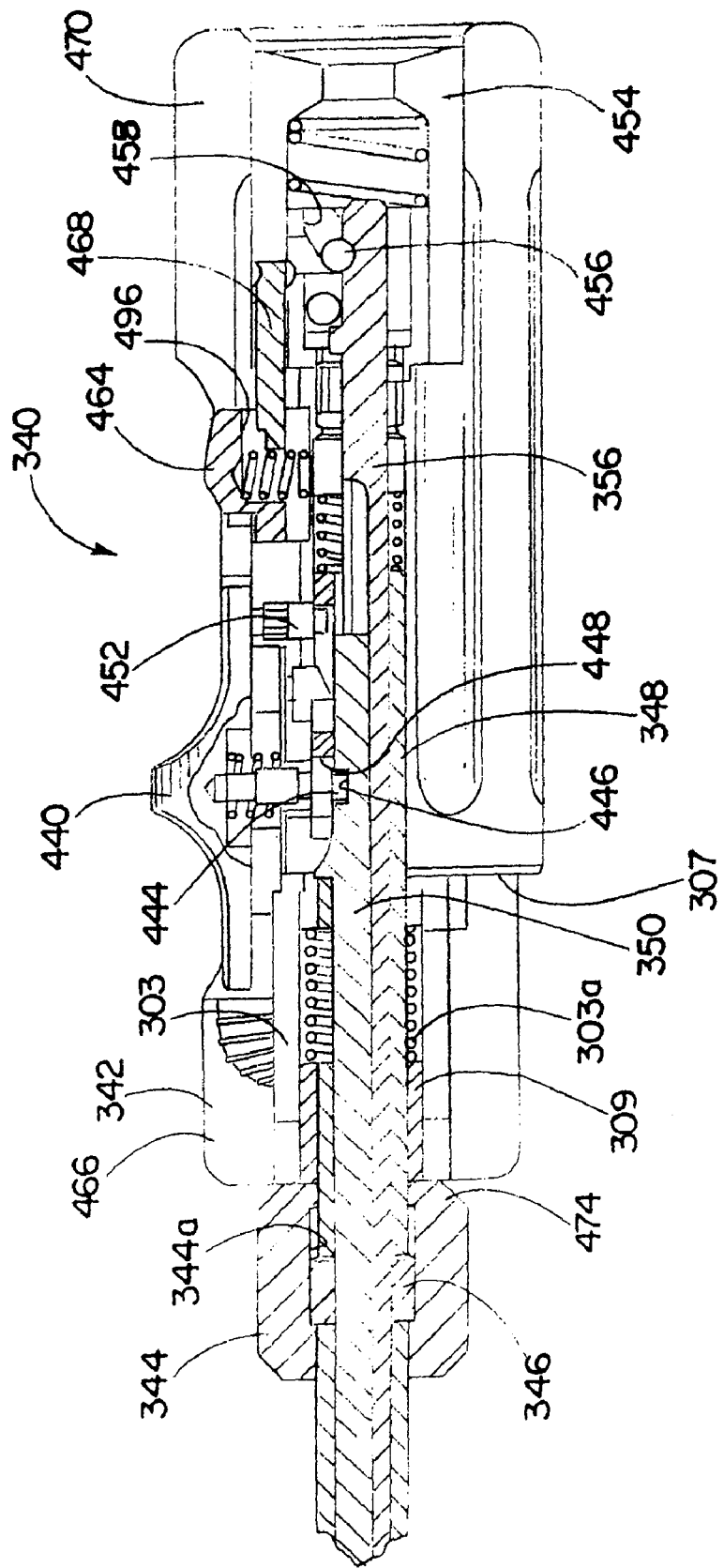
FIG. 45 is a cross-sectional view of the handle portion of the inserter of FIG. 31 showing the grip and yoke shafts secured to the handle portion.

In order to axially shift the grip shaft 348, the securement sleeve 344 has internal threads within a bore 344a that operatively engage threads 346 on grip shaft 348 so that rotating the securement sleeve 344 shifts the grip shaft 348 axially. In one form, in order to avoid interference with guide dowels 486, it will be understood that the small diameter portion 309 of the securement sleeve 344 may have a reduced axial length so that the grip shaft 348 extends rearwardly and out of the small diameter portion 309 in the vicinity of the slots 478. This avoids interfering with the path of the guide dowels 486. A biasing member such as coil spring 345 may also be eliminated for this purpose. In an alternative form, the biasing member 345 biases the securement sleeve 344 forward and within collar 303 to reduce undesirable play or shifting of the securement sleeve. To provide the guide dowels 486, however, the biasing member 345 would be eliminated since it extends between the slots 478 and the grip shaft 348 as shown in FIG. 45.

Figure 36:
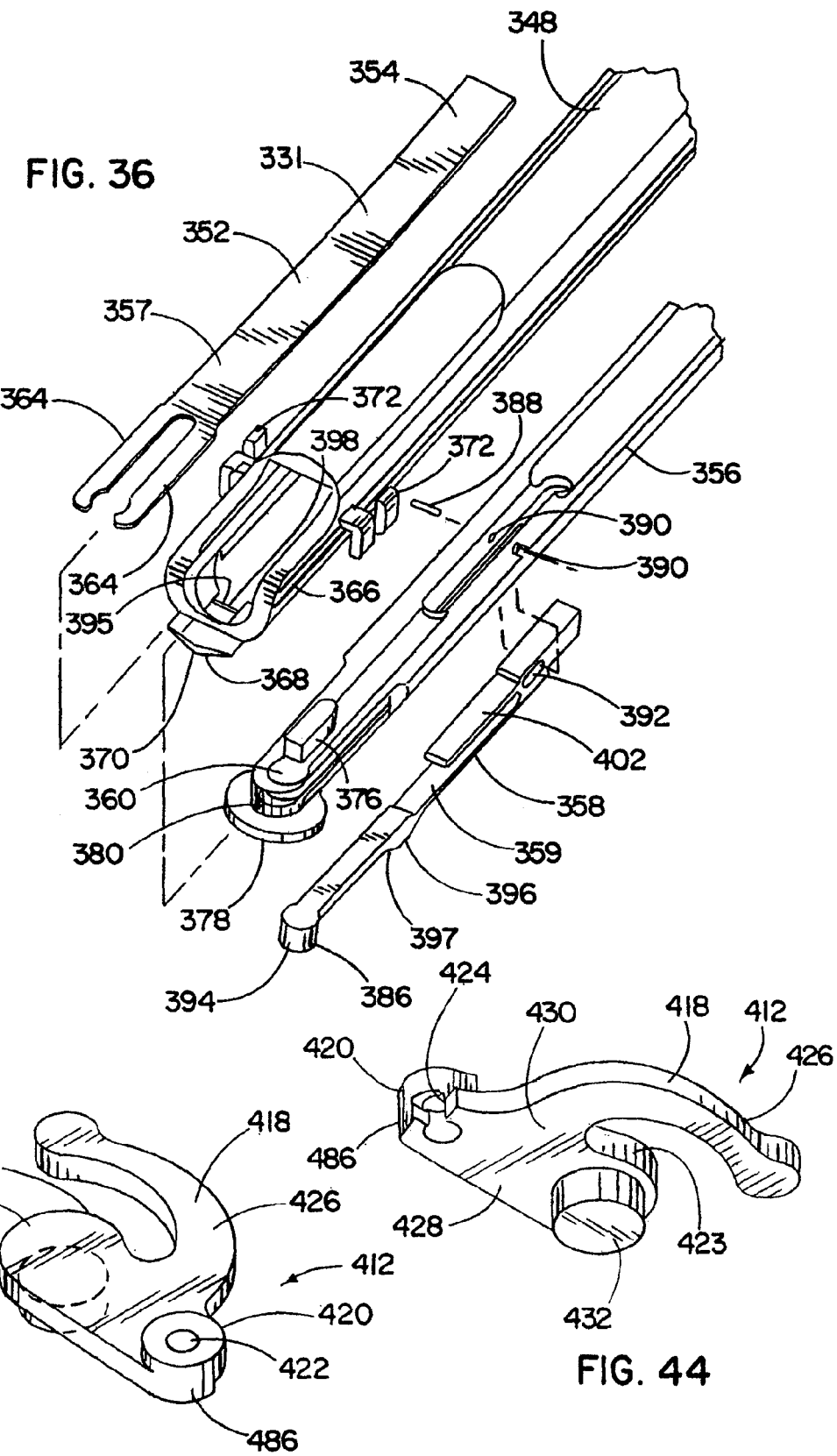
FIG. 36 is an enlarged, exploded view of the implant-holding end of the inserter of FIG. 31 showing the control and steering mechanisms that hold the implant and guide the implant during rotation and implantation thereof.

Turning now to FIG. 36, to hold the superior member 304, a yoke shaft 350 has a slit 351 for receiving a bendable or resilient yoke member or yoke grip 352 to form the yoke shaft's distal end 354. The yoke shaft 350 sits within an elongate groove 355 on the base grip member 356 and translates within the grip shaft 348.

Figure 40:
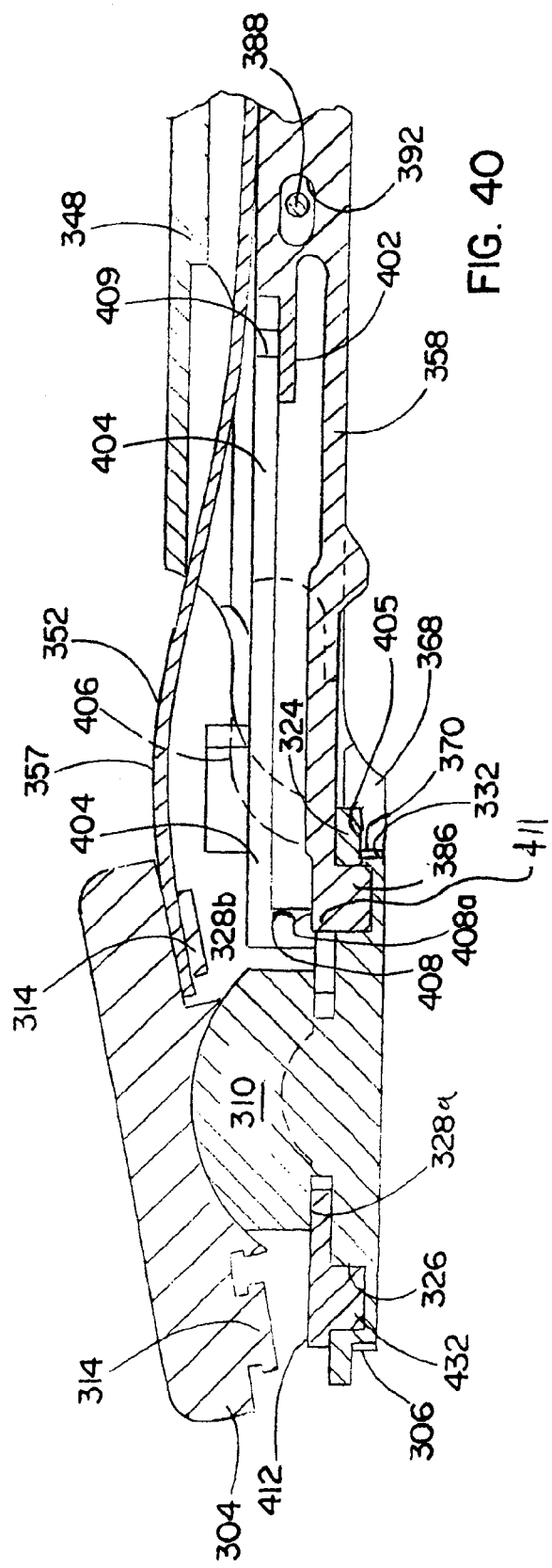
FIG. 40 is a cross-sectional view of the implant and the implant-holding end of the inserter of FIG. 31 showing the implant secured to the inserter in a wedge configuration.

As shown in FIG. 36, the yoke grip 352 is a spring member 331 similar in structure to the resilient member 58 on inserter 12. In this regard, the yoke grip 352 is of a generally flat resilient material such as spring steel. Yoke grip 352 has a distal end 357 and that bows upwardly and downwardly transverse to the longitudinal axis $L_3$ of inserter 302 in the initial or original orientation of the implant 300, as shown in FIG. 40. The yoke grip 352 holds the superior member 304 in a generally slanted position relative to the inferior member 306 so as to form the wedge configuration with the superior member tilted forwardly about bearing portion 310. The spring member 331 is resiliently flexible so that when the raised proximal end 315 of the impact member 304 engages the upper vertebrae, the superior member 304 will be pushed downward from the slanted orientation. The force from the vertebrae overcomes the bias spring force of the spring member 331 and generally flattens out the spring member as shown in FIG. 31. The spring member 331 may be provided with S-shaped, traversing windings as on resilient member 68 of inserter 12 to provide for longitudinal compressibility of the spring member 331. This allows for the tilting of the superior member 304 from a slanted, wedge orientation to a flat orientation.

The distal end 357 of the yoke grip 352 has spaced fingers 364 with a groove 365 therebetween and that are configured to grasp the neck 323 of the proximal post 314 on the superior member 304 as by a snap-fit connection. To provide further strength for holding the superior member 304, the thickness of each of the fingers 364 is sized relative to the length of neck 323 to provide a tight fit between the post head 325 and the opposing flat surface 321 on the superior member 304 to provide further strength for holding the superior member 304.

With reference to FIG. 36, to disengage the yoke grip 352 from the post 314 of the inferior member 306, the grip member 356 has a dislodging wall 376, similar to dislodging wall 286 of inserter 212, on its distal end portion 360. With the tool 302 assembled, the upstanding wall 376 is positioned in alignment with slot 365 between the fingers 364 of the yoke grip 352. This allows the wall 376 to dislodge the superior member 304 from the yoke grip 352 when the yoke grip is retracted relative to the grip member 356. In this case, the proximal motion of the superior member 304 with the yoke grip 352 is stopped, and the fingers 364 are pulled off and disengaged from the post 314, when the proximal end 315 of the superior member 304 abuts the dislodging wall 376 in interference therewith and the yoke grip 352 continues its proximal motion during retraction thereof.

Referring again to FIGS. 36 and 37, the distal end portion 366 of the grip shaft 348 includes the impact end surface 370 on a lower projection 368 extending downward from left and right sidewalls 333 of grip shaft 348. The distally facing, contoured impact surface 370 is at the end of the projection 368 and is configured to abut the concave surface 334 of shoulder 332 on the inferior member 306. The impact surface 370 applies the main, forward thrusting force to the implant 10 to place the inserter into the nuclear space and when the implant 300 encounters any resistance from the annulus or the vertebrae.

For pivoting the implant 300, the impact surface 370 can be retracted away from the shoulder 332 on inferior member 306 to avoid frictional engagement between the impact surface 370 and the implant 300, and specifically of the inferior member 306. In this case, to hold the implant 300 in a desired pivoted orientation after the implant is pivoted, the impact surface 370 may then be translated distally or forwardly to engage the proximal end 319 of the inferior member 306 to secure the inferior member 306 between the boss 386 of the boss arm 358 and the impact surface 370.

Instead of retracting the grip shaft 348, the impact surface 370 alternatively acts as a pivot guide or holder as described for impact surface 80 on inserter 12 and impact surface 290 for inserter 212 such that the implant 300 can also be pivoted while it is in contact with the impact surface 370. In this operation of the tool 302, the inferior member 306 slides or rolls against the impact surface 370 as the implant 306 is steered and pivoted. The inferior member 306 preferably pivots at one location along the impact surface 370 or one point of contact between the impact surface 370 and inferior member 306 but more may be provided.

When the impact surface 370 is held at a constant distance from rotational axis $R_2$ and boss 386, inserter 302 may limit the amount of pivoting of the implant 300 by positioning the impact surface 370 in the circular path for pivoting of the implant 300. As the implant 300 pivots, a left or right side of the implant 300 depending on the pivot direction will eventually engage an outer left or right corner 371 of the impact surface 370. This is set to occur while the implant generally extends 90 degrees from the longitudinal axis $L_2$. The implant 300 cannot pivot any farther since this requires that the implant 300 pivot about the outer corner of the impact surface 370 that the implant engages. Since the boss 386 on the holding arm 358 secures the proximal end 319 of the implant 300 both longitudinally and transversely relative to the corner of the impact surface 370, the implant 300 does not have the clearance to pivot about the corner of the impact surface 370. In other words, for pivoting beyond 90 degrees, the distance between the axis $R_2$ and the 371 needs to increase. However, with the boss 386 received in the opening 326, this distance is fixed. Thus, the impact surface 370 limits pivoting of the implant 300 to a predetermined angle such as to the left or right about 90 degrees from the longitudinal axis $L_3$.

The grip shaft 348 also has side cable guides 372 at either side thereof for guiding the cables 374 as shown in FIG. 31. The cable guides 372 are similar to those shown for inserters 12 and 212 and similarly permit axial motion of the cables 374 while keeping the cables close to the inserter and reducing effective lateral width of the inserter tool 302, particularly at the distal end portion 375 thereof that are to be advanced through the annulus incision into the intervertebral space to avoid damage to tissue or entangling of the cables. As shown in FIG. 31, the inserter 300 may have additional cable guides 472, 474, and 476 back or rearwardly along the shaft 348 (shown in dashed line) to maintain the cable 374a closer to the inserter 302.

In order to provide smooth, stable pivoting of the implant 300, the distal end 360 of the grip member 356 has a generally flat, disc-shaped, stabilizing plate 378 that extends radially outward from a front end, curved surface 380. The stabilizing plate 378 is configured for fitting in either of the undercuts 328a or 328b depending on which is positioned at the proximal side of the inferior member 306 of the implant 300 as shown in FIGS. 39-42. The front surface 380 extends upward from the stabilizing plate 378 on the distal end 360 of the grip member 356 and faces sidewall 329 on the inferior member 306 while the plate 378 is disposed within the undercut 328b. The stabilizing plate 378 preferably has a radius that corresponds to the radius of the arcuate undercuts 328a and 328b for smooth rotation of the inferior member 306 about the plate 378.

In order to minimize rocking of the implant 300 relative to the distal end 360 of the grip member 356 and the stabilizing plate 378, the undercuts 328a and/or 328b are sized to secure the stabilizing plate 378 flush against the upper surface 327 of the inferior member 306. In other words, once the stabilizing plate 378 is secured within one of the undercuts 328a or 328b, the stabilizing plate cannot lift off of upper surface 327 of the inferior member 306. Since the stabilizing plate 378 provides a relatively large contact area or bearing surface 378 flush against the upper surface 327, the inferior member 306 is restricted from pivoting either laterally about the longitudinal axis $L_2$ or longitudinally about a lateral axis extending across the implant.

Figure 37:
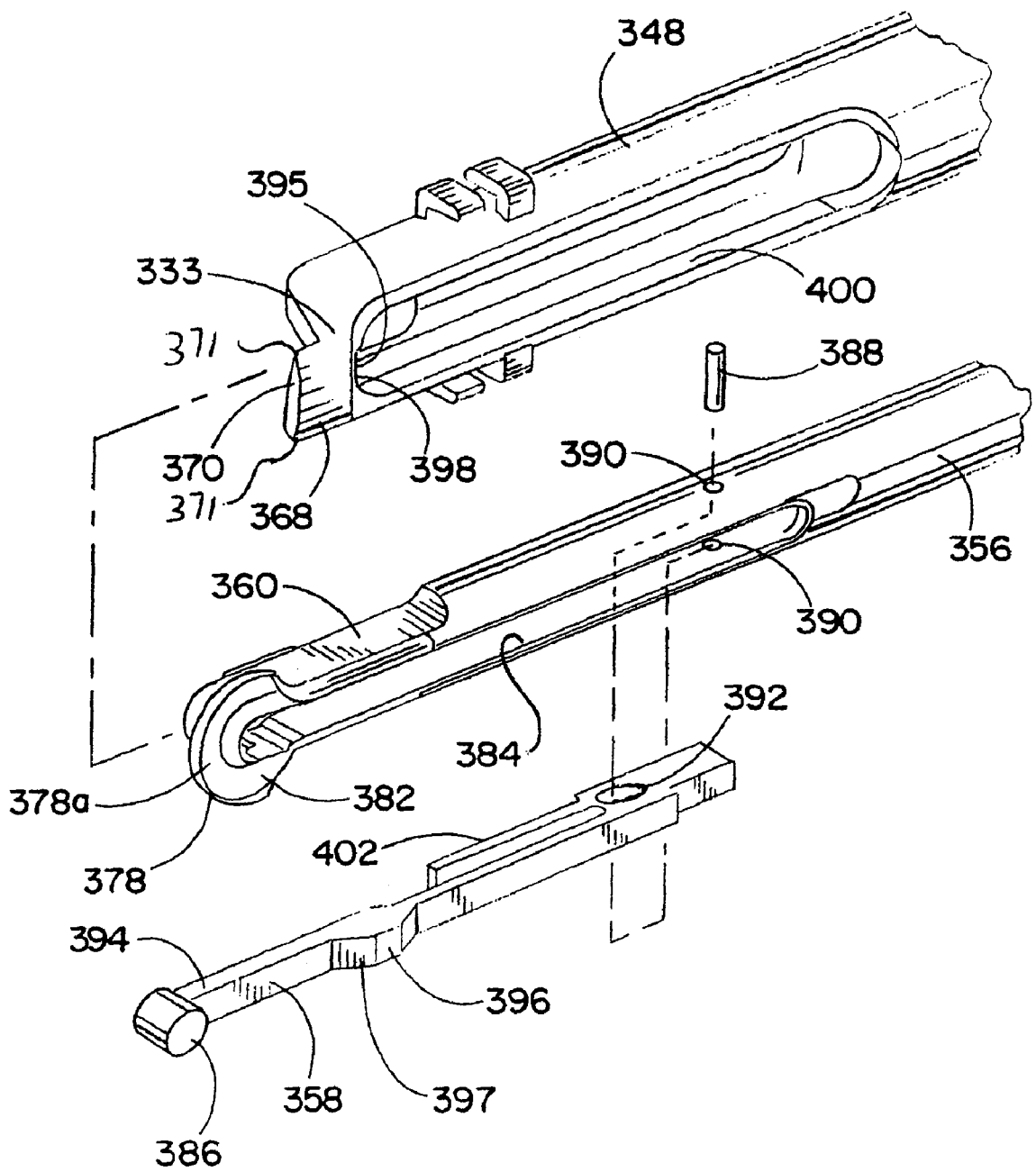
FIG. 37 is an enlarged, exploded, bottom perspective view of the implant-holding end of the inserter of FIG. 31 showing a pivot arm and its attachment to a base grip member on the inserter.

Referring to FIG. 37, to minimize or eliminate potentially destructive, high impact forces as explained above, the gripping member 356 is configured to provide smooth detachment of the holding arm 358 from the inferior member 306. A bottom side 382 of the grip member 356 has an elongate slot 384. Holding arm 358 is pivotally secured to the grip member 356 by a pivot pin 388 that extends transversely through side apertures 390 in the grip member 356 and an aligned slot 392 on the boss arm 358. The pin 388 defines the pivot axis for the holding arm 358 and extends orthogonally to both longitudinal axis $L_3$ and the implant's rotational axis $R_2$. The slot 384 extends forwardly into the stabilizing plate portion 378 and beyond the radial center thereof so that the boss 386 at the free distal end 394 of the holding arm 358 can be positioned at the radial center of the stabilizing plate 378.

For pivoting the holding arm 358 about pin 388, the holding arm has a thickened portion or depending cam protrusion 396 that is positioned to selectively engage a cam wall 398 (shown best in FIG. 36). The cam wall 398 is disposed at the forward end of a bottom opening 400 in the grip shaft 348. Pivoting of the holding arm 358 is generated by the camming action between the cooperating cam surfaces 397 and 395 on the cam protrusion 396 and the cam wall portion 398 respectively. So configured, axially translating the grip shaft 348 relative to the holding arm 358 causes the surfaces 397 and 395 to cammingly engage pivoting the arm 358 and lifting the boss 386 from the opening 326 on the inferior member 306. The holding arm 358 also has an upper stopper portion 402 generally extending above and parallel to an elongate, main portion 359 of the holding arm for abutting a top wall 404 of the grip member 356 to limit rotation of the boss arm as shown in FIG. 40 and as explained in greater detail below.

In order to avoid unintentional detachment of the implant 300 from the inserter 302, the inserter has a releasable locking mechanism for releasably holding the implant, and allowing for the inserter to be detached from the implant in a simple and easy manner. In the releasably locked configuration shown in FIG. 40, the boss 386 is received in the opening 326 of the inferior member 306. In the unlocked configuration, the holding arm 358 is pivoted about pin 388 to shift boss 386 out of the opening 326. The details of the locked and unlocked configurations are described during the following explanation of the operation of the inserter.

Referring now to FIGS. 39-42, a general explanation of how the inferior member 306 is connected to and disconnected from the inserter 302 follows. Preliminarily, it should be noted that except for FIG. 39, FIGS. 40-42 are shown in sequential order for explaining the disconnection of the implant 300 from the tool 302. Thus, these figures are discussed in reverse order for explaining the connection of the implant 300 to the inserter 302.

Figure 39:
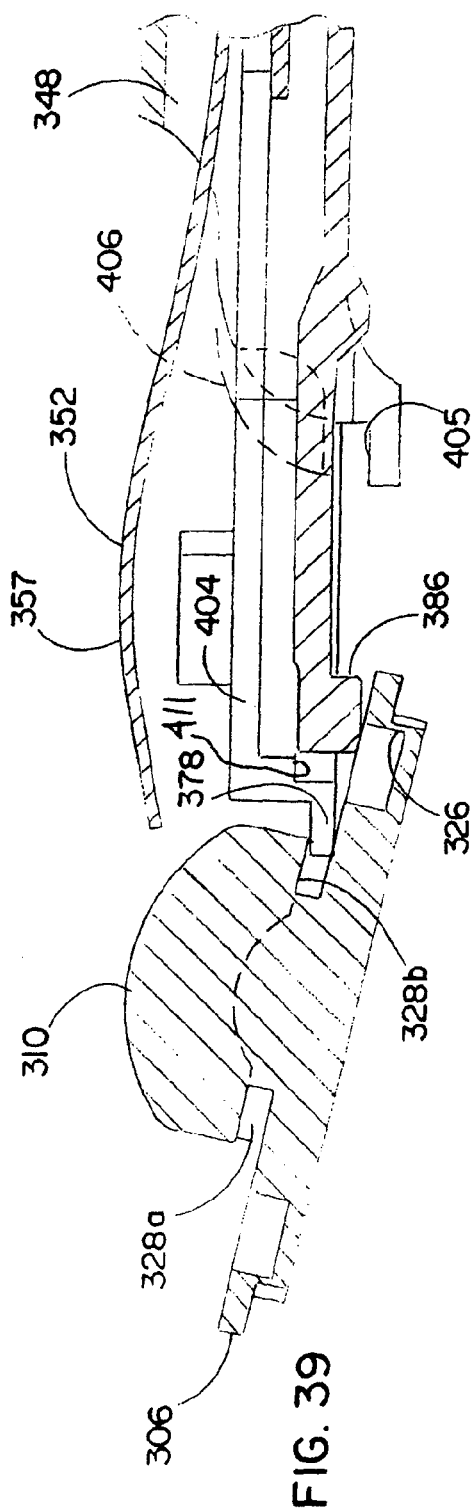
FIG. 39 is a cross-sectional view of the implant and the implant-holding end of the inserter of FIG. 31 showing the implant in a first position as the implant is being attached to the inserter.

As shown in FIG. 39, in order to connect the implant 300 to the inserter 302, the grip shaft 348 is first retracted. This positions the stabilizing plate 378 to extend forwardly beyond the distal end 366 of the grip shaft 348. This exposes the extending stabilizing plate 378 so that it can readily be inserted into one of the entrances of either undercut 328a or 328b of the inferior member 306 on the stabilizing plate 378. Simultaneously, the user tilts the inferior member 306 to provide clearance for the boss 386, which is extending downward from the holding arm 358, so that the boss 386 is oriented above the top surface 327 in which the recessed openings 326 of the inferior member 306 are formed.

Figure 42:
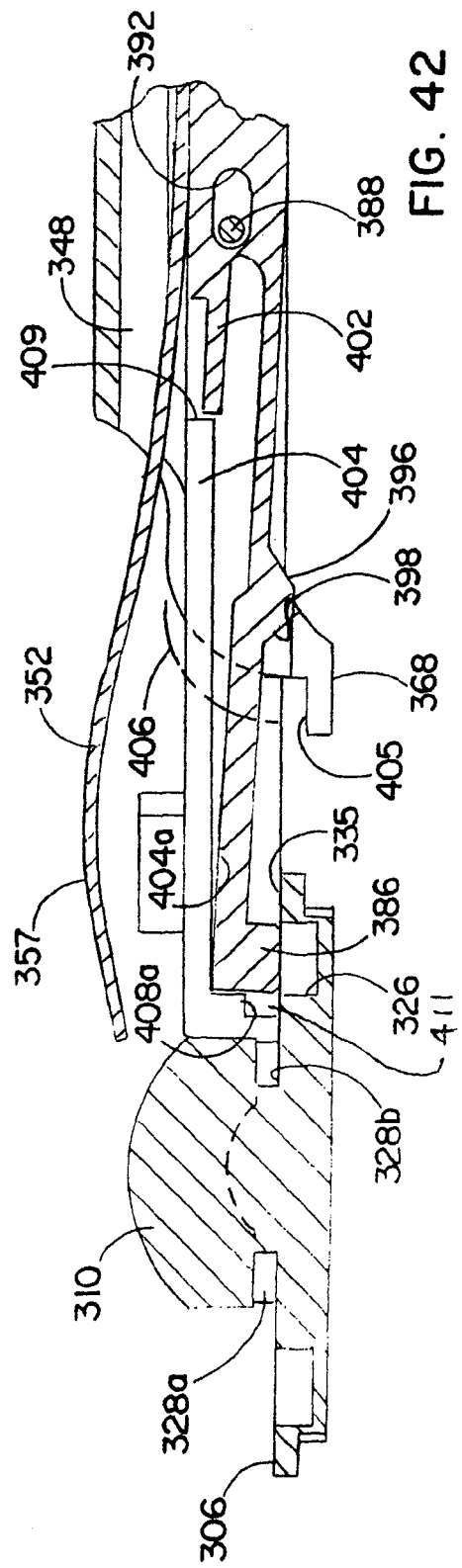
FIG. 42 is a cross-sectional view of the implant and the implant-holding end of the inserter of FIG. 31 showing a boss arm rotated to an unengaged position.

Referring to FIG. 42, once the boss 386 is above surface 327, the inferior member 306 is pivoted until the stabilizing plate 378 lays flush against top surface 327. In order to perform this while the boss 386 engages the top surface 327, the top wall 404 of the slot 384 provides a sufficiently high or upper ceiling 404a so that the holding arm including the boss 386 is pivoted into the slot 384.

Figure 41:
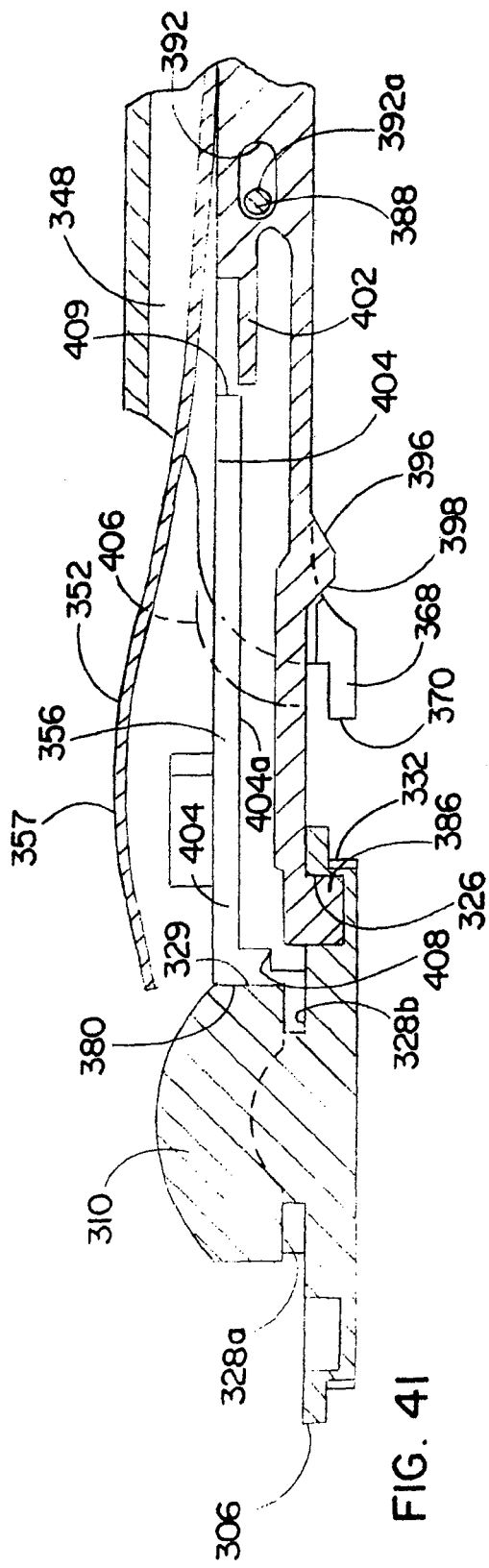
FIG. 41 is a cross-sectional view of the implant and the implant-holding end of the inserter of FIG. 31 showing a boss arm rotated to engage the implant.

As shown in FIG. 42, once the stabilizing plate 378 and boss 386 are engaged on the top surface 327, the user shifts the inferior member 306 and the inserter tool 302 toward each other such as by pushing the inferior member in the proximal direction, to shift the stabilizing plate 378 farther into the undercut 328a or 328b. The grip member 356 is shifted forwardly until the front surface 380 of the grip member 356 nears or abuts the surface 329 on the bearing portion 310. Alternatively, the grip member 356 may be translated until its stabilizing plate 378 abuts a back of the undercut 328b. So configured, this will generally locate the boss 386 over the recessed opening 326. As shown in FIG. 41, this causes the holding arm 358 to pivot and shift or drop the boss 386 into the recessed opening 326. Gravity causes the holding arm 358 to pivot since the free end 344 with the boss 386 is the heavy end of the holding arm 358.

The grip member 356 has an interior shoulder 408 that forms a lower or dropped ceiling 408a relative to upper ceiling 404a at a distal end 488 of slot 384. The lower ceiling 408a is configured to engage a top surface 490 of the free end 394 of the holding arm 358 and directly above the boss 386 while the boss 386 is disposed within the opening 326. So engaged, the lower ceiling 408a blocks upward motion of the holding arm 358 at the free end 394 and retains the boss 386 to extend out of slot 384 and within the opening 326 as shown in FIG. 40.

With the boss received in the corresponding implant opening but prior to achieving the releasably locked condition between the implant and inserter, the grip shaft can be translated axially relative to the holding arm since the impact surface is not engaged with the implant shoulder surface. To shift to the releasably locked condition the grip shaft is axially translated to bring the impact surface thereof into engagement with the implant shoulder surface at which the father forward axial translation of the gripshaft cease the holding arm to translate therewith. Axial translation of the holding arm with the boss thereof received in the corresponding implant opening is permitted by the slot of the holding arm in which pivot pin extends. Accordingly, both the grip shaft and holding arm translate together relative to the grip member with the pin translating toward the rear of the grip member slot. Forward translation of the grip shaft and holding arm, as well as the implant, relative to the grip member occurs until the boss is received in the end pocket formed at the forward end of the slot of the grip member, as shown in FIG. 40. In this position, the ceiling surface is oriented to extend over the boss so that upward pivoting of the holding arm cannot occur and the inserter and implant are in their releasably locked condition relative to each other.

In one alternative configuration, to provide stability between the inferior member 306 and the grip shaft 348, the grip shaft's distal end 366 has side walls 406 (shown in dashed lines) that extend forwardly and above the projection 368 of the grip shaft. A groove 405 is formed between the walls 406 and projection 368 to at least receive the proximal wall 324 on the inferior member 306. This structure secures the wall 324 against shifting transverse and superior-inferior directions relative to longitudinal axis $L_2$ to add stability to the releasably locked and adjustably held implant 300.

Referring to FIGS. 41 and 42, in order to disconnect the inferior member 306 from the inserter 302, the procedure described above is generally performed in reverse. It should be noted that the disconnection process can be performed while the implant 300 is in a pivoted orientation relative to the longitudinal axis $L_2$ of the inserter 302 within the nuclear or intervertebral space. Thus, the grip shaft 348 is first retracted rearwardly and away from implant 300 after placing the implant 300 in a desired orientation within the nuclear or intervertebral space. This causes the grip shaft 348 to translate axially and rearward relative to the grip member 356 and the holding arm 358. The rearward axial shifting of the grip shaft 348 also causes cam surface 345 to engage cam protrusion 396 on the holding arm 358. Because the boss is restrained from pivoting upward, the engagement between the cam portions 345 and 396 pushes the holding arm axially rearward with the grip member pin shifting forward in the holding arm slot. The slot is sized so that when the pin abuts the forward end of the slot, the boss will be retracted out from the pocket 409 away from the forward surface of the grip member, as shown in FIG. 41. In this position, the boss is disposed beneath the upper ceiling surface 404a of the grip member with a gap formed therebetween. The gap is sized to allow the boss to pivot up out of the implant opening and in the slot toward the ceiling wall 404a. Accordingly, further axially rearward translation of the grip shaft causes the cam surfaces to cammingly engage each other pivoting the holding arm and lifting the boss out of the opening in the implant in which it was seated. Also in this position, the upper stopper portion 402 of the boss arm 358 is retracted back to clear the top wall 404 of the grip member 356 so that it also has clearance to pivot upward through a top opening 408 of the grip member 356.

As shown in FIG. 42 and described above, further retraction of the grip shaft 348 causes the holding arm 358 to pivot to shift boss 386 out of opening 326. For this purpose, the cam surfaces 395 and 397 are both extend obliquely relative to the longitudinal axis $L_2$ of the inserter and extend from a lower position forwardly and upwardly. With this orientation, continued engagement and axial translation between the cam surfaces 395 and 397 causes the boss arm 358 to pivot upward about pin 388 to lift the boss 386 out of the opening. The inserter 302 can then be shifted rearwardly to slide the stabilizing plate 378 out of the undercut 328b to disengage the grip member 356 from the inferior member 306.

Referring again to FIG. 38, for the steering operation and pivoting of the implant 300, the steering actuator 410 includes the anchoring clip 412 attached to a distal end 375 of the cable 374. The cable 374 is threaded through the cable guides 372 and secured to spool 416 on one of the hilts 414 of the actuator 342 as shown on FIG. 31 and as described previously for control assemblies 110 and 235 on inserters 12 and 212.

Figure 38:
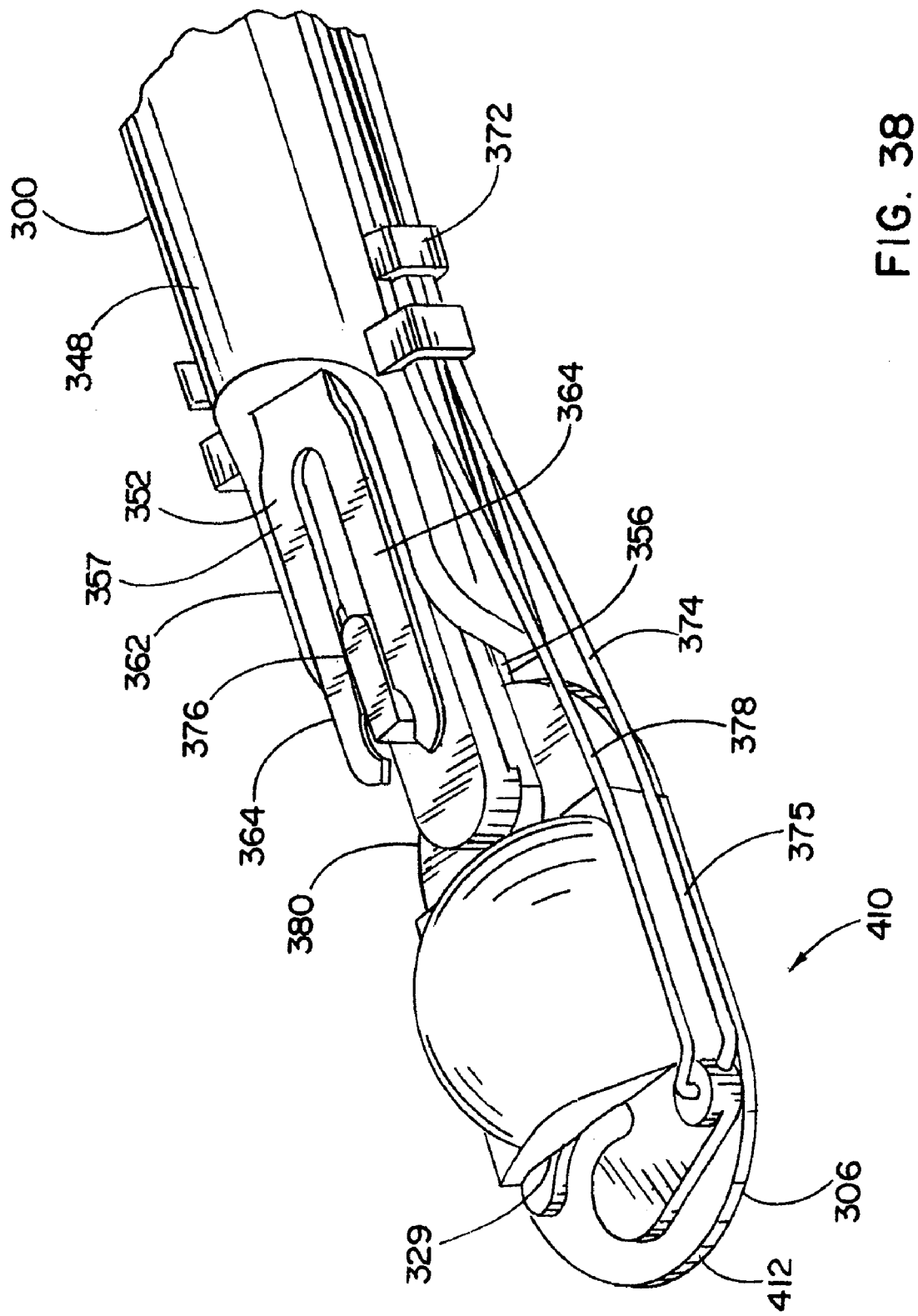
FIG. 38 is an enlarged, fragmentary view of the implant-holding end of the inserter of FIG. 31 showing the implant with a steering clip attached to cables from the inserter.

As shown in FIGS. 43 and 44, the clip 412 has a raised cylindrical portion 420 extending upward from an upper side or surface 418 of the clip. The cylindrical portion 420 has a throughbore 422 that receives the cable 374. The main body portion of the clip has a cut-out section 424 aligned with and extending into the cylindrical portion so that the cable 374 can extend through the bore of the cylindrical portion and out from the cut-out section along the upper surface of the implant member. A flexible, locking arm 426 of the clip 412 extends from a rear or proximal side 423 of a main body portion 428 of the clip. The locking arm 426 also extends generally laterally relative to the longitudinal axis $L_3$ of the implant 300 and is curved to fit within the undercut 328a or 328b of the inferior member 306 as shown in FIGS. 38 and 40. The bottom 430 of the clip 412 has a post 432 that is received within the distal seating opening 326 on the inferior member 306 as shown in FIG. 40. The locking arm 426 is spaced from the proximal side 423 of the main portion 428 as the arm 426 extends along the proximal side 423 so that the flexible arm can be sat toward one proximal side for pulling the clip's post 432 in the seating opening 326.

In order to minimize problems with entangling of the cable 374 with the implant 300 during removal of the cable from the implant, the clip 412 has a lateral extension 486 on which the cylindrical portion 420 is formed. The lateral extension projects slightly beyond a left or right side of the inferior member 306 as shown in FIG. 38. This positions the bore 422 so that the cable 374 attaches adjacent to either the left or right side of the clip 412. So configured, the cable does not need to extend around the distal end 317 of the inferior member 306 to pivot the inferior member. While a left-hand clip 412 is shown in the illustrated embodiment, the cable 374 could attach to the right side instead via a generally reversely configured right-hand clip 412 with the extension projecting beyond the right side of the implant.

Once the inferior member 306 is mounted to the inserter 302, the clip 412 is mounted to the distal end 317 of the inferior member. As with inserter 12 and implant 10, the superior member 304 may be connected to the resilient member 352 and mounted on the bearing portion 310 of the inferior member 306. As mentioned before, in the initial or original position, the superior member 304 is slanted to place the implant 300 in the wedge configuration and mounted to the inserter 302 so that the longitudinal axis $L_3$ of the implant 300 is parallel to or coaxial with the longitudinal axis $L_2$ of the inserter 302.

In this orientation, the implant 300 may be inserted through an annulus incision and into a nuclear space between vertebrae with its narrow, distal end 436 leading. The vertebrae push the superior member 304 down into a flat configuration so that the superior member 304 extends generally parallel to the inferior member 306. Once positioned within the annulus, the grip shaft 348 is retracted if desired to pivot the implant 300 as has been described earlier.

To steer the implant 300, the hilt 414 that is connected to cable 374 is pulled rearwardly and away from the implant 300 to pivot the hilt about its pivot axis H. This shifts the cable 374 rearwardly which in turn pulls the anchor clip 412 in the direction the cable 374 was pulled. The implant 300 is thereby pivoted toward the side of the inserter 302 with the pivoted hilt 414. The surgeon may maintain the implant 300 at a pivoted orientation using a pawl as described previously for hilts 116 and 118 for inserter 12. This is performed while stabilizing plate 378 provides for smooth and controlled pivoting of the implant 300 and a reduced risk that the implant 300 may unintentionally disengage from the inserter 12 during pivoting.

After the implant 300 is pivoted to a desired orientation between the vertebrae of the nuclear space, the cable 374 is cut or untied and pulled axially to disengage the cable from the clip 412. The clip 412 remains in situ with the implant 300.

Referring now to FIGS. 35 and 45, for the handle portion 340 of the inserter 302 has a similar structure to that of the handle portion on the inserter 212 (FIG. 26). Thus, in order to retract or advance the yoke grip 352 and yoke shaft 350 relative to the grip shaft 348, a slide 440 is provided on the main body 470 of the handle portion 340. The slide 440 has a post 444 that extends transversely relative to longitudinal axis $L_2$ of the inserter 302 and in a superior-inferior direction into the main body 470. The post 444 extends through a slot 448 on the grip shaft 348 to engage a notch 446 formed on a top surface of the yoke shaft 350. A slot 450 on the grip shaft 348 is displaced axially and rearward from slots 448 and receives a locking screw 452 that maintains the grip shaft on the body 470 until the screw is removed. The slide 440 covers the screw 452 and is removable to expose the screw.

With this configuration, shifting the slide 440 forward slides the yoke grip 352 forward on the grip member 356 and within grip shaft 348 for engaging the superior member 304. Retracting the slide 440 will provide the reverse operation and is performed to abut the superior member 304 against the dislodging wall 376 to disengage the superior member from the yoke grip 352 as described previously.

In order to disassemble the inserter 302, the base grip member 356 is fixed to the handle portion body 470 by a release 454 that is similar to release 209 on inserter 212. Thus, release 454 also has a securing pin 456 slidable within a diagonally extending groove 458 as shown in FIG. 45. Pushing forward on the back 460 of the release 454 moves the pin 456 upward within the slot 458 and off of a groove 462 on the grip member 356. The grip member 356 can then be pulled out of the handle portion 340.

In order to provide a further security mechanism to avoid unintentional depression of the release 454 and accidental disassembly of the inserter 302, a lock button 464 is provided on the handle portion 340. The lock button 464 is transversely reciprocal relative to the longitudinal axis $L_2$ of the inserter 302 and is disposed on the main body 470 behind slide 440. A locking pin 468 extends longitudinally through the main body 470 and has a front end 494 that is selectively received by a longitudinally extending bore 496 in the button 464 and a rear end 498 received by the release 454. So configured, the locking pin 68 axially retains the release 454 unless the lock button 464 is depressed to align the bore 496 with the locking pin 468. Once the lock button 464 is depressed, the locking pin 468 may be shifted axially forward into bore 496, by pressing the release 454 forward.

Referring to FIGS. 46-49, an implant-holding end 500 of the inserter 302 may be provided with an alternative configuration to facilitate the connection of the superior member 304 to a bowed resilient member. More specifically, the implant-holding end 500 has a resilient member 502, similar to yoke grip 352, that is biased to be bowed upwardly relative to the longitudinal axis $L_4$ of the inserter 302. While the bowed configuration of the resilient member 502 is desirable for orienting the superior member 304 to extend in a generally transverse direction relative to the implant axis with the implant 300 in its wedge configuration, a surgeon may have difficulty connecting the resilient member to the neck 323 of the post 314 on the superior member 304. This is due to the curved profile of the resilient member and the relatively small length of the neck 323 (measured in millimeters). For this reason, resilient member 502 also has a distal end 504 with additional structure 516 and 518 that increases the stiffness of the distal end 504. This structure overcomes the bias force and eliminates or reduces the bowing at the distal end 504 of the resilient member 502 without straightening an adjacent, intermediate bowed portion 506 (shown in FIG. 48) of the resilient member. The intermediate portion 506 remains bowed to maintain the straightened distal end 504 in a slanted orientation hold the superior member 304 in the slanted orientation thereof for forming the wedge configuration of the implant.

Figure 46:
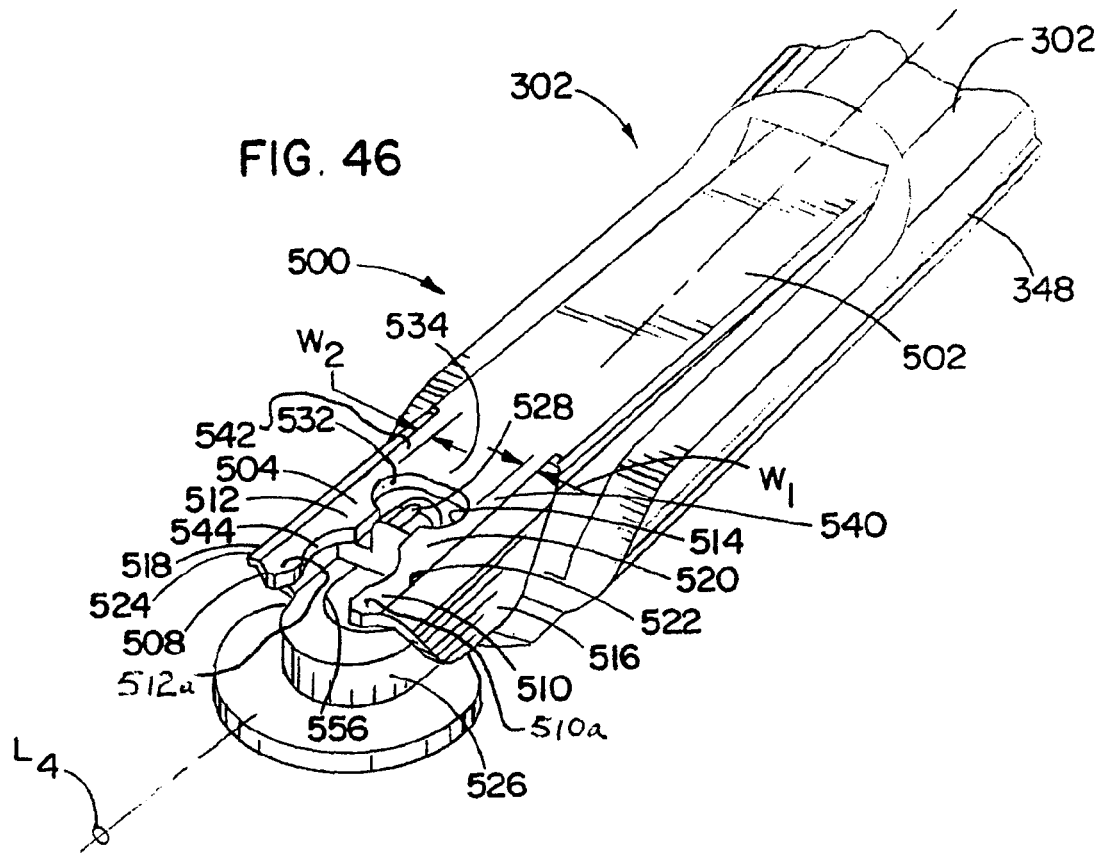
FIG. 46 is a perspective view of an alternative implant-holding end for the inserter of FIG. 31 showing a resilient member with stabilizing wings.
Figure 47:
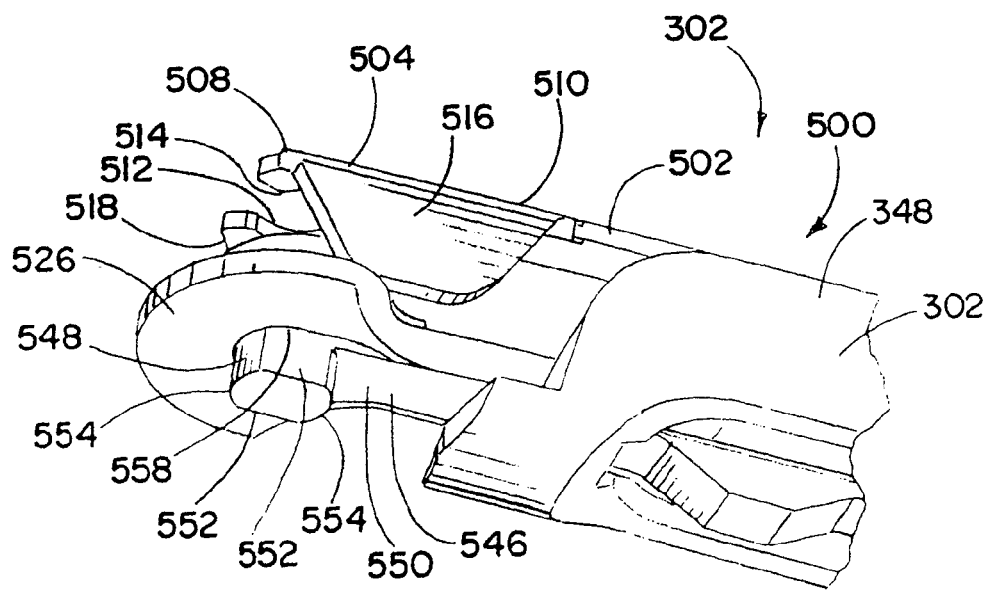
FIG. 47 is a bottom perspective view of the alternative implant-holding end of FIG. 46 showing a non-circular boss for engaging the implant.
Figure 48:
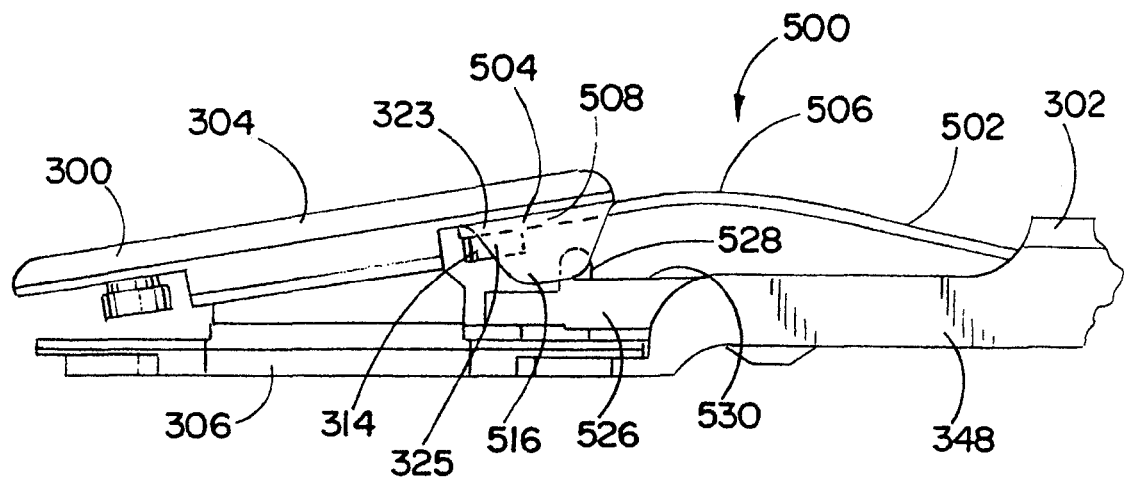
FIG. 48 is an elevational view of the inserter with the alternative implant-holding end of FIG. 46 showing the implant held in a wedge configuration.

Referring to FIG. 46, the distal end 504 of the resilient member 502 has a grasping claw 508 for engaging the neck 323 on post 314 on the superior member 304. The claw 508 has two laterally, spaced fingers 510 and 512 that form a groove 514 therebetween and similar to the gripping opening 365 between yoke fingers 364 of yoke grip 352. The additional structure 516 and 518 is respectively added to fingers 510 and 512 so that the fingers extend linearly rather than bow. This facilitates locating and aligning the fingers 510 and 512 with the neck 323 between the head 325 of the post 314 and the main wall or surface 321 of the superior member. Due to the increased stiffness of the fingers 510 and 512, this configuration also minimizes the amount the fingers bow or bend independently of each other in a superior-inferior direction. Thus, it is easier to connect the stiffened and straightened fingers 510 and 512 to the post 314. Additionally, once the superior member 314 is connected between the fingers 510 and 512, it is less likely that the fingers will tilt or pivot the superior member 314 about the implant axis or detach from the superior member. This configuration also positions upper surfaces 510a and 512a of the fingers 510 and 512 to lie flush against the main wall surface 321 of the superior member 304 for increased contact area between the fingers and surface 321 which provides further support for the superior member.

The additional structure on the distal end 504 of the resilient member 502 can be in the form of two generally trapezoidally shaped wing portions 516 and 518 respectively extending downward in a superior-inferior direction from a main, flat plate portion 520 that forms the fingers 510 and 512. The left wing 516 extends downward from, and along, a left edge 522 of the left finger 510 while the right wing 518 extends downward from, and along, a right edge 524 of the right finger 512. The wings 516 and 518 add stiffening material extending along the fingers and rearwardly beyond the fingers for overcoming the bias force of the resilient member 502 that otherwise bends to generate a bowing action along the resilient member and at the distal end thereof where the fingers are formed.

The wings 516 and 518 also act to maintain the resilient member 502 extending in a straight configuration along the axis $L_4$ minimizing lateral or transverse shifting from left to right relative to the longitudinal axis $L_4$ of the inserter 302 and this also keeps the resilient member 502 in lateral alignment with the gripping member 526 upon which the resilient member 502 is mounted. This may be needed when a surgeon actuates cables 374 to pivot the implant 300 which may cause post 314 on the superior member 304 to press laterally left or right against fingers 510 or 512 on the resilient member 502. The transverse forces could misalign the resilient member 502 relative to the grip member 526, particularly at the projecting bowed distal end portion thereof such that the implant members may be skewed relative to each other making insertion thereof through the annulus incision more difficult. In addition, when the resilient member 502 is retracted to pull the post 314 of the superior member 304 back against a dislodging wall 528 that extends upward from a top surface 530 of the grip member 526, these is a possibility that transverse forces may be generated between the post 314 and fingers 510 and 512, particularly when the implant 300 has been steered to extend laterally to the left or right relative to the inserter in the intervertebral space. The wall 528 is provided to disengage the implant 300 from the inserter 302 similar to dislodging wall 376. As stated above, retracting post 314 against the wall 528 may cause the post 314 to shift transversely against finger 510 or 512. Otherwise, the transverse force may be created by the annulus, vertebra or ligaments pressing against the implant 360.

Figure 49:
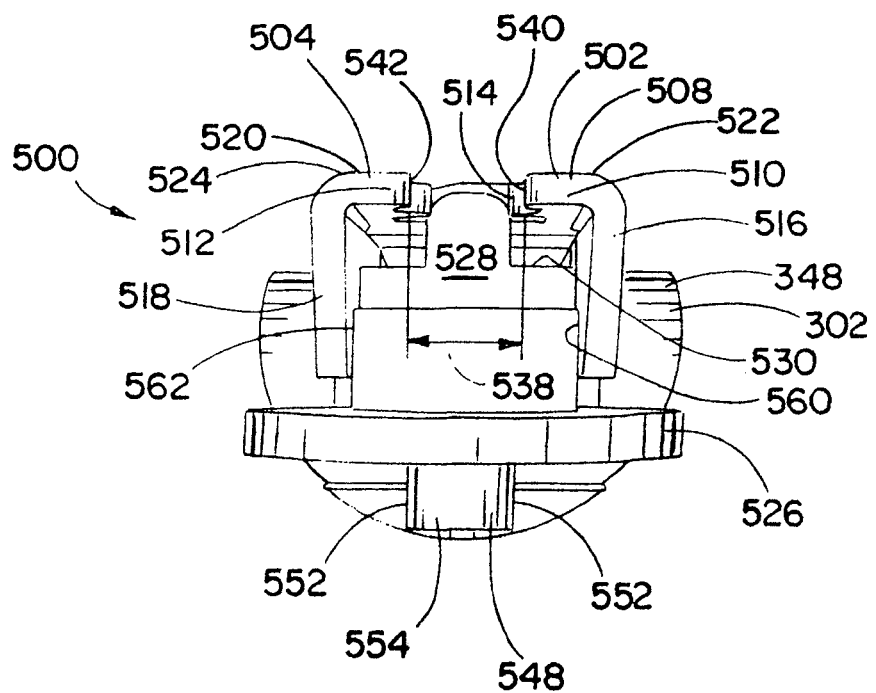
FIG. 49 is an end elevational view of the inserter with the alternative implant-holding end of FIG. 46 showing the wings on the resilient member extending down along the sides of a main gripping member.

As shown in FIG. 49, the wings 516 and 518 respectively extend down along and adjacent the left and right sides 560 and 562 of the grip member 526 with the implant 300 in the flat configuration in the intervertebral space. In this configuration, the wings 516 and 518 are positioned relative to the grip member 526 so that significant lateral or transverse left or right motion of either the resilient member 502 or the grip member 526 relative to each other is limited. Since the wings 510 or 512 will respectively engage left and right sides 560 and 562 of the grip member 526 if either the wings or the grip member are shifted laterally, very little relative lateral motion between the grip member and the resilient member is allowed.

Referring to FIG. 46, resilient member 502 also has a configuration to facilitate the insertion of the post 314 into the gripping opening or groove 514 between the fingers 510 and 512. The fingers 510 and 512 are modified to increase their flexibility in the lateral direction (transverse from left to right and relative to the longitudinal axis $L_4$ of the inserter). For this purpose, base portions 540 and 542 of the fingers are narrowed to reduce the amount of material extending laterally on the top wall 520 and at the bases 540 and 542. This structure provides both finger bases 540 and 542 with respective reduced widths $w_1$ and $w_2$ on the top wall 520 of the gripping opening 514 and between a wide end portion 532 at the rear of the gripping opening 514 and the left and right edges 522 and 524 of the resilient member 502. Since this results in widening of end portion 532 of the gripping opening 514, fingers 510 and 512 are also configured to form a forward seat portion 544 of the opening 514 for receiving and pivotally holding the post 314. The opening portions 532 and 544 are interconnected by a narrow neck portion 514a. So configured, fingers 510 and 512 easily flex laterally as the post 314 is being inserted into groove 514 between the fingers The increased flexibility of the fingers 510 and 512 permits the fingers to be shortened. The shorter fingers 510 and 512 add further strength to the distal end 504 of the resilient member 502 so as to resist the bias force thereof tending to bow or generate an arcuate configuration of the distal end portion 504. To accommodate the shortened fingers 510 and 512 and in turn the shortening of the opening 514, the dislodging wall 528 on grip member 526 is also configured so that it still fits within the groove 514 when the implant 300 is in a flat (non-wedge) configuration. In this regard, the previously described dislodging wall 376 (FIG. 36) extends longitudinally along the gripping member 526 a distance, for example, that is greater than its height. On the other hand, the wall 528 does not extend a significant longitudinal distance for fitting into the shortened or smaller length opening 514.

Also in this alternative embodiment, in order to reduce manufacturing costs, a holding arm 546 including a boss 548 is manufactured from a single flat plate of thin material rather than increasing the thickness of the plate, adding on a separate piece or using relatively expensive contoured molds to form a cylindrical boss on the end of a flat arm as with previously described holding arm 358. Thus, the holding arm 546, similar to holding arm 358, is pivotally connected to the grip member 526 and boss 548 is configured for engaging the opening 326 (shown on FIGS. 33 and 39-42) on the inferior member 306 of implant 300. In this embodiment, the boss 548 need not be entirely cylindrical and is elongated with flat sides 552 and curved longitudinal ends 554. The ends 554 are configured to align with and engage a cylindrical interior surface 326a (shown on FIG. 33) of the aperture 326 so that the implant 300 still rotates about the boss 548.

In order to provide further clearance for the post 314 on the superior member 304 while the superior member is being attached to the resilient member 502, the grip member 526 has a recess or opening 556 in front of the dislodging wall 528. This permits the superior member 304 to be slanted slightly downward as it extends proximally opposite to the direction of the superior member 304 in the wedge configuration, to connect the superior member to the claw 508 of the resilient member 502. This allows the post 314 to extend slightly into opening 556, if necessary. To facilitate cleaning of the slot 558 on the gripping member 526, the opening 556 may also open to the slot 558 of the grip member 526. Thus, the opening 556 may provide an outlet or inlet for cleaning fluids flushed through the slot 558.

Other than the configurations mentioned above, the resilient member 502, grip member 526 and holding arm 546 respectively have the same or similar features, characteristics, orientations and operation as described above for yoke grip 352, grip member 356 and holding arm 358.

It will also be appreciated that instead of yoke grip 352 or resilient member 502, the inserter 302 could be operated with bent and forked yoke grip 274 (FIG. 26) instead.

Referring now to FIGS. 50-70, a system 601 for replacing a nuclear disc preferably within an annulus may include instruments such as a spacer 600 held by an inserter 602 for determining the size of the nuclear or intervertebral space. It is desired for the implant to be properly sized for an intervertebral space to avoid causing pain to the patient and damage to anatomical structure such as the vertebrae, annulus of ligaments. The size of the intervertebral space is determined before inserting an implant into the space because removing oversized or undersized implants may be a relatively complicated and time consuming procedure. This is especially true when the implant is provided in multiple pieces and/or the implant is detached from the inserter in order to determine if the implant fits the nuclear space. Thus, the present invention includes a spinal device such as a trial spacer 600 that is adjustably held on a distal end 604 of insertion tool or holder 602 for being actively steered thereby. The inserter 602 is used to insert and steer the spacer 600 into the intervertebral space, to determine the size of the intervertebral space, and then steer and retract the spacer from the intervertebral space.

As with the implants, the trial spacer 600 is shaped to imitate the shape of a natural disc. Thus, the spacer 600 is elongated to have a narrow end 636. The end 636 is used as a leading end to face an annulus incision and lead the spacer 600 during insertion of the spacer into a nuclear space in order to minimize the required size of the incision. In order to permit the surgeon to orient the spacer so that the longitudinal axis $L_s$ of the spacer extends laterally relative to the anterior-posterior direction in the nuclear space to imitate the orientation of a natural disc within the nuclear space, the inserter 602 is configured to pivot the trial spacer 600. The pivoting also allows the spacer 600 to be injected through incisions disposed at a wide range of positions about the annulus. The incision can be disposed at a lateral position relative to the anterior-posterior direction or can be offset therefrom with the pivoting of the spacer allowing the surgeon to reorient the spacer in the nuclear space to the desired laterally extending orientation therein. The inserter 602 also provides active steering of the trial spacer 600 that minimizes pressing of the spacer against the annulus in order to further reduce the risk of damage to the annulus that passively steered systems using the wall of the annulus may generate.

Figure 50:
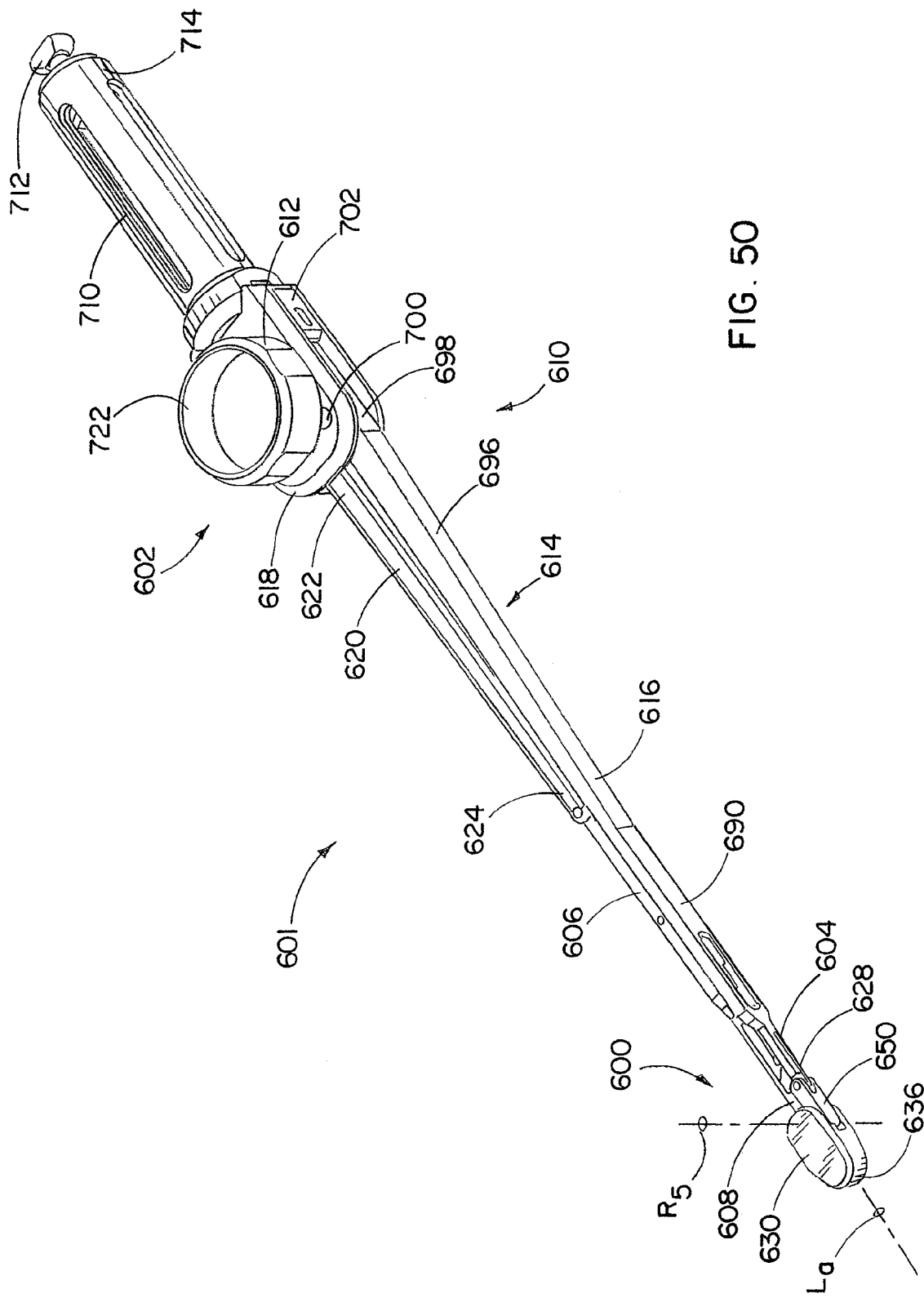
FIG. 50 is a perspective view of a trial spacer connected to an insertion tool in accordance with the present invention.
Figure 51:
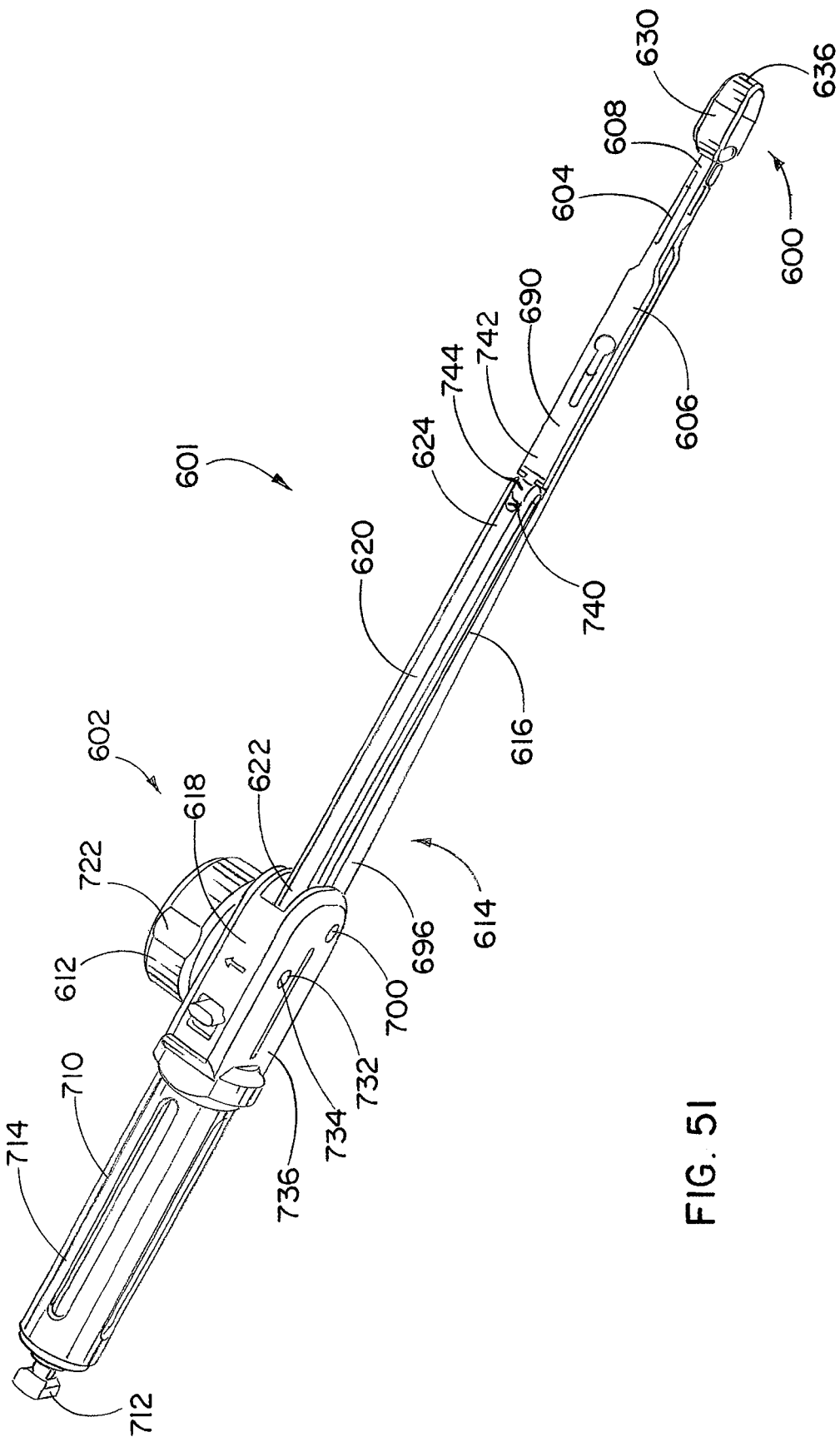
FIG. 51 is a right side perspective view of the trial spacer connected to the insertion tool.

For these purposes, the inserter 602 includes a gripping member 606 with a distal end portion 608 configured to adjustably hold the trial spacer 600 in the intervertebral space while a steering mechanism or system 610 is used to actively steer the spacer within the intervertebral or nuclear space. To provide the active steering, the steering system 610 includes a steering control device 612 operatively connected to a steering actuator 614 and the spacer 600, as shown in FIGS. 50-51. With this structure, operating the control device 612 causes the actuator 614 to pivot the spacer 600 while the spacer remains adjustably held by the gripping member 606 of the actuator 614 and within the nuclear space.

In more detail, an example set of trial spacers including spacers 600*a* to 600*c* (FIG. 53A) are provided where all the spacers in the set have the same general shape and each spacer has a slightly different size or geometry so that each spacer corresponds to at least one implant of a corresponding size or geometry. The size refers to the height of the spacer extending in a superior-inferior direction and from one vertebra to the opposite adjacent vertebra that forms the nuclear space and/or may refer to the lateral width or longitudinal length (i.e. the foot print) of the spacer. The geometry may refer to the angle of one of the outer surfaces of the spacer relative to an adjacent surface on the spacer or between the outer surfaces and the plane formed by the lateral and longitudinal central axes of the spacer.

Figure 53A:
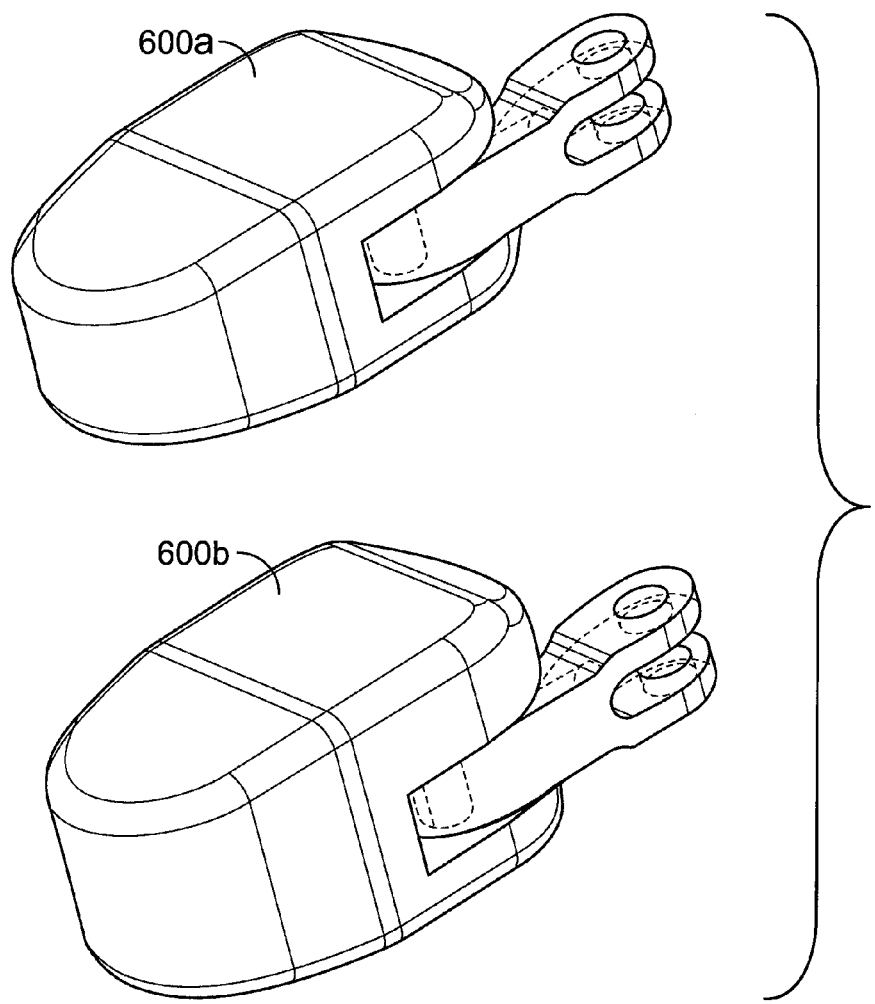
FIG. 53A is perspective view of a set of trial spacers each having different dimensions.
Figure 53B:
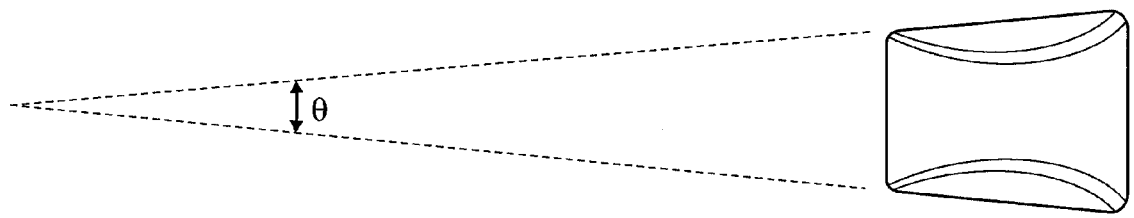
FIG. 53B is a front end view of a trial spacer in a set of trial spacers of FIG. 53A.

In order to match the lordotic or kyphotic curvature of the vertebrae, the upper and lower surfaces of the spacer may generally extend in intersecting planes x and y that form an included angle θ therebetween as shown in FIG. 53B (shown exaggerated for clarity). To form this angle, the planes are inclined toward each other as they extend transversely to the longitudinal axis of the spacer and are inclined relative to the plane formed by the central longitudinal and lateral axes of the spacer. The lordotic angle may be pre-measured by using imaging technology such as x-ray, MRI, fluoroscopic or other similar techniques.

In one example trial spacer set, the spacers 600 are provided with angles θ of 0°, 6° or 12°. The "0°" means a spacer with upper and lower surfaces that are parallel to each other and do not have planes that intersect. The 0° spacer comes in a height of about 7 mm and is preferably used to measure the footprint of the nuclear space. The spacers may come in different foot print sizes such as approximately 14. 5 mm by 25 mm or 16 mm by 28 mm. The spacers angled at θ=6° are preferably used with lordotic angles of 0 to 10°, and the spacers with θ=12° are preferably used with lordotic angles greater than 10°. The spacers with either the 6° or 12° angles may have heights of approximately 8, 9 or 10 mm. The 6° spacers also include an 11 mm height spacer, and the 12° spacers include a 10.5 mm height spacer.

To determine the size of the nuclear or intervertebral space, a surgeon inserts the spacers 600 into the intervertebral space one at a time in trial and error fashion and preferably starting with the smaller spacers and increasing the size of the spacer with each trial. The spacers 600 are inserted until one of the spacers 600 fits the intervertebral or nuclear space. The spacers 600 may also be used to distract and stretch the tissue surrounding the nuclear space as the spacers increase in size to make it easier to subsequently insert the implant into the nuclear space.

The surgeon determines whether or not the spacer 600 fits properly within the intervertebral space by using imaging technology mentioned previously. The surgeon may also determine how tightly the spacer fits in the intervertebral space by sensing how much force must be applied to the inserter 602 to shift the spacer 600 in the space. Once the proper size of spacer 600 is determined and the spacer is removed from the intervertebral space, the user then determines the proper size for the implant.

Referring to FIGS. 50-52, in order to avoid enlarging the incision on the annulus or damaging the annulus, the inserter 602 actively pivots the trial spacer 600 about rotational axis $R_5$ and relative to the distal end portion 608 of the gripping member 606 without requiring that the spacer 600 be pushed against the annulus wall or the inserter 602 against edges about the incision during insertion. Instead, to pivot the spacer 600 within the annulus, the inserter 602 is advanced longitudinally to extend through the incision on the annulus. The actuator mechanism 614 includes components that translate along the longitudinal axis $L_a$ of the inserter 602 for pivoting the spacer 600 in the intervertebral space.

In the illustrated and preferred form, the steering actuator 614 has an elongate main member 616 that is connected to the spacer 600. The gripping member 606 is axially translated relative to the main member 616.

Generally, in order to steer the spacer 600, the inserter 602 has a housing 618 for holding the steering control device 612, and the steering actuator 614 also has a drive arm 620 with one end 622 connected to the control device 612 in the housing 618. The drive arm 620 extends out of a front opening 621 of the housing 618 and to another end 624 that pivotally connects to the gripping member 606. The main member 616 of the steering actuator 614 is pivotally connected to the housing 618 at one end 626 and connected to the spacer 600 at an opposite, distal end 628. The main member 616 is also connected to the gripping member 606 to support and maintain the gripping member extending in a parallel orientation along the longitudinal axis $L_a$ of the inserter 602. With this configuration, operating the control device 612 shifts the drive arm 620 axially to axially translate the gripping member 606 relative to the main member 616. This pivots the spacer 600 since the spacer is pivotally connected to the distal end 608 of the gripping member 606 while remaining longitudinally fixed at its connection to the distal end 628 of the main member 616.

While the steering actuator 614 is referred to herein as comprising the main member 616 and drive arm 620, it will be understood that the actuator may refer to the entire insertion tool 601 or parts thereof including the steering mechanisms and gripping member 606 as well as the housing it is positioned within.

Referring to FIGS. 52-53, the spacer 600 has a spacer body 630 with generally flat, top and bottom surfaces 632 and 634 both with generally obround, oval or other elongate shapes, and that form the narrow leading end portion 636. A continuous sidewall surface 638 extends from the top surface 632 to the bottom surface 634 and forms a front, curved, and smooth outer surface for the leading end 636 and without sharp exterior edges that could damage tissue as the body 630 is inserted through an incision and into a nuclear space. The sidewall 638 is continuous with left and right longitudinal sides 640 and 642 of the main body 630 where left and right is relative to the user holding the inserter 602 connected to the spacer 600. Further, directional and other descriptions regarding various inserter components, and their configuration, as well as that of the spacer, are with respect to normal orientations, and not necessarily corresponding with those that may be found during surgery. So, for example, pivoting of the spacer may be described as occurring in lateral or left-right directions, when in surgery such pivoting occurs vertically. In order to minimize damage to the annulus as the spacer 600 is retracted from the nuclear space, a rear or proximal end 644 on the spacer body 630 and opposite the leading end 636 is also curved to avoid sharp edges.

In one form of the spacer 600, the height of the leading end portion 636 and rear or trailing end portion 644 is reduced relative to the height between the surfaces 632 and 634 so that the end portions 636 and 644 form a slight wedge insertion shape to facilitate insertion of the spacer into and through small spaces like the annulus incision and between vertebrae, similar to the implant's wedge configuration, as well as removed therefrom. Thus, the top and bottom surfaces 632 and 634 also include front, inclined surface portions 632a and 634a that are inclined relative to a plane formed by the lateral axis $L_{lat}$ of the spacer body and the central, longitudinal axis $L_s$ of the spacer body. The inclined upper and lower surface portions 632a and 634a, respectively, slant downward and upward as the surface portions extend forwardly. The rear end portion 644 of the body 630 may be reduced in size likewise by upper and lower inclined surface portions 632b and 634b that respectively extend downward and upward as the surface portions extend rearwardly.

To engage the gripping member 606, the spacer body 630 has a pocket 646 that opens rearwardly at the rear end portion 644 to receive the distal end portion 608 of the gripping member 606. The pocket 646 also opens along a rear portion 648 of the left side 640 of the spacer body 630 to provide clearance for an elongate, rigid, link 650. The link 650 is connected in the pocket 646 and may extend out of the left side 640 of the spacer body 630.

The pocket 646 is formed between upper and lower walls 652 and 654 of the spacer body 630. A grip pin 656 extends through a bore 658 formed in the lower wall 654, through the pocket 646, and into a recess in the upper wall 652 aligned with the bore 658. The bore 658 opens to an indent 680 formed on the bottom surface 634 of the spacer 630 to provide access to the grip pin 656 for assembly or disassembly purposes. The grip pin 656 also extends in a superior-inferior direction through the pocket 646 and is removably engaged by a generally U-shaped hook 660 (shown in FIG. 56) on the gripping member's distal end 608. While the spacer 300 is engaged on the hook 660, the grip pin 656 is coaxial to the rotational axis $R_s$ about which the spacer body 630 pivots. The grip pin 656 is generally centered from left to right on the spacer body so that the grip pin 656 is oriented along the longitudinal axis $L_s$ of the spacer body 630.

The link 650 is provided for quickly and conveniently connecting the spacer 600 to the inserter 602 and for releasing the spacer from the inserter 602. The link 650 extends from the pocket 646 on the spacer body 630 for releasably connecting the main member 616 to the spacer body 630. A first link pin 664 pivotally connects a first end 662 of the link 650 adjacent the left side 640 of the spacer body. A second end 668 of the link 650 opposite the first end 662 is pivotally and removably connected to a distal end 628 of the actuator's main member 616 by a second link pin 678.

So configured and as shown in FIG. 64, axially translating the gripping member 606 relative to the main member 616 causes the gripping member 606 to pull or push on the grip pin 656 and the rear end portion 644 of the spacer body 630. This occurs while the first end 662 of the link 650 pivots slightly about the second link pin 678 at the distal end 628 of the main member 616 but remains near axial position FP relative to longitudinal axis $L_a$ of the inserter and longitudinal axis $L_m$ of the main member (shown on FIG. 63). With this structure, the gripping member 606 can shift the grip pin 656 and the rear end portion 644 of the spacer 600 forwardly or rearwardly past the position FP and the first end 662 of the link 650. Since both pins 664 and 656 are disposed at fixed locations in the spacer 600, the relative axial motion causes the spacer body 630 to pivot about the grip pin 656 and the first link pin 664 and toward the side of the inserter 602 with the link 650.

In further detail, the first link pin 664 extends parallel to grip pin 656 and through the lower wall 654 on the spacer body 630. The first link pin 664 also extends through a bore 666 on the first end 662 of the link 650 and into the upper wall 652 of the spacer body 630. In order to provide a full range of approximately 90 degrees of pivoting of the spacer body 630, the first link pin 664 is placed forwardly from the grip pin 656 in the spacer body 630 with the spacer's longitudinal axis $L_s$ aligned with the inserter longitudinal axis $L_a$. This enables the grip pin 656 to axially translate both rearwardly and forwardly of the axially fixed position FP of the first link pin 664 which increases the distance the grip pin 656 can translate and in turn the amount the spacer body 630 can be pivoted. The spacer body 630 may be pivoted to a number of positions where its longitudinal axis $L_s$ extends transversely to the longitudinal axis $L_a$ of the inserter, and in one form, until the axis $L_s$ of the spacer 600 extends approximately orthogonally to the axis $L_a$ of the inserter 602 to pivot the pacer approximately 90 degrees.

Referring to FIG. 63, to align the first link pin 664 with the longitudinal axis $L_m$ of main member 616, the first link pin 664 is positioned laterally from the longitudinal axis $L_s$ of the spacer 600 and toward the left, longitudinal side 640 of the spacer body 630 for pivoting the spacer 600 to the left. It will be appreciated that the inserter 602, spacer 600 and link 650 could be configured to pivot to the right side of the inserter instead. It will also be appreciated that since the top and bottom surfaces 632 and 634 of the spacer body 630 may be symmetrical, it is possible to invert the spacer 600 and inserter 602 to steer the spacer 600 to the right rather than the left of the inserter 602.

With this preferred configuration, the link 650 does not widen the profile of the spacer 600 during insertion of the spacer 600. For insertion of the spacer 600 into a nuclear space, the spacer 600 is held in a straight, non-pivoted orientation where the longitudinal axis $L_m$ of the spacer 600 is generally coaxial to the longitudinal axis $L_a$ of the inserter 602. In this straight orientation, the link 650 extends generally coaxial to the longitudinal axis $L_m$ of the main member 616 and rearward from the spacer body 630. As the spacer 600 is shifted forwardly into a nuclear space, the axially extending link 650 will not press significantly and laterally against the annulus edges extending adjacent the incision.

Still referring to FIG. 63, in order to minimize the risk of unintentional disengagement of the spacer 600 from the gripping member 606, the first end 662 of the link 650 is configured and disposed to be in interference with the hook 660 blocking its removal from grip pin 656. While the link 650 is connected to the main member 616 within the pocket 646 on the spacer body 630, the hook 660 does not have sufficient clearance within pocket 646 to disconnect from the grip pin 656. Specifically, the hook 660 opens toward the right and away from the first end 662 of the link 650 within pocket 646. Thus, hook 660 needs to be shifted toward the left in the pocket 646 in order to disengage it from the grip pin 656. As shown in FIGS. 63 and 64, however, at least some portion of the first end 662 of the link 650 remains to the left and adjacent an outer, curved surface 720 of the hook 660 to block the leftward motion of the hook 660 at least while the link 650 is connected to the main member 616.

To provide the clearance for removing the hook 660, the second end 668 of the link 650 is disengaged from the inserter 602 in a process described in detail below. Once the second end 668 of the link 650 is free, the user can pivot spacer body 630 clockwise or to the right about the grip pin 656 while pivoting the link 650 clockwise about the first link pin 664 in spacer body 630. The spacer 600 and link 650 are pivoted until the link 650 is no longer disposed directly to the left of the hook 660 in pocket 646. This orients the link 650 in a hook removal orientation 651 shown in dash lines on FIG. 63. Once the link 650 is shifted away from the left side of the hook 660, the hook 660 can be shifted to the left within this pocket 646 in order to disengage it from the grip pin 656.

Also in the preferred embodiment, in order to secure the gripping member 606, and in turn spacer 600, in the straight insertion orientation as described above and as shown in FIG. 63, the link 650 and hook 660 cooperatively provide a releasable locking arrangement that minimizes undesirable axial shifting of the gripping member 606 relative to the link 650. In more detail, relatively strong forces may be transferred to the spacer 600 such as when a surgeon uses a hammer to hit a proximal end 714 of the inserter 602, and more specifically, a handle 710 or a force transmitting shaft 712 on the proximal end 714. The shaft 712 extends through the handle 710 and connects directly to the housing 618 of the inserter 602 to transfer force through the housing, the actuating members 606, 616 and 620, and to the spacer 600. In this case, the forces that are transmitted from the hammer blow to the gripping member 606 may cause the gripping member to translate forward relative to the main member 616 which may unintentionally pivot the spacer 600 from the injection orientation. Additionally, anatomical structure such as the vertebrae may apply sufficient force on the spacer 600 to urge the spacer to pivot and in turn to axially shift the gripping member 606.

To reduce the risk of this occurrence, the link 650 has a contoured side 716 with an indent 718 for receiving the curved outer surface 720 of the hook 660. In this configuration, the first end 662 of the link 650 extends laterally slightly in front of the hook 660 so as to be in interference with forward axial motion thereof. Similarly, the second end 668 of the link 650 extends slightly laterally rearward of the hook 660 to be in interference with rearward axial motion thereof. So disposed, the hook 660 is axially restrained against axial motion between the link ends 662 and 668 to limit such unintentional axial motion of the gripping member 606.

To disengage the above-described restraining arrangement, translating the gripping member 606 forwardly by using the control device 612 shifts the first end 662 of the link 650 laterally out of the axial path of the hook 660 and grip pin 656. More specifically, and as mentioned above, the first link pin 664 is fixed at or near axially fixed position FP shown in FIG. 63 relative to longitudinal axis $L_m$. Also, spacer 600 holds the pins 664 and 656 at a fixed distance apart from each other. Thus, translating the grip member 656 axially forwardly toward and past the axially fixed position FP and in a direction along the longitudinal axis $L_m$ causes the first link pin 664 to pivot, shifting it slightly laterally relative to axis $L_m$ and slightly back rearwardly from axial position FP. The first link pin 664 pivots away from axis $L_m$ as the grip pin 656 translates closer to the axially fixed position FP. Conversely, the first link pin 664 shifts to the right and toward axis $L_m$ back toward the axial position FP as the grip pin 656 translates axially past the link pin 664 and away therefrom. The first end 662 of the link 650 is able to shift laterally by pivoting the link 650 about second link pin 678 which is pivotally connected to the main member 616.

To connect the link 650 to the distal end 628 of the main member 616, the second end 668 of the link 650 has a clevis 670 with an upper wall 672 spaced from an opposing lower wall 674 and forming a cavity 676 therebetween. The walls 672 and 674 generally extend parallel to each other and generally parallel to the plane formed by the longitudinal and lateral axes $L_a$ and $L_{lat}$ of the spacer body 630. The second link pin 678 extends into aligned apertures 673 of the lower wall 674 and upper wall 672 both opening to cavity 676 therebetween. The second link pin 678 also extends parallel to both the grip pin 656 and the first link pin 664 in a superior-inferior direction and transverse to longitudinal axis $L_a$.

Figure 56:
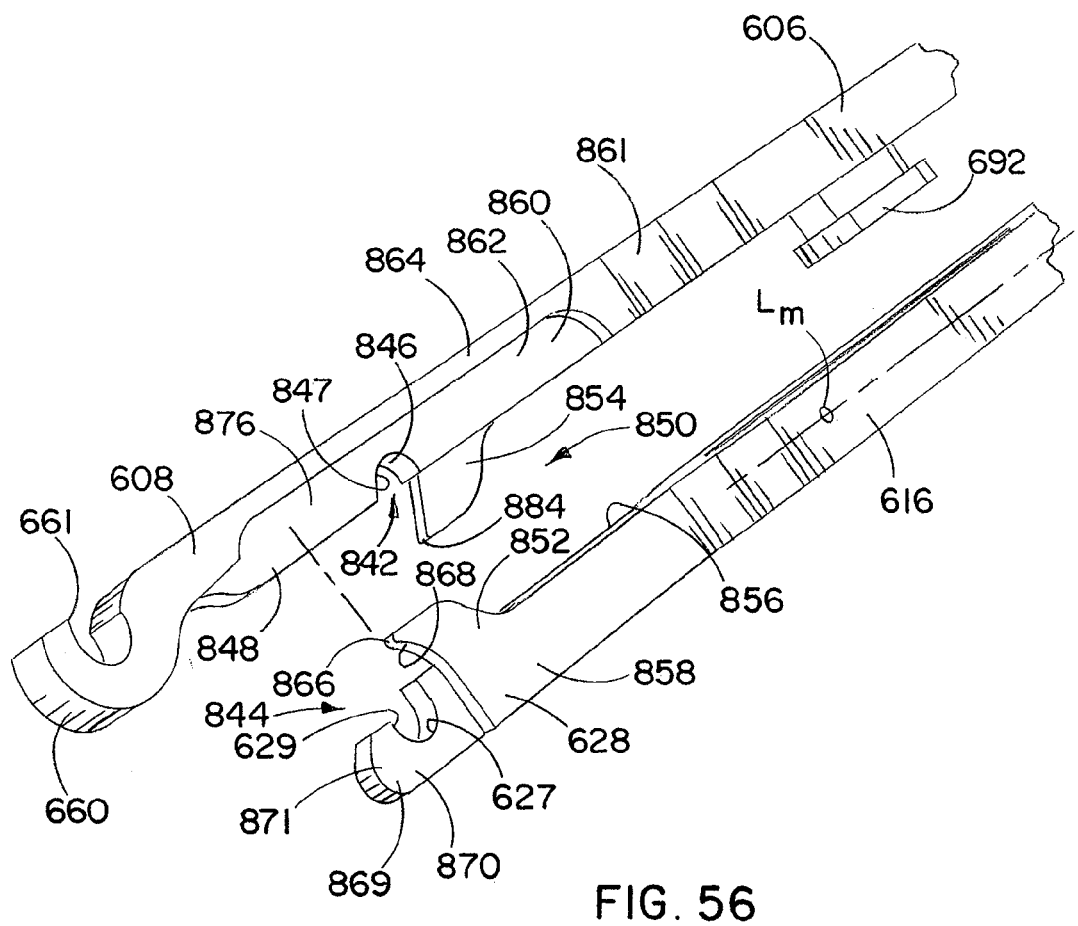
FIG. 56 is an enlarged, exploded perspective view of the spacer-holding end of the inserter showing distal end portions of a main member and a gripping member for being connected to each other and the spacer.

As shown in FIG. 56, the distal end 628 of the main member 616 has an arcuate end notch 627 that receives and holds the second link pin 678 during pivoting of the spacer 600. The end notch 627 has an opening 629 that faces a left, longitudinal side surface 848 of the adjacent gripping member 606 and is configured for receiving second link pin 678. In the pivoting orientations described below, the left side surface 848 opposes the opening 629 at a distance from the opening 629 that retains the second link pin 678 within the groove 627 as shown in FIGS. 63-64.

Referring to FIG. 50, to provide axial translation of the gripping member 606, the main member 616 has a first, distal, elongate portion 690. The first portion 690 extends along the longitudinal axis $L_m$ of the main member 616 and is connected to the spacer link 650. The first portion 690 maintains the gripping member 606 in generally parallel alignment with the longitudinal axis $L_a$ of the inserter 602 during pivoting of the spacer 600. To maintain this parallel alignment, the gripping member 606 has a protrusion 692 extending from the left side or surface 848 of the gripping member 606 as shown in FIGS. 52 and 69. The protrusion 692 is removably secured in an elongate, axially extending slot 694 on the first portion 690. The slot 694 and protrusion 692 are configured to permit the members 616 and 606 to axially translate relative to each other as explained below. In the present embodiment, the protrusion 692 and slot 694 at least provide a sufficient axial distance of relative translation between them so that the gripping member 606 may pivot the spacer 600 from the straight orientation and up to about 90 degrees to the left of the longitudinal axis of the inserter 602 as previously described.

Figure 54:
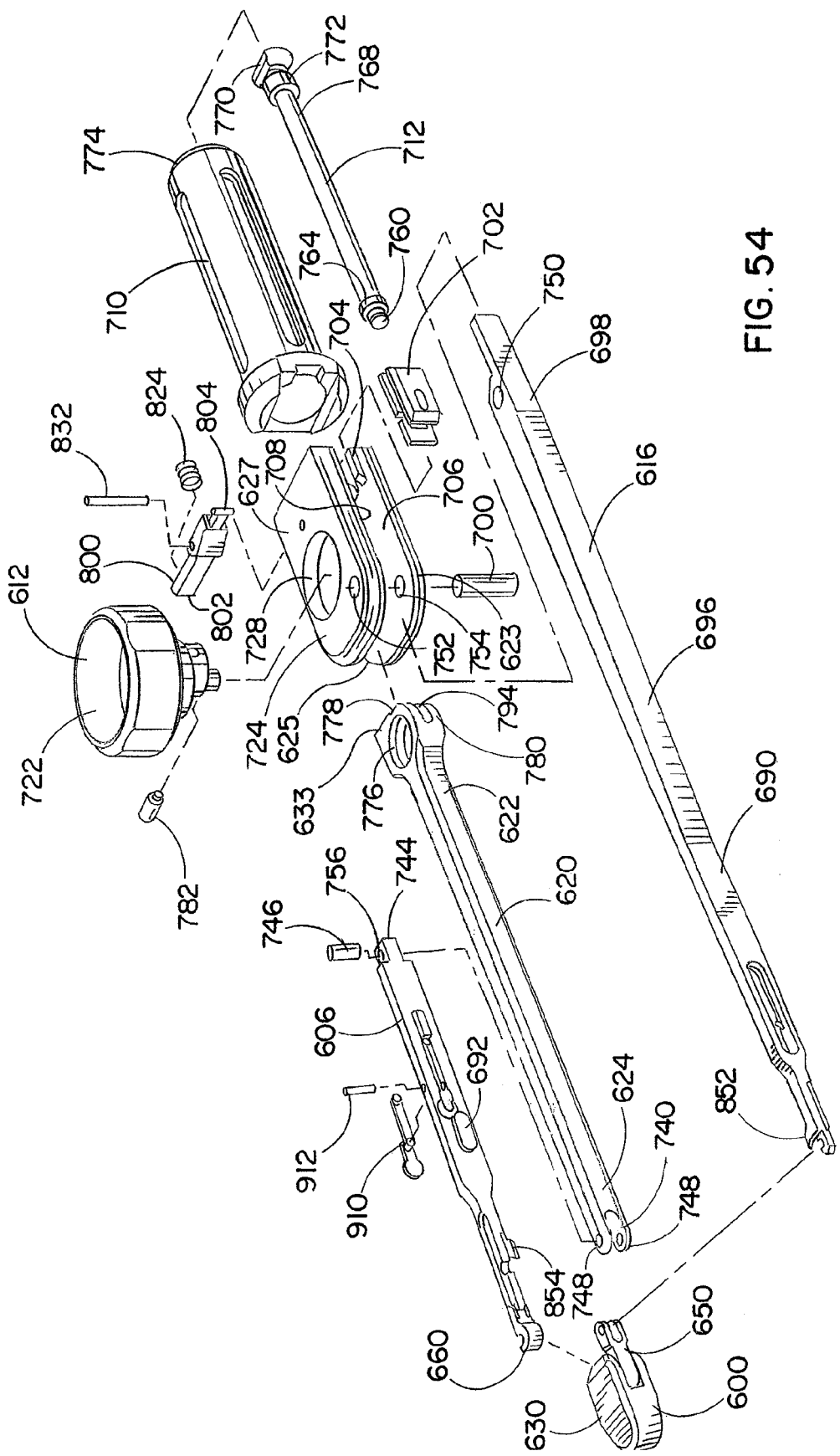
FIG. 54 is an exploded perspective view of the inserter showing the steering mechanism for the trial spacer including a steering actuator and control device thereof.
Figure 57:
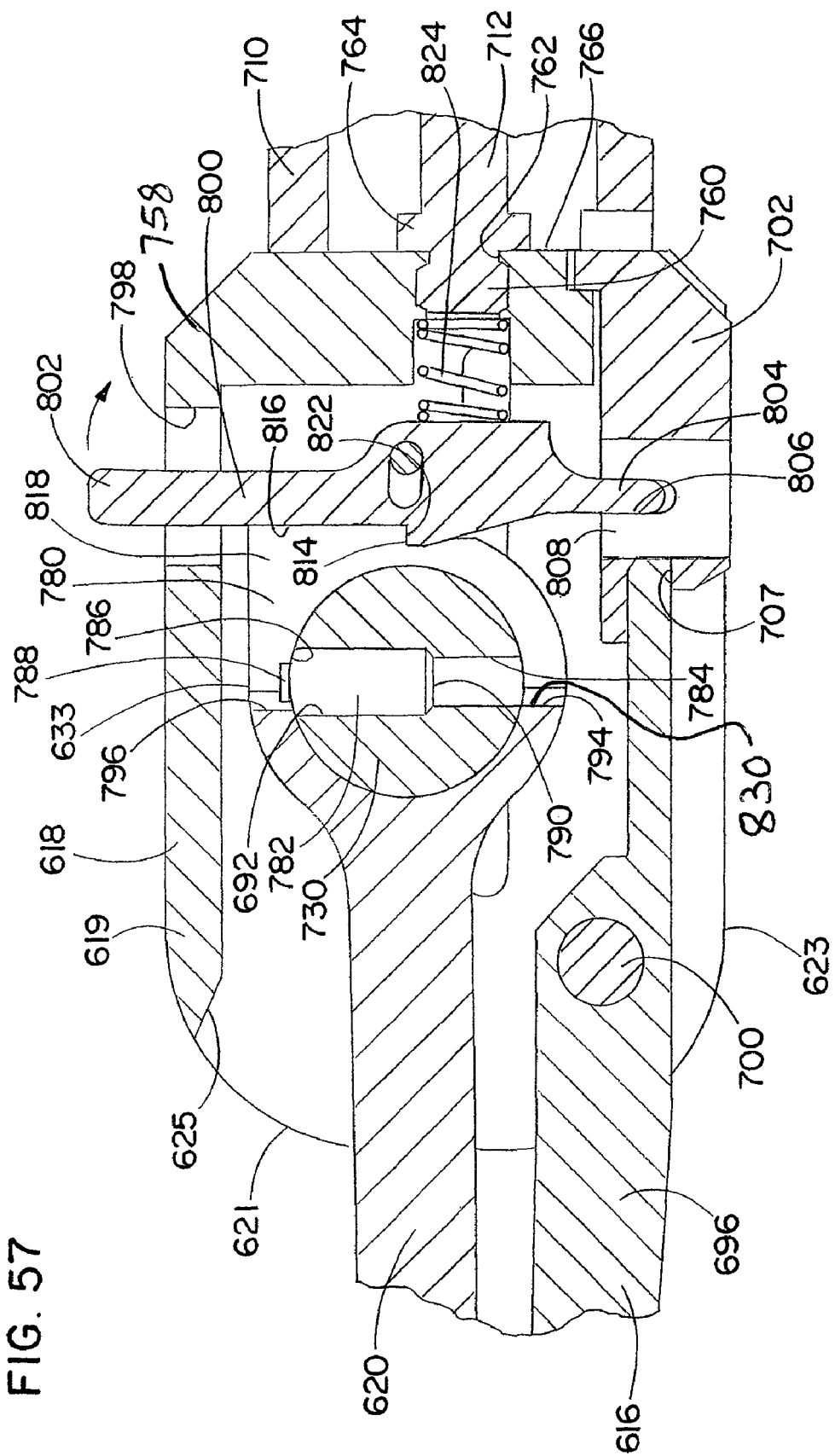
FIG. 57 is a top cross-sectional view of a housing on the inserter showing the steering control device and steering actuator in an orientation for holding the spacer at a zero degree orientation relative to the longitudinal axis of the inserter.
Figure 58:
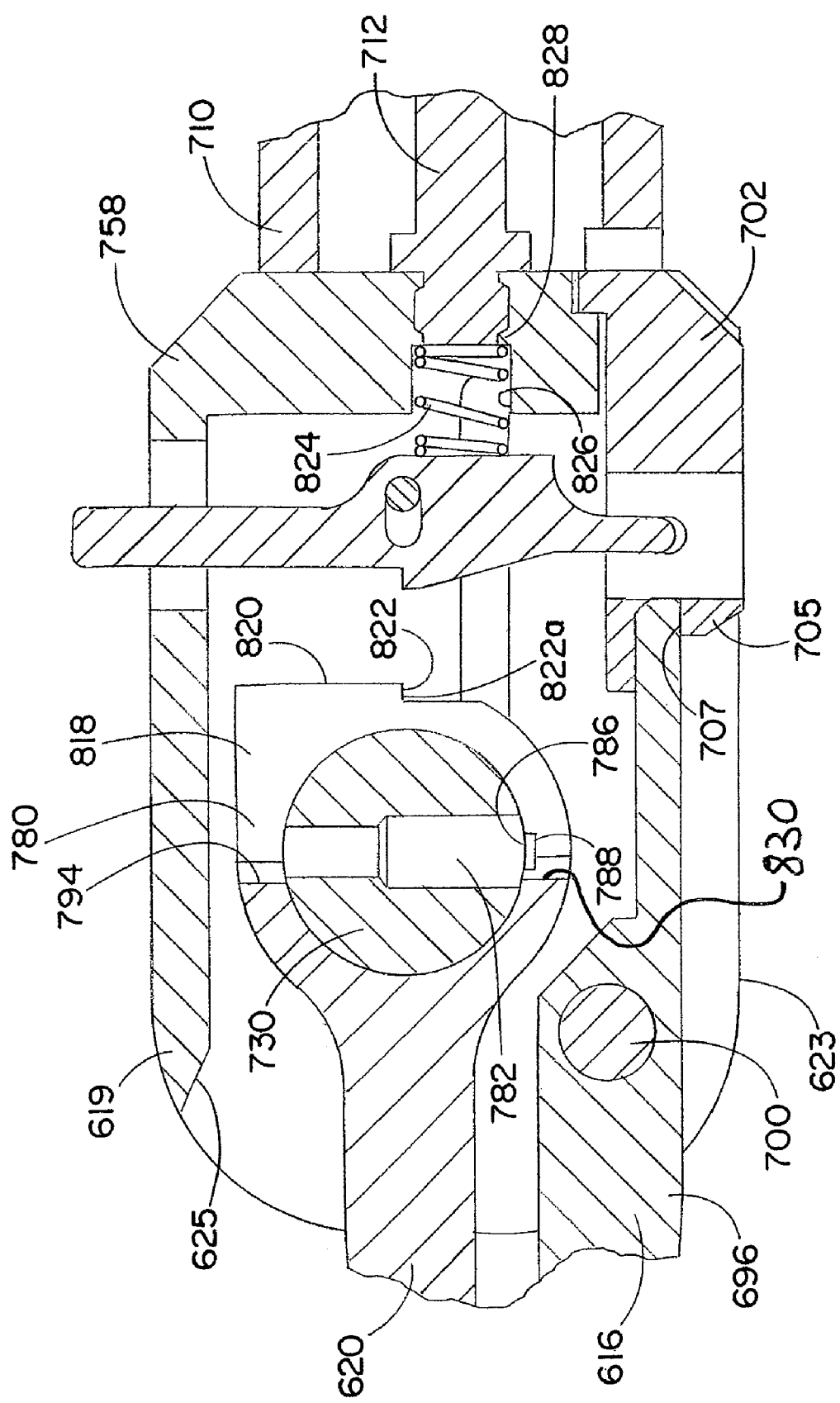
FIG. 58 is a top cross-sectional view of the housing of the inserter showing the steering control device and steering actuator in an orientation for holding the spacer at a 90 degree orientation relative to the longitudinal axis of the inserter.
Figure 59:
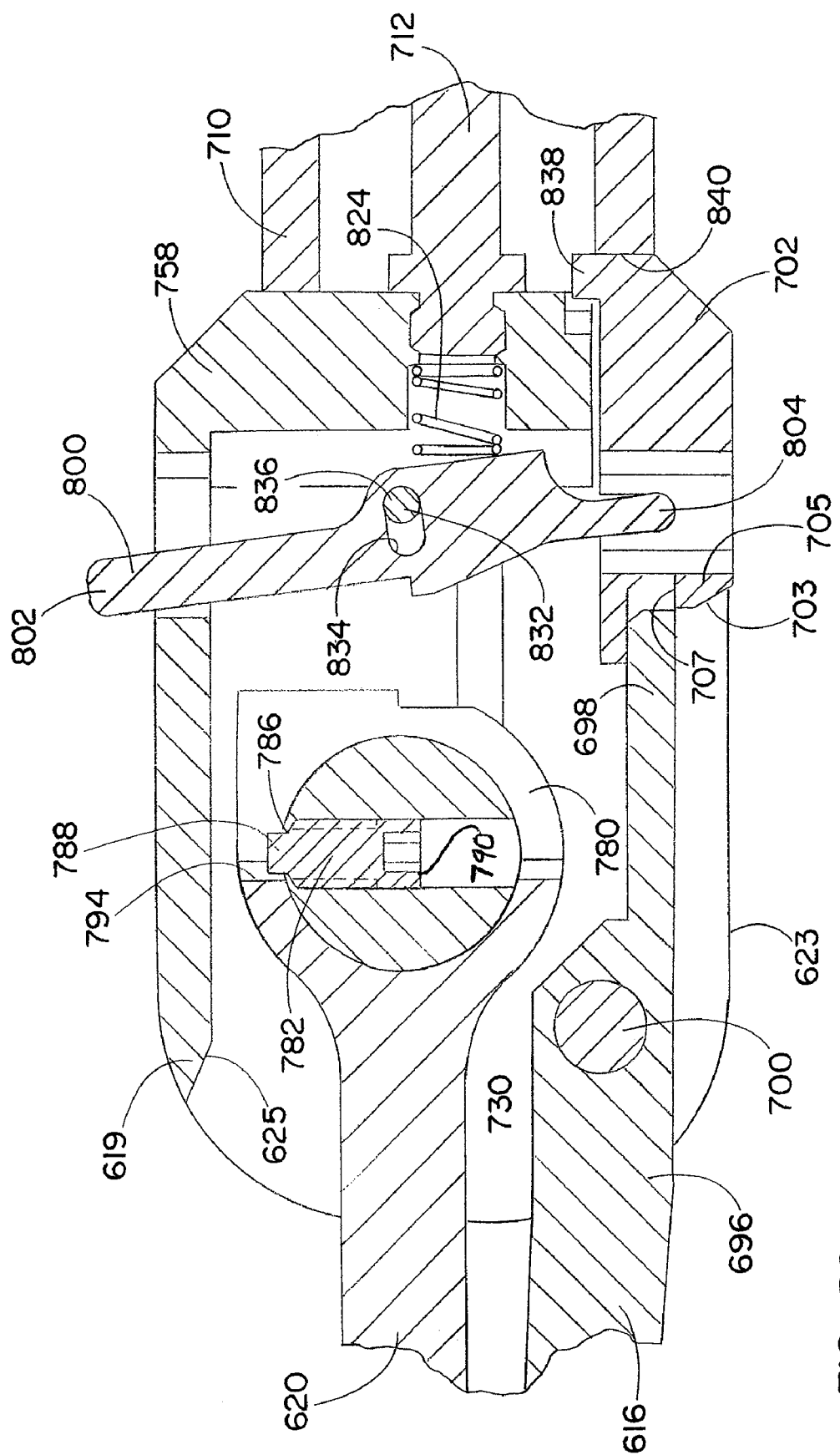
FIG. 59 is a top cross-sectional view of the housing of the inserter showing the inserter in a spacer changing orientation for connecting or disconnecting the spacer and the inserter.

Referring to FIGS. 57-59, the main member 616 has a second, elongate portion 696 extending rearwardly from the first portion 690 transverse to the longitudinal axis $L_m$ of the main member 616. The second portion 696 extends through the front 621 of the housing. An end 698 of the second portion 696 is pivotally mounted by a pin 700 to the housing 618. The pin 700 extends through a bore 750 in the end 698 and into two aligned apertures 752 and 754 of upper and lower walls 724 and 736 on the housing 618 as shown in FIG. 54. The housing 618 also has a right side wall 619 and a back wall 758 that connect the upper and lower walls 724 and 736 to each other while the front and left sides 621 and 623 of the housing 618 have a continuous opening 625 to receive the second portion 696 of the main member 616 and the drive arm 620.

To releasably secure the first portion 690, and in turn the gripping member 606, in parallel alignment with the longitudinal axis $L_a$ of the inserter 602 for pivoting of the spacer 600, the end 698 of the main member 616 engages a release slide 702 at the housing. The end 698 is secured within a retaining groove 705 formed on a front end 707 of the release slide 702. The release slide 702 is mounted on rails 704 (one is shown on FIG. 54) on two facing, interior lower and upper surfaces 706 and 708 of the housing 618. This permits the release slide 702 to slide parallel to the longitudinal axis $L_a$ of the inserter to be engaged or disengaged from the housing end 698 of the main member 616. Sliding the release slide 702 rearwardly and away from the housing end 698 of the main member 616 permits the main member to pivot for loading or unloading of the spacer 600.

Figure 55:
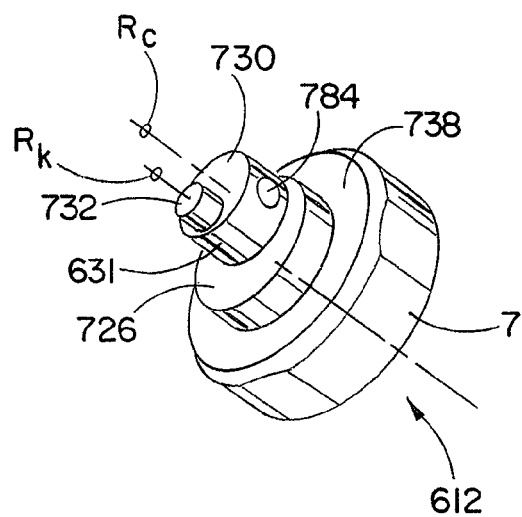
FIG. 55 is an enlarged perspective view of the control device showing an eccentric cam on a rotatable knob.

Referring now to FIGS. 54-55, the steering control device 612 is configured to provide a significant mechanical advantage so that pivoting the spacer 600 takes little effort. In order to accomplish this, the control device 612 has a relatively large knob 722 that fits comfortably in the surgeon's hand and need only be rotated about one-half turn or 180 degrees in order to pivot the spacer 600 through about 90 degrees. In addition, the control device 612 is configured for durability so to avoid damage thereto such as when the proximal end 714 of the inserter 602 is repeatedly impacted with a driving device or hammer.

For these purposes, the control device 612 includes an eccentric cam 730 relative to and extending on a large diameter shank 726. the eccentric cam 730 is connected to the drive arm 620 so that rotating the knob 722 in one direction such as clockwise will translate the drive arm 620 axially to pivot the spacer 600 toward the left side of the inserter 602. Pivoting the knob 722 in the opposite direction will return the spacer 600 to the straight, insertion orientation. The cam 730, knob 722 and shank 726 are durable due to their relatively large size. Thus, these components can withstand repeated driving impact forces applied to the inserter 602.

In more detail, the knob 722 is rotatably mounted on an exterior surface 627 of an upper wall 724 of housing 618. The shank 726 extends from a bottom surface 738 of the knob 722 that faces the upper wall 724 and through a large bore 728 in the housing upper wall 724. The cam 730 has a reduced diameter and has its center offset from the center of the shank 726 and the knob 722 thereabove. An axle portion 732 of the shank 726 extends distally from the cam 730 and is rotatably mounted in an opening 734 on the lower wall 736 of the housing 618 (shown in FIG. 51). The axle portion 732 is aligned along a central, rotational axis $R_k$ that extends through the center of the knob 722 and shank 726 offset from the center of the of the cam 730, as shown on FIG. 55. Accordingly, a central, rotational axis $R_c$ of the cam 730 extending through its center is displaced radially from the axis $R_k$ so that rotating the knob about axis $R_k$ eccentrically rotates the cam 730.

In order to connect the control device 612 to the gripping member 606, the drive arm 620 is operatively and pivotally connected to the cam 730 at rear end 622 thereof (as shown in FIGS. 57-59) and pivotally connected to a proximal end 742 of the gripping member 606 at the forward end 624 thereof. As shown in FIG. 51, the forward end 624 of the drive arm 620 has an opening 740 sized for receiving a reduced extension 744 of the gripping member 606 extending proximally therefrom. A pin 746 pivotally secures the extension 744 in the opening 740. The pin 746 extends through aligned apertures 748 at upper and lower sides of the opening 740 and through a bore 756 in the extension 744 as shown on FIGS. 51 and 54.

Referring to FIG. 57, for axially translating the drive arm 620 by rotating the cam 730, the end 622 of the drive arm 620 has an opening 776 formed by two opposing, partially spaced, upper and lower rings 778 and 780. The rings 778 and 780 are rotatably mounted about an outer cylindrical surface 631 of the cam 730 and coaxially to rotational axis $R_c$ of the cam 730. The rings 778 and 780 are axially separated from each other along slightly more than half of their circumference and on a rear-most portion 633 of the rings. Thus, an arcuately extending, backward C-shaped slot 794 is formed between the ring 778 and 780 and at the rear-most portion 633.

The rings 778 and 780 and the cam 730 are secured to each other within housing 618 by a threaded screw 782. So secured, the cam 730 and knob 722 cannot be pulled off of the upper wall 724 of the housing 618 through the large bore 728 thereof, and the drive arm 620 cannot be pulled out of the front 621 of the housing 618. For these purposes, the screw 782 has a reduced diameter end portion 788 opposite a driver receiving, enlarged head end 790. The screw 782 is threadedly engaged within a throughbore 784 extending diametrically through the cam 730 and orthogonally to axis $R_c$. The bore 784 has a reduced diameter opening 786 to retain the screw within bore 784 except for the reduced diameter end 788 which extends out of the bore 784 and into the slot 794 formed between the rings 778 and 780. The diametric bore 784 has an enlarged diameter portion to form a seat 792 for the screw end 790 in the bore 784, as shown in FIG. 59.

Referring to FIGS. 57-59 and 65-67, the cam 730 is eccentric so that rotating the knob 722 varies the longitudinal position of the cam 730 relative to the longitudinal axis $L_a$ of the inserter 602. Since shifting the cam 730 axially translates the drive arm 620 and in turn the gripping member 606, shifting the cam changes the axial distance between the distal end 608 of the gripping member 606 holding the spacer body 730 and the axially fixed, distal end 628 of the main member 616 holding the link 650, which pivots the spacer.

In order to orient the spacer 600 in the straight orientation, also referred to herein as the 0 degree orientation as shown in FIGS. 57 and 65, the knob 722 may be rotated counterclockwise to place the cam 730 in its farthest rearward position closest to the back wall 758 of the housing 618. The rotation of the cam 730 axially translates the drive arm 620 and in turn the gripping member 606 rearward and relative to the main member 616. This positions the link 650 and the spacer body 730 in the straight or 0 degree orientation.

Also in the 0 degree orientation, a right end 796 of the slot 794 between the rings 778 and 780 is configured to abut the reduced diameter end portion 788 of the screw 782 to limit further counter-clockwise rotation of the cam 730 as shown in FIG. 57. The rotation of the cam 730 is limited to less than a full 360 degree rotation in order to releasably lock the inserter 602 in the 0 degree orientation as explained below.

Figure 70:
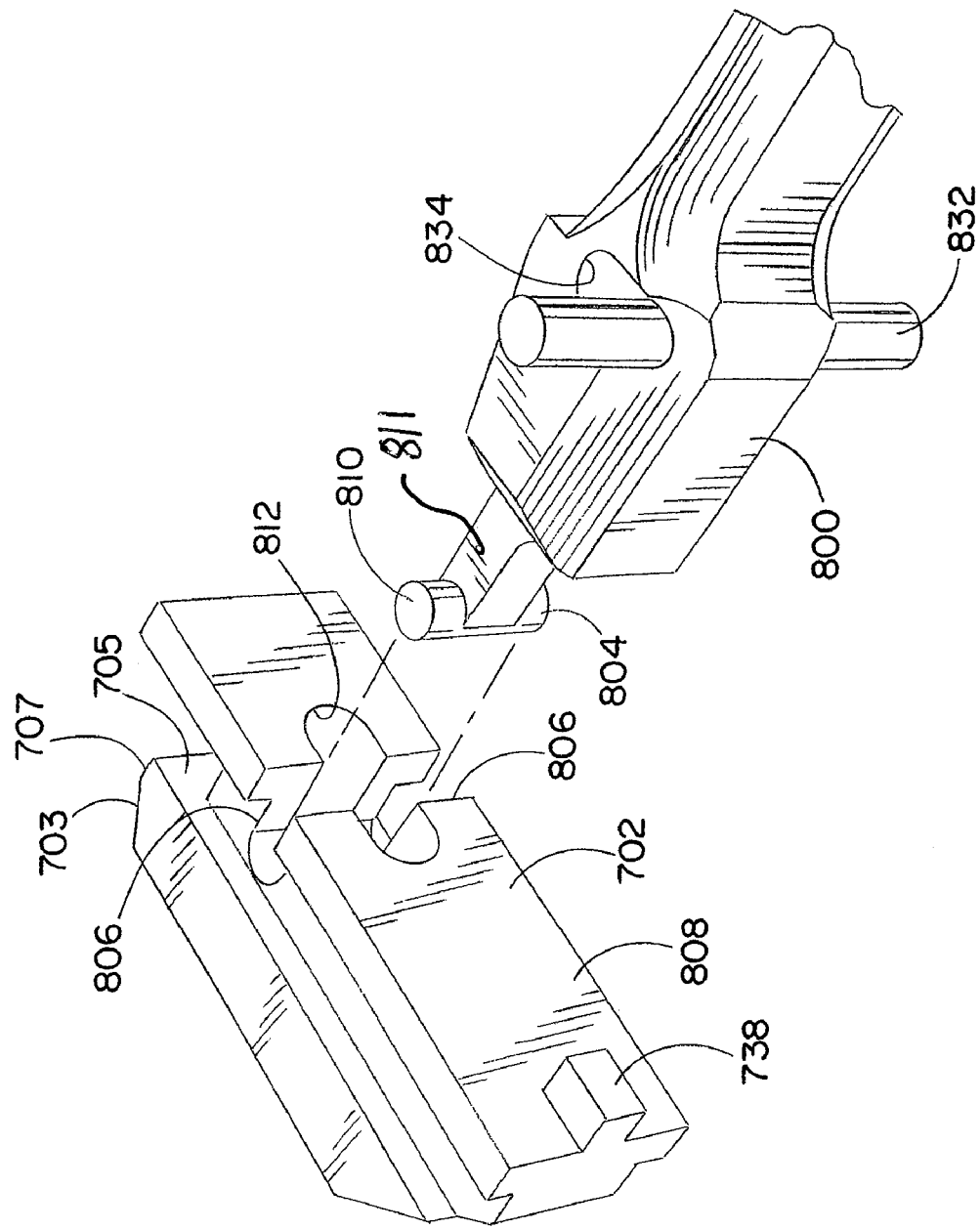
FIG. 70 is an enlarged perspective view of a locking lever and a release slide showing grooves on the release slide for engaging the locking lever.

Referring to FIGS. 57 and 70, a locking actuator or lever 800 is provided to lock the control device 612 and in turn the spacer 600 at the 0 degree or straight orientation to avoid unintentional axial translation of the drive arm 620 and in turn gripping member 606 during initial insertion of the spacer 600 through the annulus incision and into the nuclear or intervertebral space. For this purpose, the locking lever 800 is pivotally mounted within the housing 618 and has a user accessible actuator end 802. The actuator end 802 extends out through an opening 798 in the right side wall 619 of the housing 618. While disposed in the 0 degree orientation, the locking lever 800 is biased toward the drive arm 620 and has structure for engaging and retaining the drive arm which in turn retains the cam 730. So engaged, the cam 730 cannot rotate to translate the drive arm 620. To turn the knob 722 and rotate cam 730, the user shifts the actuator end 802 of the locking lever 800 rearwardly to disengage the locking lever 800 from the drive arm 620.

In the illustrated and preferred form, the locking lever 800 has a T-shaped, left end 804 opposite the actuator end 802 including a pivot pin 810 that engages the release slide 702 as shown in FIG. 70. The pin 810 fits in a groove 806 that extends transversely in an up and down direction relative to longitudinal axis $L_a$. The groove 806 opens on a right-side surface 808 of the release slide 702 facing the locking lever 800. The release slide 702 also has a longitudinally extending groove 812 that extends orthogonally through groove 806. Groove 812 provides clearance for the locking lever 800 to pivot about pin 810 with arm 811 of T-shaped end 804 swinging in the groove 812 in a direction parallel to the longitudinal axis $L_a$ of the inserter 602.

Referring to FIGS. 57 and 58, to engage the rings 778 and 780, the locking lever 800 also has a laterally facing shoulder 814 extending forwardly from a front surface 816 that faces the rings. The rings 778 and 780 both have symmetrical, rearwardly extending projections 818. The projections 818 each have an outer edge 820 with a notch 822. Each notch 822 has a laterally facing surface 822a disposed for being selectively engaged by the ledge 814 on the locking lever 800.

To bias the locking lever 800 forward and toward the drive arm 620, a coil spring 824 is placed behind the locking lever 800 in a bore 826 formed in the back wall 758 of the housing 618 where it abuts a radially inwardly extending ring portion 828. This biases the shoulder 814 into locking engagement with the notches 822 to limit clockwise rotation of the cam 730 for locking the cam 730 as seen in FIG. 57. In this configuration, the screw 782 extends laterally from left to right and abuts the end 796 of the slot 794 which limits counter-clockwise rotation of the cam 730 to provide a defined stop position with the trial spacer at its 0° orientation. In this manner, continued clockwise rotation of the cam 730 and with the knob 722 is blocked which would otherwise shift the cam 730 forwardly and away from the locking lever 800 so that it could not lock the cam 730 against rotation. So configured, the cam 730 cannot rotate about axis $R_k$ and, therefore, the inserter 602 is locked.

Also in the straight orientation, with the gripping member 600 and drive arm 620 axially locked, the inserter 602 is set to receive forwardly directed driving forces as mentioned above. Thus, to receive hammer blows at the proximal end 714 of the inserter 602, the driving shaft 712 is directly connected to a back wall 758 of the housing. So configured, hitting the shaft 712 with a driving tool, transfers a driving force in order through the shaft 712 and housing 618 and then through the shank 726 and cam 730, and in turn, through the drive arm 620, gripping member 606, and spacer 600.

As shown in FIG. 57, for securing the driving shaft 712 to the back wall 758 of the housing 618, the driving shaft 712 has a threaded end 760 received by a rearwardly open, internally threaded bore 762 in the back wall 758 aligned with spring bore 826 forwardly thereof. In order to dissipate the driving force and transfer it over a wide area on the back wall 758 rather than just through the threaded end 760, the shaft 712 also has a forward widened, force-distribution collar portion 764. The collar portion 764 is adjacent the threaded end 760 and disposed to abut an exterior surface 766 of the back wall 758. As shown in FIG. 54, the proximal end 768 of the shaft 712 has a widened impact receiving end 770 to make it an easier target to hit or to attach to hammering devices. A rearward, widened force distribution ring 772 of the shaft 712 abuts against the proximal end 774 of the handle 710 to retain the handle on the housing 618 while distributing some of the driving force through the handle and to the back 758 of the housing 618.

Referring to FIGS. 65-67, shifting the actuator end 802 of the locking lever 800 rearward in a direction away from the drive arm 620 releases the drive arm and in turn the cam 730 to be rotated clockwise about axis $R_k$ so that the spacer 600 can be pivoted by the knob 722. Pulling the actuator end 802 rearward shifts abutment shoulder 814 of the locking lever 800 rearward to clear the outer ends of the notch surfaces 822a of the drive arm 620 to allow the clockwise rotation of the knob 722. This shifts the notches 822 farther to the left and forward of the locking lever 800 where the locking lever 800 and specifically the abutment shoulder surface 814 thereof cannot engage in the notches 822. The locking lever 800 can then be released without locking the drive arm 620.

Turning the knob 722 clockwise rotates the cam 730 in a circular path about axis $R_k$ and toward the front 621 of the housing 618. This motion translates the drive arm 620 and gripping member 606 forwardly to pivot the spacer 600. Since the knob 722 is not biased to rotate to any particular orientation, the surgeon can let go of the knob 722, and the inserter 602 will hold a present position of the spacer 600.

Referring to FIGS. 58 and 67, in the illustrated and preferred form, turning the knob 722 a half-turn or about 180° from its 0 degree orientation places the cam 730 in its most distal or forward position. In this configuration, the lengths of the actuator members 606, 620, 650 and 616 for the spacer 600 are sized so that at the forward-most position of the cam 730, the spacer 600 is limited to pivoting about 90 degrees relative to the longitudinal axis $L_a$ of the inserter 602. The slot 794 extends approximately 180° about the rings 778 and 780 of the drive arm 620 so that a second, left end 830 of the slot 794 is disposed generally diametrically opposite the first end 796 of the slot 794. Accordingly, the left end 830 will abut the screw 782 on the cam 730 to limit further clockwise motion of the cam 730 with the knob turned 180° to provide a defined stop position with the trial spacer at its 90° orientation.

In another aspect of the preferred embodiment, providing the link 650 on the spacer 600 permits a surgeon to quickly and conveniently connect the spacer 600 to the inserter 602 as well as disconnect the spacer 600 from the inserter 602 for interchanging with different sizes of spacers 600a-c (FIGS. 53A-53B). In contrast to prior systems, present inserter 602 does not require inserting fasteners into small bores or the tightening or loosening of any screws (or requiring multiple inserters for the spacers) for interchanging trial spacers during the surgical procedure while the patient is under anesthesia and the nuclear space on the patient is accessible to the surgeon. To accomplish this, each spacer 600 in a set of spacers is preassembled with the link 650, the first and second link pins 664 and 678 and the grip pin 656. Thus, all three pins 656, 664 and 678 are pre-connected to their respective apertures in bores on the upper and lower walls 652 and 654 of the spacer body 630 and the upper and lower walls 672 and 674 of the link 650 such as by threading a press fit thereon.

Figure 60:
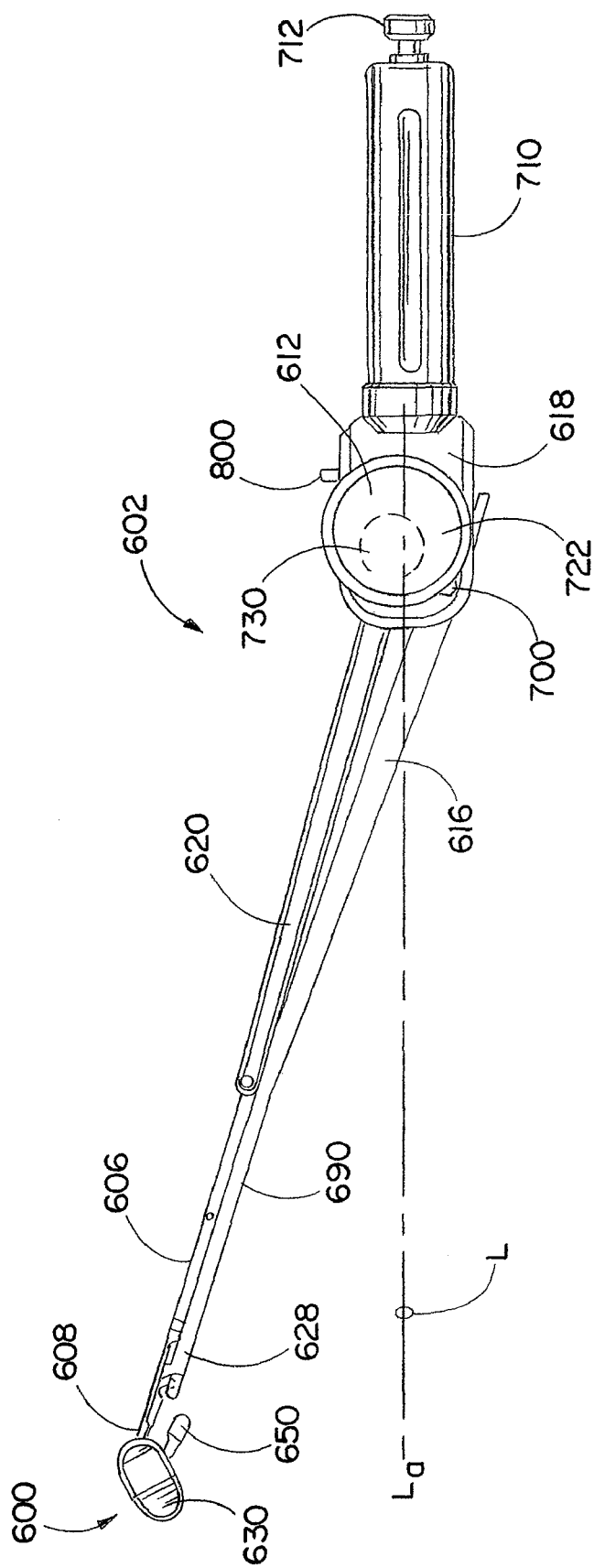
FIG. 60 is a plan view of the inserter and the spacer showing the spacer partially connected to the inserter.

To load the preassembled spacer 600 on the inserter 602, the surgeon need only mount the spacer main body 630 and link 650 on the inserter 602 while the inserter 602 is configured in a spacer changing orientation as shown in FIG. 60. The surgeon then shifts the main member 616 back to a straight orientation to be operable for inserting the spacer into the intervertebral space as has been described in order to automatically and releasably secure the spacer 600 to the inserter 602. The process is performed in reverse to remove the spacer 600 from the inserter 602 as explained in more detail below.

In the preferred embodiment, in order to first load a spacer 600 onto the inserter 602, the inserter 602 needs to be shifted to other than its 0° orientation. As shifted, the inserter is in the spacer changing orientation by pivoting the main member 616 to the right of longitudinal axis $L_a$ as shown in FIG. 60. In this orientation, the gripping member 606 is translated further forward or more distally than its axial position for holding the spacer in its 90 degree (FIG. 64) orientation. As explained above, the cam 730 limits further translation of the gripping member 606 past the 90 degree orientation while the main member 616 retains the gripping member 606 parallel to the longitudinal axis $L_a$ of the inserter 602. The main member 616 and in turn the gripping member 606 cannot pivot away from longitudinal axis $L_a$ while they are operably secured to the release slide 702.

In order to disengage the release slide 702 from the main member 616, the locking lever 800 is pivoted about pin 832 to shift the release 702 rearward and away from the main member 616. The locking lever 800 is pivotally mounted to the pin 832 that extends from the lower to the upper walls 736 and 724 of the housing 618. The pin 832 extends transversely to the length of the actuating lever 800 within a generally axially extending slot 834 formed on lever body 801 generally centrally located along the length of the locking lever 800 as shown in FIG. 70. The slot 834 extends generally along the longitudinal axis $L_a$ of the inserter 602 so that the locking lever 800 is free to translate back and forth over the pin 832 when the lever 800 is operated to selectively shift the drive arm 620 pivoting about the end pin 810 as described above for the steering operation.

Accordingly, the locking lever actuator 800 is operable for two different functions. One function is to release the cam when pivoting the lever 800 about the pin 810 with the intermediate pivot pin 832 shifting in slot 834 as necessary. The other function is to actuate the release slide 702 while pivoting the lever arm 800 about intermediate pivot pin 832 biased against the rear end of the slot 834 to allow unloading and loading of the spacer body 630 from and to the inserter 601.

Referring to FIG. 59, as mentioned previously, the drive arm 620 is disengaged from the locking lever 800 when the knob 722 is rotated to the 90 degree orientation. In this orientation, the locking lever 800 is biased forward by the spring 824 until the pin 832 extending through the central slot 834 in the locking lever body 801 is biased against a rear end 836 of the central slot 834. So configured, a user can press the user operated end 802 of the locking lever 800 forward and toward the spacer 600 to pivot the locking lever 800 about the pin 832. This operation rearwardly shifts the end 804 of the locking lever 800 which in turn shifts release slide 702. A projection 838 extends from the interior side surface 808 of the release slide 702 and is retained in a corresponding opening 840 in the handle 710 and engages a rear stop surface 840*a* thereof to limit rearward motion of the release slide 702.

Once the release slide 702 is shifted to this rearward position, the housing end 698 of the main member 616 is shifted out of and released from the channel 705 at the front end 707 of the release slide 702. With the release slide 702 disengaged, a surgeon can then manually pivot or swing the main member 616 laterally left and right relative to the longitudinal axis $L_a$ of the inserter 602 and about its pivot pin 700 fixed to the housing 618. For explanatory purposes, the longitudinal axis $L_a$ of the inserter 602 is defined to remain fixed relative to the housing 618 while the main member 616 and gripping member 606 swing out of parallel alignment with the longitudinal axis $L_a$ as explained below.

Referring to FIG. 60, since the gripping member 606 is secured to the main member 616, the swinging of the main member 616 causes the gripping member 606 and drive arm 620 to swing with the main member 616 while the drive arm 620 pivots about the cam 730. Swinging main member 616 away from longitudinal axis $L_a$ causes the gripping member 606 to translate axially forward relative to the main member 616 and distally into the spacer changing orientation shown in FIG. 60. This is due to the gripping member 606 being axially secured to the drive arm 620 so that the central axis about which the gripping member is pivoted is at the cam 730. Since the gripping member 606 and main member 616 have different but fixed centers of rotation (e.g., the cam 730 versus the pin 700, respectively), swinging the main member 616 clockwise or to the right and toward the gripping member 606 in FIG. 60 causes the gripping member to axially translate forward relative to the main member 616. A disassembly lock 910 limits axial translation of the gripping member 606 past in the spacer changing orientation, and will be described more fully hereinafter.

In order to mount the spacer body 630 on the gripping member 606 once the gripping member 606 is in the spacer changing orientation, a surgeon first uses his fingers or a tool to manually place the grip pin 656 of the spacer body 630 on the hook 660 at the distal end 608 of the gripping member 606 as shown on FIG. 61

For mounting the second end 668 of the link 650 on main member 616, the gripping member 606 has a locating portion 842 to hold the second link end 668 in an orientation for being automatically and subsequently shifted to engagement with a holding portion 844 on the main member 616 that secures the link 650 for pivoting the spacer 600. As shown in FIGS. 61 and 62A, the locating portion 842 is axially and rearwardly displaced from the hook 660 on the gripping member 606.

Referring to FIG. 56, the locating portion 842 includes a notch 846 that opens on the left side 848 of the gripping member 606 and that faces the main member 616 during the pivoting of the spacer 600. In the spacer changing orientation, the notch 846 is positioned forwardly of the distal end 628 of the main member 616 where it is accessible as shown in FIG. 61. So positioned, a surgeon is able to manually place the second link pin 678 in the notch 846.

In order to assist in locating and placing the second link pin 678 in the notch 846, the distal end 608 of the gripping member 606 and the link 650 are configured with locating structure to align pin 678 with the gripping member in a transverse superior-inferior direction. For this purpose, the upper and lower walls 672 and 674 of the link 650 extend radially outward from the second link pin 678 as shown in FIG. 53. This respectively forms an overhang or setback 682 and 684 on the walls 672 and 674 that extends from outer edges 686 and 688 of the walls to the second link pin 678.

To cooperate with this structure, the distal end 608 has a reduced thickness portion 876 forming notch 846. The reduced thickness portion 876 is configured to fit between upper and lower walls 672 and 674 of link 650. Thus, the distal end 608 has a first recess 862 formed by an upwardly facing surface 860 and recessed downward from a top surface 861 as shown in FIG. 56. Similarly, the distal end 608 has a second recess 872 formed by a lower surface 874 recessed upward from a bottom side or surface 886 as shown in FIG. 61. The first and second recesses 862 and 872 form the reduced thickness wall or portion 876 therebetween. The recesses 862 and 872 also respectively provide clearance for the upper and lower walls 627 and 674 of link 650. The reduced thickness portion 876 extends longitudinally along distal end 608 and forms a distal portion of the left side 848 of the distal end 608. So structured, the second link pin 678 can be placed against and shifted along left side 848 to shift the pin 678 into notch 846.

For automatically shifting the second link pin 678 from the notch 846 to the holding portion 844 for pivoting the spacer 600, a surgeon swings the main member 616 counterclockwise or back toward the left and closer to the longitudinal axis $L_a$ of the inserter. More specifically, this swings the front portion 690 to extend closer to parallel to the longitudinal axis $L_a$.

The holding portion 844 is the groove 627 at the distal end 628 of the main member 616 that receives the second link pin 678 for pivoting and securing the spacer 600. The swinging of the main member 616 to the left translates the gripping member 606 rearwardly relative to the main member 616 which eventually aligns the opening 629 of groove 627 with the notch 846 as shown in FIG. 62A. This orientation is also used to shift the second link pin 678 back to the notch 846 from the groove 627 to unload the spacer.

Referring again to FIG. 56, the inserter 602 includes shifting structure 850 that shifts the second end 668 of the link 650 from engagement with the notch 846 to engagement with the groove 627 when loading a spacer 600 onto the main member 616. For automatic operation, the shifting structure 850 is configured so that swinging of the main member 616 back toward the longitudinal axis $L_a$ causes the shifting structure 850 to axially translate and press against the second end 668 of the link 650. With this motion, the shifting structure 850 cams the second end 668 from the notch 846 to the groove 627. This process is reversed to remove the spacer 600.

In one preferred form, the shifting structure 850 includes an engagement hook or protrusion 852 extending from main member 616 and a disengagement protrusion 854 extending from the gripping member 606. The protrusions 852 and 854 are respectively configured to engage curved outer edges 686 and 688 of the upper and lower walls 672 and 674 of the second link end 668.

The engagement protrusion 852 is connected to the main member 616 and may be integrally formed with the main member 616 so that the engagement protrusion 852 translates with the main member 616. The engagement protrusion 852 also extends laterally from a longitudinal, right side 856 of the main member 616 and toward the gripping member 606. Further, the engagement protrusion 852 extends from a top side 858 of the main member 616 and over the upwardly facing surface 860 of first recess 862 on the distal end 608 of the gripping member 606. The first recess 862 has a longitudinally extending back wall or shoulder 864 that extends upward from the upwardly facing surface 630. The shoulder 864 opposes a translating, pointed tip 866 of the engagement protrusion 852 to protect anatomical structure such as the annulus from the tip. So configured, axially translating the engagement protrusion 852 along the first recess 862 and toward the notch 846 on the gripping member 606 causes the engagement protrusion 852 to engage the outer edge 686 of the upper wall 672 on the link 650.

For engaging and shifting the upper wall 672, the engagement protrusion 852 is generally cusp-shaped with a concave, curved, front edge 868 that corresponds to the curve of the upper wall 672 as shown in FIG. 62A. As shown in FIG. 56, the front edge 868 extends from the main member 616 at a location slightly rearward and set back from the notch 846 on the gripping member 616 in order to match the overhang 682 on the second link pin 678. This permits the front edge 868 of the engagement protrusion 852 to engage the outer edge 868 of the upper wall 672 while the second link pin 668 is still disposed in the notch 846 on the gripping member 606.

In order to fit the distal end 628 of the main member 616 between the upper and lower walls 672 and 674 of link 650, the front edge 868 also extends upwardly from a reduced thickness end portion 869 on distal end 628. The reduced end portion 869 forms the groove 627 and has a reduced thickness to fit between the upper and lower walls 672 and 674 while the second link pin 678 is engaged in the groove 627. The reduced thickness end portion 869 is formed between a bottom recess 878 and a top recess 870 on distal end 628. The bottom recess 878 is formed by a downwardly facing surface 880 recessed upward from a bottom surface 879 of the main member 616 as shown on FIG. 61. The top recess 870 is formed by an upwardly facing surface 871 recessed downward from an upper surface or side 858 of the main member 616. The bottom recess 878 also has an elongate, axially extending shoulder 882 to cover an axially translating tip 884 (shown on FIG. 56) of the disengagement protrusion 854 that slides on the bottom recess 878.

Referring to FIG. 62A, once the second link pin 678 is disposed in the notch 846 and the upper wall 672 of the link 650 is disposed over the notch 846, the second end 668 of the link 650 is set to be automatically shifted from the notch 846 to the groove 627. With this configuration, continued counterclockwise swinging of the main member 616 toward longitudinal axis $L_a$ and translation of the main and gripping members 616 and 606 causes the engagement protrusion 852 to engage and advance the upper wall 672 of the link 650. This in turn causes the second link pin 678 to engage an axially forward, tapered edge 847 of the notch 846. The tapered edge 847 extends toward the left side 848 of the gripping member 606 as the tapered edge 847 extends forwardly or distally. Thus, translating the engagement protrusion 852 forward shifts the second link pin 678 forwardly and against the tapered edge 847. This action slides or cams the second link pin 678 laterally toward the main member 616.

When the second link pin 678 engages the tapered edge 847, the gripping member 606 and main member 616 have translated so that the notch 846 on the gripping member 606 opposes the groove 627 on the main member 616 as shown in FIG. 62A. Further translation and advancement of the engagement protrusion 852 causes the protrusion 852 to press the second link pin 678 out of the notch 846 and into the groove 627 on the main member 616.

After the second link pin 678 is engaged in the groove 627 on the main member 616, swinging the main member 616 closer to the longitudinal axis $L_a$ of the inserter 602 places the housing end 698 of the main member 616 in position for reengagement with the release slide 702. Even though the release slide 702 is biased forward by spring 824 and locking lever 800, the main member 616 can be swung until its housing end 698 overcomes the forwardly directed bias force of the release slide 702 and snaps into the groove 705 on the release slide 702. The front end 707 of the release slide 702 has a tapered surface 703 that extends forwardly as it extends laterally and toward the groove 705 on the release slide 702. So configured, the housing end 698 of the main member 616 cams against surface 703 and presses the release slide 702 rearward as the housing end 698 is swung into the housing 618 and then snaps into the groove 705.

In order to remove the spacer 600 from the inserter 602, the disengagement protrusion 854 is configured to automatically shift the second link pin 678 from the groove 627 of the holding portion 844 into the notch 846 of the locating portion 842. Once in the locating portion 842, the second link pin 678 is accessible to be manually removed from the notch 846 by a surgeon grasping the link 650 with his fingers or a grasping tool.

To perform the shifting operation, the main member 616 and gripping member 606 are swung to the spacer changing orientation (FIG. 60) from the pivoting orientation as explained above. This translates the gripping member 606 axially and forwardly relative to the main member 616. As the gripping and main members 606 and 616 translate relative to each other and into the spacer changing orientation, the disengagement protrusion 854 is axially translated forward to engage and shift the second end 668 of the link 650.

Referring to FIGS. 56 and 62B, for engaging the lower wall 674 of link 650, the disengagement protrusion 854 is generally cusp-shaped and extends from the bottom side 886 and the left side 848 of the gripping member 606. The disengagement protrusion 854 also extends transversely relative to the longitudinal dimension of the gripping member 606 and underneath bottom surface 878 of the main member 616.

A front edge 888 of the disengagement protrusion 854 is slanted or curved relative to the longitudinal axis $L_m$ of the first portion 690 of the main member 616. The front edge 888 slants distally or forward as it extends transversely outward from the left side 848 of the gripping member 606. The front edge 888 provides this configuration to engage and direct, or more specifically cam, the lower wall 674 toward notch 846 on the gripping member 606 as the front edge 888 is translated forward. The front edge 888 also is set back slightly rearward from the notch 846 on the gripping member 616 to match the setback 684 on the lower wall 674 from the second link pin 678 to the outer edge 688 of the lower wall 674.

So configured, when swinging the main member 616 toward the spacer changing orientation, the disengagement protrusion 854 is translated with the gripping member 606 and forwardly against the lower wall 674 of the link 650. While the disengagement protrusion 854 engages the lower wall 674, the groove 627 on the main member 616 is aligned with the notch 846 on the gripping member 606. As shown in FIG. 62B, further translation of the gripping member 606 causes the front edge 888 of the disengagement protrusion 854 to shift or cam the lower wall 674 toward the gripping member 606 and over the notch 846. This in turn shifts the second link pin 678 from the groove 627 to the notch 846.

Once the inserter 602 is configured in the spacer changing orientation as shown in FIG. 60 and the second link pin 678 is shifted to the notch 846 on the gripping member, the gripping member 606 has translated the notch 846 past and axially forward of the distal end 628 of the main member 616 as shown in FIG. 61. The notch 846 is then accessible for a surgeon to manually remove the second end 668 of the link 650 from the notch 846.

Once the second end 668 of the link 650 is removed from the notch 846, the spacer body 730 is free to pivot about the grip pin 656 still grasped by the hook 660. The spacer body 730 as well as the link 650 can be pivoted clockwise, for the present embodiment, until the hook 660 has sufficient clearance within the pocket 646 as explained previously to be disengaged from the grip pin 656 on the spacer 600. A different spacer 600 can then be quickly and conveniently loaded on the inserter 602 as explained above.

Referring again to FIG. 61, the front edge 888 of the disengagement protrusion 854 also is disposed and configured to aid the surgeon in directing the link 650 toward the notch 846 when the surgeon is first loading a new spacer 650 onto the inserter 602. For this reason, the front edge 888 of the disengagement protrusion 854 is continuous with a shoulder 890 that extends downward from the bottom surface 874 of the second recess 872 of the gripping member 606. The shoulder 890 also extends generally axially along the gripping member 606 and axially forward of the front edge 888. The shoulder 890 and front edge 888 connect to cooperatively form a concave, curved surface 892. This structure permits a surgeon to push the lower wall 674 of the second end 668 of the link 650 against the curved surface 892 to cam or shift the lower wall 674 toward and over the notch 846. This in turn shifts the second link pin 678 into the notch 846. Thus, the curved surface 892 is contoured to extend generally toward the notch 846 and then around the notch 846 but at a distance from the notch 846 that corresponds to the length of the setback 684 described above.

Referring now to FIGS. 68-69, the inserter 602 is configured for easy disassembly while minimizing the risk of unintentional disengagement of the gripping member 606 from the main member 616. As mentioned above, in order to laterally secure the gripping member 606 to the main member 616, locking protrusion 692 extends from the left side surface 848 of the gripping member 606 and is engaged within locking slot 644 on the main member 616.

In a preferred form, the protrusion 692 has a neck 894 and an enlarged end 896 received within slot 694. The slot 694 which is formed on the right side surface 856 of the main member 616 that faces the gripping member 606. To releasably secure the gripping member 606 to the main member 616 during pivoting of the spacer 600 or while spacers 600 are being replaced on the inserter 602, the locking slot 694 has two opposing lip flanges 900 that extend in parallel and axially along a track portion 902 of the slot 694. The lip flanges 900 are spaced from each other on opposite sides of the neck 894 of the protrusion 692 with the neck 894 therebetween so that the enlarged head resides laterally of each lip flange 900. So configured, the head 896 does not have clearance to pass between the lip flanges 900 and is therefore retained by the lips 900 in the slot 894. The lip flanges 900 are spaced sufficiently from the neck 894 to still permit the protrusion 692 to translate axially between them. In order to disassemble the members 606 and 616 from each other, a non-flanged open portion 906 of the locking slot 694 is provided. Thus, a user can translate protrusion 692 to the non-flanged open portion 906 by swinging the main member 616, as explained above, to remove the protrusion 692 from the locking slot 694.

To minimize the risk of unintentional disengagement of the gripping member 606 from the main member 616, a disassembly lock 910 on the gripping member 606 extends into the main member 616 and selectively retains the locking protrusion 692 along the lipped portion 902 of the locking slot 694. For this purpose, the disassembly lock 910 includes an elongate body 908 with a central portion 898 pivotally mounted on a pin 912. The pin 912 extends laterally left and right relative to longitudinal axis $L_a$ and within a cavity 914 on the gripping member 606 that receives the disassembly lock 910. The cavity 914 opens on the left side 848 of the gripping member 606 and opens to a corresponding recess or chamber 916 open on right side 856 of the main member 616. The chamber 916 extends axially along the main member 616 and is disposed rearwardly or proximally from the locking slot 694. The chamber 916 is separated from the locking slot 694 by a chamber wall 918 that forms the distal end of the chamber.

In order to retain the protrusion 692 on the lipped portion 902 of the locking slot 694, the body 908 of the disassembly lock 910 has an end 920 with a projection 922 for extending into the chamber 916 and abutting the chamber wall 918. A tapered, coil spring 930 biases the body 908 to a pivoted position about pin 912 that extends the projection 922 into chamber 916.

For disengaging the disassembly lock 910, the body 908 has a button end 924 that can be depressed to pivot the disassembly lock 910 and release the projection 922 from the chamber 916. The button end 924 is disposed opposite the projection end 920 on the body 908 and is accessible to a user through an opening 926 on the right side surface 928 of the gripping member 606. The tapered coil spring 930 is disposed under the button end 924 and on a bottom surface 932 of the cavity 914 to bias projection 922 into the chamber 916. Tabs 934 (only one is shown) on opposite sides of the disassembly lock 910 are disposed to engage two corresponding ledges 936 at the opening 926 on the right side 928 of the gripping member 606. The ledges 936 engage the tabs 934 to retain the tabs 936 and the button end 924 in the opening 926 of the cavity 914.

In the preferred form, the gripping member 606 also has a second projection 938 extending from the left side 848 of the gripping member 606 and that is received by the chamber 916. The second protection 938 is free to translate axially within the chamber 916 and is provided to maintain the gripping member 616 in transverse upward and downward (superior-inferior) alignment with the main member 616.

In operation, in order to separate the gripping member 606 from the main member 616 for disassembly of the inserter 602, the main member 616 is disengaged from the release slide 702, and the main member is swung toward the spacer changing orientation (FIG. 60) which translates the gripping member 606 forward as explained previously. The gripping member 606 translates forward until the projection 922 of the disassembly lock 910 abuts the chamber wall 918 which limits further forward translation of the gripping member 606. Then, depressing the button end 924 of the disassembly lock 910 pivots the disassembly lock 910 about the pin 912 which retracts the projection 922 from the chamber 916. The gripping member 606 can then be translated until the locking protrusion 692 is aligned with the non-lipped portion 906 of the locking slot 694 for removing the protrusion 692 from the locking slot 694.

Referring now to FIGS. 71-81, in another embodiment, a system for replacing a natural nuclear disc may include an insertion tool 1000 capable of steering a spinal device in at least one predetermined increment. Like the embodiment described in FIGS. 50-70, the present embodiment includes a spinal device such as a trial spacer 600 that is adjustably held on a distal end 1002 of the insertion tool 1000 or holder for being actively steered thereby. The inserter 1000 is used to insert and steer the spacer 600 into the intervertebral space to determine the size of the intervertebral space, and then steer and retract the spacer 600 from the intervertebral space. Additional structural details, such as the geometry of the trial spacer 600 and the manner in which the trial spacer 600 is connected to and removed from the inserter 1000 are similar to the embodiment disclosed above. However, one principal distinction of the present embodiment from the embodiments described in FIGS. 50-70 is in the steering mechanism or system 1004, which will be described in greater detail below.

As opposed to the insertion tool as described above, in which the steering control device is embodied by a knob 722 combined with an eccentric cam 730 which engages the drive arm 620 to allow for continuous adjustment of the trial spacer position, the steering control device 1004 of the present embodiment allows for incremental positional adjustment of the trial spacer. Specifically, the trial spacer may be shifted at predetermined increments or angular distances through the axial translation of the drive arm 1006 shifted by a drive in the form of a ratcheting mechanism 1008 in engagement with the drive arm 1006.

Figure 77A:
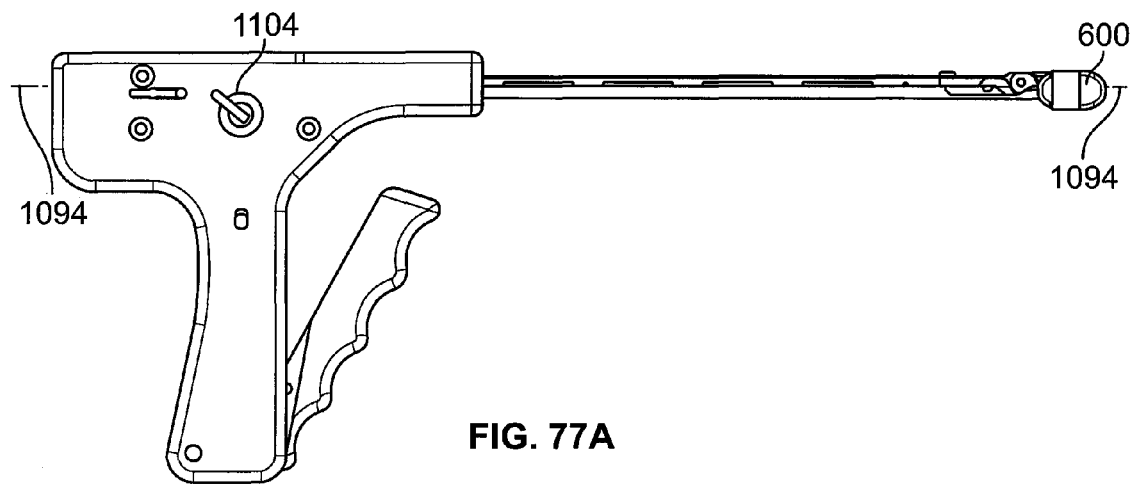
FIG. 77a is a plan view of the insertion tool and trial spacer with the spacer in a 0 degree orientation relative to the longitudinal axis of the insertion tool.
Figure 77B:
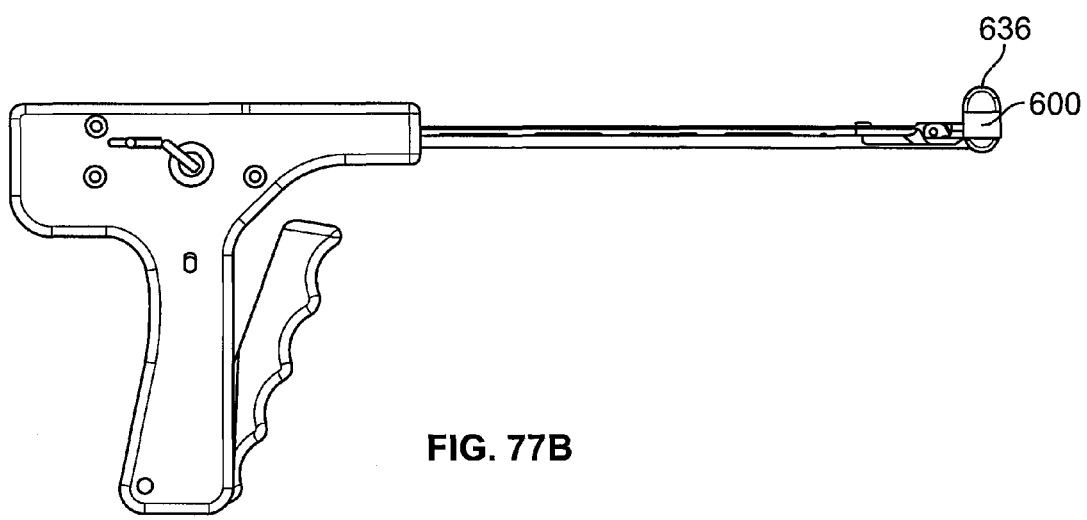
FIG. 77b is a plan view of the insertion tool and trial spacer with the spacer in a 90 degree orientation relative to the longitudinal axis of the insertion tool.
Figure 77C:
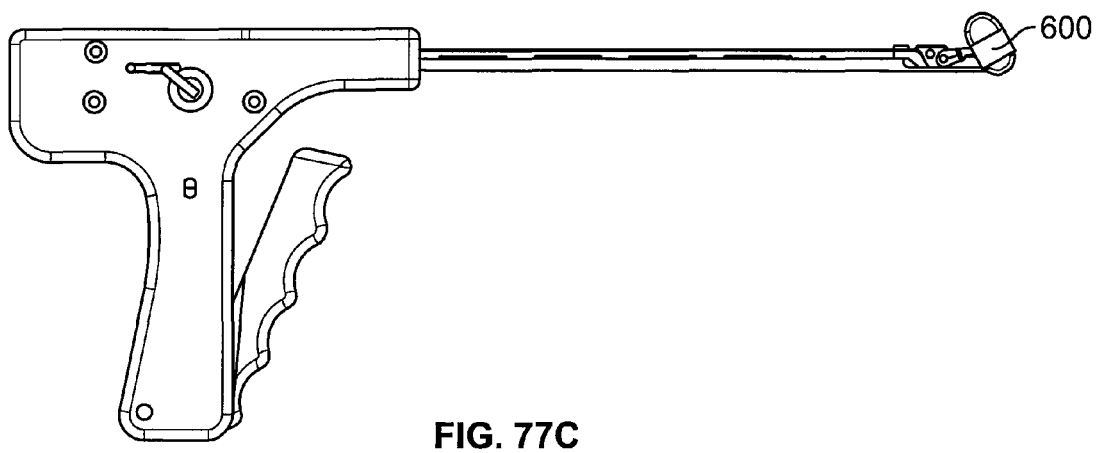
Figure 78:
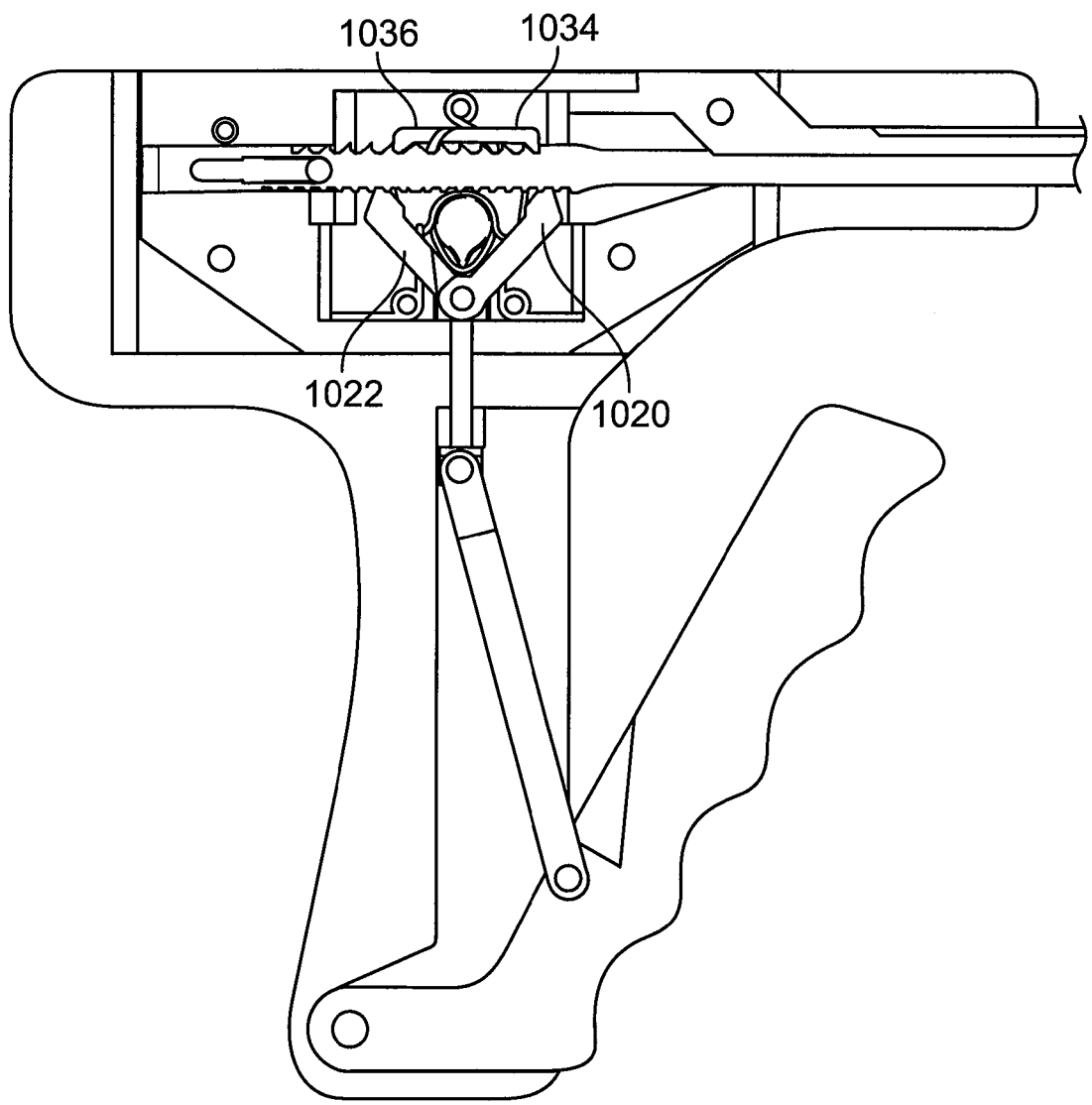
FIG. 78 is an enlarged plan view of the inserter with the ratchet mechanism in a locked position.
Figure 79:
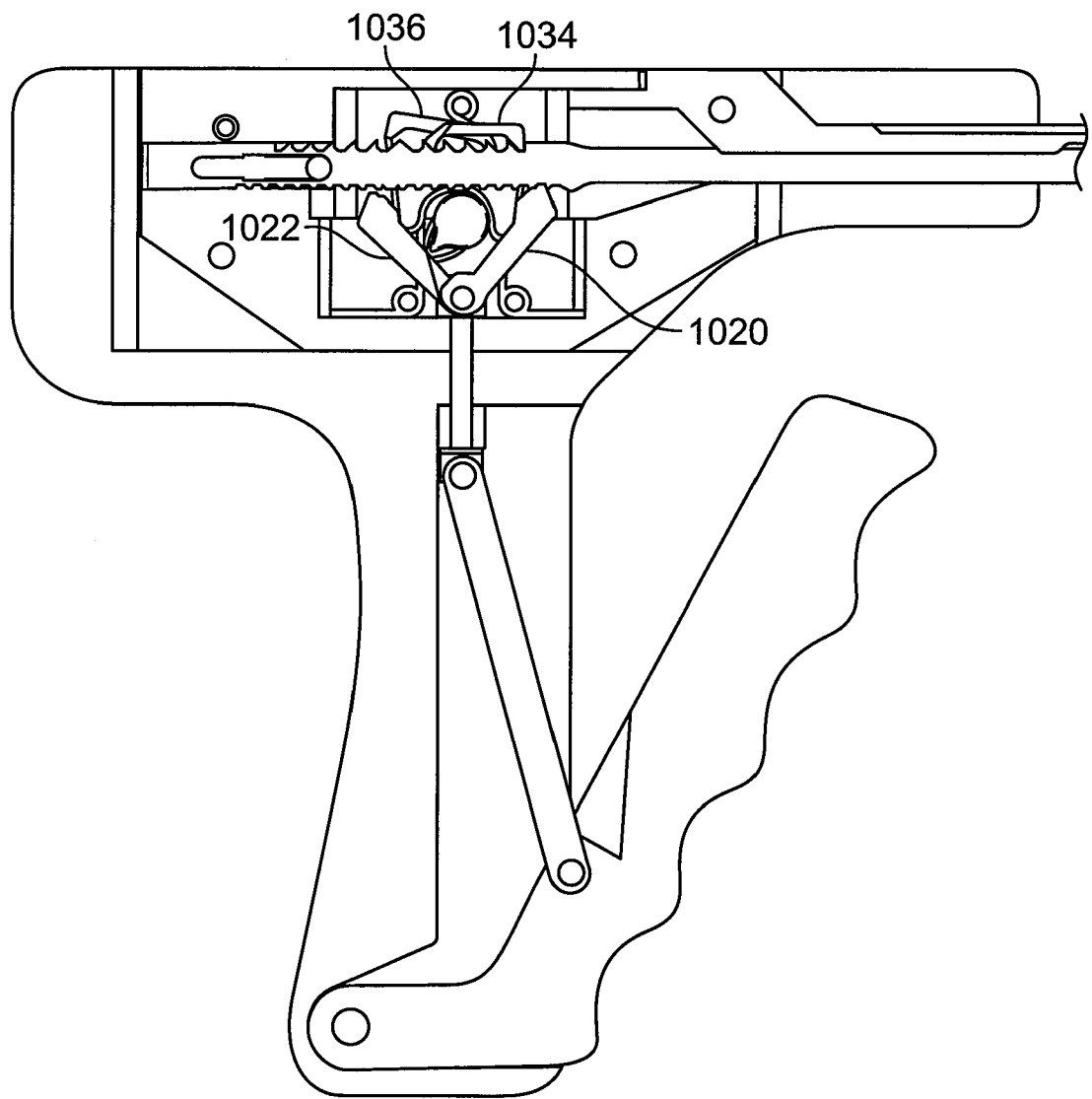
FIG. 79 is an enlarged plan view of the inserter with the ratchet mechanism in an advancing mode prior to depression of the trigger.
Figure 80:
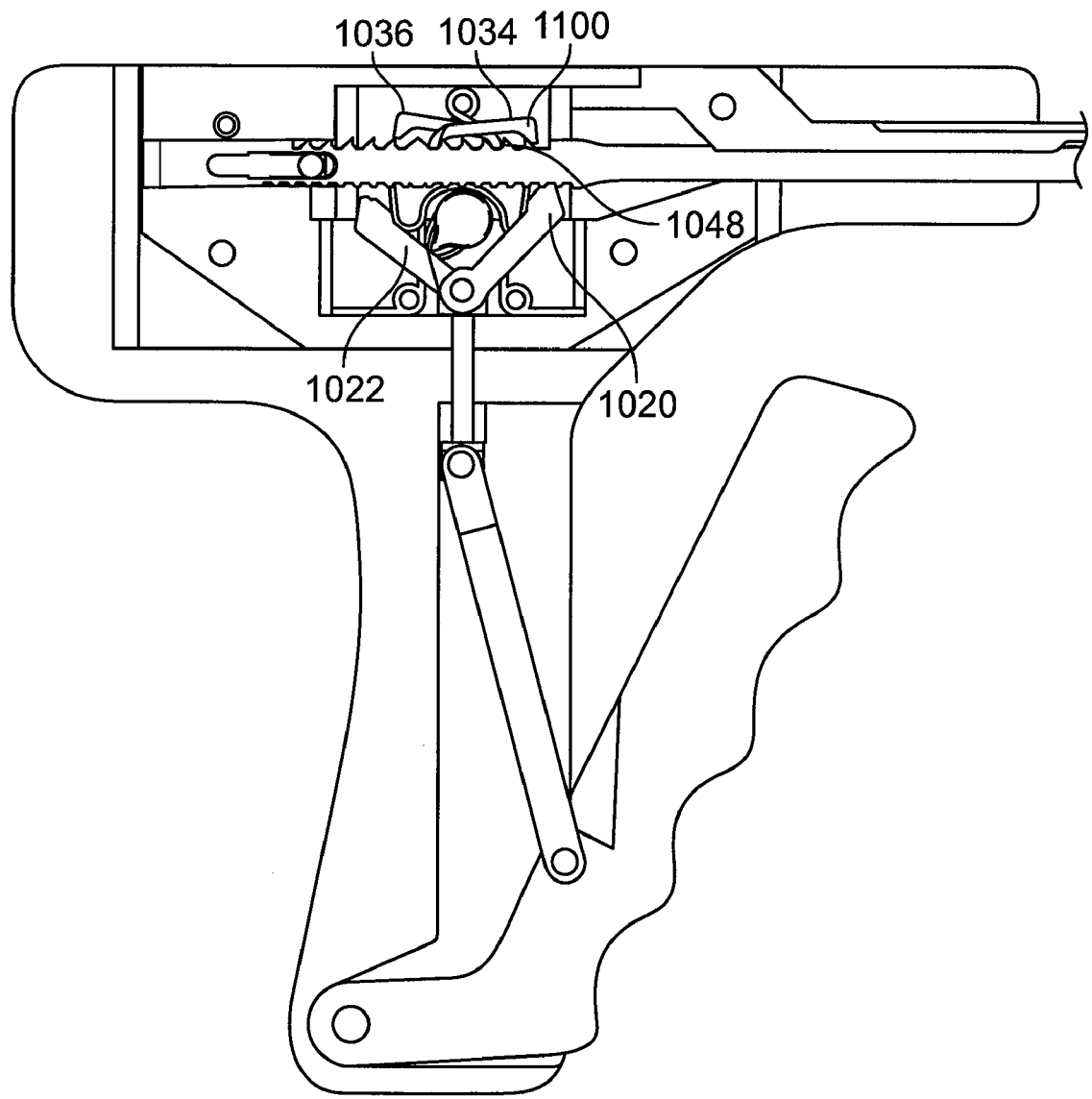
FIG. 80 is an enlarged plan view of the inserter with the ratchet mechanism in an advancing mode showing the drive arm being advanced by the depression of the trigger.
Figure 81:
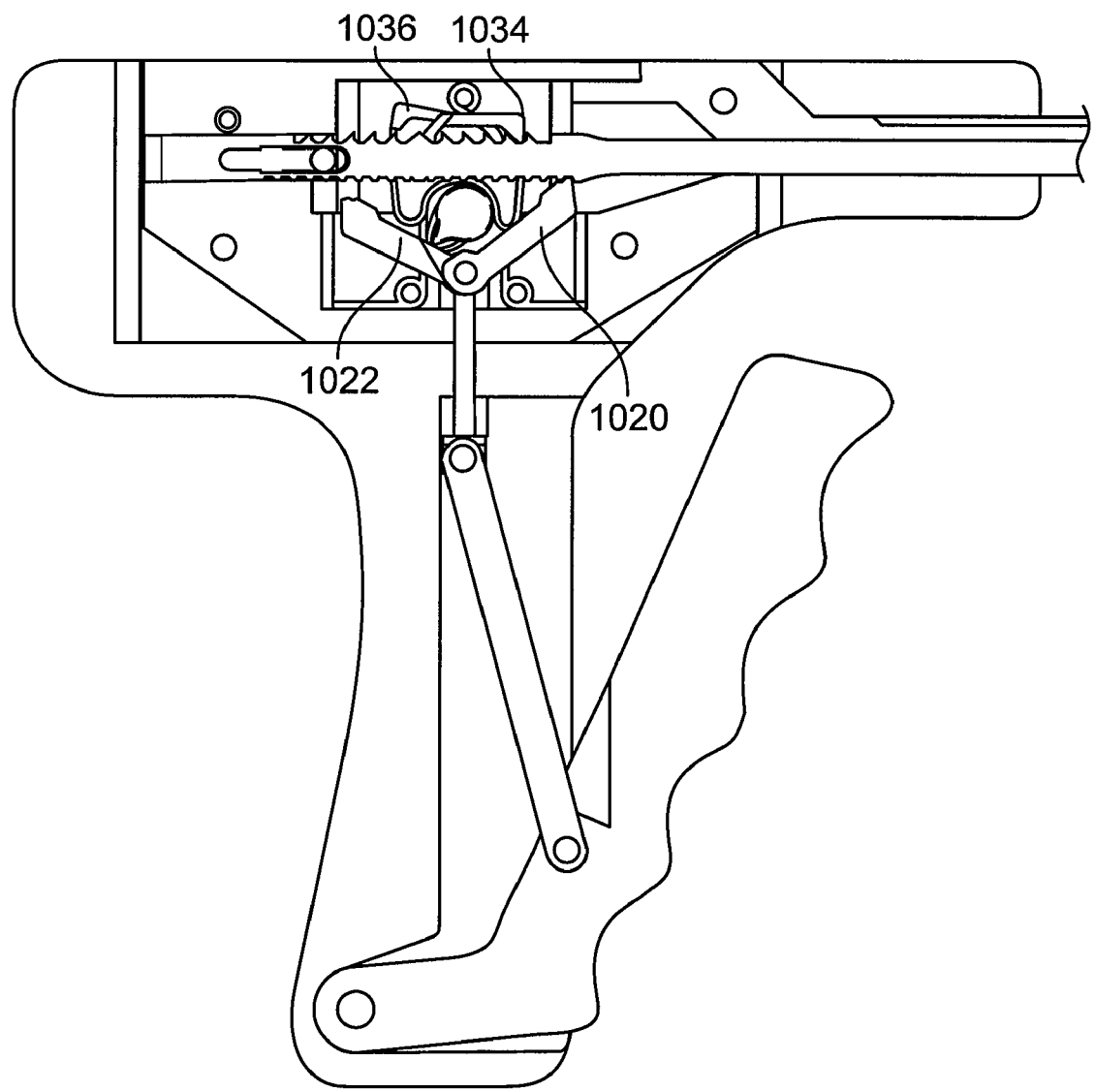
FIG. 81 is an enlarged plan view of the inserter with the ratchet mechanism in an advancing mode showing the drive arm advanced from its initial position in FIG. 79.

In a preferred embodiment shown in FIGS. 71-73, the ratcheting mechanism 1008 is actuated by an actuator, such as a trigger 1010 pivotally attached to a pistol-grip type handle 1012. The pistol-grip handle 1012 is connected to the housing 1014 of the inserter 1000 to extend transversely thereto, and more particularly preferably at a substantially perpendicular angle to the longitudinal axis 1094 of the inserter. As shown in FIG. 77a-c, the trial spacer 600 is removably mounted to the distal end of the inserter with its lateral axis in a horizontal position. The trial spacer may be pivoted by the insertion tool from an initial horizontal position shown in FIG. 77a, into a vertical orientation shown in FIG. 77b, in which the longitudinal axis of the trial spacer is transverse to the longitudinal axis 1094 of the inserter.

With this orientation, the pistol-grip handle 1012 allows the user to implement the tool with one hand having their wrist in a generally neutral position. The neutral wrist position may be defined as the alignment of the hand to the forearm without significant pronation, supination, flexion, extension nor ulnar or radial deviation. In addition, the user's arm may be positioned in a more natural position when manipulating the inserter. During the procedure of replacing an affected disc or nucleus, a surgeon may approach the affected disc from an anterior lateral or anterolateral direction. If the patient is lying supine on the operating table, the affected disc's lateral axis will be horizontal and its anterior-posterior axis will be vertical. Therefore, the surgeon may approach the affected disc with the inserter at a downward angle between the anterior and lateral axes of the disc. As discussed above, the desired position of the trial spacer is with its longitudinal axis spanning the lateral axis of the spine. As the trial spacer will be inserted into the disc space at an anterolateral angle, it must be turned towards the anterior axis to be properly aligned with the lateral axis of the spine. Hence, in this configuration, the inserter will be in a proper position to insert and shift the trial spacer 600 to an appropriate lateral orientation when the inserter is held with a neutral wrist position. Thus, an inserter with a pistol grip may be more ergonomic and comfortable to use, while increasing the maneuverability of the inserter and reducing the likelihood of unnecessary trauma to the patient.

Because the disc device is not typically visible when inserted into the patient, a surgeon must determine the position of the disc device by other means. In a preferred form, the ratchet mechanism 1008 audibly emits a sound, such as a clicking sound produced by the ratchet mechanism components when actuated. Thus, a clicking sound will accompany each positional change of the disc device. As a result, a surgeon, knowing the predetermined increment that the disc device will shift with each actuation of the ratchet mechanism 1008, may simply listen for the clicking sound to determine the orientation of the disc device. In this form, the steering mechanism 1004 generates audible feedback to provide information regarding the steered position of the disc device. In addition, the steering mechanism 1004 may emit tactile feedback through the inserter 1000, such that the surgeon can feel with his hand when the mechanism has been actuated, and thus determine the steered position of the disc device.

The trigger 1010 is pivotally connected to a trigger link 1016, which in turn is pivotally connected to one end of a push rod 1018, which is constrained for movement in alignment with a vertically oriented, narrow and elongate slot opening 1066 between opposing walls 1068 of the handle 1012 such that it may only move along an axis perpendicular to the drive arm 1006. The trigger 1010 has a lower foot 1070 extending into the slot 1066 and having a pivoting connection 1074 at its rear end 1076 to the handle 1012. The pivot connection 1072 of the trigger 1010 to the link 1016 is toward the lower end of the obliquely extending gripping portion 1078 of the trigger 1010 and at the lower end 1080 of the link 1016. The upper end 1082 of the link 1016 is pivotally connected to the lower end 1084 of the vertically oriented push rod 1018. Thus, the pulling or squeezing of the trigger 1010 towards the handle 1012 into the slot 1066 thereof pivots the trigger 1010 about its bottom rear pivot connection 1074 to the handle 1012, causing the link 1016 to shift upwardly and causing the push rod 1018 to be pivotally driven upwardly in the handle 1012.

The push rod 1018 is pivotally connected through a pin linkage at its opposite upper end to forward and reverse pawls 1020, 1022, which selectively engage the drive arm 1006 to advance or retract the drive arm 1006, respectively, or operate in tandem to simultaneously engage the drive arm 1006 to block movement of the drive arm 1006 and corresponding shifting of the trial spacer.

Referring now to FIGS. 74a and 74d, the drive arm 1006 includes four sets of teeth 1024 on its upper and lower faces 1086 and 1088 to facilitate the axial translation of the drive arm 1006 when acted on by one of the pawls 1020, 1022. The teeth on the upper face include advancing and retracting teeth 1026, 1028, and the lower face also has advancing teeth and retracting teeth 1030, 1032 formed thereon. The advancing teeth 1026, 1030 are used to generate forward advancement of the drive arm 1006 and are disposed forwardly towards the distal end 1002 of the inserter along the drive arm 1006 relative to the rearward retracting teeth 1028 and 1032. The advancing teeth 1026, 1030 have ramped surfaces 1090 that are inclined rearwardly relative to the longitudinal axis while the retracting teeth 1028 and 1032 have ramp surfaces 1090 oppositely inclined in the forward direction relative to the longitudinal axis 1094. Abutment surfaces 1096 of all the teeth 1026-1032 generally extend from their tip ends 1098 orthogonal to the longitudinal axis 1094 with the advancing teeth 1026, 1030 having their abutment surfaces 1096 rearwardly of their ramp surfaces 1090, and the retracting teeth 1028, 1032 having their abutment surfaces 1096 forwardly of the ramp surfaces 1092, as best shown in FIG. 74d.

Acting in tandem with the forward and reverse directional pawls are forward and reverse locking wings 1034, 1036, shown in FIGS. 74a-c, which are in biased engagement with the drive arm 1006 through torsion spring 1038. The forward locking wing 1034 has a downward projecting portion 1100 that engages against an abutment surface 1096 of one of the advancing teeth 1026 on the upper face 1086 of the drive arm 1006 to keep the drive arm 1006 from moving in a rearward direction when forward pawl is advancing the drive arm 1006. The reverse locking wing 1036 has a projecting portion 1102 that operates in the same manner on the upper reversing teeth 1028 to keep the drive arm 1006 from moving in a forward direction when the reverse pawl 1022 is retracting the drive arm 1006. The drive arm 1006 may be operatively connected to the gripping member 1040, similar to the embodiment shown in FIG. 54, or the drive arm 1006 and gripping member 1040 may be integrated into one element, as shown in FIG. 72.

Both the locking wings 1034, 1036 and the pawls 1020, 1022 are selectively operable through the operation of a directional selector. Referring now to FIGS. 72, 75c-d, the directional selector in one embodiment takes the form of a directional knob 1042 connected to a directional shaft 1044 having axially spaced camming surfaces 1046 to engage the wings and pawls to selectively move them into an engaged and disengaged orientation with the teeth 1024 of the drive arm 1006. Referencing FIG. 71, when the directional knob 1042 is turned in a clockwise direction, corresponding to a forward direction, the camming surfaces 1046 engage both the reverse pawl 1022 and wing 1036 and move both against their spring bias away from the teeth 1024, leaving the forward pawl 1020 and wing 1034 in biased engagement with the teeth 1024. When the directional knob 1042 is in a neutral position, as shown in FIG. 71, both the forward and reverse pawls 1020, 1022 and wings 1034, 1036 are in engagement with the teeth 1024, as best shown in FIG. 73, effectively blocking any fore-and-aft movement of the drive arm 1006. Thus, the trigger 1010 may not be actuated or pivoted and pulled rearwardly toward the handle 1012 when the directional knob 1042 is in the neutral position, effectively acting as a "safety" position. A surgeon may use the neutral position to avoid accidental pivotal movement of the trial spacer when manipulating the inserter within the body of the patient. To reverse the drive arm 1006, the directional knob 1042 is placed in reverse mode by turning the knob 1042 counterclockwise from the neutral position. In the same manner as the forward mode, the camming surfaces 1046 of the directional shaft 1044 engage the forward pawl 1020 and wing 1034 and move both against their spring bias away from the teeth 1026, 1030. Thus, the reverse pawl 1022 and wing 1036 are left in biased engagement with the teeth 1028, 1032.

When the user selects forward mode by turning the directional knob clockwise so that the bar indicator portion 1104 thereof projects upwardly and rearwardly (FIG. 77), the ratcheting mechanism is operable to move the drive arm in a forward direction and consequently rotate the trial spacer 600 away from a longitudinal orientation. As shown in FIGS. 78-81, when the trigger 1010 is depressed, the forward directional pawl 1020 is actuated by the push rod 1018, the pawl advances the drive arm 1006 in a forward direction. As the drive arm 1006 advances, the forward wing projecting portion 1100 travels along a ramped surface 1048 of an upper advancing tooth 1030 until it clears the peak or tip end 1098 of the tooth and drops back into the valley 1050 of next most rearward tooth. When the trigger 1010 is released and the push rod 1018 begins returning to its original position, the pawl 1020 is pulled away from the lower advancing teeth 1030 and the biasing spring 1052 forces the pawl 1020 rearwards until it engages the next most rearward tooth on the lower face 1088. While the pawl 1020 is moving to the next most rearward tooth, the forward wing blocks rearward movement of the drive arm 1006. When the reverse mode is selected by turning the directional knob 1042 counterclockwise so that the bar indicator portion 1104 thereof projects downwardly and rearwardly, the reverse pawl 1022 and wing 1036 become operable on the lower and upper reversing teeth 1028, 1032 in a corollary manner to retract the drive arm 1006 and shift the trial spacer 600 back towards a longitudinal orientation with respect to the inserter 1000.

In a similar manner to the embodiment described in FIGS. 50-70, the trial spacer may be pivoted from an initial or longitudinal position of 0 degrees, where the longitudinal axis 1094 of the trial spacer is coaxial with the longitudinal axis 1094 of the inserter 1000 (FIG. 77*a*), to a position of 90 degrees, where the longitudinal axis of the trial spacer is turned perpendicular to the longitudinal axis 1094 of the inserter 1000 (FIG. 77*b*). To advance the trial spacer from a position of 0 degrees to 90 degrees, the directional knob 1042 must be in the forward direction. The user actuates the ratchet mechanism by squeezing or depressing the trigger 1010. With each depression of the trigger 1010, the drive arm 1006 advances a predetermined increment or distance, which is dictated by the tooth geometry and the pawl and wing configuration. In turn, the trial spacer 600 will be pivoted or rotated a predetermined increment or amount corresponding to the distance advanced by the drive arm 1006.

In a preferred embodiment, each squeeze of the trigger 1010 results in a rotation of the trial spacer 600 of approximately 30 degrees, such that three sequential depressions of the trigger 1010 will pivot the trial spacer 600 approximately 90 degrees. However, the predetermined rotational increment may be a different size, such that more or fewer depressions of the trigger 1010 are required to pivot the spacer 600 to the desired position. For example, the steering mechanism components may be selected such that a single actuation of the trigger 1010 results in a rotation of 90 degrees. In a like manner, the trial spacer 600 may be shifted from a 90 degree position to a 0 degree position by shifting the directional knob 1042 to the reverse direction and depressing the trigger 1010 in the same manner as described above.

In addition, the trial spacer 600 may be passively steered using intervertebral surfaces such as the annulus to help guide the trial spacer 600 into position. For example, when the directional knob 1042 is in the forward position, the drive arm 1006 is free to be pulled forward due to the orientation of the upper and lower advancing teeth 1026, 1030. Thus, if the distal end 636 of the trial spacer 600 is acted on by an external force in the direction of rotation of the trial spacer 600, the trial spacer 600 will pivot about the distal end 1002 of the inserter and pull the drive arm 1006 forward. In this manner, the surgeon may combine active with passive steering while inserting the trial spacer 600. Nevertheless, while in the forward position, the forward pawl 1020 and locking wing 1034 will prevent the trial spacer 600 from being rotated back towards a longitudinal position. In a similar manner, the trial spacer 600 may be passively steered while the inserter 1000 is in reverse mode, in that the trial spacer 600 may be pushed back towards a longitudinal position.

As shown in FIG. 74*d*, the motion of the drive arm 1006 may be limited by a release pin 1054 disposed through a channel 1056 defined in a proximal portion of the drive arm 1006. The channel 1056 is comprised of a forward groove 1058 and a rearward groove 1060 having separate but parallel longitudinal axes. The grooves are interconnected near the center 1062 of the channel 1056 at a rearward portion of the forward groove 1058 and a forward portion of the rearward groove 1060. Referring to FIG. 75*b*, the release pin 1054 is an elongate shaft with an enlarged portion 1064 between its ends sized to fit within the grooves 1058,1060 and is biased with a spring within the housing 1014 of the inserter to prevent the pin from inadvertently traveling from the forward 1058 to the rearward groove 1060 when the trial spacer 600 is orientated at 90 degrees with respect to the longitudinal axis of the inserter 1000. In normal operation, the enlarged portion 1064 is disposed within the forward groove 1058. The forward end of the forward groove 1058 prevents the drive arm 1006 from retracting beyond a predetermined position, such as one corresponding to the spacer having a 0 degree orientation. The rearward end of the forward groove 1058 prevents the spacer from rotating beyond a different predetermined position, such as one corresponding to a spacer having a 90 degree orientation. To remove the spacer, the release pin 1054 must be shifted through the center connection point 1062 between the two grooves and into the rearward groove 1060. As shown in FIG. 77*c*, the drive arm 1006 may then be extended further to allow the trial spacer 600 to be removed, similar to the previous embodiment wherein the second link pin 678 of the trial spacer 600 may be removed from the engagement hook 852.

Once the trial spacer 600 is removed and replaced with another trial spacer, the directional knob 1042 is set to a reverse direction to retract the drive arm 1006 and rotate the trail spacer back to 90 degrees and lock the trial spacer 600 onto the inserter 1000. The release pin 1054 is then shifted back to the forward groove 1058, which will allow the drive arm 1006 to continue to be fully retracted until the spacer is in a longitudinal or 0 degree position.

While some embodiments of the insertion tools have been described above in combination with a trial spacer, it will be appreciated that the tools may be used with a prosthetic implant instead.

It will be appreciated that while a number of the features on the embodiments described above are configured with a disc nucleus prosthesis (DNP) in mind, any of the features of the inserters or implants described herein can be used with total disc prosthesis (TDP) instead.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A system for replacing a natural nuclear disc in an intervertebral space, the system comprising:
    a spinal device configured for placement in the intervertebral space;
    an insertion tool configured for holding the spinal device while the spinal device is inserted into the intervertebral space;
    a gripping member of the insertion tool having an end configured for adjustably holding the spinal device within the intervertebral space;
    a steering actuator of the insertion tool being operably connected to the spinal device and being configured for pivoting the adjustably held spinal device within the intervertebral space and for being controlled remotely from the intervertebral space;
    wherein the gripping member and the steering actuator have portions selectively opposed to each other and being configured for alternatively engaging the spinal device; and
    wherein the spinal device has a body and a link pivotally mounted on the body and having a selectively free end, and wherein the selectively opposed portions are configured for receiving the free end of the link.

2. The system of claim 1, wherein the gripping member further includes a locating portion configured and disposed for engaging and locating the spinal device at a predetermined orientation on the gripping member for being subsequently shifted into engagement with the steering actuator.

3. The system of claim 1 wherein the gripping member and steering actuator are configured for manually loading of the spinal device onto the gripping member and automatically shifting of the spinal device between engagement with the gripping member and engagement with the steering actuator.

4. A system for replacing a natural nuclear disc in an intervertebral space, the system comprising:
- a spinal device configured for placement in the intervertebral space;
- an insertion tool configured for holding the spinal device while the spinal device is inserted into the intervertebral space;
- a gripping member of the insertion tool having an end configured for adjustably holding the spinal device within the intervertebral space;
- a steering actuator of the insertion tool being operably connected to the spinal device and being configured for pivoting the adjustably held spinal device within the intervertebral space and for being controlled remotely from the intervertebral space;
- wherein the gripping member and steering actuator are configured for manual loading of the spinal device onto the gripping member and automatic shifting of the spinal device between engagement with the gripping member and engagement with the steering actuator; and
- wherein the insertion tool further includes shifting structure extending from at least one of the gripping member and steering actuator for engaging the spinal device to shift the spinal device between the gripping member and steering actuator.

5. The system of claim 4, wherein the steering actuator has an elongate main member extending generally parallel to the gripping member and having a distal end interconnected to the spinal device, and wherein both the gripping member and main member have at least one protrusion extending toward the other of the gripping and main member for engaging and shifting the spinal device while the spinal device is engaged on the other member.

6. The system of claim 4, wherein the steering actuator includes a ratchet mechanism operably connected to the gripping member for shifting the spinal device by a predetermined increment.

7. A system for replacing a natural nuclear disc in an intervertebral space, the system comprising:
- a spinal device configured for placement in the intervertebral space;
- an insertion tool configured for holding the spinal device while the spinal device is inserted into the intervertebral space;
- a gripping member of the insertion tool having an end configured for adjustably holding the spinal device within the intervertebral space; and
- a steering actuator of the insertion tool being operably connected to the spinal device and being configured for pivoting the adjustably held spinal device within the intervertebral space and for being controlled remotely from the intervertebral space, wherein the steering actuator includes a ratchet mechanism operably connected to the gripping member for shifting the spinal device by a predetermined increment;
- wherein the ratchet mechanism further comprises a drive arm connected to the gripping member and the drive arm comprises a set of teeth for incrementally advancing and retracting the gripping member and thereby shifting the spinal device by a predetermined increment.

8. The system of claim 7, wherein the steering actuator further comprises a trigger mechanism operatively connected to the ratchet mechanism for incrementally translating the drive arm to incrementally shift the spinal device by a corresponding predetermined increment.

9. The system of claim 7, wherein the insertion tool further comprises a pistol-grip handle operably connected to the steering actuator for allowing the user to operate the insertion tool with a generally neutral wrist position.

* * * * *